US008623381B2

(12) United States Patent
Crance et al.

(10) Patent No.: US 8,623,381 B2
(45) Date of Patent: Jan. 7, 2014

(54) VIRAL STRAINS DERIVED FROM THE VACCINIA VIRUS LISTER VACV-107 AND USES THEREOF

(75) Inventors: Jean-marc Crance, La Tronche Cedex (FR); Daniel Garin, La Tronche Cedex (FR); Daniele Gratier, La Tronche Cedex (FR); Anne-Laure Favier, La Tronce Cedex (FR); Robert Drillien, Illkirch (FR); Matthias Hebben, Illkirch (FR); Daniele Spehner, Illkirch (FR); Karine Pradeau, Illkirch (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/119,812

(22) PCT Filed: Sep. 18, 2009

(86) PCT No.: PCT/EP2009/062114
§ 371 (c)(1),
(2), (4) Date: Mar. 18, 2011

(87) PCT Pub. No.: WO2010/031837
PCT Pub. Date: Mar. 25, 2010

(65) Prior Publication Data
US 2011/0171256 A1 Jul. 14, 2011

(30) Foreign Application Priority Data
Sep. 19, 2008 (EP) .................................. 08305570

(51) Int. Cl.
*A61K 39/12* (2006.01)
*A61K 39/275* (2006.01)
(52) U.S. Cl.
USPC ................... 424/205.1; 424/199.1; 424/232.1
(58) Field of Classification Search
USPC ...................................................... 424/205
See application file for complete search history.

(56) References Cited

U.S. PATENT DOCUMENTS

2005/0031643 A1 2/2005 Szalay et al.

OTHER PUBLICATIONS

CDC Advisory Committee, Vaccinia (Smallpox) Vaccine Recommendations of the Advisory Committee on Immunization Practices (ACIP), 2001, 50(RR10), PDF pp. 1-30.*
Ober et al.; "Immunogenicity and Safety of Defective Vaccinia Virus Lister: Comparison with Modified Vaccinia Virus Ankara"; Journal of Virology, vol. 76, No. 15, Aug. 2002, pp. 7713-7723.
Kidokoro et al.; "Geneticlally Stable and Fully Effective Smallpox Vaccine Strain Constructed from Highly Attenuated Vaccinia LC16m8"; Proceedings of the National Academy of Sciences of the United States of America, vol. 102, No. 11, Mar. 2005, pp. 4152-4157.
Garcel et al.; "Genomic Sequence of a Clonal Isolate of the Vaccinia Virus Lister Strain Employed for Smallpox Vaccination in France and it's Comparison to Other Orthopoxviruses"; Journal of General Virology, vol. 88, No. Part 7, Jul. 2007, pp. 1906-1916.
Meyer et al.; "Mapping of Deletions in the Genome of the Highly Attenuated Vaccinia Virus MVA and Their Influence on Virulence"; Journal of General Virology, vol. 72, Jan. 1991, pp. 1031-1038.

* cited by examiner

*Primary Examiner* — Louise Humphrey
*Assistant Examiner* — Barry A Chestnut
(74) *Attorney, Agent, or Firm* — Whitham, Curtis, Christofferson & Cook, PC

(57) ABSTRACT

The present invention relates to viral strains derived from the vaccinia virus Lister VACV-107 and to pharmaceutical composition containing the viral strains. More particularly, the present invention relates to a viral strain derived from the vaccinia virus Lister VACV-107 wherein strain contains in its genomic sequence (SEQ ID N°1) at least one deletion selected from the group consisting of: deletion of the nucleotides 19758 to 28309 in the sequence ID NO°1 ($\Delta$18), deletion of the nucleotides 161293 to 164811 in the sequence ID NO°1 ($\Delta$20), deletion of the nucleotides 181231 to 183304 in the sequence ID NO°1 ($\Delta$21), deletion of the nucleotides 6118 to 9677 in the sequence ID NO°1 ($\Delta$22), deletion of the nucleotides 1833 to 3574 and 185848 to 187589 in the sequence ID NO°1 ($\Delta$23).

7 Claims, 9 Drawing Sheets

SEQUENCE LISTING

```
<160> NUMBER OF SEQ ID NOS: 37

<210> SEQ ID NO 1
<211> LENGTH: 189421
<212> TYPE: DNA
<213> ORGANISM: Vaccinia virus

<400> SEQUENCE: 1
ctgaaaggaa ataggaatag gaataggaat agtgtcataa tcgtatcaca ctattgagac     60
agaaaaagaa gaagtcgcga gaggtaactt tttgtgaatg tagttaagaa cattttttgtt    120 ttgcaaaccg gaatatagtg tccggtacac ttttttaatt cgtggtgtgc ctgaatcgtt    180
cgattaaccc tactcatcca atttcagatg aatagagtta tcgattcaga cacacgcttt    240
gagttttgtt gaatcgatga gtgaagtatc atcggttgca ccttcagatg ccgatccgtc    300
gacatacttg aatccatcct tgacctcaag ttcagatgat tccttgcaca tgtctccgat    360
acgaacgcta aactctagat ttttgacgca ttttgtatcg acgatcgttg aaccgatgat    420
atcttcgtaa ctcactttct tatgagagat gttagacccg agtactggat gggtcttgat    480
gtcgctgtct ttctcttctt cgctacatct gatgtcgata gacacctcac agtctttgat    540
catagcaaga gcttcttcat gagtgatcgc gggagagtcc ttaccttgtc ctggggacac    600
gctggacaat ctagcattca ctgtgtttcc atcagcggat tctgagatgg atttaatctg    660
aggacatttg gtgaatccaa agttcattct cagacctcca ccgatgatgg agtaataagt    720
ggtaggagga tctacatcct cgactgatgt ggaatcatct tctgattcca cctcgggatc    780
tggatctgac tcggactctg taatttccgt tacggattgg caaatcttat cattggtcgg    840
tgtttggtct tgctttgtga ctttgataat aacatcgatt cccatatgat gtttgttttc    900
ttcttccgta cacgaggagg aggatgagga tgattgctga agactggcag gcatagcagc    960
tgccgccagg cacatgcatg ccaggacgat atattgtttc ataattgcta ttgattgagt    1020
actgttcttt atgattctac ttccttaccg tgcaataaat tagaatatat tttctacttt    1080
tacgagaaat taattattgt atttattatt tatgggtgaa aaacttacta taaaaagtgg    1140
gtgggtttgg aattagtgat cagtttatgt atatcgcaac taccgggcat atggctatcg    1200
acatcgagaa cattacccac atgataagag attgtatcag tttcgtagtc ttgagtattg    1260
gtattactat atagtatata gatgtcgccc actagagtta ctgtctccga atgcggcatg    1320
```

```
atagtatcat tctttgcttt cgttaactgt ttggaggaag aatctttgtt attgcattta   1380
atctcgaaat tcagagtgca caccttctc ctgtaaagaa acctgaagtt gctaccttat   1440
taaggacgga gaagtattcc tcacgaaaga cgggattaca gtctttatga ttcatagtaa   1500
tagttagttc cgacgttgag atggattcgc tgagaccggt agtggtcgtc cgagtacacg   1560
atgtgtcgtt aactggatac aggttaattt ccacatcgat atagttaaag gtatttctgg   1620
gtacgggttc gcattatct gcggaagaga cggtgtgaga atatgttccg agaccacacg   1680
gagaacagat gacgtctccg gatactccgt atcctattcc acattttgtt tgggaaacac   1740
atgccttgca tccggatgat cctttgagaa gacaataata tccgggagag cattcacaga   1800
ttctattgtg agtcgtgtta cacgatcgcg tcttccgtta caacttagac aagcgggtaa   1860
atgattattg cgagatgtga aggtacccga accacacggc gtacattgtg tgttagtctt   1920
gctatcgcat aatctggaag cgtatgttcc cggacacaaa ttatggcgtt tgtattcgtt   1980
gtctttacac tttccatcgg atggtgcatg cggtgctata tctcttccgt ttattattat   2040
acatgagaga aacaatatat acgagtataa tacggacttc atgatttaat aatgtagtaa   2100
tcgtcgtctt gttcctgttt cctacttctc caatcatata gatattttct ttctatcatg   2160
gataatattt gtaatggttc tttccgtaca acatactgtt tagatgatat tgcgcataat   2220
ttccggaggc aaatacgata gtctagattg accgatggta gactctaatt tattgagtgc   2280
tttgtcgacg agtttacttt tacgctccat cgatagatgg cactgttcta tgagatcgtc   2340
gtacatggga aatgaaatgt gtctgtccga atgtatggct ttaagatagc tgtgataccg   2400
tatacaggtc ggtgtcggag attcgaatct ctttaaggcg acttatgtca cgatgatgga   2460
atctatctta tcgaatgata tatttttcat aaatacactt ttatagtcct cgtttaaaca   2520
gaatttacta tgtagttccg cgaatgactc gtcccttaat aggcagtagg ctagtatctt   2580
ttttacgtag taatcgtcgt agggagagac atcttgtaga acaacgattt aatcataggt   2640
agagatactt tcagtctgtg gtggatgatg tcattcacaa catccgcctt gtatatgatg   2700
tttctgtttt caaacaccaa gtcgaatacc gtctttagtc ggaaggttga tgtcgtatcc   2760
gatgtatgag gcaacattgt tgttacaatt ttgaaaggcg gtattatagt attcgtcttt   2820
ctgaatgtcg aacctatcta gtagataccg tagtatattg agagtgtatc cttgattatg   2880
ttttatgaat agataaagta gatgttgtcc ttcttccttt tgttcgtgcc aagtgagtaa   2940
cattatgaga atatgacctg ttgcacaatc gttccatgat gggtgtacaa tcaagattat   3000
tacgtatcct cgagataaaa gagcatacac cacacgagga ctatgtttgg tatactgttg   3060
aaggtaagtg tgtaaccgcg ttaatgtttg ctccataatc tattatcgcg tagatgaatc   3120
gcttctcggc tcgcatctta gtgtgactta acttgtaata attgctttcg tagaacgtgg   3180
atatgtgttt acagtagtaa tgaagagaag tgagttcatc ctcgtcggcg caattagggt   3240
cggatccttt gtacagaacg taatagttta agctcccatt gaatttatat ctaagataac   3300
acagcaatag atcggatgat ttactaaagt catcaatggt gtccgttagt atatcaaaga   3360
tcttgttatc gattgatagt ggtcatcctt gctatcaaag ttacgcatgc cgtggtgtaa   3420
caatatcttt aatacagatg gattaaatcg tgtattcatc gtatagcaat gtaatggaga   3480
gttacctcgt ttattcagat cgcagtgttt aataactagc ttaaacagat gagacgatgt   3540
atccacatca aagaacgtga aatacatatg acagacattg ttgacagaaa cgtgaccttc   3600
attcttaccg tcgtccataa atacgttagg tataaaccac atactatcgc gaacgatgcg   3660
tacaatctcg tccatctcat aatgatttac tttttcataa ttagagatgt acgaaagaaa   3720
```

```
aagaaaaaga aaaagaaaaa cagaacaata tattttttta gtaatgttta tgcgagacat    3780
ataaaataaa ctccgtgttt atgatgccgg taaatgtttt tatcatcttg gacggaatcg    3840
attttgtaat atgtcatgga aacaaatgaa acaggacatt atcgctccat gataaattat    3900
ttaatggagt aataaagtat ctccatgggt aatttcgaaa tcaagttatc gtctgtatta    3960
atgttgtcca ctatggagtc gatcctctca ttgttcttta cagtttctgt aatgatggac    4020
gttagttctt ttttgtacca tttgatgtcg gattctttgc gtatctcaat ctgtggcgtt    4080
tgcttcgttt aaataatata tcaaacatgg agacgcctga tatgtagaca ttcttcattc    4140
tattaatgtc tgctctatag cgctttagtt ccttatgacg accggcgata tcatacttta    4200
ctttagaagg aaaatcatca tctaggatta aggcgtatct gatacaggcg aataatggtt    4260
caggatatag atagcgtata tctctattaa atgcgtcaat catagtctct agagtgggat    4320
ggtaactcag taataaatca actagcttcg ttttgttttc tcttctgtaa ctgcttttct    4380
ggatggccgt attgattatc gagcgtgaca ctcgctccat attccaataa ccgctttgca    4440
aattgtatat tattgacatc gaccgcgtaa tatagtagag ttatcgatca tatctatatc    4500
atccatgtac ttgcttagta tatcaaatac atctatcagt atggtttcat aacagtgata    4560
cccgcaatta ttaaatctcg ataatatcag accgtacata catagacggc cattgttcga    4620
tatgtgattt acagccgcgt gtccatattt tccacgataa accttacgac gtttacatcg    4680
acgagattat tattaacaaa gtagtcgtgc agaggatagt tgttgtccgt cgtcttatcc    4740
atggttgctc cgttatccaa catgcattga atgataggta tacttaccat atcgccgtaa    4800
tgtaagtagt ttatcaacat ggcttgtaca tcctgttgtc taaatctctt tagaatgtta    4860
tcgatgatgt agtggttata ttctctggaa tcgtacgaag taatactacg cattacgtcg    4920
acaagagtat gacgtctctc aataagaaga ttaacgattt ccatgtctac attatatggg    4980
gttactctaa atcgcttgtt tagataatac gcctctaata tagggctgac gtcgtatact    5040
ctacacgtgt ccacatcctt tattaataat ttaacaatct ctatatctat ggttgagcaa    5100
gaccagtagt attggatggg taaagatcct ccttcgtctc tgccatggat ggaaacattg    5160
ttatcgatca aacatttaat tacatccttg gatagagatt gagattctct atgagacgat    5220
atatagtaat gaagagagtt cttacacata tcactgtcgt acatacaggt acgaaatacg    5280
taaccggtgc tgtaacattc tgatttaaga agccatagca atacttctgg tctcggatta    5340
ggcgtcgtta cgtatatatc caccaatccg agaccattga ttgcataatt cgtattcttg    5400
gacgacgtta tccgtttatc cacaattagg tattttagca gacgtaagtc gatattatcc    5460
gaatacagat cgaaatcatt tatattcgac ttgagttcgt tagaggaatt cgaatagctg    5520
gatatcagta gatgcacaat ctgagatttg acgtatctat gcttactgta tgctcctagc    5580
ggagttaatc cttcgttgtt tctacaaagt ctctcgactc cgcgagagag taacagccga    5640
acaatcttaa tgtctgtatc gcatttattg aagacgtaac aatgtagcgc attgtttcct    5700
cgtctatcta tatgtttga taagttgtga cacgtttcaa tctctggttt tattttttg    5760 tacgtcacat cttcatccag tagacgacat aaaatagtgc actctctacc acaataatcc    5820
atagctattc tggtgctaat tattcctatt tcacgaaggc aatcattcct cataagatga    5880
taaaaagtgt agtgagagag catgaaggag atttagtatt tagcagtgcg gatatgatcc    5940
aagagggtga gatagtcgtt ctcgttcaga atctttcgca gcataagtag tatgtcgata    6000
tacttatcgt tgaagactct tccagagacg atagctgatt gagtacaaag tccaatgatt    6060
gcacgaagtt cttcggcggt tttcatggag tcatttctga tgaaacattt aatgatctcc    6120
```

```
acgcaattgt cccacggaag tgaatccttc aactcaccac caaagagctc cgttgcatca   6180
gttctgaaag agatgagaag cctgtagaga gaccctgcgc tttctctatg ggtccatcta   6240
tgagaaaccc acaggatgta ttcagtcaga caatgtctga cgtcggccac ggtattcagg   6300
gagtccttag tagcgtggca atgacagggt ctgaacttgg cacaaggaga ggccattgtg   6360
aaggtagacc tgtagccgtc tatgctaata gagggcttta atttccattt ttttaatggg   6420
gttgtggatg aggaatgaga gtgatatcat attgagatac gtagttatgt agaggtgtat   6480
ttcctatatt atttactttc ggtttcatat tttaccaact cttaaataaa tttcttttca   6540
cgatgcatct tattaaatga cgttttctca taagtggaca tatagatgca aaagtaatga   6600
agaaaagtat tacctctatc atctacataa ttagggtctg ctccttttt taacaactta    6660
tacagtacgt agtagtagtt tatcggtttt aaatcaagtc tagaatatat agtggattaa   6720
tatatttta tattcgctaa agctatctat actatcagaa agcatatcat tctcaacttc    6780
atcatgagtt aaatatttgt gtaatggaat gtgaccatca ctgtcatgac atactccttt   6840
aataggtttt ttaaaacaga tgattcaaat ccttcattca ttagataaca gtgtaacgga   6900
gtcgtacctt ctactagttt gtttatatca cagcattcta caaacagtct aaacaataga   6960
gaagacggac agactttaac gtataaatga cacatgttat cgatattcgt tgatgaatta   7020
ttattaaacg tagttatgat aaatgattct aacgacatct ctcgctagag ataaaatcta   7080
gtatcgtatc atactcgcat agcatagttt ttcataatta atacaatatt taaaagactt   7140
attcggaaag tattttaata catgtatcat cgatggagat ccatatgagg agtcacttgt   7200
agttcttcag tagtaataac agtgctatca tcgatagtat aattatatgt tgttgtaatt   7260
ggagtaactg ttggtagttc ttccgtggaa tcaataatta tactaacagc aatagtataa   7320
ttatataaat atgttccgtt gatatcacat attttaatga actcatttct aacaccctca   7380
gctatatctg tccaattaaa tgtagccaac aatctactac gttctctttg attgactact   7440
tgtacggtag cgacgctaca ctatctttat tgtcttctac atgctccaat tgaatgtcat   7500
gatacaacgc agttttttctt atgcatgttt cataacacca cgaacatgtc gcagtaagat   7560
aatttctgta aattcatgat tgccggtcat aaacaagccc gtcaataatt gtggctatat   7620
attcagttta tagagcaaaa taattaagca caatagcgct taatctcaaa atatgttatg   7680
tttatttttt tcatattaaa catactggtt aaaatcctct aaaggctgat cttcatctat   7740
aaatcaagat cataattaca tttagacagt ggtttcatgt ttataaaaat gttcttttg    7800
tgtgaataag gaatatacta atcaataatc aaccatcgac cccattacga tagtatgcag   7860
gcaaccccc attagagagg tacgtgtaat cagtctctcc agttttagta ttttttataag   7920
tcattgttac ataaacggct tttaaacagt ctcctcgata ataagccata tctggaaatt   7980
tattaaatac tcgagtcatt ttacgcacgg tcaaaaaagt aagtaatgtc gacgacttct   8040
tacattctat agaacaccct agaatactca ttttcttttg gaaaatatcc tcagactctg   8100
atttgaacaa tgcacgacct atagtaaacc gtgaccaata agttatatta gtcaatggta   8160
tatccaaacc atcaggtgtg gatagtacgc cgatagtcca gtctttggta tcgatagtgt   8220
agttattgaa ctgagaagtt accgtatagt cttttttggtc atctctaaac aaggaaacta   8280
ataccttctac actattgaac gatttatctt ccgtaatggg tggaataacg ggaatataaa   8340
gtggactagc gatggatgaa gtcacgaata taagacacgc tattaatccg tatatcatca   8400
ttttgatatt acttataata acgatttgtt taatttttag tttatactat taattgtaaa   8460
tgatattatt atttttttt aagtattatc agctttagtt tatactatta ctatttgtaa   8520
```

-continued

```
tatttagaca tagataaacg tgataaaagt ctatttgttt atatttattg cggatagcag    8580
tatttcccta taaaaagtat acgtcctgtg ttgtctttaa tcatgtacat gaatggatgg    8640
tttatgtaga ccttcgtacg atataccatc gaaaagttag tcataaatac tcctgtaacg    8700
gccgatgctt ctgtatactc ctcattaaca tctataaacg tcgtatgtag aaattttct    8760
acagtgatag tttcattaca catcttgcta aaatctgcat aatatccgaa tatattagta    8820
agtcctaaat tttctaaaat cggtaccaga ttatacggtt ctgtcatttc cacttttaaac   8880
tttggcatat acaagtctat acttttagta gataacatac cacaccattt tttaaatttt    8940
tcatctgtta tattttttc tatgttatat ataccttcta tgtcgtccgg tagtataatt    9000
accatactag agtttccctc gtatggaata tcgataatag agaatcctcc gaataattca    9060
ttaatatgta catattgcaa gttattctcg gtacccacca tcatatcaac gctggtaact    9120
atattcttag aaatataaaa cttgtctgta tatgtaagat gtttagaaaa tggatatttc    9180
cacattgctt taaatggac ggcgctaaca actgtcatac gagtattaat ggatagcgga    9240
ctagtcaata aggaattaat tttaccattt gtcattgtct taacccattc gttgattagt    9300
tcctttgttt ggttagcatt attaaagttt acagtttgaa atcgtctttt tattttttgt   9360
aggaaggagg catggaactc gatactatcg ctaccgtata ttttatttgc ggtagctagt    9420
gtcgcacaat acggaatatc tacgtccatg tcattattgt catcgggtgt attctcattc    9480
atattctcta tatattttga tagttgttca gctgtagaac cagctgctcc atgatttaga    9540
atagataaag tagataaaat agaaactgga gaaatcaaaa cattttcatc agggtgtttt    9600
acgattagtt ctttaaagat atccatggta tagaccaaac aataacgata acgatatata    9660
tcataaataa ataatgttaa atttcagttt atgtttgtac cccgtattca tacttaacaa    9720
attggtattg cgtacacaat caatcatatt acataccatt aataatgcaa gcataaaaaa    9780
tcgttagtag atgtttctaa atataggttc cgtaagcaaa gaatataaga atgaagcggt    9840
aatgataaaa tcaattgtta tctaaaatga tcatactcat ttatttatt ctattatatt    9900
aacacataca tttttaacag caacacattc aatattgtat tgttatttt atattattta    9960
cacaattaac aatatattat tagttttatat tactgaatta ataatataaa attcccaatc   10020
ttgtcataaa cacacactga gaaacagcat aaacacaaaa tccatcaaaa atgttgataa   10080
attatctgat gttgttgttc gctgctatga taatcagatc attcgccgat agtggtaacg   10140
ctatcgaaac gacatcgcca gaaattacaa acgctacaac agatattcca gctatcagat   10200
tatgcggtcc agagggagat ggatattgtt tacacggtga ctgtatccac gctagagata   10260
ttgacggtat gtattgtaga tgctctcatg gttatacagg cattagatgt cagcatgtag   10320
tattagtaga ctatcaacgt tcagaaaacc caaacactac aacgtcatat atcccatctc   10380
ccggtattat gcttgtatta gtaggcatta ttattattac gtgttgtcta ttatctgttt   10440
ataggttcac tcgacgaact aaactactta tacaagatat ggttgtgcca taatttttat   10500
aaattttttt tatgagtatt tttacaaaaa tgtataaagt gtatgtctta tgtatattta   10560
taaaaatgct aaatatgcga tgtatctatg ttatttgtat ttatctaaac aatacctcta   10620
cctctagata ttatacaaaa attttttatt tcggcatatt aaagtaaaat ctagttacct   10680
tgaaaatgaa tacagtgggt ggttccgtat caccagtaag aacataatag tcgaatacag   10740
tatccgattg agattttgca tacaatacta gtctagaaag aaatttgtaa tcattttctg   10800
tgacgggagt ccatatatct gtatcatcgt ctagtttatc agtgtcccat gctatattcc   10860
tgttatcatc attagttaat gaaaataact ctcgtgcttc agaaaagtca aatattgtat   10920
```

```
ccatacatac atctccaaaa ctatcgctta tacgtttatc tttaacgata cctatatccta   10980
gatggttatt tactaacaga cattttccag atctattgac tataactcct atagtttcca   11040
catcaaccaa gtaatgatca tctattgtta tataacaata acataactct tttccatttt   11100
tatcagtatg tatatctata tcaacgtcgt cgttgtagtg aatagtagtc attgatctat   11160
tatatgaaac ggatatgtct agaacggcaa ttgttttacg tccagttaac actttctttg   11220
atttaaagtc tagagtcttt gcaaacataa tatccttatc cgactttata tttcctgtag   11280
ggtggtataa ttttatttg cctccacata tcggtgtttc caaatatatt actagacaat   11340
attccatata gttattagtt aagggtaccc aattagaaca cgtacgctta ttatcatcat   11400
ttggatcgta tttcataaaa gttattgtac tatcgatgtc aacacattct acatttttta   11460
atcgtctata tagtatttt ctgatatttt ctataatatc agaattgtct tccatcggaa   11520
gttgtatact atcggaatca gttacatgtt taaataattc tctgatgtca ttccttatac   11580
aatcaaattc attattaaac agtttaatag tctgtagacc tttattgtcg taaatatcca   11640
ttgtcttatt agttacgctt attttatgt gttttacgtt gctttattat attttataag   11700
aatgattgtt tgacgaatca cgagaactat taagacacat tattaggtat atattataaa   11760
aaagtttttg attacgatgt tataagagga aagaggacac attaacatca tacatcaatt   11820
aactacattc ttataacatc gtaatcaaaa gaattgcaat tttgatgtat aacaactgtc   11880
aatgggttat ggaattgtat attacatatt atacggtatg ttggtaacga caaataccgg   11940
tcggtaattg tctgccggtg taatagaatt atatatatct atctattaca ccggccttgt   12000
atacataata ataagttgtg gtagtatgat ctccatatt ataatttagg actttgtatt   12060
cagtattttt ggaatcataa aaaataaaaa aagttttac taatttaaaa tttaaaaagt   12120
atttacattt ttttcactgt ttagtcgcgg atatggaatt cgatcctgcc aaaatcaata   12180
catcatctat agatcatgta acaatattac aatacataga tgaaccaaat gatataagac   12240
taacagtatg cattatccga atattaata acattacata ttatatcaat atcacaaaaa   12300
taaatacaca tttggctaat caatttcggg cttggaaaaa acgtatcgcc ggaagggact   12360
atatgactaa cttatctaga gatacaggaa tacaacaatc aaaacttact gaaactatac   12420
gtaactgtca aaaaaataga aacatatatg gtctatatat acactacaat ttagttatta   12480
attggataac cgatgtgatt gttcaatcaa tattaagagg gttggtaaat tggtacatag   12540
ctaataatac ctatactcca aatacaccca ataatacaac aaccatttct gagttggata   12600
tcatcaaaat actggataaa tacgaggacg tgtatagagt aagtaaagaa aaagaatgtg   12660
gaatttgcta tgaagttgtt tactcaaaac gatagatact ttggtttatt ggattcgtgt   12720
aatcatatat tttgcataac atgtatcaat atatggcata gaacacgaag agaaaccggt   12780
gcgtcggata attgtcctat atgccgtacc cgttttagaa acataacaat gagcaagttc   12840
tataagctag ttaactaata aataaaaagt ttaatttgtt gacgacgtat gtcgttattt   12900
tttctcgtat aaaagattaa tttgattcta atataatctt tagtattgga taaatatcaa   12960
ttcaaattaa ttccattaga ttatatcata aataaaaata gtagcacgca ctacttcagc   13020
caaatattct tttttgaaac gccatctatc gtagtgagga cacaagtgaa cctataatta   13080
tcaaatttat tagtatcagt cacatgaagg actttctgta gagtgacgat tccactatct   13140
gtggtacgaa cggtttcatc ttctttgatg ccatcaccca gatgttctat aaacttggta   13200
tcctcgtccg atttcatatc ctttgctaac caatacatat agctaaactc aggcatatgt   13260
tccacacatc ctgaacaatg aaattctcca gaagatgtta caatgtctag atttggacat   13320
```

```
ttggtttcaa ccgcgttaac atatgagtga acacacccat acatgaaagc gatgagaaat    13380
aggattctca tcttgccaaa atatcactag aaaaaattta tttatcaatt ttaaaggtat    13440
aaaaaatact tattgttgct cgaatatttt gtatttgatg gtatacggaa gattagaaat    13500
gtaggtatta tcatcaactg attctatggt tttatgtatt ctatcatgtt tcactattgc    13560
gttggaaata atatcatatg cttccacata tattttattt tgttttaact cataatactc    13620
acgtaattct ggattattgg catatctatg aataatttta gctccatgat cagtaaatat    13680
taatgagaac atagtattac cacctaccat tattttttc atctcattca attcttaatt    13740
gcaaagatct ataataatcat tatagcgttg acttatggac tctggaatct tagacgatgt    13800
acagtcatct ataatcatgg catatttaat acattgtttt atagcatagt cgttatctac    13860
gatgttagat atttctctca atgaatcaat cacataatct aatgtaggtt tatgacataa    13920
tagcattttc agcagttcaa tgtttttaga ttcgttgatg gcaatggcta tacatgtata    13980
tccgttattt gatctaatgt tgacatctga accggattct agcagtaaag atactagaga    14040
ttgtttatta tatctaacag ccttgtgaag aagtgtttct cctcgtttgt caatcatgtt    14100
aatgtcttta agataaggta ggcaaatgtt tatagtacta agaattgggc aagcataaga    14160
catgtcacaa agacccttt tgtatgtata agtgtaaaaa ttataacatc catagttgga    14220
tttacatagg tgtccaatcg ggatctctcc atcatcgaga taattgatgg catctccctt    14280
ccttttttag tagatatttc atcgtgtaag aatcaatatt aatatttcta aagtatccgt    14340
gtatagcctc tttatttacc acagttccat attccactag agggatatcg ccgaatgtca    14400
tatactcaat tagtatatgt tggaggacat ccgagttcat tgttttcaat atcaaagaga    14460
tggtttcctt atcatttctc catagtggta caatactaca cattatttcg tgcggctttc    14520
cattttccaa aaacaatttg accaaatcta aatctacatc tttattgtat ctataatcac    14580
tatttagata atcagccata attactcgag tgcaacatgt tagatcgtct atatatgaat    14640
aagccgtgtt atctattcct ttcattaaca atttaacgat gtctatatct atatgagatg    14700
acttaatata atattgaaga gctgtacaat agttttatc tataaaagac ggcttgattc    14760
cgtgattaat tagacattta acaacttccg gacgcacata tgctctcgta tccgactctg    14820
aatacagatg agagatgata tacagatgca atacggtacc gcaatttcgt agttgataat    14880
catcatacgc gtatcagtac tcgtcctcat aaagaacact gcagccattt tctatgaaca    14940
aatcaataat tttaggaaca ggatcattgt cattacataa ttttctataa ctgaacgatg    15000
gttttcacat ttaacactca agtcaaatcc atgttctacc aacacccttta ttaagtcaac    15060 gtctacatt ttggatttca tatagctgaa tatattaaag tcatttatgt tgctaaatcc    15120
agtggcttct agtagagcca tcgctatatc ctttaacttt aacatgtcta ctatttgtgt    15180
attcttctaa tggggtagct gtctccaatt tttgcgtaat ggattagtgc cactgtctag    15240
tagtagtttg acgacctcga cattattaca atgctcatta aaaaggtatg cgtgtaaagc    15300
attattcttg aattggttcc tggtatcatt aggatctctg tctttcaaca tctgtttaag    15360
ttcatcgaga gccacctcct cattttccaa atagtcaaac attttgactg aatgagctac    15420
tgtgaactct atacacccac acaactaatg tcattaaata tcatgtcaaa aacttgtaca    15480
attattaata aaaataattt agtgtttaaa ttttaccagt tccagatttt acacctccgt    15540
taatacctcc attaacccca ctggacgatc ctcctcccca cattccaccg ccaccagatg    15600
tataagtttt agatccttta ttactaccat catgtccatg gataaagaca ctccacatgc    15660
cgccactacc cccttagaa gacatattaa taagacttaa ggacaagttt aacaataaaa    15720
```

```
ttaatcacga gtaccctact accaacctac actattatat gattatagtt tctattttta   15780
cagtaccttg actaaagttt ctagtcacaa gagcaatact accaacctac actattatat   15840
gattatagtt tctattttta taggaacgcg tacgagaaaa tcaaatgtct aatttctaac   15900
ggtagtgttg ataaacgatt atcgtcaatg gatacctcct ctatcatgtc gtctattttc   15960
ttactttgtt ctattaactt attagcatta tatattattt gattataaaa cttatattgc   16020
ttattagccc aatctgtaaa tatcggatta ttaacatatc gtttctttgt aggtttatt    16080
aacttgtaca tcactgtaag catgtcctta ccatttattt taatttgacg catatccgca   16140
atttcttttt cgcagtcggt tataaattct atatatgatg gatacatgct acatgtgtac   16200
ttataatcga ctaatatgaa gtacttgata catatttcca gtaacgattt attattacca   16260
cctatgaata agtacctgtg atcgtctagg taatcaactg ttttcttaat acattcgatg   16320
gttggtaatt tactcagaat aatttccaat atcttaatat ataattctgc tatttctggg   16380
atatatttat ctgccagtat aacacaaata gtaaatacatg taaacccata ttttgttatt   16440
atattaatgt ctgcgccatt atctattaac cattctacta ggctgacact atgcgactca   16500
atacaatgat aaagtatact acatccatgt ttatctattt tgtttatatc atcaatatac   16560
ggcttacaaa gttttagtat cgataacaca tccaactcac gcatagagaa ggtagggaat   16620
aatggcataa tatttattag gttatcatca ttgtcattat ctacaactaa gtttccattt   16680
tttaaaatat actcgacaac tttaggatct ctattgccaa attttgaaa atatttattt    16740
atatgcttaa atctatataa tgtagctcct tcatcaatca tacatttaat aacattgatg   16800
tatactgtat gataagatac atattctaac aatagatctt gtatagaatc tgtatatctt   16860
ttaagaattg tggatattag gatattatta cgtaaactat tacacaattc taaaatataa   16920
aacgtatcac ggtcgaataa tagttgatca actatataat tatcgatttt gtgattttc    16980
ttcctaaact gtttacgtaa atagttagat agaatattca ttagttcata accactatag   17040
ttactatcga ataacgcgtc aaatatttcc cgtttaatat cgcatttgtc aagataataa   17100
tagagtgtgg tatgttcacg ataagtataa taacgcatct cttttcgtg tgaaattaaa    17160
tagtttatca cgtccaaaga tgtagcataa ccatcttgtg acctagtaat aatataataa   17220
tagagaactg ttttacccat tctatcatca taatcagtgg tgtaatcgta atcgtaatcg   17280
tctaattcat catcccaatt ataatattca ccagcacgtc taatctgttc tattttgatc   17340
ttgtatccat actgtatgtt gctacatgta ggtattcctt tatccaataa tagtttaaac   17400
acatctacat tgggatttga tgttgtagcg tatttttcta caatattaat accatttttg   17460
atactattta tttctatacc tttcgaaatt agtaatttca ataagtctat atcgatgtta   17520
ttagaacata gatattcgaa tatatcaaaa tcattgatat ttttatagtc gactgacgac   17580
aataacaaaa tcacaacatc gttttttgata ttattatttt tcttggtaac gtatgccttt   17640
aatggagttt caccatcata ctcatataat ggatttgcac cactttctat caatgattgt   17700
gcactgctgg catcgatgtt aaatgtttta caactatcat agagtatctt atcgttaacc   17760
atgattggtt gttgatgcta tcgcatttt tggtttcttt catttcagtt atgtatggat    17820
ttagcacgtt tgggaagcat gagctcatat gatttcagta ctgtagtgtc agtactatta   17880
gtttcgatca gatcaatgtc tagatctata gaatcaaaac acgataggtc agaagataat   17940
gaatatctgt acgcttcttt ttgtactgta acttctggtt ttgttagatg gttgcatcgt   18000
gctttaacgt caatggtaca aatttttatcc tcgctttgtg tatcatattc gtctctacta   18060
taaaattgta tattcagatt atcatgagat gtgtatacgc taacggtatc aataaacgga   18120
```

```
gcacaccatt tagtcataac cgtaatccaa aaatttttaa agtatatctt aacgaaagaa   18180
gttgtgtcat tgtctacggt gtatggtact agatcctcat aagtgtatat atctagagta   18240
atgtttaatt tatcaaatgg ttgataatat ggatcgtcgt ggcaatttcc taagacgaaa   18300
ataagacata aacacgcaat aaatctaatc gaagacatgg ttactcctta aaaaaatacg   18360
aataatcacc ttggctattt agtaagtgtc atttaacact atactcatat taatccatgg   18420
actcataatc tctatacggg attaacggat gttctatata cggggatgag tagttctctt   18480
ctttaacttt atacttttta ctaatcatat ttagactgat gtatgggtaa tagtgtttga   18540
agagctcgtt ctcatcatca gaataaatca atatctctgt ttttttgtta tacagatgta   18600
ttacagcctc atatattacg taatagaacg tgtcatctac cttattaact ttcaccgcat   18660
agttgtttgc aaatacggtt aatcctttga cctcgtcgat ttccgaccaa tctgggcgta   18720
taatgaatct aaactttaat ttcttgtaat cattcgaaat aattttttagt ttgcatccgt   18780 agttatcccc tttatgtaac tgtaaatttc tcaacgcgat atctccatta ataatgatgt   18840
cgaattcgtg ttgtataccc atactgaatg gatgaacgaa tatcaacggc gttaatagta   18900
atttactttt tcatctttac atattgggta ctagttttac tatcataagt ttataaattc   18960
cacaagctac tatggaataa gccaaccatc ttagtataac acacatgtct taaagtttat   19020
taattaatta catgttgttt tatatatcgc tacgaattta aacagagaaa tcagtttagg   19080
aaaaaaaatt atctatctac atcatcacgt ctctgtattc tacgatagag tgctacttta   19140
agatgagaca tatccgtgtc atcaaaaata tactccatta aaatgattat tccggcagcg   19200
aacttgatat tggatatatc acaacctttg ttaatatcta cgacaataga cagcagtccc   19260
atggttccat aaacagtgag tttatctttc ttttgaagaga tattttgtag agatcttata   19320
aaactgtcga atgacatcgc atttatattt ttagctaaat cgtatatgtt accatcgtaa   19380
tatctaaccg cgtctatctt aaacgtttcc atcgctttaa agacgtttcc gatagatggt   19440
ctcatttcat cagtcatact gagccaacaa atataatcgt gtataacatc tttgatagaa   19500
tcagactcta aagaaaacga atcggcttta ttatacgcat tcatgataaa cttaatgaaa   19560 aatgttttc gttgtttaag ttggatgaat agtatgtctt aataattgtt attatttcat   19620
taattaatat ttagtaacga gtacactcta taaaaacgag aatgacataa ctagttatca   19680
aagtgtctag gacgcgtaat tttcatatgg tatagatcct gtaagcattg tctgtattct   19740
ggagctattt tctctatcgc attagtgagt tcagaatatg ttataaattt aaatcgaata   19800
acgaacataa ctttagtaaa gtcgtctata ttaactctt tatttttctag ccatcgtaat   19860 accatgttta agatagtata ttctctagtt actacgatct catcgttgtc tagaatatca   19920
catactgaat ctacatccaa ttttagaaat tggtctgtgt tacatatctc ttctatatta   19980
ttgttgatgt attgtcgtag aaaactatta cgtagaccat tttctttata aaacgaatat   20040
atagtactcc aattatcttt accgatatat ttgcacacat aatccattct ctcaatcact   20100
acatctttaa gattttcgtt gttaagatat ttggctaaac tatataattc tattagatca   20160
tcaacagaat cagtatatat ttttctagat ccaaagacga actctttggc gtcctctata   20220
atattcccag aaaagatatt ttcgtgtttt agtttatcga gatctgatct gttcatatac   20280
gccatgattg tacggtacgt tatgataacc gcataaaata aaaatccatt ttcattttta   20340
accaatacta ttcataattg agattgatgt aatactttgt tactttgaac gtaaagacag   20400
tacacggatc cgtatctcca acaagcacgt agtaatcaaa tttggtgttg ttaaacttcg   20460
caatattcat caatttagat agaaacttat actcatcatc tgtttaggga atccatgtat   20520
```

-continued

```
tattaccact ttccaactta tcattatccc aggctatgtt tcgtccatca tcgttgcgca    20580
gagtgaataa ttcttttgta ttcggtagtt caaatatatg atccatgcat agatcggcaa    20640
agctattgta gatgtgattt ttcctaaatc taatataaaa ctcgtttact agcaaacact    20700
ttcctgattt atcaaccaag acacatatgg tttctaaatc tatcaagtgg tggggatcca    20760
tagttatgac gcagtaacat atattattac attcttgact gtcgctaata tctaaatatt    20820
tattgttatc gtattggatt ctgcatatag atggcttgta tgtcaaagat atagaacaca    20880
taaccaattt atagtcgcgc tttacattct cgaatctaaa gttaagagat ttagaaaaca    20940
ttatatcctc ggatgatgtt atcactgttt ctggagtagg atatattaaa gtctttacag    21000
atttcgtccg attcaaataa atcactaaat aatatcccac attatcatct gttagagtag    21060
tatcattaaa tctattatat tttatgaaag atatatcact gctcacctct atatttcgta    21120 cattttaaa ctgtttgtat aatatctctc tgatacaatc agatatatct attgtgtcgg    21180
tagacgatac cgttacattt gaattaatgg tgttccattt tacaactttt aacaagttga    21240
ccaattcatt tctaatagta tcaaactctc catgattaaa tattttaata gtatccattt    21300
tatatcacta cggacacaaa gtagctgaca taaaccattg tataatttt atgttttatg     21360 tttattagcg tacacatttt ggaagttccg gcttccatgt atttcctgga gagcaagtag    21420
atgatgagga accagatagt ttatatccgt acttgcactt aaagtctaca ttgtcgttgt    21480
atgagtatga tcttttaaac ccgctagaca agtatccgtt tgatattgta ggatgtggac    21540
atttaacaat ctgacacgtg ggtggatcgg accattctcc tcctgaacac aggacaccag    21600
agttaccaat caacgaatat ccactattgc aactataagt tacaacgctc ccatcggtat    21660
aaaaatcctc gtatccgtta tgtcttccgt tggatataga tggagggat tggcatttaa     21720 cagattcaca aataggtgcc tcgggattcc ataccataga tccagtagat cctaattcac    21780
aatacgattt agattcaccg atcaaatgat atccgctatt acaagagtac gttatactag    21840
agccaaagtc tactccacca atatcaagtt ggccattatc gatatctcga ggcgatgggc    21900
atctccgttt aatacattga ttaaagagtg tccatccagt acctgtacat ttagcatata    21960
taggtcccat ttttgctttt ctgtatccag gtagacatag atattctata gtgtctccta    22020
tgttgtaatt agcattagca tcagtctcca cactattctt aaatttcata ttaatgggtc    22080
gtgacggaat agtacagcat gatagaacgc atcctattcc caacaatgtc aggaacgtca    22140
cgctctccac cttcatattt atttatccgt aaaaatgtta tcctggacat cgtacaaata    22200 ataaaagcc catatatgtt cgctattgta gaaattgttt ttcacagttg ctcaaaaacg     22260
atggcagtga cttatgagtt acgttacact ttggagtctc atctttagta aacatatcat    22320
aatattcgat attcgagtt gacatatcga acaaattcca agtatttgat tttggataat     22380
attcgtattt tgcatctgct ataattaaga tataatcacc gcaagaacac acgaacatct    22440
ttcctacatg gttaaagtac atgtacaatt ctatccattt gtcttcctta actatatatt    22500
tgtatagata attacgagtc tcgtgagtaa ttccagtaat tacatagatg tcgccgtcgt    22560
actctacagc ataaactata ctatgatgtc taggcatggg agactttttt atccaacgat    22620
ttttagtgaa acattccaca tcgtttaata ctacatattt ctcatacgtg gtataaactc    22680
cacccattac atatatatca tcgtttacga ataccgacgc gcctgaatat ctaggagtaa    22740
ttaagtttgg aagtcttatc catttcgaag tgccgtgttt caaatattct gccacacccg    22800
ttgaaataga aaattctaat cctcctatta catataactt tccatcgtta acacaagtac    22860
taacttctga ttttaacgac gacatattag taaccgtttt ccatttttc gttttaagat     22920
```

```
ctacccgcga tacggaataa acatgtctat tgttaatcat gccgccaata atgtatagac   22980
aattatgtaa aacatttgca ttatagaatt gtctatctgt attaccgact atcgtccaat   23040
attctgttct aggagagtaa tgggttattg tggatatata atcagagttt ttaatgacta   23100
ctatattatg ttttatacca tttcgtgtca ctggctttgt agatttggat atagttaatc   23160
ccaacaatga tatagcattg cgcatagtat tagtcataaa cttgggatgt aaaatgttga   23220
tgatatctac atcgtttgga ttttatgta tccactttaa taatatcata gctgtaacat   23280
cctcatgatt tacgttaacg tcttcgtggg ataagatagt tgtcagttca tcctttgata   23340
attttccaaa ttctggatcg gatgtcaccg cagtaatatt gttgattatt tctgacatcg   23400
acgcattata tagttttta attccatatc ttttagaaaa gttaaacatc cttatacaat   23460
ttgtgaaatt aatattatga atcatagttt ttacacatag atctactaca ggcggaacat   23520
caattattat ggcagcaact agtatcattt ctacattgtt tatggtgatg tttatcttct   23580
tccagcgcat atagtctaat agcgattcaa acgcgtgata gtttatacca ttcaatataa   23640
tcgcttcatc ctttagatgg tgatcctgaa tgcgtttaaa aaaattatac ggagacgccg   23700
taataatttc cttattcact tgtataattt ccccattgat agaaaatatc acgctttcca   23760
ttcttaaagt actataagta attatagtat aatgtaaacg tttatatatt caatattttt   23820
ataaaaatca ttttgacatt aattcctttt taaatttccg tctatcatct atagaaacat   23880
attctatgaa tttataaaat gcttttacgt gtcctatcgt aggcgataga accgctaaaa   23940
agcctattga atttctacaa aagaatctgt tatatggtat agggagagta taaaacatta   24000
aatgtccgta cttattaaag tattcagtag ccaatcctaa ctctttcgaa tacttattaa   24060
tggctcttgt tctgtacgaa tctatttttt tgaacaacgg acctagtggt atatcttgtt   24120
ctatgtatct aaaataatgt ctgactagat ccgttagttt aatatccgca gtcatcttgt   24180
ctagaatggc aaatctaact gcgggtttag gctttagttt agtttctata tctacatcta   24240
tgtctttatc taacaccaaa aatataatag ctaatatttt attacaatca tccggatatt   24300
cttctacgat ctcactaact aatgtttctt tggttatact agtatagtca ctatcggaca   24360
aataaagaaa atcagatgat cgatgaataa tacatttaaa ttcatcatct gtaagatttt   24420
tgagatgtct cattagaata ttattagggt tagtactcat tatcattcgg cagctattac   24480 ttatttttatt atttttcacc atatagatca atcattagat catcaaaata tgtttcaatc   24540
atcctaaaga gtatggtgaa tgactcttcc catctaattt ctgaacgttc accaatgtct   24600
ctagccactt tggcactaat agcgatcatt cgcttagcgt cttctatatt attaactggt   24660
tgattcaatc tatctagcaa tggaccgtcg gacagcgtca ttctcatgtt cttaatcaat   24720
gtacatacat cgccgtcatc taccaattca tccaacaaca taagctttt aaaatcatca   24780 ttataatagg tttgatcgtt gtcatttctc caaagaatat atctaataag tagagtcctc   24840
atgcttagtt aacaactatt ttttatgtta aatcaattag tacaccgcta tgtttaatac   24900
ttattcatat tttagttttt aggattgaga atcaatacaa aaaattaatg catcattaat   24960
tttagaaata cttagtttcc acgtagtcaa tgaaacattt gaactcatcg tacaggacgt   25020
tctcgtacag gacgtaacta taaaccggtt tatatttgtt caagatagat acaaatccga   25080
taactttttt tacgaattct acgggatcca ctttaaaagt gtcataccgg gttctttta   25140 ttttttaaa cagatcaatg gtgtgatgtt gattaggtct tttacgaatt tgatatagaa   25200
tagcgtttac atattctcca taatggtcaa tcgccatttg ttcgtatgtc ataaattctt   25260
taattatatg acactgtgta ttgtttagtt catccttgtt cattgttagg aatctatcca   25320
```

```
aaatggcaat tatactagaa ctataggtgc gttgtataca catattgatg tgtctgttta   25380
tacaatccat gatatttgga tccatgctac taccttcggg taaaattgta gcatcatata   25440
ccatttctag tactttaggt tcattattat ccattgcaga ggacgtcatg atcgaatcat   25500
aaaaaaatat attatttta tgttattttg ttaaaaataa tcatcgaata cttcgtaaga    25560
tactccttca tgaacataat cagttacaaa acgtttatat gaagtaaagt atctacgatt   25620
tttacaaaag tccggatgca taagtacaaa gtacgcgata acggaataa taatagattt    25680
atctagtcta tctttttcta tagctttcat agttagatac atggtctcag aagtaggatt   25740
atgtaacatc agcttcgata aaatgactgg gttatttagt cttacacatt cgctcataca   25800
tgtatgaccg ttaactacag agtctacact aaaatgattg aacaatagat agtctaccat   25860
tgtttcgtat tcagatagta cagcgtagta catggcatct tcacaaatta tatcattgtc   25920
taatagatat ttgacgcatc ttatggatcc cacttcaaca gccatcttaa aatcggtaga   25980
atcatattgc tttcctttat cattaataat ttctagaaca tcatctctat cataaaagat   26040
acaaatatta actgtttgat ccgtaataac attgctagtc gatagcaatt tgttaataag   26100
atgcgctggg ctcaatgtct taataagaag tgtaagagga ctatctccga atttgttttg   26160
tttattaaca tccgttgatg gaagtaaaag atctataatg tctacattct tgactgtttt   26220
agagcataca atatggagag gtgtatttcc atcatgatct ggttttgagg gactaattcc   26280
tagtttcatc atccatgaga ttgtagaagc ttttggattg tctgacataa gatgtctatg   26340
aatatgattt ttgccaaatt tatccactat cctggcttcg aatccgatgg acattatttt   26400
tttaaacact ctttctgaag gatctgtaca cgccaacaac ggaccacatc cttcttcatc   26460
aaccgagttg ttaatcttgg ctccatactg taccaataaa tttattctct ctatgacttc   26520
atcatctgtt cccgagagat aatatagagg cgttttatgc tgtttatcac acgcgtttgg   26580
atctgcgccg tgcgtcagca gcatcgcgac tattctatta ttattaattt tagaagctat   26640
atgcaatgga taatttccat catcatccgt ctcatttgga gagtatcctc tatgaagaag   26700
ttcttcgaca aatcgttcat ctagtccttt aattccacaa tacgcatgta gaatgtgata   26760
attatttcca gaaggttcga tagcttgtag catattccta aatacatcta aattttttact 26820
attatatttg gcataaagag atagataata ctcggccgac ataatgttgt ccattgtagt   26880
ataaaaatta atatttctat ttctgtatat ttgcaacaat ttactctcta taacaaatat   26940
cataacttag ttcttttatg tcaagaaggc actggtttag ttcatctata aatgtcacgc   27000
cataactacc acgcatgcca tactcagaat tatgataaag atatttatcc ttggggtgta   27060
ggtaatgggg attaatcttt gttggatcag tctctaagtt aacacatgtc acacatgatc   27120
catttatagt tatatcacac gatgatgatt tatgaattga ttccggaaga tcgctatcgt   27180
attttgtggt tccacaattc atttccatac atgttattgt cacactaata ttatgatgaa   27240
ctttatctag ccgctgagtg gtaaacaaca gaacagatag tttattatct ttaccaacac   27300
cctcagccgc tgccacaaat ctctgatccg tatccatgat ggtcatgttt atttctagtc   27360
cgtatccagt caacactatg ttagcatttc tgtcgtatat gctttcactc atatgacact   27420
caccaataat agtagaatta atgtcgtaat ttacaccaat agtgagttcg gcggcaaagt   27480
accaataccg gtaatcttgt cgaggaggac atatagtatt cttgtattct actgaatacc   27540
cgagagatgc gatacaaaag agtaagacta atttgtaaac catcttactc aaaatatgta   27600
acaatagtac gatgcaatga gtaagacaat aggaaatcta tcttatatac acataattat   27660
tctatcaatt ttaccaatta gttagtgtaa tgttaacaaa aatgtgggag aatctaatta   27720
```

```
gtttttcttt acacaattga cgtacatgag tttgagttcc ttgttttttgc taattatttc   27780
atccaattta ttattcttga ctatatcgag atcttttgta taggagtcag acttgtattc   27840
aacatgcttt tctataatca ttttagctat ttcggcatca tccaatagta catttttccag  27900
attagcagaa tagatattaa tgtcgtattt gaacagagcc tgtaacatct caatgtcttt   27960
attatctata gccaatttaa tgtccggaat gaagagaagg gaattattgg tgtttgtcga   28020
cgtcatatag tcgagcaaga gaatcatcat atccacgtgt ccattttta tagtgatgtg    28080
aatacaacta aggagaatag ccagatcaaa agtagatggt atctctgaaa gaaagtagga   28140
aacaatactt acatcattaa gcatgacggc atgataaaat gaagttttcc atccagtttt   28200
cccatagaac atcagtctcc aatttttctt aacaaacagt tttaccgttt gcatgttacc   28260
actatcaacc gcataataca atgcagtgtt tcccttgtca tcaaattgtg aatcatccag   28320
tccactgaat agcaaaatct ttactatttt ggtatcttcc aatgtggctg cctgatgtaa   28380
tggaaattca ttctctagaa gattttttcaa tgctccagcg ttcaacaacg tacatactag  28440
acgcacgtta ttatcagcta ttgcataata caaggcacta tgaccgttga tatccgcctt   28500
aaatgcatct ttgctagaga gaaagctttt cagctgctta gacttccaag tattaattcg   28560
tgacagatcc atgtctgaaa cgagacgcta attagtgtat atttttttcat tttttataat  28620
tttgtcatat tgcaccagaa ttaataatat ctctaataga tctgattagt agatacatgg   28680
ctatcgcaaa acaacatata cacatttaat aaaaataata tttattaaga aaattcagat   28740
ttcacgtacc catcaatata aataaaataa tgattcctta caccgtaccc atattaagga   28800
gattccacct tacccataaa caatataaat ccagtaatat catgtctgat gatgaacaca   28860
aatggtgtat taaattccag ttttttcagga gatgatctcg ccgtagctac catgatagta   28920
gatgcctctg ctacagttcc ttgttcgtcg acatctatct ttgcattctg aaacatttta   28980
taaatatata atgggtccct agtcatatgt ttaaacgacg cattatctgg attaaacata   29040
ctaggagcca tcatttcggc tatcgactta atatccctct tattttcgat agaaaattta   29100
gggagtttaa gattgtacac tttattcccct aattgagacg accaatagtc taattttgca  29160
gccgtgatag aatctgtgaa atgggtcata ttatcaccta ttgccaggta catactaata   29220
ttagcatcct tatacggaag gcgtaccatg tcatattctt cgtcatcgat tgtgattgta   29280
tttccttgca atttagtaac tacgttcatc atgggaaccg ttttcgtacc gtacttatta   29340
gtaaaactag cattgcgtgt tttagtgata tcaaacggat attgccatat acctttaaaa   29400
tatatagtat taatgattgc ccatagagta ttattgtcga gcatattaga atctactaca   29460
ttagacatac cggatctacg ttctactata gaattaattt tattaaccgc atctcgtcta   29520
aagtttaatc tatataggcc gaatctatga tattgttgat aatacgacgg tttaatgcac   29580
acagtattat ctacgaaact ttgataagtt agatcagtgt acgtatattt agatgttttc   29640
agcttagcta atcctgatat taattctgta atgctggac ccagatctct ttttctcaaa    29700
tccatagtct tcaataattc tattctagta ttacctgatg caggcaatag cgacataaac   29760
atagaaaacg aatagccaaa cggcgagaag acaatattat catcttgaat atttttatac   29820
gctactatac cggcattggt aaatccttgc agacgatagg tagacgctga acacgctaac   29880
gatagtatca ataacgcaat catgattta tggtattaat aattaacctt attttttatgt   29940
tcggtataaa aaaattattg atgtctacac atccttttgt aattgacatc tatatatcct   30000
tttgtataat caactctaat cacttttaact tttacagttt tccctaccag tttatcccta   30060
tattcaacat atctatccat atgcatctta acactctctg ccaagatagc ttcagagtga   30120
```

```
ggatagtcaa aaagataaat atatagagca taatcattct cgtatactct gcccttttatt   30180
acatcacccg cattgggcaa cgaataacaa aatgcaagca tcttgttaac gggctcgtaa   30240
attgggataa aaattatgtt tttattgatt ttatatctat tttattcaag agaatattca   30300
ggaatttctt tttccggttg tatctcgtcg cagtatatat catttgtaca ttgtttcata   30360
tttttttaata gtttacacct tttagtagga ctagtatcgt acaattcata gctgtatttt   30420
gaattccaat cacgcataaa aatatcttcc aattgttgac gaagacctaa tccatcatcc   30480
ggtgtaatat taatagatgc tccacatgta tccgtaaagt aatttcctgt ccaatttgag   30540
gtacctatat aggccgtttt atcggttacc atatatttgg catggtttac cctagaatac   30600
ggaatgggag gatcagcatc tggtacaata aatagcttta cttctatatt tatgttttta   30660
gattttagca tagcgataga tcttaaaaag tttctcatga taaacgaaga tcgttgccag   30720
caactaatca atagcttaac ggatacttgt ctgtctatag cggatcttct taattcatct   30780
tctatataag gccaaaacaa aattttaccc gccttcgaat aaataatagg gataaagttc   30840
ataacagata cataaacgaa tttactcgca tttctaatac atgacaataa agcggttaaa   30900
tcattggttc tttccatagt acatagttgt tgcggcgcag aagcaataaa tacagagtgt   30960
ggaacgccgc ttacgttaat actaagagga tgatctgtat tataatacga cggataaaag   31020
tttttccaat tatatggtag attgttaact ccaagatacc agtatacctc aaaaatttga   31080
gtgagatccg ctgccaagtt cctattattg aagatcgcaa tacccaattc tttgacctga   31140
gttagtgatc tccaatccat gttagcgctt cctaaataaa tatgtgtatt atcagatatc   31200
caaaattttg tatgaagaac tcctcctagg atatttgtaa tatctatgta tcgtacttca   31260
actccggcca tttgtagtct ttcaacatcc tttaatggtt tgttagattt attgacggct   31320
actctaactc gtactcctct tttgggtaat tgtacaatct cgtttaatat tatcgtgccg   31380
aaattcgtac ccacttcatc cgataaactc caataaaaag atgatatatc tagtgttttt   31440
gtggtattgg atagaatttc cctccacatg ttaaatgtag acaaatatac tttatcaaat   31500
tgcataccta taggaatagt ctctgtaatc actgcgattg tattatccgg attcatttta   31560
tttgttaaaa aataatccta tatcacttca ctctattaaa aatccaagtt tctatttctt   31620
tcatgactga ttttttaact tcatccgttt ccttatgaag atgatgtttg gcaccttcat   31680
aaattttat ttctctatta caatttgcat gttgcatgaa ataatatgca cctaaaacat   31740
cgctaatctt attgtttgtt ccctggagta tgagagtcgg gggggtgtta atcttggaaa   31800
ttattttttct aaccttgttg gtagccttca agacctgact agcaaatcca gccttaattt   31860
tttcatgatt gattaatggg tcgtattggt atttataaac tttatccata tctctagata   31920
ctgattctgg acatagcttt ccgactggcg catttggtgt gatggttccc ataagtttgg   31980
cagctagcag attcagtctt gaaacagcat ctgcattaac tagaggagac attagaatca   32040
ttgctgtaaa caagtttgga ttatcgtaag aggctagtat agaaattgtt gctcccatgg   32100
aatgacccaa taagtagatt taatagttac cacgtgctgt accaaagtca tcaatcatca   32160
ttttttcacc attacttctt ccatgtccaa tatgatcatg tgagaatact aaaattccta   32220
acgatgatat gttttcagct agttcgtcat aacgtccaga atgtttacca gctccatgac   32280
ttatgaatac taatgcctta ggatatgtaa taggttttcca atatatgtaa tcattgtcca   32340
gattgaacat acagtttgca ctcatgattc acgttatata actatcaata ttaacagttc   32400
gtttgatgat catattattt ttatgtttta ttgataattg taaaaacata caattaaatc   32460
aatatagagg aaggagacgg ctactgtctt ttgtgagata gtcatggcga ctaaattaga   32520
```

```
ttatgaggat gctgttttt actttgtgga tgatgataaa atatgtagtc gcgactccat      32580
catcgatcta atagatgaat atattacgtg gagaaatcat gttatagtgt ttaacaaaga      32640
tattaccagt tgtggaagac tgtacaagga attgatgaag ttcgatgatg tcgctatacg      32700
gtactatggt attgataaaa ttaatgagat tgtcgaagct atgagcgaag gagaccacta      32760
catcaatttt acaaaagtcc atgatcagga aagtttattc gctaccatag gaatatgtgc      32820
taaaatcact gaacattggg gatacaaaaa gatttcagaa tctagattcc aatcattggg      32880
aaacattaca gatctgatga ccgacgataa tataaacatc ttgatacttt ttctagaaaa      32940
aaaattgaat tgatgatata ggggtcttca taacgcataa ttattacgtt agcattctat      33000
atccgtgtta aaaaaaatta tcctatcatg tatttgagag ttttatatgt agcaaacatg      33060
atagctgtga tgccaataag ctttagatat tcacgcgtgc tagtgttagg gatggtatta      33120
tctggtggtg aaatgtccgt tatataatct acaaaacaat catcgcatat agtatgcgat      33180
agtagagtaa acatttttat agtttttact ggattcatac atcgtctacc caattcggtt      33240
ataaatgaaa ttgtcgccaa tcttacaccc aacccttgt tatccattag tatagtatta      33300
acttcgttat ttatgtcata aactgtaaat gattttgtag atgccatatc atacatgata      33360
ttcatgtccc tattataatc attactaact ttatcacaat atatgttgat aatatctata      33420
tatgatctag tctttgtggg caactgtcta tacaagtcgt ctaaacgttg tttactcata      33480
tagtatcgaa cagccatcat tacatggtcc cgttccgttg atagataatc gagtatgtta      33540
gtggacttgt caaatctata taccatattt tctggaagtg gatatacata gtcgtgatca      33600
acattattgc tagcctcatc ttctatatcc tgtactatac cattatctat atcatctaca      33660
taatctacga tattattaca cataaacatc gacaacatac tattgtttat tatctaagtc      33720
ctgttgatcc aaacccttga tctcctctat ttgtactatc tagagattgt acttcttcca      33780
gttctggata atatatacgt tgatagatta gctgagctat tctatctcca gtatttacat      33840
taaacgtaca ttttccatta ttaataagaa tgactcctat gtttccccta taatcttcgt      33900
ctattcacac gcctcctata tcaatgcctt ttagtgacag accagaccta ggagctattc      33960
taccatagca gaacttaggc atggacatac taatatctgt cttaattaac tgtctttctc      34020
ctggagggat agtataatcg taagcgctat acaaatcata tccggcagca cccggcgatt      34080
gcctagtagg agatttagct ctgttagttt ccttaacaaa tctaactggt gagttaatat      34140
tcatgttgaa cataaaacta atatttatt tcaaaattat ttaccatccc atatattcca      34200
tgaataagtg tgatgattgt acacttctat agtatctata tacgattcac gataaaatcc      34260
tcctatcaat agcagtttat tatccactat gatcaattct ggattatccc tcggataaat      34320
aggatcatct atcagagtcc atgtattgct ggattcacaa taaaattccg catttctacc      34380
aaccaagaat aaccttctac cgaacactaa cgcgcatgat ttataatgag gataataagt      34440
ggatggtcca aactgccact gatcatgatt gggtagcaaa tattctgtag ttgtatcagt      34500
ttcagaatgt cctcccatta cgtatataac attgtttata gatgccactg ctggattaca      34560
tctaggtttc agaagactcg gcatattaac ccaagcagca tccccgtgga accaacgctc      34620
aacagatgtg ggatttggta gacctcctac tacgtataat ttattgttag cgggtatccc      34680
gctagcatac agtctggggc tattcatcgg aggaattgga atccaattgt ttgatatata      34740
atttacagct atagcattgt tatgtatttc attgttcatc catccaccga tgagatatac      34800
tacttctcca acatgagtac ttgtacacat atggaatata tctataattt gatccatgtt      34860
cataggatac tctatgaatg gatacttgta tgatttgcgt ggttgtttat cacaatgaaa      34920
```

```
tattttggta cagtctagta tccattttac attatttata cctctgggag aaagataatt   34980
tgacctgatt acattttga taaggagtag cagatttcct aatttatttc ttcgctttat   35040
ataccactta atgacaaaat caactacata atcctcatct ggaacattta gttcatcgct   35100
ttctagaata agttttatag atagataatc aaaattgtct atgatgtcat cttccagttc   35160
caaaaagtgt ttggcaataa agttttttagt atgacataag agattggata gtccgtattc   35220 tatcccatc atgtaacact cgacacaata ttccttttcta aaatctcgta agataaagtt   35280
tatacaagtg tagatgataa attctacaga ggttaatata gaagcacgta ataaattgac   35340
gacgttatga ctatctatat ataccttttcc agtatacgag taaataacta tagaagttaa   35400
actgtgaatg tcaaggtcta gacaaaccct tgtaactgga tctttatttt tcgtgtattt   35460
ttgacgtaaa tgtgtgcgaa agtaaggaga taacttttc aatatcgtag aattgactat   35520
tatattgcca cctatagcat caataattgt tttgaatttc ttagtcatag acaatgctaa   35580
tatattctta cagtacacag tattgacaaa tatcggcatt tatgtttctt aaaaagtcaa   35640
catctagaga aaaatgatta tcttttttgag acataactcc cattttttgg tattcaccca   35700 cacgttttc gaaaaaatta gttttcctt ccaatgatat attttccatg aaatcaaacg   35760
gattggtaac attataaatt ttttaaatc ccaattcaga aatcaatcta tccgcgacga   35820
attctatata tgttttcatc atttcacaat tcattcctat aagtttaact ggaagagccg   35880
cagtaagaaa ttcttgttca atggataccg catctgttat aatagatcta acggtttctt   35940
cactcggtgg atgcaataaa tgtttaaaca tcaaacatgc gaagtcgcag tgtagaccct   36000
cgtctctact aattagttcg ttggaaaacg tgagtccggg cattaggcca cgcttttttaa   36060 gccaaaatat ggaagcgaat gatccagaaa agaaaattcc ttctactgca gcaaaggcaa   36120
taagtctctc tccataaccg cgcctgtcat gtatccactt ttgagcccaa tcggccttct   36180
tttttacaca aggcatcgtt tctatggcat taaagagata gttttttttca ttactatctt   36240 taacataagt atcgatcaaa agactataca tttccgaatg aatgttttca atggccatct   36300
gaaatccgta gaaacatcta gcctcggtaa tctgtacttc tgtacaaaat cgttccgcca   36360
aattttcatt cactattccg tcactggctg caaaaaacgc caatacatgt tttataaaat   36420 attttcgtc tggtgttagt ttattccaat cattgatatc tttagatata tctacttctt   36480
ccactgtcca aaatgatgcc tctgcctttt tatacatgtt ccagatgtca tgatattgga   36540
ttgggaaaat aacaaatcta tttggatttg gtgcaaggat gggttccata actaaattaa   36600
caataacaat aaattttttt tcagttatct atatgcctgt acttggatct tttgtacatc   36660
gatatcgccg caatcactac aataattaca agtattattg atagcattgt tattagtact   36720
atcataatta aattatcgac attcatgggt gctgaataat cgttattatc atcattatca   36780
ttttgtaatt gtgacatcat actagataaa tcgtttgcga gattgttgtg ggaagcgggc   36840
atggaggatg cattatcatt attatttaac gccttccatt tggattcaca aatgttacgc   36900
acattcaaca ttttatggaa actataattt tgtgaaaaca gataacaaga aaactcgtca   36960
tcgttcaaat ttttaacgat agtaaaccga ttaaacgtcg agctaatttc taacgctagc   37020
gactctgttg gatatgggtt tccagatata tatctttca gttccctac gtatctataa   37080 tcatctgtag gaaatggaag atatttccat ttatctactg ttcctaatat catatgtggt   37140
ggtgtagtag aaccattaag cgcgaaagat gttatttcgc atcgtatttt aacttcgcaa   37200 taattctgg ttagataacg cactctacca gtcaagtcaa tgatattagc ctttacagat   37260
atattcatag tagtcgtaac gatgactcca tcttttagat gcgatactcc tttgtatgta   37320
```

```
ccagaatctt cgtacctcaa actcgatata tttaaacaag ttaatgagat attaacgcgt   37380
tttatgaatg atgatatata accagaagtt ttatcctcgg tggctagcgc tataaccttg   37440
tcattataat accaactagt gtgattaata tgtgacacgt tagtgtgggt acaaatatgt   37500
acattatcgt ctacgtcgta ttcgatacat ccgcatacag ccaacaaata taaaatgaca   37560
aatactctaa cgccgttcgt acccatcttg atgcggttta ataaatgttt tgatttcaat   37620
ttattgtaaa aaaagattcg gttttatact gttcgatatt ctcattgctt atattttcat   37680
ctatcatctc cacacagtca aatccgtggt tagcatgcac ctcatcaacc ggtaaaagac   37740
tatcggactc ttctatcatt taactctag aatatttaat ttggtcatta ttaatcaagt   37800
caattatctt attttaaca aacgtgagta ttttactcat ttttttataaa aacttttaga   37860 aatatacaga ctctatcgtg tgtctatatc ttctttttat atccaatgta tttatgtctg   37920 attttttcttc atttatcata tataatggtc caaattctac acgtgcttcg gattcatcca   37980
gatcattaag gttcttataa ttgtaacatc cttctcttcc ctcttctaca tcttccttct   38040
tattcttatt cttagcgtca cagaatctac cacagcagga tcccatgacg agcgtcatat   38100
taaactaatc cattttcaat tataatatat gattagtaat gaccattaaa ataaaaaata   38160
ttcttcataa ccggcaagaa agtgaaaagt tcacattgaa actatgtcag tagtatacat   38220
catgaaatga gatgaaatga gatgaaatga tgatatatat attctctatt ttggtggagg   38280
attatatgat ataattcgtg gataatcatt tttaagcaca atttcttat tcgtaaatct   38340 tttcacgtta aatgagtgtc catattttgc aatttcttca tatgatggcg gtgtacgtgg   38400
acgaggctgc tcctgttctt gttgtagtcg ccgactgtcg tgtctgcgtt tagatccctc   38460
cattatcgcg attgcgtaga tggagtacta ttttatacct tgtaattaaa tttttttatt   38520
aattaaacgt ataaaaacgt tccgtatctg tatttaagag ccagatttcg tctaatagaa   38580
caaatagcta cagtaaaaat aactagaata attgctacac ccactagaaa ccacggatcg   38640
taatacggca atcggttttc gataataggt ggaacgtata ttttatttaa ggacttaaca   38700
attgtctgta aaccacaatt tgcttccgcg gatcctgtat taactatctg taaaagcata   38760
tgttgaccgg gcggagccga acattctccg atatctaatt tctgtatatc tataatatta   38820
ttaacctccg catacgcatt acagttcttt tctagcttgg ataccgcact aggtacatcg   38880
tctagatcta ttcctatttc ctcagcgata gctcttctat ccttttccgg aagcaatgaa   38940
atcacttcaa taaatgattc aaccatgagt gtgaaactaa gtcgagaatt actcatgcat   39000
ttgttagtta ttcggagcgc gcaattttta aactgtccta taacctctcc tatatgaata   39060
gcacaagtga cattagtagg gatagaatgt tgagctaatt tttgtaaata actatctata   39120 aaagattat acaagtttt aaactcttta gtttccgcca tttatccagt ctgagaaaat   39180
gtctctcata ataatttttt ccaagaaact aattgggtga agaatggaaa cctttaatct   39240
atatttatca cagtctgtct tggtacacat gatgaattct tctaatgctg tactaaattc   39300
gatatctttt tcgatttctg gatatgtttt taataaagta tgaacaaaga aatggaaatc   39360
gtaataccag ttatgttcaa ctttgaaatt gttttttatt ttcttgttaa tgattccagc   39420
cacttgggaa aagtcaaagt cgtttaatgc cgatttaata cgttcattaa aaacaaactt   39480
tttatccttt agatgaatta ttattggttc attggaatca aaaagtaaga tattatcggg   39540
tttaagatct gcgtgtaaaa agttgtcgca acagggtagt tcgtagattt taatgtataa   39600
cagagccatc tgtaaaaaga taaactttat gtattgtacc aaagatttaa atcctaattt   39660
gatagctaac tcggtatcta ctttatctgc cgaatacagt gctaggggaa aaattataat   39720
```

```
gtttcctctt tcatattcgt agttagttct cttttcatgt tcgaaaaagt gaaacatgcg    39780
gttaaaatag tttataacat taatattact gttaataact gccggataaa agtgggatag    39840
taatttcacg aatttgatac tgtcctttct ctcgttaaac gcctttaaaa aaactttaga    39900
agaatatctc aatgagagtt cctgaccatc catagtttgt atcaataata gcaacatatg    39960
aagaacccgt ttatacagag tatgtaaaaa tgttaattta tagtttaatc ccatggccca    40020
cgcacacacg attaattttt tttcatctcc ctttagattg ttgtatagaa atttgggtac    40080
tgtgaactcc gccgtagttt ccatgggact ataaattttt gtggcctcga atacaaattt    40140
tactacatag ttatctatct taaagactat accatatcct cctgtagata tgtgataaaa    40200
atcgtcgttt ataggataaa atcgtttatc cttttgttgg aaaaaggatg aattaatgta    40260
atcattctct tctatcttta gtagtgtttc cttattaaaa ttcttaaaat aatttaacaa    40320
tctaactgac ggagcccaat tttggtgtaa atctaattgg gacattatat tgttaaaata    40380
caaacagtct cctaatataa cagtatctga taatctatgg ggagacatcc attgatattc    40440
aggggatgaa tcattggcaa cacccattta ttgtacaaaa agccccaatt tacaaacgaa    40500
agtccaggtt tgatagagac aaacaattaa ctattttgtc tctgttttta acacctccac    40560
agtttttaat ttctttagta atgaaattat tcacaatatc agtatcttct ttatctacca    40620
gagattttac taacttgata accttggctg tctcattcaa tagggtagta atatttgtat    40680
gtgtgatatt gatatctttt tgaattgttt cttttagaag tgattctttg atggtgccag    40740
catacgaatt acaataatgc agaaactcgg ttaacatgca ggaattatag taagccaatt    40800
ccaattgttg cctgtgttgt attagagtgt caatatgagc aatggtgtcc ttgcgtttct    40860
ctgatagaat gcgagcagcg attttggcgt tatcatttga cgatatttct ggaatgacga    40920
atcctgtttc tactaacttt ttggtaggac aaagtgaaac aatcaagaag atagcttctc    40980
ctcctatttg tggaagaaat tgaactcctc tagatgatct actgacgata gtatctcctt    41040
gacagatatt ggaccgaatt acagaagtac ctggaatgta aagccctgaa accccctcat    41100
tttttaagca gattgttgcc gtaaatcctg cactgtgacc aagatagaga gctccttttgg   41160 tgaatccatc tctatgtttc agtttaacca agaaacagtc agctggtcta aaatttccat    41220
ctctatctaa tacagcatct aacttgatgt caggaactat gaccggttta atgttatatg    41280
taacattgag taaatcctta agttcataat catcactgtc atcagttatg tacgatccaa    41340
acaatgtttc taccggcata gtggatacga agatgctatc catcagaatg tttccctgat    41400 tagtatttc tatatagcta ttcttcttta aacgattttc caaatcagta actatgttca    41460
tttttttagg agtaggacgc ctagccagta tggaagagga ttttctagat cctctcttca    41520
acatctttga tctcgatgga atgcaaaacc ccatagtgaa acaaccaacg ataaaaataa    41580
tattgttttt cacttttat aatttaccatctgactcat ggattcatta atatctttat    41640
aagagctact aacgtataat tctttataac tgaactgaga tatatacacc ggatctatgg    41700
tttccataat tgagtaaatg aatgctcggc aataactaat ggcaaatgta taaaacaacg    41760
aaattatact agagttgtta aagttaatat tttctatgag ctgttccaat aaattatttg    41820
ttgtgactgc gttcaagtca taaatcatct tgatactatc cagtaaaccg ttttaagtt    41880 ctggaatatt attatcccat tgtaaagccc ctaattcgac tatcgaatat cctgctctga    41940
tagcagtttc aatatcgacg gacgtcaata ctgtaataaa ggtggtagta ttgtcatcat    42000
cgtgataaac tactgggaata tggtcgttag taggtacggt aactttacac aacgcgatat    42060
ataactttcc ttttgtacca ttttaacgt agttgggacg tcctgcaggg tattgttttg    42120
```

```
aagaaatgat atcgagaaca gatttgatac gatatttgtt ggattcctga ttattcacta   42180
taatataatc tagacagata gatgattcga taaatagaga aggtatatcg ttggtaggat   42240
aatacatccc cattccagta ttctcggata ctctattgat gacactagtt aagaacatgt   42300
cttctattct agaaaacgaa aacatcctac atggactcat taaaacttct aacgctcctg   42360
attgtgtctc gaatgcctcg tacaaggatt tcaaggatgc catagattct ttgaccaacg   42420
atttagaatt gcgtttagca tctgattttt ttattaaatc gaatggtcgg ctctctggtt   42480
tgctacccca atgataacaa tagtcttgta aagataaacc gcaagaaaat ttatacgcat   42540
ccatccaaat aaccctagca ccatcggatg atattaatgt attattatag attttccatc   42600
cacagttatt gggccagtat actgttagca acggtatatc gaatagatta ctcatgtaac   42660
ctactagaat gatagttcgt gtactagtca taatatcttt aatccaatct aagaaattta   42720
aaattagatt ttttacactg ttaaagttaa caaaagtatt acccggatac gtggatatca   42780
tatatggcat tggtccatta tcagtaatag ctccataaac tgatacggcg atggttttta   42840
tatgtgtttg atctaacgag gaagaaattc gcgcccacaa ttcatctcta gatatgtatt   42900
taatatcaaa cggtaacaca tcaatttcgg gacgcgtata tgtttctaaa tttttaatcc   42960
aaatataatg atgacctata tgccctatta tcatactgtc aactatagta cacctaggga   43020
acttacgata catctgtttc ctgtaatcgt taaattttac aaatctataa catgctaaac   43080
cttttgacga caaccattca ttaatttctg atatggaatc tgtattctca ataccgtatc   43140
gttctaaagc cagtgctata tctccctgtt cgtgggaacg ctttcgtata atatcgatca   43200
acggataatc tgaagttttt ggagaataat atgactcatg atctatttcg tccataaaca   43260
atctagacat aggaattgga ggcgatgatc ttaattttgt gcaatgagtc gtcaatccta   43320
taacttctaa tcttgtaata ttcatcatcg acataatact atctatgtta tcatcgtata   43380
ttagtatacc atgaccttct tcatttcgtg ccaaaatgat atacagtctt aaataattac   43440
gcaatatctc aatagtttca taattgttag ctgttttcat caaggtttgt atcctgttta   43500
acatgatggc gttctataac gtctctattt tctattttta attttttaaa tttttaacga   43560
tttactgtgg ctagataccc aatctctctc aaatattttt ttagcctcgc ttacaagctg   43620
tttatctata ctattaaaac tgacgaatcc gtgattttgg taatgggttc cgtcgaaatt   43680
tgccgaagtg atatgaacat attcgtcgtc gactatcaac aattttgtat tattctgaat   43740
agtgaaaacc ttcacagata gatcattttg aacacacaac gcatctagac ttttggcggt   43800
tgccatagaa tatacgtcgt tcttatccca attaccaact agaagtctga tcttaactcc   43860
tctattaatg gctgcttcta taatggagtt gtaaatgtcg ggccaatagt agctattacc   43920
gtcgacacgt gtagtgggaa ctatggccaa atgttcaata tctatactag tcttagccga   43980
cttgagttta tcaataacta catcggtatc tagatctcta gaatatccca ataggtgttc   44040
cggagaatca gtaaagaaca ctccacctat aggattctta atatgatacg cagtgctaac   44100
tggcaaacaa caagccgcag agcataaatt caaccatgaa ttttttgcgc tattaaaggc   44160
tttaaaagta tcaaatcttc tacgaagatc tgtggccagc gggggataat cagaatatac   44220
acctaacgtt ttaatcgtat gtatagatcc tccagtaaat gacgcgtttc ctacataaca   44280
tctttcatca tctgacaccc aaaaacaacc gagtagtagt cccacattat tttttttatc   44340
tatattaacg gttataaaat ttatatccgg gcagtgactt tgtagctctc ccagatttct   44400
tttccctcgt tcatctagca aaactattat tttaatccct ttttcagatg cctctttag    44460
tttatcaaaa ataagcgctc ccctagtcgt actcagagga ttacaacaaa aagatgctat   44520
```

```
gtatatatat ttcttagcta gagtgataat ttcgttaaaa cattcaaatg ttgtcaaatg    44580
atcggatcta aaatccatat tttctggtag tgtttctacc agcctacatt ttgctcccgc    44640
aggtaccggt gcaaatggcc acatttagtt aacataaaaa cttatacatc ctgttctatc    44700
aacgattcta gaatatcatc ggctatatcg ctaaaatttt catcaaagtc gacatcacaa    44760
cctaactcag tcaatatatt aagaagttcc atgatgtcat cttcgtctat ttctatatcc    44820
gtatccattg tagattgttg accgattatc gagtttaaat cattactaat actcaatcct    44880
tcagaataca atctgtgttt cattgtaaat ttataggcgg tgtatttaag ttggtagatt    44940
ttcaattatg tattaatata gcaacagtag ttttgctcc tccttgattc tagcatcctc    45000
ttcattattt tcttctacgt acataaacat gtccaatacg ttagacaaca caccgacgat    45060
ggcggccgcc acagacacga atatgactaa accgatgacc atttaaaaac ccctctctag    45120
ctttcactta aactgtatcg atcattcttt tagcacatgt ataatataaa aaaacattat    45180
tctatttcga atttaggctt ccaaaaattt ttcatccgta aaccgataat aatatatata    45240
gacttgttaa tagtcggaat aaatagatta atgcttaaac tatcatcatc tccacgatta    45300
gagatacaat atttacattc ttttttgctgt ttcgaaactt tatcaataca cgttaataca    45360
aacccaggaa ggagatattg aaactgaggc tgttgaaaat gaaacggtga atacaataat    45420
tcagataatg taaaatcatg attccgtatt ctgatgatat tagaactgct aatggatgtc    45480
gatggtatgt atctaggagt atctatttta acaaagcatc gatttgctaa tatacaatta    45540
tccttttgat taattgttat tttattcata ttcttaaaag gtttcatatt tatcaattct    45600
tctacattaa aaatttccat ttttaattta tgtagccccg caatactcct cattacgttt    45660 catttttgt ctataatatc cattttgttc atctcggtac atagattatc caattgagaa    45720
gcgcatttag tagttttgta catttaagt ttattgacga atcgtcgaaa actagttata    45780
gttaacattt tattatttga taccctgata ttaatacccc tgccgttact attatttata    45840
actgatgtaa tccacgtaac attagaatta attatcgata gtaatgcatc gacgcttcca    45900
aaattgtcta ttataaactc accgataatt ttttttattgc atgttttcat attcattagg    45960
attatcaaat ctttaatctt attacgattg tatgcgttga tattgcaaga cgtcattcta    46020
aaagacggag gatctccatc aaatgccaaa caatcacgta caaagtacat ggaaataggt    46080
tttgttctat tgcgcatcat agatttatat agaacacccg tagaaatact aatttgtttt    46140
actctataaa atactaatgc atctatttca tcgttttgta taacgtcttt ccaagtgtca    46200
aattccaaat ttttttcatt gatagtacca aattcttcta tctctttaac tacttgcata    46260
gataggtaat tacagtgatg cctacatgcc gttttttgaa actgaataga tgcgtctaga    46320
agcgatgcta cgctagtcac aatcaccact ttcatattta gaatatatgt atgtaaaaat    46380
atagtagaat ttcattttgt tttttctat gctataaatg aattctcatt ttgcatctgc    46440
tcatactccg ttttatatca ataccaaaga aggaagatat ctggttctaa aagccgttaa    46500
agtatgcgat gttagaactg tagaatgcga aggaagtaaa gcttcctgcg tactcaaagt    46560
agataaaccc tcatcgcccg cgtgtgagag aagaccttcg tccccgtcca gatgcgagag    46620
aatgaataac cctggaaaac aagttccgtt tatgaggacg gacatgctac aaaatatgtt    46680
cgcggctaat cgcgataatg tagcttctag acttttgtcc taaaatacta ttatatcctt    46740
ttcgatatta ataaatccgt gtcgtccagg ttttttatct ctttcagtat gtgaatagat    46800
aggtatttta tctctattca tcatcgaatt taagagatcc gataaacatt gtttgtattc    46860
tccagatgtc agcatctgat acaacaatat atgtgcacat aaacctctgg cacttatttc    46920
```

```
atgtaccttc cccttatcac taaggagaat agtatttgag aaatatgtat acatgatatt    46980
atcatgaatt agatatacag aatttgtaac actctcgaaa tcacacgatg tgtcggcgtt    47040
aagatctaat atatcactcg ataacacatt ttcatctaga tacactagac attttttaaa    47100
gctaaaatag tctttagtag taacagtaac tatgcgatta ttttcatcga tgatacattt    47160
catcggcata ttattacgct taccatcaaa gactatacca tgtgtatatc taacgtattc    47220
tagcatagtt gccatacgcg cattaaactt ttcaggatct ttggatagat cttccaatct    47280
atctatttga gaaaacattt ttatcatgtt caatagttga aacgtcggat ccactatata    47340
gatattatct ataagatttt taggaactac gttcatggta tcctggcgaa tattaaaact    47400
atcaatgata tgattatcgt tttcatcttt tatcaccata tagtttctaa gatatgggat    47460
tttacttaat ataatattat ttcccgtgat aaatttttatt agaaaggcca aatctataag    47520
aaaagtccta gaattagtct gaagaatatc tatatcgccg tatagtatat ttggattaat    47580
tagatataga gaatatgatc cgtaacatat acaactttta ttatggcgtc taagatattc    47640
ttccatcaac ttattaacat ttttgactag ggaagataca ttatgacgtc ccattacttt    47700
tgccttgtct attactgcga cgttcataga atttagcata tctcttgcca attcttccat    47760
tgatgttaca ttataagaaa ttttagatga aattacattt ggagctttaa tagtaagaac    47820
tcctaatatg tccgtgtatg tggtcactaa tacagattgt agttctataa tcgtaaataa    47880
tttacctata ttatatgttt gagtctgttt agaaaagtag ctaagtatac gatcttttat    47940
ttctgatgca gatgtatcaa catcggaaaa aaatctttttt ttattctttt ttactaaaga    48000
tacaaatatg tctttgttaa aaacagttat tttctgaata tttctagctt gtaattttaa    48060
catatgatat tcgttcacac taggtactct gcctaaatag gtttctataa tctttaatgt    48120
aatattagga aaagtattct gatcaggatt cctattcatt ttgaggatttt aaaactctga    48180
ttattgtcta atatggtctc tacgcaaact ttttcacaga gcgatagagt ttttgataac    48240
tcgttttttct taagaaatat aaaactactg tctccagagc tcgctctatc tttttatttta    48300
tctaattcga tacaaactcc tgatactggt tcagaaagta attcattaat tttcagtcct    48360
ttatagaaga tatttaatat agataataca aaatcttcag tttttgatat cgatctgatt    48420
gatcctagaa ctagatatat taataacgtg ctcattaggc agtttatggc agcttgataa    48480
ttagatatag tatattccag ttcatatta ttagataccg cattgcccag attttgtatat    48540
tctatgaatt cctctgaaaa taaatccaaa ataactagac attctatttt tgtggatta    48600
gtgtactctc ttccctctat catgttcact actggtgtcc acgatgataa atatctagag    48660
ggaatataat atagtccata ggatgccaat ctagcaatgt cgaataactg taatttgatt    48720
cttcgttctt cattatgaat tgattcttga ggtataaacc taacacaaat tatattatta    48780
gactttttcgt atgtaatgtc tttcatgtta taagttttta atcctggaat agaatctatt    48840
ttaatgagge ttttaaacgc agagttctcc aacgagtcaa agcataatac tctgttgttt    48900
ttcttatata cgatgttacg attttcttct ttgaatggaa taggttttttg aattagttta    48960
taattacaac ataatagata aggaagtgtg caaatagtac gcggaaaaaa cataatagct    49020
cccctgtttt catccatggt tttaagtaaa tgatcactgg cttctttagt caatggatat    49080
tcgaacatta accgtttcat catcattgga cagaatccat atttcttaat gtaaagagtg    49140
atcaaatcat tgtgtttatt gtaccatctt gttgtaaatg tgtattcggt tatcggatct    49200
gctccttttt ctattaaagt atcgatgtcg atctcgtcta agaattcaac tatatcgaca    49260
tatttcattt gtatacacat aaccattact aacgtagaat gtataggaag agatgtaacg    49320
```

```
ggaacagggt tgttgattc gcaaactatt ctaatacata attcttctgt taatacgtct   49380
tgcacgtaat ctattataga tgccaagata tctatataat tattttgtaa gatgatgtta   49440
actatgtgat ctatataagt agtgtaataa ttcatgtatt ttgatatatg ttccaactct   49500
gtctttgtga tgtctagttt cgtaaatatct atagcatcct caaaaaatat attcgcatat   49560
attcccaagt cttcagttct atcttctaaa aaatcttcaa cgtatggaat ataataatct   49620
attttacctc ttctgatatc attaatgata taattttga cactatcttc tgtcaattga   49680
ttcttattca ctatatctaa gaaacggata gcgtccctag gacgaactac tgccattaat   49740
atctctatta tagcttctgg acataattca tctattatac cagaattaat gggaactatt   49800
ccgtatctat ctaacatagt tttaagaaag tcagaatcta agacctgatg ttcatatatt   49860
ggttcataca tgaaatgatc tctattgatg atagtgacta tttcattctc tgaaaattgg   49920
taactcattc tatatatgct ttccttgttg atgaaggata gaatatactc aatagaattt   49980
gtaccaacaa actgttctct tatgaatcgt atatcatcat ctgaaataat catgtaaggc   50040
atacatttaa caattagaga cttgtctcct gttatcaata tactattctt gtgataattt   50100
atgtgtgagg caaatttgtc cacgttcttt aattttgtta tagtagatat caaatccaat   50160
ggagctacag ttcttggctt aaacagatat agttttctg gaacaaattc tacaacatta   50220
ttataaagga ctttgggtag ataagtggga tgaaatccta ttttaattaa tgcgatagcc   50280
ttgtcctcgt gcagatatcc aaacgctttt gtgatagtat ggcattcatt gtctagaaac   50340
gctctacgaa tatctgtgac agatatcatc tttagagaat atactagtcg cgttaatagt   50400
actacaattt gtatttttta atctatctca ataaaaaaat taatatgtat gattcaatgt   50460
ataactaaac tactaactgt tattgataac tagaatcaga atctaatgat gacgtaacca   50520
agaagtttat ctactgccaa tttagctgca ttatttttag catctcgttt agattttcca   50580
tcggccttat cgaatactct tccgtcgata tctacacagg cataaaatgt aggagagtta   50640
ctaggcccaa ctgattcaat acgaaaagac caatctctcc tagtaatttg gcagtactca   50700
ttaataacgg tgacaggggtt agcatctttc caatcaataa ttttttttagc cggaataaca   50760
tcatcaaaag acttatgatc ctctctcatt gattttcgc gggatacatc atctattatg   50820
gcgtcagcca taacatcagc atccggctta tccgcctccg ttgtcataaa ccaacgagga   50880
ggaatatcgt cggagctgta caccatagca ctacgttgaa gatcgtacag agctttatta   50940
acttctcgct tctccatatt aagttgtcta gttagttgtg cagcagtagc tccttcgatt   51000
ccaatggttt taatagcctc acacacaatc tctgcgttag aacgttcgtc gatatagatt   51060
ttagacattt ttagagagaa ctaacgcaat cagtaataaa actaatttat tttatcattt   51120
ttttattcat catcctctgg tggttcgtcg ttcctatcga atgtggatct gattaacccg   51180
tcatctatag gtgatgctgg ttctggagat tctggaggag atggattatt atctggaaga   51240
atctctgtta tttccttgtt ttcatgtatc gattgcgttg taacattaag attgcgaaat   51300
gctctaaatt tgggaggctt aaagtgttgt ttgcaatctc tacacgcgtg tctaactagt   51360
ggaggttcgt cagctgctct agtttgaatc atcatcggtg tagtattcct acttttacag   51420
ttaggacacg gtgtattgta tttctcgtcg agaacgttaa aataatcgtt gtaactcaca   51480
tccttttattt tatctatatt gtattctact cctttcttaa tgcatttttat accgaataag   51540
agatagcgaa ggaattcttt ttcggtgccg ctagtaccct taatcatatc acatagtgtt   51600
ttatattcca aatttgtggc aatagacggt ttatttctat acgatagttt gtttctggaa   51660
tcctttgagt attctatacc aatattattc tttgattcga atttagtttc ttcgatatta   51720
```

```
gattttgtat taccatatt cttgatgtag tactttgatg attttttccat ggcccattct   51780
attaagtctt ccaagttggc atcatccaca tattgtgata gtaattctcg gatatcagta   51840
gcggttaccg ccattgatgt tgttcattg gatgagtaac tactaatgta tacatttcc    51900
atttataaca cttatgtatt aactttgttc atttatattt tttcattatt atgttgatat   51960
taacaaaagt gaatatatat gttaataatt gtattgtggt tatacggcta caatttata    52020
atgagtgaaa gtcagtgtcc gatgatcaat gacgatagct ttactctgaa agaaagtat    52080
caaatcgata gtgcggagtc aacaataaaa atggataaga agaggacaaa gtttcagaat   52140
agagccaaaa tggtaaaaga aataaatcag acaataagag cagcacaaac tcattacgag   52200
acattgaaac taggatacat aaaatttaag agaatgatta ggactactac tctagaagat   52260
atagcaccat ctattccaaa taatcagaaa acttataaac tattctcgga catttcagcc   52320
atcggcaaag catcacagaa tccgagtaag atggtatatg ctctgctgct ttacatgttt   52380
cccaatttgt ttggagatga ccatagattc attcgttata gaatgcatcc aatgagtaaa   52440
atcaaacaca agatcttctc tcctttcaaa cttaatctta ttagaatatt agtggaagaa   52500
agattctata ataatgaatg cagatctaat aaatggaaaa taattggaac acaagttgat   52560
aaaatgttga tagctgaatc tgataaatat acaatagatg caaggtataa cctaaaaccc   52620
atgtatagaa tcaagggaga atctgaagaa gataccctct tcatcaaaca gatggtagaa   52680
caatgtgtga catcccagga attggtggaa aaagtgttga agatactgtt tagagatttg   52740
ttcaagagtg gagaatacaa agcgtacaga tacgatgatg atgtagaaaa tggattcatt   52800
ggattggata cactaaaatt aaacattgtt catgatatag ttgaaccatg tatgcctgtt   52860
cgtaggccag tggctaagat actgtgtaaa gaaatggtaa ataaatactt tgagaatccg   52920
ctacatatta ttggtaaaaa tcttcaagag tgcattgact ttgttagtga ataggcattt   52980
catctttctc caatactaat tcaaattgtt aaattaataa tggatagtat aaatagttat   53040
tagtgataaa atagtaaaaa taattattag aataagagtg tagtatcata gataactctc   53100
ttctataaaa atggatttta ttcgtagaaa gtatcttata tacacagtag aaaataatat   53160
agatttttta aaggatgata cattaagtaa agtaaacaat tttaccctca atcatgtact   53220
agctctcaag tatctagtta gcaattttcc tcaacatgtt attactaagg atgtattagc   53280
taataccaat ttttttgttt tcatacatat ggtacgatgt tgtaaagtgt acgaagcggt   53340
tttacgacac gcatttgatg cacccacgtt gtacgttaaa gcattgacta agaattattt   53400
atcgtttagt aacgcaatac aatcgtacaa ggaaaccgtg cataaactaa cacaagatga   53460
aaaattttta gaggttgccg aatacatgga cgaattagga gaacttatag gcgtaaatta   53520
tgacttagtt cttaatccat tatttcacgg aggggaaccc atcaaagata tggaaatcat   53580
tttttaaaa ctgtttaaga aaacagactt caaagttgtt aaaaaattaa gtgttataag   53640
attacttatt tgggcatacc taagcaagaa agatacaggc atagagtttg cggataatga   53700
tagacaagat atatacactt tatttcaaca aactggtaga atcgtccata gcaatctaac   53760
agaaacgttt agagattata tctttcccgg agataagact agctattggg tgtggttaaa   53820
cgaaagtata gctaatgatg cggatattgt tcttaataga cacgccatta ccatgtatga   53880
taaaattctt agttatatat actctgagat aaaacaagga cgcgttaata aaaacatgct   53940
taagttagtt tatatctttg agcctgaaaa agatatcaga gaacttctgc tagaaatcat   54000
atatgatatt cctggagata tcctatctat tattgatgca aaaaacgacg attggaaaaa   54060
atattttatt agttttata aagctaattt tattaacggt aatacattta ttagtgatag   54120
```

```
aacgtttaac gaggacttat tcagagttgt tgttcaaata gatcccgaat atttcgataa    54180
tgaacgaatt atgtctttat tctctacgag tgctgcggac attaaacgat ttgatgagtt    54240
agatattaat aacagttata tatctaatat aatttatgag gtgaacgata tcacattaga    54300
tacaatggat gatatgaaga agtgtcaaat ctttaacgag gatacgtcgt attatgttaa    54360
ggaatacaat acatacctgt ttttgcacga gtcggatccc atggtcatag agaacggaat    54420
actaaagaaa ctgtcatcta taaaatccaa gagtagacgg ctgaacttgt ttagcaaaaa    54480
cattttaaaa tattatttag acggacaatt ggctcgtcta ggtcttgtgt tagatgatta    54540
taaaggagac ttgttagtta aaatgataaa ccatcttaag tctgtggagg atgtatccgc    54600
attcgttcga ttttctacag ataaaaaccc tagtattctt ccatcgctaa tcaaaactat    54660
tttagctagt tataatattt ccatcatcgt cttatttcaa aggttttga gagataatct    54720 atatcatgta gaagaattct tggataaaag catccatcta accaagacgg ataagaaata    54780
tatacttcaa ttgataagac acggtagatc atagaacaga ccaaatatat tattaataat    54840
ttgtatatac atagatataa ttatcacaca ttttttgataa atgggaactg ctgcaacaat    54900
tcagactccc accaaattaa tgaataaaga aaatgcagaa atgattttgg aaaaaattgt    54960
tgatcatata gttatgtata ttagtgacga atcaagtgat tcagaaaata atcctgaata    55020
tattgatttt cgtaacagat acgaagacta tagatctctc attataaaaa gtgatcacga    55080
gtttgtaaag ctatgtaaaa atcatgcaga gaaaagttct ccagaaacgc aacaaatgat    55140
tatcaaacac atatacgaac aatatcttat tccagtatct gaagtactat taaaaacctat   55200 aatgtccatg ggtgacataa ttacatataa cggatgtaaa gacaatgaat ggatgctaga    55260
acaactctct accctaaact ttaacaatct ccgcacatgg aactcatgta gcataggcaa    55320
tgtaacgcgt ctgttttata cattttttag ttatctgatg aaagataaac taaatatata    55380
agtataatcc cattctaata ctttaacctg atgtattagc atcttattag aatattaacc    55440
taactaaaag acataacata aaaactcatt acatagttga taaaaagcgg taggatataa    55500
atattatggc tgccaccgtt ccgcgttttg acgacgtgta caaaaatgca caaagaagaa    55560
ttctagatca agaaacattt tttagtgagg gtctaagtag accgttaatg aaaaacacat    55620
atctatttga taattacgcg tatggatgga taccagaaac tgcaatttgg agtagtagat    55680
acgcaaacct agatgctagt gactattatc ccatttcgtt gggattactt aaaaagttcg    55740
agtttctcat gtctctatat aaaggtccta ttccagtata cgaagaaaaa gtaaatactg    55800
aattcattgc taatggatcg ttctctggta gatacgtatc atatcttaga aagttttctg    55860
ctcttccaac aaacgagttt attagttttt tgttactgac ttccattcca atctataata    55920
tcttgttctg gttaaaaat acacagtttg atattactaa acacacatta ttcagatacg    55980
tctatacaga taatgccaaa cacctggcgt tggctaggta tatgcatcaa acaggagact    56040
ataagccttt gtttagtcgt ctcaaagaga attatatatt taccggtccc gttccaataa    56100
gtatcaaaga tatagatcac cctaatctta gtagagcaag aagtccatcc gattatgaga    56160
cattagctaa tattagtact atattgtact ttaccaagta tgatccggta ttaatgtttt    56220
tattgtttta cgtacctggg tattcaatta ctacaaaaat tactccagcc gtagaatatc    56280
taatggataa actgaatcta acaaagagcg acgtacaact gttgtaaatt attttatgct    56340
tcgtaaaatg taggttttga accaaacatt cttttcaaaga atgagatgca taaaacttta    56400
ttatccaata gattgactat ttcggacgtc aatcgtttaa agtaaacttc gtaaatatt    56460 ctttgatcac tgccgagttt aaaacttcta tcgataattg tttcatatgt tttaatattt    56520
```

```
acaagttttt tggtccatgg tacattagcc ggacaaatat atgcaaaata atatcgttct    56580
ccaagttcta tagtttctgg attattttta ttatattcag taaccaaata catattaggg    56640
ttatctgcgg atttataatt tgagtgatgc attcgactca acataaataa ttctagagga    56700
gacgatctac tatcaaattc ggatcgtaaa tctgtttcta aagaacggag aatatctata    56760
catacctgat tagaattcat ccgtccttca gacaacatct cagacagtct ggtcttgtat    56820
gtcttaatca tattcttatg aaacttggaa acatctcttc tagtttcact agtaccttta    56880
ttaattctct caggtacaga ttttgaattc gacgatgctg agtatttcat cgttgtatat    56940
ttcttcttcg attgcataat cagattctta tataccgcct caaactctat tttaaaatta    57000
ttaaacaata ctctactatt aatcagtcgt tctaactcct ttgctatttc tatggactta    57060
tctacatctt gactgtctat ctctgtaaac acggagtcgg tatctccata cacgctacga    57120
aaacgaaatc tgtaatctat aggcaacgat gttttcacaa tcggattaat atctctatcg    57180
tccatataaa atggattact taatggattg gcaaaccgta ataccgtt agataactct      57240
gctccattta gtaccgattc tagatacaag atcattctac gtcctatgga tgtgcaactc    57300
ttagccgaag cgtatgagta tagagcacta tttctaaatc ccatcagacc atatactgag    57360
ttggctacta tcttgtacgt atattgcatg gaatcataaa tggccttttc agttgaactg    57420
gtagcctgtt ttagcatctt tttatatctg gctctctctg ccaaaaatgt tcttaatagt    57480
ctaggaatgg ttccttctat cgatctatcg aaaattgcta tttcagagat gaggttcggt    57540
agtctaggtt cacaatgaac cgtaatatat ctaggaggtg gatatttctg aagcaagagc    57600
tgattattta tttcttcttc caatctattg gtactaacaa cgacaccgac taatgtttcc    57660
ggagatagat ttccaaagat acacacatta ggatacagac tgttataatc aaagattaat    57720
acattattac taaacatttt tgttttgga gcaaataccet taccgccttc ataaggaaac    57780
ttttgttttg tttctgatct aactaagata gttttagttt ccaacaatag ctttaacagt    57840
ggacccttga tgactgtact cgctctatat tcgaatacca tggattgagg aagcacatat    57900
gttgacgcac ccgcgtctgt ttttgtttct actccataat actcccacaa atactgacac    57960
aaacaagcat catgaataca gtatctagcc atatctaaag ctatgtttag attataatcc    58020
ttatacatct gagctaaatc aacgtcatcc tttccgaaag ataatttata tgtatcatta    58080
ggtaaagtag gacataatag tacgacttta aatccatttt cccaaatatc tttacgaatt    58140
actttacata taatatcctc atcaacagtc acataattac ctgtggttaa aacctttgca    58200
aatgcagcgg ctttgccttt cgcgtccgta gtatcgtcac cgatgaacgt catttctcta    58260
actcctctat ttaatacttt acccatgcaa ctgaacgcgt tcttggatat agaatccaat    58320
ttgtacgaat ccaattttc aaattttga atgaatgaat atagatcgaa aaatatagtt      58380
ccattattgt tattaacgtg aaacgtagta ttggccatgc cgcctactcc cttatgacta    58440
gactgatttc tctcataaat acagagatgt acagcttcct ttttgtccgg agatctaaag    58500
ataatcttct ctcctgttaa taactctaga cgattagtaa tatatctcag atcaaagtta    58560
tgtccgttaa aggtaacgac gtagtcgaac gttagttcca acaattgttt agctattcgt    58620
aacaaaacta tttcagaaca tagaactagt tctcgttcgt aatccatttc cattagtgac    58680
tgtatcctca aacatcctct atcgacggct tcttgtattt cctgttccgt taacatctct    58740
tcattaatga gcgtaaacaa taatcgttta ccacttaaat cgatataaca gtaacttgta    58800
tgcgagattg ggttaataaa tacagaagga aacttcttat cgaagtgaca ctctatatct    58860
agaaataagt acgatcttgg gatatcgaat ctaggtattt ttttagcgaa acagttacgt    58920
```

```
ggatcgtcac aatgataaca tccattgtta atctttgtca aatattgctc gtccaacgag   58980
taacatccgt ctggagatat cccgttagaa atataaaacc aactaatatt gagaaattca   59040
tccatggtgg cattttgtat gctgcgtttc tttggctctt ctatcaacca catatctgcg   59100
acggagcatt ttctatcttt aatatctaga ttataactta ttgtctcgtc aatgtctata   59160
gttctcatct ttcccaacgg cctcgcatta aatggaggag gagacaatga ctgatatatt   59220
tcgtccgtca ctacgtaata aaagtaatga ggaaatcgta taaatacggt ctcaccattt   59280
cgacatctgg atttcagata taaaaatctg ttttcaccgt gactttcaaa ccaattaatg   59340
caccgaacat ccatttatag aatttagaaa tatattttca tttaaatgaa tcccaaacat   59400
tggggaagag ccgtatggac cattatttt atagtacttt cgcaagcggg tttagacggc   59460
aacatagaag cgtgtaaacg aaaactatat actatagtta gcactcttcc atgtcctgca   59520
tgtagacggc acgcgactat tgctatagag acaataatg tcatgtctag cgatgatctg   59580
aattatattt attatttttt catcagatta tttaacaatt tggcatctga tcccaaatac   59640
gcgatcgatg tgacaaaggt taacccttta taaacttaac ccattataaa acttatgatt   59700
agtcacgact gaaataaccg cgtgattatt ttttggtata attctacacg gcatggtttc   59760
tgtgactatg aattcaaccc ccgttacatt agtgaaatct ttaacaaaca gcaagggttc   59820
gtcaaagaca taaaactcat tgtttacaat cgaaatagac ccctatcac acttaaaata   59880 aaaaatatcc ttatccttta ccaccaaata aaattctgat tggtcaatgt gaatgtattc   59940
acttaacagt tccacaaatt tatttattaa ctccgaggca catacatcgt cggtattttt   60000
tatggcaaac tttactcttc cagcatccgt ttctaaaaaa atattaacga gttccattta   60060
tatcatccaa tattattgaa atgacgttga tggacagatg atacaaataa gaaggtacgg   60120
tacctttgtc caccatctcc tccaattcat gctctatttt gtcattaact ttaatgtatg   60180
aaaacagtac gccacatgct tccatgacag tgtgtaacac tttggataca aaatgtttga   60240
cattagtata attgtccaag actgtcaatc tataatagat agtagctata atatattcta   60300
tgatggtatt gaagaagatg acaaccttgg catattgatc atttaacaca gacatggtat   60360
caacagatag cttgaatgaa agagaatcag taattggaat aagcgtcttc tcgatagagt   60420
gtccgtatac caacatgtct gatattttga tgtattccat taaattattt agttttttct   60480
ttttattttc gttaaacagc atttctgtca acggaccccca acatcgttga ccgattaagt   60540
tttgattgat ttttccgtgt aatgcgtatc tagtcagatc gtatagccta tccaataatc   60600
catcatctgt gcgtagatca catcgtacac ttttttaattc tctatagaag agcgacagac   60660
atctggagca attacagaca gcaatttctt tattctctac agatgtaaga tacttgaaga   60720
cattcctatg atgatgcaga attttggata acacggtatt gatggtatct gttaccataa   60780
ttcctttgat ggctgatagt gtcagagcac aagatttcca atctttgaca atttttagca   60840
ccattatctt tgttttgata tctatatcag acagcatggt gcgtctgaca acacagggat   60900
taagacggaa agatgaaatg attctctcaa catcttcaat agatacctttg ctattttttc   60960 tggcattatc tatatgtgcg agaatatcct ctagagaatc agtatccttt ttgatgatag   61020
tggatctcaa tgacatggga cgtctaaacc ttcttattct atcaccagat tgcatggtga   61080
tttgtcttct ttcttttatc ataatgtaat ctctaaattc atcggcaaat tgtctatatc   61140
taaaatcata atatgagatg tttacctcta caaatatctg ttcgtccaat gttagagtat   61200
ttacatcagt tttgtattcc aaattaaaca tggcaacgga tttaattttta tattcctcta   61260 ttaagtcctc gtcgataata acagaatgta gataatcatt taatccatcg tacatggttg   61320
```

```
gaagatgctt gttgacaaaa tctttaattg tcttgatgaa ggtgggacta tatctaacat   61380
cttgattaat aaaatttata acattgtcca taggatactt tgtaactagt tttatacaca   61440
tctcttcatc ggtaagttta gacagaatat cgtgaacagg tggtatatta tattcatcag   61500
atatacgaag aacaatgtcc aaatctatat tgtttaatat attatataga tgtagcgtag   61560
ctcctacagg aatatcttta actaagtcaa tgatttcatc aaccgttaga tctattttaa   61620
agttaatcat ataggcattg atttttaaaa ggtatgtagc cttgactaca ttctcattaa   61680
ttaaccattc caagtcactg tgtgtaagaa gattatattc tatcataagc ttgactacat   61740
ttggtcccga taccattaaa gaattctat gatataagga aacagatttt aggtactcat   61800
ctactctaca agaattttgg agagccttaa cgatatcagt gacgtttatt atttcaggag   61860
gaaaaaacct aacattgaga atatcggaat taatagcttc cagatacagt gattttggca   61920
atagtccgtg taatccataa tccagtaaca cgagctggtg cttgctagac accttttcaa   61980 tgtttaatt ttttgaaata agctttgata aagccttcct cgcaaattcc ggatacatga   62040
acatgtcggc gacatgatta agtattgttt tttcattatt tttatatttt ctcaacaagt   62100
tctcaatacc ccaatagatg atagaatatc acccaatgcg tccatgttgt ctatttccaa   62160
caggtcgcta tatccaccaa tagaagttttt cccaaaaaag attctaggaa cagttctacc   62220
accagtaatt tgttcaaaat aatcccgcaa ttcattttcg ggtttaaatt ctttaatatc   62280
gacaatttca tacgctcctc ttttgaaact aaacttattt agaatatcca gtgcatttct   62340
acaaaaagga catgtatact tgacaaaaat tgtcactttg ttattggcca acctttgttg   62400
tacaaattcc tcggccattt taatatttaa gtgatataaa actatctcga cttatttaac   62460
tctttagtcg agatatatgg acgcagatag ctatatgata gccaactaca gaaggcaaac   62520
gctataaaaa acataattac aacgagcata tttataaata tttttattca gcattacttg   62580
atatagtaat attaggcaca gtcaaacatt caaccactct cgatacatta actctctcat   62640
tttctttaac aaattctgca atatcttcgt aaaaagattc ttgaaacttt ttagaatatc   62700
tatcgactct agatgaaata gcgttcgtca acatactatg ttttgtatac ataaaggcgc   62760
ccattttaac agtttctagt gacaaaatgc tagcgatcct aggatccttt agaatcacat   62820
agattgacga ttcgtctctc ttagtaactc tagtaaaata atcatacaat ctagtacgcg   62880
aaataatatt atccttgact tgaggagatc taaacaatct agttttgaga acatcgataa   62940
gttcatcggg aatgacatac atactatctt taatagaact cttttcatcc agttgaatgg   63000
attcgtcctt aaccaactga ttaatgagat cttctatttt atcattttcc agatgatatg   63060
tatgtccatt aaagttaaat tgtgtagcgc ttctttttag tctagcagcc aatactttaa   63120
catcactaat atcgatatac aaaggagatg atttatctat ggtattaaga attcgttttt   63180
cgacatctgt caaaccaat tccttttgc ctgtatcatc cagttttcca tcctttgtaa   63240
agaaattatt ttctactaga ctattaataa gactgataag gattcctcca taattgcaca   63300
atccaaactt tttaacaaaa ctagacttta caagatctac aggaatgcgt acttcaggtt   63360
tcttagcttg tgattttttc ttttgcggac attttctagt aaccaactca tctaccattt   63420
cattgatttt agcagtgaaa taagctttca atgcacgggc actgatacta ttgaaaacga   63480
gttgatcttc aaattccgcc atttaagttc accaaacaac ttttaaatac aaatatatca   63540
atagtagtag aataagaact ataaaaaaaa taataattaa ccaataccaa ccccaacaac   63600
cggtattatt agttgatgtg actgttttct catcacttag aacagattta acaatttcta   63660
taaagtctgt caaatcatct tccggagacc ccataaatac accaaatata gcggcgtaca   63720
```

```
acttatccat ttatacattg aatattggct tttctttatc gctatcttca tcatattcat   63780
catcaatatc aacaagtccc agattacgag ccagatcttc ttctacattt tcagtcattg   63840
atacacgttc actatctcca gagagtccga taacgttagc caccacttct ctatcaatga   63900
ttagtttctt gagcgcgaat gtaattttg tttccgttcc ggatctatag aagacgatag    63960
gtgtgataat tgccttggcc aattgtcttt ctcttttact gagtgattct agttcacctt   64020
ctatagatct gagaatggat gattctccag tcgaaacata ttctaccatg gatccgttta   64080
atttgttgat gaagatggat tcatccttaa atgttttctc tgtaatagtt tccaccgaaa   64140
gactatgcaa agaatttgga atgcgttcct tgtgcttaat gtttccatag acggcttcta   64200
gaagttgata caacatagga ctagccgcgg taacttttat ttttagaaag tatccatcgc   64260
ttctatcttg tttagattta tttttataaa gtttagtctc tccttccaac ataataaaag   64320
tggaagtcat ttgactagat aaactatcag taagttttat agagatagac gaacaattag   64380
cgtattgaga agcatttagt gtaacgtatt cgatacattt tgcattagat ttactaatcg   64440
attttgcata ctctataaca cctgcacaag tctgtagaga atcgctagat gcagtaggtc   64500
ttggtgaagt ttcaactctc ttcttgatta ccttactcat gattaaacct aaataattgt   64560
actttgtaat ataatgatat atattttcac tttatctcat ttgagaataa aaatgttttt   64620
gtttaaccac tgcatgatgt acagatttcg gaatcgcaaa ccaccagtgg ttttatttta   64680
tccttgtcca atgtgaattg aatgggagcg gatgcgggtt tcgtacgtag atagtacatt   64740
cccgttttta gaccgagact ccatccgtaa aaatgcatac tcgttagttt ggaataactc   64800
ggatctgcta tatggatatt catagattga ctttgatcga tgaaggctcc cctgtctgca   64860 gccatttta tgatcgtctt ttgtggaatt tcccaaatag ttttataaac tcgcttaata    64920
tcttctggaa ggtttgtatt ctgaatggat ccaccatctg ccataatcct attcttgatc   64980
tcatcattcc ataattttct ctcggttaaa actctaagga gatgcggatt aactacttga   65040
aattctccag acaatactct ccgagtgtaa atattactgg tatacggttc caccgactca   65100
ttatttccca aaatttgagc agttgatgca gtcggcatag gtgccaccaa taaactattt   65160
ctaagaccgt atgttctgat tttatctttt agaggttccc aattccaaag attcgacggt   65220
acaacattcc aaagatcata ttgtagaata ccgttactgg cgtacgatcc tacatatgta   65280
tcgtatggtc cttccttctc agctagttca caactcgcct ctaatgcacc gtaataaatg   65340
gtttcgaaga tcttcttatt tagatcttgt gcttccaggc tatcaaatgg ataatttaag   65400
agaataaacg cgtccgctaa tccttgaaca ccaataccga taggtctatg tctcttatta   65460
gagatttcag cttctggaat aggataataa ttaatatcta aattttatt gagatttctg    65520 acaattactt tgaccacatc cttcagtttg agaaaatcaa atcgcccatc tattacaaac   65580
atgttcaagg caacagatgc cagattacaa acggctacct cattagcatc cgcatattgt   65640
attatctcag tgcaaagatt actacacttg atagttccta aattttgttg attactcttt   65700
ttgttacacg catccttata aagaatgaat ggagtaccag tttcaatctg agattctata   65760
atcgctttcc agacgactcg agcctttatt atagatttgt atctcctttc tctttcgtat   65820
agtgtataca atcgttcgaa ctcgtctccc caaacattgt ccaatccagg acattcatcc   65880
ggacacatca acgaccactc tccgtcatcc ttcactcgtt tcataaagag atcaggaatc   65940
caaagagcta taaatagatc tctggttcta tgttcctcgt ttcctgtatt cttttttaaga  66000 tcgaggaacg ccataatatc agaatgccac ggttccaagt atatggccat aactccaggc   66060
cgtttgtttc ctccctgatc tatgtatcta gcggtgttat tataaactct caacattgga   66120
```

```
ataataccgt tgatatacc attggtaccg gagatatagc ttccactggc acgaatatta   66180
ctaattgata gacctattcc ccctgccatt ttagagatta atgcgcatcg ttttaacgtg   66240
tcatagatac cctctatgct atcatcgatc atgttaagta gaaaacagct agacatttgg   66300
tgacgactag ttcccgcatt aaataaggta ggagaagcgt gcgtaaacca tttttcagaa   66360
agtagattgt acgtctcaat agctgagtct atatcccatt gatgaattcc tactgcgaca   66420
cgcattaaca tgtgctgagg tcttcaacg atcttgttgt ttattttcaa caagtaggat    66480
ttttccaaag ttttaaaacc aaaatagttg tatgaaaagt ctcgttcgta aataataacc   66540
gagttgagtt tatccttata tttgttaact atatccatgg tgatacttga aataatcgga   66600
gaatgtttcc catttttagg attaacatag ttgaataaat cctccatcac ttcactaaat   66660 agttttttg tttccttgtg tagatttgat acggctattc tggcggctag aatggcataa    66720
tccggatgtt gtgtagtaca agtggctgct atttcggctg ccagagtgtc caattctacc   66780
gttgttactc cattatatat tccttgaata accttcatag ctattttaat aggatctata   66840
tgatccgtgt ttaagccata acataatttt ctaatacgag acgtgatttt atcaaacatg   66900
acattttcct tgtatccatt tcgtttaatg acaaacattt tgttggtgt aataaaaaaa    66960 ttatttaact tttcattaat agggatttga cgtatgtagc gtacaaaatg atcgttcctg   67020
gtatatagat aaagagtcct atatatttga aaatcgttac ggctcgatta aactttaatg   67080
attgcatagt gaatatatca ttaggattta actccttgac tatcatggcg gcgccagaaa   67140
ttaccatcaa aagcattaat acagttatgc ctatcgcagt tagaacggtt atagcatcca   67200
ccatttatat ctaaaaatta gatcaaagaa tatgtgacaa agtcctagtt gtatactgag   67260
aattgacgaa acaatgtttc ttacatattt ttttcttatt agtaactgac ttaatagtag   67320
gaactggaaa gctagacttg attattctat aagtatagat acccttccaa ataatattct   67380
ctttgataaa agttccagaa aatgtagaat tttttaaaaa gttatctttt gctattacca   67440
agattgtgtt tagacgctta ttattaatat gagtgatgaa atccacaccg cctctagata   67500
tcgcctttat ttccacatta gatggtaaat ccaatagtga aactatcttt ttaggaatgt   67560
atggactcgc gtttagagga gtgaacgtct tgggcgtcgg aaaggatgat tcgtcaaacg   67620
aataaacaat ttcacaaatg gatgttaatg tattagtagg aaattttttg acgctagtgg   67680
aattgaagat tctaatggat gatgttctac ctatttcatc cgataacatg ttaatttccg   67740
acaccaacgg ttttaatatt tcgatgatat acggtagtct ctctttcgga cttatatagc   67800
ttattccaca atacgagtca ttatatactc caaaaaacaa aataactagt ataaaatctg   67860
tatcgaatgg gaaaaacgaa attatcgaca taggtataga atccggaaca ttgaacgtat   67920
taatacttaa ttcttttttct gtggtaagta ccgataggtt attgacattg tatggtttta   67980
aatattctat aacttgagac ttgatagata ttagtgatga attgaaaatt attttatca    68040 ccacgtgtgt ttcaggatca tcgtcgacgc ccgtcaacca accgaatgga gtaaaataaa   68100
tatcattaat atatgctcta gatattagta tttttatcaa tcctttgatt atcatcttct   68160
cgtaggcgaa tgattccatg atcaagagtg atttgagaac atcctccgga gtattaatgg   68220
gcttagtaaa cagtccatcg ttgcaataat aaaagttatc caagttaaag gatattatgc   68280
attcgtttaa agatatcacc tcatctgacg gagacaattt tttggtaggt tttagagact   68340
ttgaagctac ttgtttaaca aagttattca tcgtcgtcta ctattctatt taattttgta   68400
gttaatttat cacatatcac attaattgac tttttggtcc atttttccat acgtttatat   68460
tcttttaatc ctgcgttatc cgtttccgtt atatccaggg atagatcttg caagttaaat   68520
```

```
agaatgctct taaataatgt cattttctta tccgctaaaa atttaaagaa tgtataaacc    68580
tttttcagag atttgaaact cttaggtggt gtcctagtac acaatatcat aaacaaacta    68640
ataaacattc cacattcaga ttccaacagc tgattaactt ccacattaat acagcctatt    68700
ttcgctccaa atgtacattc gaaaaatctg aataaaacat cgatgtcaca atttgtatta    68760
tccaatacag aatgtctgtg attcgtgtta aaaccatcgg agaaggaata aaaataaaaa    68820
ttattatagt ggtggaattc agttggaata ttgcctccgg agtcataaaa ggatactaaa    68880
cattgttttt tatcataaat tacacatttc caatgagaca aataacaaaa tccaaacatt    68940
acaaatctag aggtagaact tttaattttg tctttaagta tatacgataa gatatgttta    69000
ttcataaacg cgtcaaattt ttcatgaatc gctaaggagt ttaagaatct catgtcaaat    69060
tgtcctatat aatccacttc ggatccataa gcaaactgag agactaagtt cttaatactt    69120
cgattgctca tccaggctcc tctctcaggc tctattttca tcttgacgac ctttggattt    69180
tcaccagtat gtattccttt acgtgataaa tcatcgattt tcaaatccat ttgtgagaag    69240
tctatcgcct tagatacttt ttcccgtagt cgaggtttaa aaaaatacgc taacggtata    69300
ctagtaggta actcaaaaac atcatatata gaatggtaac gcgtctttaa ctcgtcggtt    69360
aactctttct tttgatcgag ttcgtcgcta ctattgggtc tgctcaggtg ccccgactct    69420
actagttcca acatcatacc gataggaata caagacactt gccggcggt tgtagattta    69480 tcatatttct ccactacata tccgttacaa tttgttaaaa atttagatac atctatattg    69540
ctacataatc cagctagtga atatatatga cataataaat tggtaaatcc tagttctggt    69600
attttactaa ttactaaatc tgtatatctt tccatttatc atggaaaaga atttaccaga    69660
tatcttcttt tttccaaact gcgttaatgt attctcttac aaatattcac aagatgaatt    69720
cagtaatatg agtaaaacgg aacgtgatag tttctcattg gcggtgtttc cagttataaa    69780
acatagatgg cataacgcac acgttgtaaa acataaagga atatacaaag ttagtacaga    69840
agcacgtgga aaaaaagtat ctcctccatc actaggaaaa cccgcacaca taaacctaac    69900
cgcgaagcaa tatatataca gtgaacacac aataagcttt gaatgttata gttttctaaa    69960
atgtataaca aatacagaaa tcaattcgtt cgatgagtat atattaagag gactattaga    70020
agctggtaat agtttacaga tattttccaa ttccgtaggt aaacgaacag atactatagg    70080
tgtactaggg aataagtatc catttagcaa aattccattg gcctcattaa ctcctaaagc    70140
acaacgagag atattttcag cgtggatttc tcatagacct gtagttttaa ctggaggaac    70200
tggagtgggt aagacgtcac aggtacccaa gttattgctt tggtttaatt atttatttgg    70260
tggattctct actctagata aaatcactga cttttcacgaa agaccagtca ttctatctct    70320
tcctaggata gctttagtta gattgcatag caataccatt ttaaaatcat tgggatttaa    70380
ggtactagat ggatctccta tttctttacg gtacggatct ataccggaag aattaataaa    70440
caaacaacca aaaaaatatg gaattgtatt ttctacccat aagttatctc taacaaaact    70500
atttagttat ggcactctta ttatagacga agttcatgag catgatcaaa taggagatat    70560
tattatagca gtagcgagaa agcatcatac gaaaatagat tctatgtttt taatgactgc    70620
cacgttagag gatgaccgag aacggctaaa agtattttta cctaatcccg catttataca    70680
tattcctgga gatacactgt ttaaaattag cgaggtattt attcataata agataaatcc    70740
atcttccaga atggcataca tagaagaaga aaagagaaat ttagttactg ctatacagat    70800
gtatactcct cctgatggat catccggtat agtctttgtg gcatccgttg cacagtgtca    70860
cgaatataaa tcatatttag aaaaaagatt accgtatgat atgtatatta ttcatggtaa    70920
```

```
ggtcttagat atagacgaaa tattagaaaa agtgtattca tcacctaatg tatcgataat   70980
tatttctact ccttatttgg aatccagcgt tactatacgc aatgttacac acatttatga   71040
tatgggtaga gttttgtcc ccgctccttt tggaggatcg caacaattta tttctaaatc   71100
tatgagagat caacgaaaag gaagagtagg aagagttaat cctggtacat acgtctattt   71160
ctatgatctg tcttatatga agtctataca gcgaatagat tcagaatttc tacataatta   71220
tatattgtac gctaataagt ttaatctaac actccccgaa gatttgttta taatccctac   71280
aaatttggat attctatggc gtacaaagga atatatagac tcgttcgata ttagtacaga   71340
aacatggaat aaattattat ccaattatta tatgaagatg atagagtatg ctaaacttta   71400
tgtactaagt cctattctcg ctgaggagtt ggataacttt gagaggacgg gagaattaac   71460
tagtattgta cgagaagcca ttttatctct aaatttacga attaagattt taaattttaa   71520
acataaagat gatgatacgt atatacactt ttgtaaaata ttattcggtg tctataacgg   71580
aacaaacgct actatatatt atcatagacc tctaacggga tatatgaata tgatttcaga   71640
tactatattt gttcctgtag ataataacta aaaatcaaac tctaatgacc acatcttttt   71700
ttagagatga aaaattttcc acatctcctt ttgtagacac gactaaacat tttgcagaaa   71760
aaagtttatt agtgtttaga taatcgtata cttcatcagt gtagatagta aatgtgaaca   71820
gataaaaggt attcttgctc aatagattgg taaattccat agaatatatt aatcctttct   71880
tcttgagatc ccacatcatt tcaaccagag acgttttatc caatgattta cctcgtacta   71940
taccacatac aaaactagat tttgcagtga cgtcgtacct ggtattccta ccaaacaaaa   72000
ttttactttt agttctttta gaaaattcta aggtagaatc tctatttgcc aatatgtcat   72060
ctatggaatt accactagca aaaaatgata gaaatatata ttgatacatc gcagctggtt   72120
ttgatctact atactttaaa aacgaatcag attccataat tgcctgtata tcatcagctg   72180
aaaaactatg ttttacacgt attccttcgg catttctttt taatgatata tcttgtttag   72240
acaatgataa agttatcatg tccatgagag acgcgtctcc gtatcgtata aatatttcat   72300
tagatgttag acgcttcatt agggtatac ttctataagg tttcttaatc agtccatcat   72360
tggttgcgtc aagaactact atcggatgtt gttgggtatc tctagtgtta cacatggcct   72420
tactaaagtt tgggtaaata actatgatat ctctattaat tatagatgca tatatttcat   72480
tcgtcaagga tattagtatc gacttgctat cgtcattaat acgtgtaatg taatcatata   72540
aatcatgcga tagccaagga aaattcaaat agatgttcat catataatcg tcgctataat   72600
tcatattaat acgttgacat tgactaattt gtaaatagc ctcgccacga agaaagctct   72660
cgtattcagt ttcatcgata aaggataccg ttaaatataa ctggttgccg atagtctcat   72720
agtctattaa gtggtaagtt tcgtacaaat acagaatccc taaaatatta tctaatgttg   72780
gattaatctt taccataact gtataaaatg gagacggagt cataactatt ttaccgtttg   72840
tacttactgg aatagatgaa ggataatct ccggacatgc tggtaaagac ccaaatgtct   72900
gtttgaagaa atccaatgtt ccaggtccta atctcttaac aaaaattacg atattcgatc   72960
ccgatatcct ttgcattcta tttaccagca tatcacgaac tatattaaga ttatctatca   73020
tgtctattct cccaccgtta tataaatcgc ctccgctaag aaacgttagt atatccatac   73080
aatggaatac ttcatttcta aaatagtatt cgtttctaa ttctttaatg tgaaatcgta   73140
tactagaaag ggaaaaatta tctttgagtt ttccgttaga aaagaaccac gaaactaatg   73200
ttctgattgc gtccgatttc gttgctgaat taatggattt acaccaaaaa ctcatataac   73260
ttctagatgt agaagcattc gctaaaaaat tagtagaatc aaaggatata agtagatgtt   73320
```

```
ccaacaagtg agcaattccc aagatttcat ctatatcatt ctcgaatccg aaattagaaa   73380
ttcccaagta gatatccttt ttcatccgat cgttgatgaa aatacgaact ttattcggta   73440
agacaatcat ttactaagga gtaaaatagg aagtaatgtt cgtatgtcgt tatcatcgta   73500
taaattaaag gtgtgttttt taccattaag tgacattata attttaccaa tattggaatt   73560
ataatatagg tgtatttgcg cactcgcgac ggttgatgca tcggtaaata tagctgtatc   73620
taatgttcta gtcggtattt catcatttcg ctgtctaata atagcgtttt ctctatctgt   73680
ttccattaca gctgcctgaa gtttattggt cggataatat gtaaaataat aagaaataca   73740
tacgaataac aaaaataaaa taagatataa taaagatgcc atttagagat ctaattttgt   73800
ttaacttgtc caaattccta cttacagaag atgaggaatc gttggagata gtgtcttcct   73860
tatgtagagg atttgaaata tcttataatg acttgataac ttactttcca gataggaaat   73920
accataaata tatttctaaa gtatttgaac atgtagattt atcggaggaa ttaagtatgg   73980
aattccatga tacaactctg agagatttag tctatcttag attgtacaag tattccaagt   74040
gtatacggcc gtgttataaa ttaggagata atctaaaagg catagttgtt ataaaggaca   74100
ggaatattta tattagggaa gcaaatgatg acttgataga atatctcctc aaggaataca   74160
ctcctcagat ttatacatat tctaatgagc gcgtccccat aactggttca aaattaattc   74220
tttgtggatt ttctcaagtt acatttatgg cgtatacaac gtcgcatata acaacaaata   74280
aaaaggtaga tgttctcgtt tccaaaaaat gtatagatga actagtcgat ccaataaatt   74340
atcaaatact tcaaaattta tttgataaag gaagcggaac aataaacaaa atactcagga   74400
agatatttta ttcggtaaca ggtggccaaa ctccataatt tgcttttttct atttcggatt   74460 ttagaatttc caaattcacc agcgatttat cggttttggt gaaatccaag gatttattaa   74520
tgtccacaaa tgccatttgt tttgtctgtg gattgtattt gaaaatggaa acgatgtagt   74580
tagatagatg cgctgcgaag tttcctatta gggttccgcg cttcacgtca cccagcatac   74640
ttgaatcacc atcctttaaa aaaaatgata agatatcaac atggagtata tcatactcgg   74700 atttttaattc ttctactgca tcactgacat tttcacaaat actacaatac ggtttaccga   74760
aaataatcag tacgttcttc atttatgggt atcaaaaact taaaatcgtt actgctggaa   74820
aataaatcac tgacgatatt agatgataat ttatacaaag tatacaatgg aatatttgtg   74880
gatacaatga gtatttatat agccgtcgcc aattgtgtca gaaacttaga agagttaact   74940
acggtattca taaaatacgt aaacggatgg gtaaaaaagg gagggcatgt aaccctttt   75000 atcgatagag gaagtataaa aattaaacaa gacgttagag acaagagacg taaatattct   75060
aaattaacca aggacagaaa aatgctagaa ttagaaaagt gtacatccga aatacaaaat   75120
gttaccggat ttatggaaga agaaataaag gcagaaatgc aattaaaaat cgataaactt   75180
acatttcaaa tatatttatc tgattctgat aacataaaaa tatcattgaa tgagatacta   75240
acacatttca acaataatga gaatgttaca ttatttttatt gtgatgaacg agacgcagaa   75300
ttcgttatgt gtctcgaggc taaaacacat ttctctacca caggagaatg gccgttgata   75360
ataagtaccg atcaggatac tatgctattt gcatctgctg ataatcatcc taagatgata   75420
aaaaacttaa ctcaactgtt taaatttgtt ccctcggcag aggataacta tttagcaaaa   75480
ttaacggcgt tagtgaatgg atgtgatttc tttcctggac tctatgggc atctataaca   75540 cccaccaact taaacaaaat acaattgttt agtgattta caatcgataa tatagtcact   75600
agtttggcaa ttaaaaatta ttatagaaag actaactcta ccgtgacgt gcgtaatatt   75660 gttacgttta taaacgatta cgctaattta gacgatgtct actcgtatat tcctccttgt   75720
```

```
caatgcactg ttcaagaatt tatattttcc gcattagatg aaaaatggaa tgaatttaaa    75780
tcatcttatt tagaaagcgt gccgttaccc tgtcaattaa tgtacgcgtt agaaccacgc    75840
aaggagattg atgtttcaga agttaaaact ttatcatctt atatagattt cgaaaatact    75900
aaatcagata tcgatgttat aaaatctata tcctcgatct tcggatattc taacgaaaac    75960
tgtaacacga tagtattcgg catctataag gataatttac tactgagtat aaatagttca    76020
ttttacttta acgatagtct gttaataacc aatactaaaa gtgataatat aataaatata    76080
ggttactaga ttaaaaatgg tgttccaact cgtgtgctct acgtgcggta agatatttc     76140 tcacgaacga tataaattga ttatacgaaa aaaatcatta aaggatgtac tcgtcagtgt    76200
aaagaacgaa tgttgtaggt taaaattatc tacacaaata gaacctcaac gtaacttaac    76260
agtgcaacct ctattggata taaactaata tggatccggt taattttatc aagacatatg    76320
cgcctagagg ttctattatt tttattaatt ataccatgtc attaacaagt catttgaatc    76380
catcgataga aaaacatgtg ggtatttatt atggtacgtt attatcggaa cacttggtag    76440
ttgaatctac ctatagaaaa ggagttcgaa tagtcccatt ggatagtttt tttgaaggat    76500
atcttagtgc aaaagtatac atgttagaga atattcaagt tatgaaaata gcagctgata    76560
cgtcattaac tttattgggt attccgtatg gatttggtca taatagaatg tattgtttta    76620
aattggtagc tgaatgttat aaaaatgccg gtattgatac atcgtctaaa cgaatattgg    76680
gcaaagatat ttttctgagc caaaacttca caaacgataa tagatggata aagatatatg    76740
attctaataa tttaacattt tggcaaattg attaccttaa agggtgagtt aatatgcata    76800
actactcctc cgttgttttt tccctcgttc ttttcttaa cgttgtttgc catcactctc     76860
ataatgtaaa gatattctaa aatggtaaac ttttgcatat cggacgcaga aattggtata    76920
aatgttgtaa ttgtattatt tcccgtcaat ggactagtca cagctccatc agtttatat     76980 cctttagagt atttctcact cgtgtctagc attctagagc attccatgat ctgtttatcg    77040
ttgatattgg ccggaaagat agattttta ttttttatta tattactatt ggcaattgta     77100
gatataactt ctggtaaata ttttttctacc ttttcaatct cttctatttt caagccggct   77160
atatattctg ctatattgtt gctagtatca ataccttttc tggctaagaa gtcatatgtg    77220
gtattcacta tatcagtttt aactggtagt tccattagcc tttccacttc tgcagaataa    77280
tcagaaattg gttctttacc agaaaatcca gctactataa taggctcacc gatgatcatt    77340
ggcaaaatcc tatattgtac cagattaatg agagcatatt tcatttccaa taattctgct    77400
agttcttgag acattgattt atttgatgaa tctagttggt tctctagata ctctaccatt    77460
tctgccgcat acaataactt gttagataaa atcagggtta tcaaagtgtt tagcgtggct    77520
agaatagtgg gcttgcatgt attaaagaat gcggtagtat gagtaaaccg ttttaacgaa    77580
ttatatagtc tccagaaatc tgtggcgtta catacatgag ccgaatgaca tcgaagattg    77640 tccaatatttt ttaatagctg ctctttgtcc attatttcta tatttgactc gcaacaattg   77700
tagataccat taatcaccga ttccttttc gatgctggac aatagcacaa ttgtttagct     77760
ttggactcta tgtattcaga attaatagat atatctctca atacagattg cactatacat    77820
tttgaaacta tgtcaaaaat tgtagaacga cgctgttctg cagccattta actttaaata    77880
atttacaaaa atttaaaatg agcatccgta taaaaatcga taaactgcgc caaattgtgg    77940 catattttttc agagttcagt gaagaagtgt ctataaatgt agactcgacg gatgagttaa   78000 tgtatattttt tgccgccttg ggcggatctg taaacatttg ggccattata cctctcagtg   78060
catcagtgtt ctaccgagga gccgaaaaca ttgtgtttaa tcttcctgtg tccaaggtaa    78120
```

```
aatcgtgttt gtgtagtttt cacaatgatg ccatcataga tatagaacct gatctggaaa   78180
ataatctagt aaaactttct agttatcatg tagtaagtgt cgattgtaac aaggaactga   78240
tgcctattag gacagatact actatttgtc taagtataga tcaaaagaaa tcttatgtgt   78300
ttaattttca caagtatgaa gaaaaatgtt gtggtagaac cgtcattcat ctagaatggt   78360
tgttgggctt tatcaagtgt attagtcagc atcagcatct ggctattatg tttaaagatg   78420
acaatattat tatgaagact cctggtaata ctgatgcatt ttccagggaa tattctatga   78480
ctgaatgttc tcaagaacta caaaagtttt ctttcaaaat agctatctcg tctctcaaca   78540
aactacgagg attcaaaaag agagtcaatg tttttgaaac tagaatcgta atggataatg   78600
acgataacat tttaggaatg ttgttttcgg atagagttca atcctttaag atcaacatct   78660
ttatggcgtt tttagattaa tactttcaat gagataaata tgggtggcgg agtaagtgtt   78720
gagctcccta aacgggatcc gcctccggga gtacccactg atgagatgtt attaaacgtg   78780
gataaaatgc atgacgtgat agctcccgct aagcttttag aatatgtgca tataggacca   78840
ctagcaaaag ataaagagga taaagtaaag aaaagatatc cagagtttag attagtcaac   78900
acaggacccg gtggtctttc agcattgtta agacaatcgt ataatggaac cgcacccaat   78960
tgctgtcgca cttttaatcg tactcattat tggaagaagg atggaaagat atcagataag   79020
tatgaagagg gtgcagtatt agaatcgtgt tggccagacg ttcacgacac tggaaaatgc   79080
gatgttgatt tattcgactg gtgtcagggg gatacgttcg atagaaacat atgccatcag   79140
tggatcggtt cagcctttaa taggagtgat agaactgtag agggtcaaca atcgttaata   79200
aatctgtata ataagatgca aacattatgt agtaaagatg ctagtgtacc aatatgcgaa   79260 tcattttgc atcatttacg cgcacacaat acagaagata gcaaagagat gatcgattat   79320
attctaagac aacagtctgc ggactttaaa cagaaatata tgagatgtag ttatcccact   79380
agagataagt tagaagagtc attaaaatat gcggaacctc gagaatgttg ggatccagag   79440
tgttcgaatg ccaatgttaa tttcttacta acacgtaatt ataataattt aggactttgc   79500
aatattgtac gatgtaatac tagcgtgaac aacttacaga tggataaaac ttcctcatta   79560
agattgtcat gtggattaag caatagtgat agattttcta ctgttcccgt caatagagca   79620
aaagtagttc aacataatat taaacattcg ttcgacctaa aattgcattt gatcagttta   79680
ttatctctct tggtaatatg gatactaatt gtagctattt aaatgggtgc cgcggcaagc   79740
atacagacga cggtgaatac actcagcgaa cgtatctcgt ctaaattaga acaagaagcg   79800
aatgctagtg ctcaaacaaa atgtgatata gaaatcggaa atttttatat ccgacaaaac   79860
catggatgta acctcactgt taaaaatatg tgctctgcgg acgcggatgc tcagttggat   79920
gctgtgttat cagccgctac agaaacatat agtggattaa caccggaaca aaaagcatac   79980
gtgccagcta tgtttactgc tgcgttaaac attcagacga gtgtaaacac tgttgttaga   80040
gattttgaaa attatgtgaa acagacttgt aattctagcg cggtcgtcga taacaaatta   80100
aagatacaaa acgtaatcat agatgaatgt tacggagccc caggatctcc aacaaatttg   80160
gaatttatta atacaggatc tagcaaagga aattgtgcca ttaaagcgtt gatgcaattg   80220
acgactaagg ccactactca aatagcacct agacaagttg ctggtacagg agttcagttt   80280
tatatgattt ttatcggtgt tataatattg gcagcgttgt ttatgtacta tgccaagcgt   80340
atgctgttca catccaccaa tgataaaatc aaacttattt tagccaataa ggaaaacgtc   80400
cattggacta cttacatgga cacattcttt agaacttctc cgatggttat tgctaccacg   80460
gatatgcaaa actgaaaata tattgataat attttaatag attaacatgg aagttatcgc   80520
```

```
tgatcgtcta gacgatatag tgaaacaaaa tatagcggat gaaaaatttg tagattttgt   80580
tatacacggt ctagagcatc aatgtcctgc tatacttcga ccattaatta ggttgtttat   80640
tgatatacta ttatttgtta tagtaattta tattttacg gtacgtctag taagtagaaa    80700
ttatcaaatg ttgttggcgt tggtggcgct agtcatcaca ttaactattt tttattactt   80760
tatactataa tagtactaga ctgacttcta acaaacatct cacctgccat aaataaatgc   80820
ttgatattaa agtcttctat ttctaacact attccatctg tggaaaataa tactctgaca   80880
ttatcgctaa ttgacacatc ggtgagtgat atgcctataa agtaataatc ttctttgggc   80940
acatatacca gtgtaccagg ttctaacaac ctatttactg gtgctcctgt agcatacttt   81000
ttctttacct tgagaatatc catcgtttgc ttggtcaata gcgatatgtg attttttatc   81060
aaccactcga aaaagtaatt ggagtgttca tatcctctac gggctattgt ctcatggccg   81120
tgtatgaaat ttaagtaaca cgactgtggt agatttgttc tatagagccg gttgccgcaa   81180
atagatagaa ctaccaatat gtctgtacaa atgttaaaca ttaattgatt aacagaaaaa   81240
acaatgttcg ttctgggaat agaaaccaga ttaaaacaaa attcgttaga atatatgcca   81300
cgtttataca tggaatataa aataactaca gtttgaaaaa taacagtatc atttaaacat   81360
ttaacttgcg gggttaattt cacaacttta ctgttttttga actgttcaaa atatagcata  81420
gatccgtgag aaatacgttt agccgccttt aatagaggaa atcccaccgc ctttctggat   81480
ctcaccaacg acgatagttc tgaccagcaa ctcatttctt catcatccac ctgttttaac   81540
atataatagg caggagatag atatccgtca ttgcaatatt ccttctcgta ggcacacaat   81600
ctaatattga taaaatctcc attctcttct ctgcatttat tatcttgttt cggtggctga   81660
ttaggctgta gtcttggttt aggctttggt atatcgttgt tgaatctatt ttggtcatta   81720
aatctttcat ttcttcctgg tatattttta tcacctcgtt tggttggatt tttgtctata   81780
ttatcgtttg taacatcggt acgggtattc atttatcaca aaaaaaactt ctctaaatga   81840
gtctactgct agaaaacctc atcgaagaag ataccatatt ttttgcagga agtatatctg   81900
agtatgatga tttacaaatg gttattgccg gcgcaaaatc caaatttcca agatctatgc   81960
tttctatttt taatatagta cctagaacga tgtcaaaata tgagttggag ttgattcata   82020
acgaaaatat cacaggagca atgtttacca caatgtataa tataagaaac aatttgggtc   82080
taggagatga taaactaact attgaagcca ttgaaaacta tttcttggat cctaacaatg   82140
aagttatgcc tcttattatt aataatacgg atatgactgc cgtcattcct aaaaaaagtg   82200
gtaggagaaa gaataagaac atggttatct tccgtcaagg atcatcacct atcttgtgca   82260
ttttcgaaac tcgtaaaaag attaatattt ataaagaaaa tatggaatcc gcgtcgactg   82320
agtatacacc tatcggagac aacaaggctt tgatatctaa atatgcggga attaatgtcc   82380
tgaatgtgta ttctccttcc acatccataa gattgaatgc catttacgga ttcaccaata   82440
aaaataaact agagaaactt agtactaata aggaactaga atcgtatagt tctagccctc   82500
ttcaagaacc cattaggtta aatgattttc tgggactatt ggaatgtgtt aaaaagaata   82560
ttcctctaac agatattccg acaaaggatt gattactata aatggagaat gttcctaatg   82620
tatactttaa tcctgtgttt atagagccca cgtttaaaca ttctttatta agtgtttata   82680
aacacagatt aatagttttta tttgaagtat tcgttgtatt cattctaata tatgtatttt   82740
ttagatctga attaaatatg ttcttcatgc ctaaacgaaa aatacccgat cctattgata   82800
gattacgacg tgctaatcta gcgtgtgaag acgataaatt aatgatctat ggattaccat   82860
ggatgacaac tcaaacatct gcgttatcaa taaatagtaa accgatagtg tataaagatt   82920
```

```
gtgcaaagct tttgcgatca ataaatggat cacaaccagt atctcttaac gatgttcttc    82980
gcagatgatg attcattttt taagtatttg gctagtcaag atgatgaatc ttcattatct    83040
gatatattgc aaatcactca atatctagac tttctgttat tattattgat ccaatcaaaa    83100
aataaattag aagccgtggg tcattgttat gaatctcttt cagaggaata cagacaattg    83160
acaaaattca cagactttca agattttaaa aaactgttta acaaggtccc tattgttaca    83220 gatgaaggg tcaaacttaa taaaggatat ttgttcgact ttgtgattag tttgatgcga     83280
ttcaaaaaag aatcctctct agctaccacc gcaatagatc ctgttagata catagatcct    83340
cgtcgcgata tcgcattttc taacgtgatg gatatattaa agtcgaataa agtgaacaat    83400
aattaattct ttattgtcat catgaacggc ggacatattc agttgataat cggccccatg    83460
ttttcaggta aaagtacaga attaattaga cgagttagac gttatcaaat agctcaatat    83520
aaatgcgtga ctataaaata ttctaacgat aatagatacg gaacgggact atggacgcat    83580
gataagaata attttgaagc attggaagca actaaactat gcgatgtctt ggaattaatt    83640
acagatttct ccgtgatagg tatcgatgaa ggacagttct ttccagacat tgttgaattc    83700
tgtgagcgta tggcaaacga aggaaaaata gttatagtag ccgcactcga tgggacattt    83760
caacgtaaac cgtttaataa tattttgaat cttattccat tatctgaaat ggtggtaaaa    83820
ctaactgctg tgtgtatgaa atgctttaag gaggcttcct tttctaaacg attgggtgag    83880
gaaaccgaga taaaaataat aggaggtaat gatatgtatc aatcggtgtg tagaaagtgt    83940
tacatcgact cataatatta tattttttat ctaaaaaact aaaaataaac attgattaaa    84000
ttttaatata atacttaaaa atggatgttg tgtcgttaga taaaccgttt atgtattttg    84060
aggaaattga taatgagtta gattacgaac cagaaagtgc aaatgaggtc gcaaaaaaac    84120
tgccgtatca aggacagtta aaactattac taggagaatt attttttctt agtaagttac    84180
agcgacacgg tatattagat ggtgccaccg tagtgtatat aggatctgct cccggtacac    84240
atatacgtta tttgagagat catttctata atttaggagt gatcatcaaa tggatgctaa    84300
ttgacggccg ccatcatgat cctattctaa atggattgcg tgatgtgact ctagtgactc    84360
ggttcgttga tgaggaatat ctacgatcca tcaaaaaaca actgcatcct tctaagatta    84420
ttttaatttc tgatgtaaga tccaaacgag gaggaaatga acctagtacg gcggatttac    84480
taagtaatta cgctctacaa aatgtcatga ttagtatttt aaaccccgtg gcatctagtc    84540
ttaaatggag atgcccgttt ccagatcaat ggatcaagga cttttatatc ccacacggta    84600
ataaaatgtt acaaccttt gctccttcat attcagctga aatgagatta ttaagtattt     84660
ataccggtga gaacatgaga ctgactcgag ttaccaaatt agacgctgta aattatgaaa    84720
aaaagatgta ctaccttaat aagatcgtcc gtaacaaagt agttgttaac tttgattatc    84780
ctaatcagga atatgactat tttcacatgt actttatgct gaggaccgtg tactgcaata    84840
aaacatttcc tactactaaa gcaaaggtac tatttctaca acaatctata tttcgtttct    84900
taaatattcc aacaacatca actgaaaaag ttagtcatga accaatacaa cgtaaaatat    84960
ctagcaaaaa ttctatgtct aaaaacagaa atagcaagag atccgtacgc ggtaataaat    85020
agaaacgtac tactgagata tactaccgat atagagtata atgatttagt tactttaata    85080
accgttagac ataaaattga ttctatgaaa actgtgtttc aggtatttaa cgaatcatcc    85140
ataaattata ctccggttga tgatgattat ggagaaccaa tcattataac atcgtatctt    85200
caaaaaggtc ataacaagtt tcctgtaaat tttctataca tagatgtggt aatatctgac    85260
ttatttccta gctttgttag actagatact acagaaacta atatagttaa tagtgtacta    85320
```

```
caaacaggtg atggtaaaaa gactcttcgt cttcccaaaa tgttagagac ggaaatagtt   85380
gtcaagattc tctatcgccc taatatacca ttaaaaattg ttagatttt  ccgcaataac   85440 atggtaactg gagtagagat agccgataga tctgttattt cagtcgctga ttaatcaatt   85500
agtagagatg agataagaac attataataa tcaataatat atcttatatc ttatatctta   85560
tatcttgttt agaaaaatgc taatattaaa atagctaacg ctagtaatcc aatcggaagc   85620
catttgatat ctataatagg gtatctaatt tcctgattta aatagcggac agctatattc   85680
tcggtagcta ctcgtttgga atcacaaaca ttatttacat ctaatttact atctgtaatg   85740
gaaacgtttc ccaatgaaat ggtacaatcc gatacattgc attttgttat attttttttt   85800
aaagaggctg gtaacaacgc atcgcttcgt ttacatggct cgtaccaaca ataatagggt   85860
aatcttgtat ctattcctat ccgtactatg cttttatcag gataaataca tttacatcgt   85920
atatcgtctt tgttagcatc acagaatgca taaatttgtt cgtccgtcat gataaaaatt   85980
taaagtgtaa atataactat tattttatta gttgtaataa aaagggaaat ttgattgtat   86040
actttcggtt ctttaaaaga aactgacttg ataaaaatgg ctgtaatctc taaggttacg   86100
tatagtctat atgatcaaaa agagattaat gctacagata ttatcattag tcatgttaaa   86160
aatgacgacg atatcggtac cgttaaagat ggtagactag gtgctatgga tggggcatta   86220
tgtaagactt gtgggaaaac ggaattggaa tgtttcggtc actggggtaa agtaagtatt   86280
tataaaactc atatagttaa gcctgaattt atttcagaaa ttattcgttt actgaatcat   86340
atatgtattc actgcggatt attgcgttca cgagaaccgt attccgacga tattaaccta   86400
aaagagttat cgggacacgc tcttaggaga ttaaggata  aaatattatc caagaaaaag   86460
tcatgttgga acagcgaatg tatgcaaccg tatcaaaaaa ttacttttc  aaagaaaaag   86520 gtttgtttcg tcaacaagtt ggatgatatt aacgttccta attctctcat ctatcaaaag   86580
ttaatttcta ttcatgaaaa gttttggcca ttattagaaa ttcatcaata tccagctaac   86640
ttattttata cagactactt tcccatccct ccgttgatta ttagaccggc tattagtttt   86700
tggatagata gtatacccaa agaaaccaat gaattaactt acttattagg tatgatcgtt   86760
aagaattgta acttgaatgc tgatgaacag gttatccaga aggcggtaat agaatacgat   86820
gatattaaaa ttatttctaa taacactacc agtatcaatt tatcatatat cacatccggc   86880
aaaaataata tgattagaag ttatatcgtc gcccggcgaa aagatcagac cgctagatct   86940
gtaattggtc ccagtacatc tatcaccgtt aatgaggtag gaatgcccgc atatattaga   87000
aatacactta cagaaaagat atttgttaat gcctttacag tggataaagt taaacaacta   87060
ttagcgtcaa accaagttaa attttacttt aataaacgat taaaccaatt aacaagaata   87120
cgccaaggaa agtttatcaa aaataaaata catttattgc ctggtgattg ggtagaagta   87180
gctgttcaag aatatacaag tattattttt ggaagacagc cgtctctaca tagatacaac   87240
gtcatcgctt catctatcag agctaccgaa ggagatacta tcaaaatatc tcccggaatt   87300
gccaactctc aaaatgctga tttcgacgga gatgaagaat ggatgatatt agaacaaaat   87360
cctaaagctg taattgaaca agtattctt  atgtatccga cgacgttact caaacacgat   87420
attcatggag ccccgtttta tggatctatt caagatgaaa tcgtagcagc gtattcattg   87480
tttaggatac aagatctttg tttagatgaa gtattgaaca tcttggggaa atatggaaga   87540
gagttcgatc ctaaaggtaa atgtaaattc agcggtaaag atatctatac ttacttgata   87600
ggtgaaaaga ttaattatcc gggtctctta aaggatggtg aaattattgc aaacgacgta   87660
gatagtaatt ttgttgtggc tatgaggcat ctgtcattgg ctggactctt atccgatcat   87720
```

```
aagtcgaacg tggaaggtat caactttatt atcaagtcat cttatgtttt taagagatat   87780
ctatctattt acggttttgg ggtgacattc aaagatctga gaccaaattc gacgttcact   87840
aataaattgg aggccatcaa cgtagaaaaa atagaactta tcaaagaagc atacgccaaa   87900
tatctcaacg atgtaagaga cgggaaaata gttccattat ctaaagcttt agaggcggac   87960
tatgtggaat ccatgttatc caacttgaca aatcttaata tccgagagat agaagaacat   88020
atgagacaaa cgctgataga tgatccagat aataacctcc tgaaaatggc caaagcgggt   88080
tataaagtaa atcccacaga actaatgtat attctaggta cgtatggaca acaaaggatt   88140
gatggtgaac cagcagagac tcgagtattg ggtagagttt taccttacta tcttccagac   88200
tctaaggatc cagaaggaag aggttacatt cttaattctt taacaaaagg attaacaggt   88260
tctcaatatt acttttcgat gctggttgcc agatctcaat ctactgatat cgtctgtgaa   88320
acatcacgta ccggaacact ggctagaaaa atcattaaaa agatggagga tatggtggtc   88380
gacggatacg gacaagtagt tataggtaat acgctcatca agtacgccgc caattatacc   88440
aaaattctag gctcagtatg taaacctgta gatcttatct atccagatga gtccatgact   88500
tggtatttgg aaattagtgc tctgtggaat aaaataaaac agggattcgt ttactctcag   88560
aaacagaaac ttgcaaagaa gacattggcg ccgtttaatt tcctagtatt cgtcaaaccc   88620
accactgagg ataatgctat taaggttaag gatctgtacg atatgattca taacgtcatt   88680
gatgatgtga gagagaaata cttctttacg gtatctaata tagatttat ggagtatata   88740 ttcttgacgc atcttaatcc ttctagaatt agaattacaa agaaacggc tatcactatc   88800 tttgaaaagt tctatgaaaa actcaattat actctaggtg gtggaactcc tattggaatt   88860
atttctgcac aggtattgtc tgagaagttt acacaacaag ccctgtccag ttttcacact   88920
actgaaaaaa gtggtgccgt caaacaaaaa cttggtttca acgagtttaa taacttgact   88980
aatttgagta agaataagac cgaaattatc actctggtat ccgatgatat ctctaaactt   89040
caatctgtta agattaattt cgaatttgta tgtttgggag aattaaatcc aaacatcact   89100
cttcgaaaag aaacagatag gtatgtagta gatataatag tcaatagatt atacatcaag   89160
agagcagaaa ttaccgaatt agtcgtcgaa tatatgattg aacgattcat ctcctttagc   89220
gtcattgtaa aggaatgggg tatgaaaaca ttcattgagg atgaggataa tattagattt   89280
actgtctacc taaatttcgt tgaaccggaa gaattgaatc ttagtaagtt tatgatggtt   89340
cttccgggtg ccgccaacaa gggcaagatt agtaaattca agattcctat ctctgattat   89400
acgggttatg acgacttcaa tcaaacaaaa agctcaata agatgactgt agaactcatg   89460
aatctaaaag aattgggttc tttcgatttg gaaaacgtca acgtgtatcc tggagtatgg   89520
aatacatacg atatcttcgg tatcgaggcc gctcgtgaat acttgtgcga agccatgtta   89580
aacacctatg gagaagggtt cgattatctg tatcagcctt gtgatcttct cgctagttta   89640
ctatgtgcta gttacgaacc agaatcagtg aataaattca agttcggcgc agctagtact   89700
cttaagagag ctacgttcgg agacaataaa gcattgttaa acgcggctct tcataaaaag   89760
tcagaaccta ttaacgataa tagtagctgc cactttttta gcaaggtccc taatatagga   89820
actggatatt acaaatactt tatcgacttg ggtcttctca tgagaatgga aaggaaacta   89880
tctgataaga tatcttctca aaagatcaag gaaatggaag aaacagaaga cttttaattc   89940
ttatcaataa catatttttc tatgatctgt cttttaaacg atggattttc cacaaatgcg   90000
cctctcaagt ccctcataga atgatacacg tataaaaaat atagcatagg caatgactcc   90060 ttattttag acattagata tgccaaaatc atagccccgc ttctatttac tcccgcagca   90120
```

```
caatgaacca acacgggctc gtttcgttga tcacatttag ataaaaaggc ggttacgtcg    90180 tcaaatatt tactaatatc ggtagttgta tcatctacca acggtatatg aataatatta    90240
atattagagt taggtaatgt atatttatcc atcgtcaaat ttaaaacata tttgaactta    90300
acttcagatg atggtgcatc catagcattt ttataatttc ccaaatacac attattggtt    90360
acccttgtca ttatagtggg agatttggct ttgtgcatat ctccagttga acgtagtagt    90420
aagtatttat acaaactttt cttatccatt tataacgtac aaatggataa aactacttta    90480
tcggtaaacg cgtgtaattt agaatacgtt agagaaaagg ctatagtagg cgtacaagca    90540
gccaaaacat caaacacttat attctttgtt attatattgg caattagtgc gctattactc    90600
tggtttcaga cgtctgataa tccagtcttt aatgaattaa cgagatatat gcgaattaaa    90660
aatacggtta acgattggaa atcattaacg gatagcaaaa caaaattaga aagtgataga    90720
ggtaaacttc tagccgctgg taaggatgat atattcgact tcaaatgtgt ggatttcggc    90780
gcctatttta tagctatgcg attggataag aaaacatatc tgccgcaagc tattaggcga    90840
ggtactggag acgcgtggat ggttaaaaag gcggcaaagg tcgatccatc tgctcaacaa    90900
ttttgtcagt atttgataaa acacaagtct aataatgtta ttacttgtgg taatgagatg    90960
ttaaatgaat taggttatag cggttatttt atgttaccgc attggtgttc cgattttagt    91020 aatatgaat agtgttagat aaatgcggta acgaatgttc ctgtaaggaa ccataacagt    91080
ttagatttaa cgttaaagat gagcataaac ataataaaca aaattacaat caaacctata    91140
acattaatat caaacaatcc aaaaaatgaa atcagtggag tagtaaacgc gtacataact    91200
cctggataac gtttagcagc tgccgttcct attctagacc aaaaatttgg tttcatgttt    91260
tcgaaacggt attctgcaac aagtcgagga tcgtgttcta catatttggc ggcgttatcc    91320
agtatctgcc tattgatctt catttcgttt tcgattctgg ctatttcaaa ataaaatccc    91380
gatgatagac ctccagactt tataatttca tctacgatgt tcagcgccgt agtaactcta    91440
ataatatagg ctgataagct aacatcatac cctcctgtat atgtgaatat ggcatgattt    91500
ttgtccatta caagctcggt tttaactttta ttgcctgtaa taattctct catctgtagg    91560 atatctattt ttttgtcatg cattgccttc aagacgggac gaagaaacgt aatatcctca    91620
ataacgttat cgttttctac aataactaca tattctacct ttttattttc taactcggta    91680
aaaaaattag aatcccatag ggctaaatgt ctagcgatat ttcttttcgt ttcctctgta    91740
cacatagtgt tacaaaaccc tgaaagaag tgagtatact tgtcatcatt tctaatgttt    91800
cctccagtcc actgtataaa cgcataatcc ttgtaatgat ctggatcatc cttgactacc    91860
acaacatttc ttttttctgg cataacttcg ttgtcctttta catcatcgaa cttctgatca    91920
ttaatatgct catgaacatt aggaaatgtt tctgatggag gtctatcaat aactggcaca    91980
acaataacag gagttttcac cgccgccatt tagttattga aattaatcat atacaactct    92040
ttaatacgag ttatattttc gtctatccat tgtttcacat tgacatattt cgacaaaaag    92100
atataaaatg cgtattccaa tgcttctctg tttaatgaat tactaaaata tacaaacacg    92160
tcactgtctg gcaataaatg atatcttaga atattgtaac aatttatttt gtattgcaca    92220
tgttcgtgat ctatgagttc ttcttcgaat ggcataggat ctccgaatct gaaaacgtat    92280
aaataggagt tagaataata atatttgaga gtattggtaa tatataaact ctttagcggt    92340
ataattagtt ttttttctctc aatttctatt tttagatgtg atggaaaaat gactaatttt    92400
gtagcattag tatcatgaac tctaatcaaa atcttaatat cttcgtcaca cgttagctct    92460
ttgaagtttt taagagatgc atcagttggt tctacagatg gagtaggtgc aacaattttt    92520
```

```
tgttctacac atgtatgtac tggagccatt gttttaacta taatggtgct tgtatcgaaa  92580
aactttaatg cagatagcgg aagctcttcg ccgcgactttt ctacgtcgta attgggttct  92640
aacgccgatc tctgaatgga tactagttttt ctaagttcta atgtgattct ctgaaaatgt  92700
aaatccaatt cctccggcat tatagatgtg tatacatcgg taaataaaac tatagtatcc  92760
aacgatccct tctcgcaaat tctagtctta accaaaaaat cgtatataac cacggagatg  92820
gcgtatttaa gagtggattc ttctaccgtt ttgttcttgg atgtcatata ggaaactata  92880
aagtccgcac tactgttaag aatgattact aacgcaacta tatagttcaa attaagcatt  92940
ttggaaacat aaaataactc tgtagacgat acttgactttt cgaataagtt tgcagacaaa  93000
cgaagaaaga acagacctct cttaatttca gaagaaaact ttttttcgta ttcctgacgt  93060
ctagagttta tcaataag aaagttaaga attagtcggt taatgttgta tttcattacc  93120
caagtttgag atttcataat attatcaaaa gacatgataa tattaaagat aaagcgctga  93180
ctatgaacga aatagctata tggttcgctc aaaaatatag tcttgttaaa cgtggaaacg  93240
ataactgtat tttaatcac gtcagcggca tctaaattaa atataggtat atttattcca  93300
cacactctac aatatgccac accatcttca taataaataa attcgttagc aaaattatta  93360
attttagtga aatagttagc gtcaactttc atagcttcct tcaatctaat ttgatgctcg  93420
cacggtgcga attccactct aacatcccttt ttccatgcct caggttcatc gatctctata  93480
atatctagtt ttttgcgttt cacaaacaca ggctcgtctc tcgcgatgag atctgtatag  93540
taactatgta aatgataact agatagaaag atgtagctat atagatgacg atcctttaag  93600
agaggtataa taactttacc ccaatcagat agactgttgt tatggtcttc ggaaaaagaa  93660
tttttataaa ttttttccagt atttttccaaa tatacgtact taacatctaa aaaatccttta  93720 atgataatag gaatggataa tccgtctatt ttataaagaa atacatatcg cacattatac  93780
ttttttttgg aaatgggaat accgatgtgt ctacataaat atgcaaagtc taaatatttt  93840
ttagagaatc ttagttggtc caaattcttt tccaagtacg gtaatagatt tttcatattg  93900
aacggtatct tcttaatctc tggttctagt tccgcattaa atgatgaaac taagtcacta  93960 ttttttataac taacgattac atcacctcta acatcatcat ttaccagaat actgatcttc  94020
ttttgtcgta aatacatgtc taatgtgtta aaaaaaagat catacaagtt atacgtcatt  94080
tcatctgtgg tattcttgtc attgaaggat aaactcgtac taatctcttc tttaacagcc  94140
tgttcaaatt tatatcctat atacgaaaaa atagcaacca gtgtttgatc atccgcgtca  94200
atattctgtt ctatcgtagt gtataacaat cgtatatctt cttctgtgat agtcgatacg  94260
ttataaaggt tgataacgaa aatatttttta tttcgtgaaa taaagtcatc gtaggattttt  94320 ggacttatat tcgcgtctag taaatatgct tttattttg gaatgatctc aattagaata  94380 gtctcttttag agtccatttta aagttacaaa caactaggaa attggtttat gatgtataat  94440
ttttttagtt tttatagatt ctttattcta tacttaaaaa atgaaaataa atacaaaggt  94500
tcttgagggt tgtgttaaat tgaaagcgag aaataatcat aaattatttc attatcgcga  94560
tatccgttaa gtttgtatcg taatggcgtg gtcaattaca aataaagcgg atactagtag  94620
cttcacaaag atggctgaaa tcagagctca tctaaaaaat agcgctgaaa ataaagataa  94680
aaacgaggat attttcccgg aagatgtaat aattccatct actaagccca aaaccaaacg  94740
agccactact cctcgtaaac cagcggctac taaaagatca accaaaaagg aggaagtgga  94800
agaagaagta gttatagagg aatatcatca aacaactgaa aaaaattctc catctcctgg  94860
agtcagcgac attgtagaaa gcgtggctgc tgtagagctc gatgatagcg acgggatga  94920
```

```
tgaacctatg gtacaagttg aagctggtaa agtaaatcat agtgctagaa gcgatctttc   94980
tgacctaaag gtggctaccg acaatatcgt taaagatctt aagaaaatta ttactagaat   95040
ctctgcagta tcgacggttc tagaggatgt tcaagcagct ggtatctcta gacaatttac   95100
ttctatgact aaagctatta caacactatc tgatctagtc accgagggaa aatctaaagt   95160
tgttcgtaaa aaagttaaaa cttgtaagaa gtaaatgcgt gcactttttt ataaagatgg   95220
taaactcttt accgataata attttttaaa tcctgtatca gacgataatc cagcgtatga   95280
ggttttgcaa catgttaaaa ttcctactca tttaacagat gtagtagtat atgaacaaac   95340
gtgggaggag gcgttaacta gattaatttt tgtgggaagt gattcaaaag gacgtagaca   95400
atacttttac ggaaaaatgc atgtacagaa tcgcaacgct aaaagagatc gtattttgt   95460 tagagtatat aacgttatga aacgaattaa ttgttttata aacaaaaata taagaaaatc   95520
gtccacagat tccaattatc agttggcggt ttttatgtta atggaaacta tgttttttat   95580
tagatttggt aaaatgaaat atcttaagga gaatgaaaca gtagggttat taacactaaa   95640
aaataaacac atagaaataa gtcccgatga aatagttatc aagtttgtag gaaaggacaa   95700
agtttcacat gaatttgttg ttcataagtc taatagacta tataaaccgc tattgaaact   95760
gacggatgat tctagtcccg aagaatttct gttcaacaaa ctaagtgaac gaaaggtata   95820
cgaatgtatc aaacagtttg gtattagaat caaggatctc cgaacgtatg gagtcaatta   95880
tacgttttta tataattttt ggacaaatgt aaagtccata tctcctcttc cgtcaccaaa   95940
aaagttaata gcattaacta tcaaacaaac tgctgaagtg gtaggtcata ctccatcaat   96000
ttcaaaaaga gcttatatgg caacgactat tttagaaatg gtaaaggata aaaattttt   96060 agatgtagta tctaaaacta cgttcgatga attcctatct atagtcgtag atcacgttaa   96120
atcatctacg gatggatgat atagatcttt acacaaataa ttacaagacc gataaatgga   96180
aatggataag cgtatgaaat ctctcgcaat gacagctttc ttcggagagc taaacacatt   96240
agatattatg gcattgataa tgtctatatt taaacgccat ccaaacaata ccatttttc   96300 agtggataag gatggtcagt ttatgattga tttcgaatac gataattata aggcttctca   96360
atatttggat ctgaccctca ctccgatatc tggagatgaa tgcaagactc acgcatcgag   96420
tatagccgaa caattggcgt gtgcggatat tattaaagag gatattagcg aatatatcaa   96480
aactactccc cgtcttaaac gatttataaa aaaataccgc aatagatcag atactcgcat   96540
cagtcgagat acagaaaagc ttaaaatagc tctagctaaa ggcatagatt acgaatatat   96600
aaaagacgct tgttaataag taaatgaaaa aaaactagtc gtttataata aaacacgata   96660
tggatgccaa cgtagtatca tcttctacta ttgcgacgta tatagacgct ttagcgaaga   96720
atgcttcgga attagaacag aggtctaccg catacgaaat aaataatgaa ttggaactag   96780
tatttattaa gccgccattg attactttga caaatgtagt gaatatctct acgattcagg   96840
aatcgtttat tcgatttacc gttactaata aggaaggtgt taaaattaga actaagattc   96900
cattatctaa ggtacatggt ctagatgtaa aaaatgtaca gttagtagat gctatagata   96960
acatagtttg ggaaaagaaa tcattagtga cggaaaatcg tcttcacaaa gaatgcttgt   97020
tgagactatc gacagaggaa cgtcatatat ttttggatta caagaaatat ggatcctcta   97080
tccgactaga attagtcaat cttattcaag caaaaacaaa aaactttacg atagacttta   97140
agctaaaata ttttctagga tccggtgccc aatctaaaag ttctttatta cacgctatta   97200
atcatccaaa gtcaaggcct aatacatctc tggaaataga attcacacct agagacaatg   97260
aaacagttcc atatgatgaa ctaataaagg aattgacgac tctatcacgt catatattta   97320
```

```
tggcttctcc agagaatgta attctttctc cgcctattaa cgcgcttata aaacccttta   97380
tgttgcctaa acaagatata gtaggtttgg atctggaaaa tctatatgcc gtaactaaga   97440
ctgacggcat tcctataact atcagagtta catcaaacgg gttgtattgt tattttacac   97500
atcttggtta tattattaga tatcctgtta agagaataat agattccgaa gtagtagtct   97560
ttggtgaggc agttaaggat aagaactgga ccgtatatct cattaagcta atagagcctg   97620
tgaatgcaat caatgataga ctagaagaaa gtaagtatgt tgaatctaaa ctagtggata   97680
tttgtgatcg gatagtattc aagtcaaaga aatacgaagg tccgtttact acaactagtg   97740
aagtcgtcga tatgttatct acatatttac caaagcaacc agaaggtgtt attctgttct   97800
attcaaaggg acctaaatct aacattgatt ttaaaattaa aaaggaaaat actatagacc   97860
aaactgcaaa tgtagtattt aggtacatgt ccagtgaacc aattatcttt ggagaatcgt   97920
ctatctttgt agagtataag aaatttagca acgataaagg ctttcctaaa gaatatggtt   97980
ctggtaagat tgtgttatat aacggcgtta attatctaaa taatatctat tgtttggaat   98040
atattaatac acataatgaa gtgggtatta agtccgtggt tgtacctatt aagtttatag   98100
cagaattctt agttaatgga gaaatactta aacctagaat cgataaaacc atgaaatata   98160
ttaactcaga agattattat ggaaatcaac ataatatcat agtcgaacat ttaagagatc   98220
aaagcatcaa aataggagat atctttaacg aggataaact atcggatgtg ggacatcaat   98280
acgccaataa tgataaattt agattaaatc cagaagttag ttattttacg aataaacgaa   98340
ctagaggacc gttgggaatt ttatcaaact acgtcaagac tcttcttatt tctatgtatt   98400
gttccaaaac attttagac gattccaaca aacgaaaggt attggcgatt gattttggaa    98460
acggtgctga cctggaaaaa tactttttatg gagagattgc gttattggta gcgacggatc   98520
cggatgctga tgctatagct agaggaaatg aaagatacaa caaattaaac tctggaatta   98580
aaaccaagta ctacaaattt gactacattc aggaaactat tcgatccgat acatttgtct   98640
ctagtgtcag agaagtattc tattttggaa agtttaatat catcgactgg cagttttgcta  98700
tccattattc tttccatccg agacattatg ctaccgtcat gaataactta tccgaactaa   98760
ctgcttctgg aggcaaggta ttaatcacta ccatggacgg agacaaatta tcaaaattaa   98820
cagataaaaa gacttttata attcataaga atttacctag tagcgaaaac tatatgtctg   98880
tagaaaaaat agctgatgat agaatagtgg tatataatcc atcaacaatg tctactccaa   98940
tgactgaata cattatcaaa agaacgata tagtcagagt gtttaacgaa tacggatttg    99000
ttcttgtaga taacgttgat ttcgctacaa ttatagaacg aagtaaaaag tttattaatg   99060
gcgcatctac aatggaagat agaccgtcta caaaaaactt tttcgaacta aatagaggag   99120
ccattaaatg tgaaggttta gatgtcgaag acttacttag ttactatgtt gtttatgtct   99180
tttctaagcg gtaaataata atatggtatg ggttctgata tccccgttct aaatgcatta   99240
aataattcca atagagcgat ttttgttcct ataggacctt ccaactgtgg atactctgta   99300
ttgttaatag atatattaat acttttgtcg ggtaacagag gttctacgtc ttctaaaaat   99360
aaaagtttta taacatctgg cctgttcata aataaaaact tggcgattct atatatactc   99420
ttattatcaa atctagccat tgtcttatag atgtgagcta ctgtaggtgt accatttgat   99480
tttcttttcta atactatata tttctctcga agaagttctt gcacatcatc tgggaataaa   99540
atactactgt tgagtaaatc agttattttt tttatatcga tattgatgga cattttttata  99600
gttaaggata ataagtatcc caaagtcgat aacgacgata acgaagtatt tatactttta   99660
ggaaatcaca atgactttat cagattaaaa ttaacaaaat taaggagca tgtattttt    99720
```

```
tctgaatata ttgtgactcc agatacatat ggatctttat gcgtcgaatt aaatgggtct    99780 agtttttcagc acggcggtag atatatagag gtggaggaat ttatagatgc tggaagacaa   99840
gttagatggt gttctacatc caatcatata tctaaagata tacccgaaga tatgcacact    99900
gataaatttg tcattatga tatatacact tttgacgctt tcaagaataa acgattggta     99960
ttcgtacagg tacctccgtc gttaggagat gatagtcatt tgactaaccc gttattgtca  100020
ccgtattatc gtaattcagt agccagacaa atggtcaata atatgatttt taatcaagat  100080
tcatttttaa aatatttatt agaacatctg attagaagcc actatagagt ttctaaacat  100140 ataacaaatag ttagatacaa ggataccgaa gaattaaatc taacgagaat atgttataat 100200
agagataagt ttaaggcgtt tgtattcgct tggtttaacg gcgtttcgga aaatgaaaag  100260
gtactagata cgtataaaaa ggtatctaat ttgatataat gaattcagtg actgtatcac  100320
acgcgccata tactattact tatcacgatg attgggaacc agtaatgagt caattggtag  100380
agttttataa cgaagtagcc agttggctgc tacgagacga gacgtcgcct attcctgata  100440
agttctttat acagttgaaa caaccgctta gaaataaacg agtatgtgtg tgtggtatag  100500
atccgtatcc gaaagatgga actggtgtac cgttcgaatc accaaatttt acaaaaaaat  100560
caattaagga gatagcttca tctatatcta gattaaccgg agtaattgat tataaaggtt  100620
ataaccttaa tataatagac ggggttatac cctggaatta ttacttaagt tgtaaattag  100680
gagaaacaaa aagtcacgcg atttactggg ataaaatttc taagttactg ctgcagcata  100740
taactaaaca cgttagtgtt ctttattgtt tgggtaaaac agatttctcg aatatacggg  100800
ccaagttaga atccccggta actaccatag tcggatatca tccagcggct agagaccgcc  100860
aattcgagaa agatcgatca tttgaaatta tcaacgtttt actggaatta gacaacaagg  100920
cacctataaa ttgggctcaa gggtttattt attaatgctt tagtgaaatt ttaacttgtg  100980
ttctaaatgg atgcggctat tagaggtaat gatgttatct ttgttcttaa gactataggt  101040
gtcccgtcag cgtgcagaca aaatgaagat ccaagatttg tagaagcatt taaatgcgac  101100
gagttagaaa gatatattga gaataatcca gaatgtacac tattcgaaag tcttagggat  101160
gaggaagcat actctatagt cagaattttc atggatgtag atttagacgc gtgtctagac  101220
gaaatagatt atttaacggc cattcaagat tttattatcg aggtgtcaaa ctgtgtagct  101280
agattcgcgt ttacagaatg cggtgccatt catgaaaatg taataaaatc catgagatct  101340 aattttttcat tgactaagtc tacaaataga gataaaacaa gttttcatat tatcttttta  101400
gatacgtata ccactatgga tacattgata gctatgaaac gaacactatt agaattaagt  101460
agatcatctg aaaatccact aaccagatcg atagacactg ccgtatatag gagaaaaaca  101520
actcttcggg ttgtaggtac taggaaaaat ccaaattgcg acactattca tgtaatgcaa  101580
ccacctcatg ataatataga agattaccta ttcacttacg tggatatgaa caacaatagt  101640
tattactttt ctctacaaca acgattggag gatttagttc ctgataagtt atgggaacca  101700
gggtttattt cattcgaaga cgctataaaa agagtttcaa aaatattcat taattctata  101760
ataaacttta atgatctcga tgaaaataat tttacaacgg taccactggt catagattac  101820
gtaacacctt gtgcattatg taaaaaacga tcgcataaac atccgcatca actatcgttg  101880
gaaaatggtg ctattagaat ttacaaaact ggtaatccac atagttgtaa agttaaaatt  101940
gttccgttgg atggtaataa actgtttaat attgcacaaa gaattttaga cactaactct  102000
gttttattaa ccgaacgagg agaccatata gtttggatta ataattcatg gaaatttaac  102060
agcgaagaac ccttgataac aaaactaatt ttgtcaataa gacatcaact acctaaggaa  102120
```

```
tattcaagcg aattactctg tccgaggaaa cgaaagactg tagaagctaa catacgagac   102180
atgttagtag attcagtgga gaccgatacc tatccggata aacttccgtt taaaaatggt   102240
gtattggacc tggtagacgg aatgttttac tctggagatg atgctaaaaa atatacgtgt   102300
actgtatcaa ccggatttaa atttgacgat acaaagttcg tcgaagacag tccagaaatg   102360
gaagagttaa tgaatatcat taacgatatc caaccattaa cggatgaaaa taagaaaaat   102420
agagagctat atgaaaaaac attatctagt tgtttatgtg gtgctaccaa aggatgttta   102480
acattctttt ttggagaaac tgcaactgga aagtcgacaa ccaaacgttt gttaaagtct   102540
gctatcggtg acctgtttgt tgagacgggt caaacaattt taacagatgt attggataaa   102600
ggacctaatc catttatcgc taacatgcat ttgaaaagat ctgtattctg tagcgaacta   102660
cctgattttg cctgtagtgg atcaaagaaa attagatctg acaatattaa aaagttgaca   102720
gaaccttgtg tcattggaag accgtgtttc tccaataaaa ttaataatag aaaccatgcg   102780
acaatcatta tcgatactaa ttacaaacct gtttttgata ggatagataa cgcattaatg   102840
agaagaattg ccgtcgtgcg attcagaaca cacttttctc aaccttctgg tagagaggct   102900
gctgaaaata atgacgcgta cgataaagtc aaactattag acgagggggtt agatggtaaa   102960 atacaaaata atagatatag attcgcattt ctatacttgt tggtgaaatg gtacagaaaa   103020
tatcatgttc ctattatgaa actatatcct acacccgaag agattcctga ctttgcattc   103080
tatctcaaaa taggtactct gttagtatct agctctgtaa agcatattcc attaatgacg   103140
gacctctcca aaaagggata tatattgtac gataatgtgg ttactcttcc gttgactact   103200
ttccaacaga aaatatccaa gtattttaat tctagactat ttggacacga tatagagagc   103260
ttcatcaata gacataagaa atttgccaat gttagtgatg aatatctgca atatatattc   103320
atagaggata tttcatctcc gtaaatatat gctcatatat ttatagaaga tatcacatat   103380
ctaaatgaat accggaatca tagatttatt tgataatcat gttgatagta taccaactat   103440
attacctcat cagttagcta ctctagatta tctagttaga actatcatag atgagaacag   103500
aagcgtgtta ttgttccata ttatgggatc aggtaaaaca ataatcgctt tgttgttcgc   103560
cttggtagct tccagattta aaaaggttta cattctagtg ccgaacatca acatcttaaa   103620
aattttcaat tataatatgg gtgtagctat gaacttgttt aatgacgaat tcatagctga   103680
gaatatcttt attcattcca caacaagttt ttattctctt aattataacg ataacgtcat   103740
taattataac ggattatctc gctacaataa ctctatttt atcgttgatg aggcacataa   103800
tatctttggg aataatactg gagaacttat gaccgtgata aaaaataaaa acaagattcc   103860
ttttttacta ttgtctggat ctcccattac taacacacct aatactctgg gtcatattat   103920
agatttaatg tccgaagaga cgatagattt tggtgaaatt attagtcgtg gtaagaaagt   103980
aattcagaca cttcttaacg aacgcggtgt gaatgtactt aaggatttgc ttaaaggaag   104040
aatatcatat tacgaaatgc ctgataaaga tctaccaacg ataagatatc acggacgtaa   104100
gtttctagat actagagtag tatattgtca catgtctaaa cttcaagaga gagattatat   104160
gattactaga cgacagcta t gttatcatga aatgtttgat aaaaatatgt ataacgtgtc   104220
aatggcagta ttgggacaac ttaatctgat gaataattta gatactttat ttcaggaaca   104280
ggataaggaa ttgtacccaa atctgaaaat aaataatggc gtgttatacg agaagaatt   104340 ggtaacgtta aacattagtt ccaaatttaa atactttatt aatcggatac agacactcaa   104400
cggaaaacat tttatatact tttctaattc tacatatggc ggattggtaa ttaaatatat   104460
catgctcagt aatggatatt ctgaatataa tggttctcag ggaactaatc cacatatgat   104520
```

```
aaacggcaaa ccaaaaacat tgctatcgt tactagtaaa atgaaatcgt ctttagagga    104580
tctattagat gtgtataatt ctcctgaaaa cgatgatggt agtcaattga tgttttgtt    104640 ttcatcaaac attatgtccg aatcctatac tctaaaagag gtaaggcata tttggtttat   104700
gactatccca gatactttt ctcaatacaa ccaaattctt ggacgatcta ttagaaaatt    104760
ctcttacgcc gatatttctg aaccagttaa tgtatatctt ttagccgccg tatattccga   104820
tttcaatgac gaagtgacgt cattaaacga ttacacacag gatgaattga ttaatgtttt   104880
accatttgac atcaaaaagc tgttgtatct aaaatttaag acgaaagaaa cgaatagaat   104940
atactctatt cttcaagaga tgtctgaaac gtattctctt ccaccacatc catcaattgt   105000
aaaagtttta ttgggagaat tggtcagaca atttttttat aataattctc gtattaagta   105060
taacgatacc aagttactta aaatggttac atcagttata aaaaataaag aagacgctag   105120
gaattacata gatgatattg taaacggtca cttctttgta tcgaataaag tatttgataa   105180
atctctttta tacaaatacg aaaacgatat tattacagta ccgtttagac tttcctacga   105240
accatttgtt tggggagtta actttcgtaa agaatataac gtggtatctt ctccataaaa   105300
ctgatgagat atataaagaa ataaatgtcg agctttgtta ccaatggata cctttccgtt   105360
acattggaac ctcatgagct gacgttagac ataaaaacta atattaggaa tgccgtatat   105420
aagacgtatc tccatagaga aattagtggt aaaatggcca agaaaataga aattcgtgaa   105480
gacgtggaat tacctctcgg cgaaatagtt aataattctg tagttataaa cgttccgtgt   105540 gtaataaccct acgcgtatta tcacgttggg gatatagtca gaggaacatt aaacatcgaa   105600
gatgaatcaa atgtaactat tcaatgtgga gatttaatct gtaaactaag tagagattcg   105660
ggtactgtat catttagcga ttcaaagtac tgctttttc gaaatggtaa tgcgtatgac   105720
aatggcagcg aagtcactgc cgttctaatg gaggctcaac aaggtatcga atctagtttt   105780 gttttctcg cgaatatcgt cgactcataa aaaagagaat agcggtaagt ataaacacga   105840
atactatggc aataattgcg aatgttttat tctcttcgat atattttga taatatgaaa    105900 aacatgtctc tctcaaatcg gacaaccatc tcataaaata gttctcgcgc gctggagagg   105960
tagttgctgc tcgtataatc tctccagaat aatatacttg cgtgtcgtcg ttcaatttat   106020
acggatttct atagttctct gttatataat gcggttttcc atcatgatta gacgacgaca   106080
atagtgttct aaatttagat agttgatcag aatgaatgtt tattggcgtt ggaaaaatta   106140
tccatacagc gtctgcagag tggttgatag ttgttcctag atatgtaaaa taatccaact   106200
tactaggcag caaattgtct agataaaata ctgaatcaaa cggtgcagac gtattggcgg   106260
atctaatgga atccaattga ttaactatct tttgaaaata tacatttta tgatccaata   106320 cttgtaagaa tatagaaata atgataagtc catcatcgtg ttttttgcc tcttcataag   106380 aactatattt tttcttattc caatgaacaa gattaatctc tccagagtat ttgtacacat    106440
ctatcaagtg attggatcca taatcgtctt ccttttcccca atatatatgt agtgatgata   106500
acacatattc attggggaga aaccctccac ttatatatcc tcctttaaaa ttaatcctta   106560
ctagttttcc agtgttctgg atagtggttg gtttcgactc attataatgt atgtctaacg   106620
gcttcaatcg cgcgttagaa attgcttttt tagtttctat attaatagga gatagttgtt   106680
gcggcatagt aaaaatgaaa tgataactgt ttaaaaatag ctcttagtat gggaattaca   106740
atggatgagg aagtgatatt tgaaactcct agagaattaa tatctattaa acgaataaaa   106800
gatattccaa gatcaaaaga cacgcatgtg tttgctgcgt gtataacaag tgacggatat   106860
ccgttaatag gagctagaag aacttcattc gcgttccagg cgatattatc tcaacaaaat   106920
```

```
tcagattcta tctttagagt atccactaaa ctattacggt ttatgtacta caatgaacta    106980
agagaaatct ttagacggtt gagaaaaggt tctatcaaca atatcgatcc tcactttgaa    107040
gagttaatat tattgggtgg taaactagat aaaaggaat ctattaaaga ttgtttaaga     107100
agagaattaa aagaggaaag tgatgaacgt ataacagtaa aagaatttgg aaatgtaatt    107160
ctaaaactta caacacggga taaattattt aataaagtat atataagtta ttgcatggcg    107220
tgttttatta atcaatcgtt ggaggattta tcgcatacta gtatttacaa tgtagaaatt    107280
agaaagatta aatcattaaa tgattgtatt aacgacgata aatacgaata tctgtcttat    107340
atttataata tgctagttaa tagtaaatga acttttacag atctagtata attagtcaga    107400
ttattaagta taatagacga ctagctaagt ctattatttg cgaggatgac tctcaaatta    107460
ttacactcac ggcattcgtt aaccaatgcc tatggtgtca taaacgagta tccgtgtccg    107520
ctattttatt aactactgat aacaaaatat tagtatgtaa cagacgagat agttttctct    107580
attctgaaat aattagaact agaaacatgt ttagaaagaa acgattattt ctgaattatt    107640
ccaattattt gaacaaacag gaaagaagta tactatcgtc attttttttct ctagatccag    107700 ctactactga taatgataga atagacgcta tttatccggg tggcataccc aaaaggggtg    107760
agaatgttcc agagtgttta tccagggaaa ttaaagaaga agttaatata gacaattctt    107820
ttgtattcat agacactcgg ttttttattc atggcatcat agaagatacc attattaata    107880 aatttttga ggtaatcttc tttgtcggaa gaatatctct aacgagtgat caaatcattg       107940
atacatttaa aagtaatcat gaaatcaagg atctaatatt tttagatccg aattcaggta    108000
atggactcca atacgaaatt gcaaaatatg ctctagatac tgcaaaactt aaatgttacg    108060
gccatagagg atgttattac gaatcattaa aaaaattaac tgaggatgat tgattagaaa    108120
atataaatta atttaccatc gtgtattttt ataacgggat tgtccggcat atcatgtaga    108180
tagttaccgt ctacatcgta tactcgacca tctacgcctt taaatcctct atttattgac    108240
attaatctat tagaattgga ataccaaata ttagtaccct caattagttt attggtaata    108300
ttttttttag acgatagatc gatggctctt gaaaccaagg ttttccaacc ggactcattg    108360
tcgatcggtg agaagtcttt ttcattagca tgaatccatt ctaatgatgt atgtttaaac    108420
actctaaaca attggacaaa ttctttgat ttgctttgaa tgatttcaaa taggtcttcg     108480
tctacagtag gcataccatt agataatcta gccattataa agtgcacgtt tacatatcta    108540
cgttctggag gagtaagaac gtgactattg agacgaatgg ctcttcctac tatctgacga    108600
agagacgcct cgttccatgt catatctaaa atgaagatat cattaattga gaaaaaacta    108660
ataccctcgc ctccactaga agagaatacg catgttttaa tgcattctcc gttagtgttt    108720
gattcttggt taaactcagc caccgccttg attctagtat ctttttgttct agatgagaac    108780 tctatattag ataccaaa gactttgaaa tatagtaata agatttctat tcctgactga      108840
ttaacaaatg gttcaaagac tagacattta ccatgggatg ctaatattcc caaacataca    108900
tctataaatt tgacgctttt ctcttttaat tcagtaaata gagagatatc agccgcacta    108960
gcatcccctt tcaatagttc tccctttta aaggtatcta atgcggattt agaaaactct      109020
ctatctctta atgaattttt aaaatcatta tatagtgttg ctatctcttg cgcgtattcg    109080
cccggatcac gattttgtct ttcaggaaag ctatcgaacg taaacgtagt agccatacgt    109140
ctcagaattc taaatgatga tatacctgtt tttatttcag cgagtttagc cttttgataa    109200
atttcttctt gctttttcga catattaacg tatcgcatta atactgtttt cttagcgaat    109260
gatgcagacc cttctacgtc atcaaaaata gaaaactcgt tattaactat atacgaacat    109320
```

```
agtcctccta gtttggagac taattctttt tcatcgacta gacgtttatt ctcaaatagc    109380
gattggtgtt gtaaggatcc tggtcgtagt aagttaacca acatggtgaa ttcttgcaca    109440
ctattgacga taggtgtagc cgataaacaa atcatcttat ggtttttaa cgcgatggtc     109500 ttagataaaa aattatatac tgaacgagta ggacggatct taccatcttc tttgattaat    109560
gatttagaaa tgaagttatg acattcatca ataatgacgc atattctact cttggaatta    109620
atagttttga tattagtaaa aaatttattt ctaaaatttt gatcatcgta attaataaaa    109680
atacaatcct tcgttatctc tggagcgtat ctgagtatag tgttcatcca aggatcttct    109740
atcaaagcct ttttcaccaa taagataata gcccaatttg tataaatatc cttaagatgt    109800
ttgagaatat atacagtagt cattgtttta ccgacacccg tttcatggaa caataaaaga    109860
gaatgcatac tgtctaatcc taagaaaact cttgctacaa aatgttgata atccttgagg    109920
cgtactacgt ccgaccccat catttcaacg ggcatattag tagttctgcg caatgcataa    109980
tcgatatagg ccgcgtgtga tttactcatt tatgagtgat aagtaataac tatgttttaa    110040
aaatcacagc agtagtttaa ctagtcttct ctgatgtttg ttttcgatac tttttgaatc    110100
agaagtcata ctagaataaa gcaacgagtg aacgtaatag agagcttcgt atactctatt    110160
cgaaaactct aagaacttat taatgaattc cgtatccact ggattgttta aaatactaaa    110220
ttgaacactg ttcacatcct tccaagaaga agacttagtg acggacttaa catgagacat    110280
aaataaatcc aaatttttt tacaaacatc actagccacc ataatggcgc tatctttcaa     110340
ccagctatcg cttacgcatt ttagcagtct aacatttta aagagactac aatatattct      110400
catagtatcg attacacctc taccgaataa agttggaagt taataatac aatatttttc      110460 gtttacaaaa tcaaataatg gtcgaaacac gtcgaaggtt aacatcttat aatcgctaat    110520
gtatagattg ttttcagtga gatgattatt agatttaata gcatctcgtt cacgtttgaa    110580
cagtttattg cgtgcgctga ggtcggcaac tacggcgtcc gctttagtac tcctcccata    110640
atactttacg ctattaatct ttaaaatttc atagacttta tctagatcgc tttctggtaa    110700
catgatatca tgtgtaaaaa gttttaacat gtcggtcggc attctattta gatcattaac    110760
tctagaaatc tgaagaaagt aattagctcc gtattccaga ctaggtaatg ggcttttacc    110820
tagagacaga ttaagttctg gcaatgtttc ataaaatgga agaaggacat gcgttccctc     110880
ccggatattt tttacaattt catccatta caactctata gtttgttttc attattatta       110940
gttattatct cccataatct tggtaatact tacccttga tcgtaagata ccttatacag      111000
gtcattacat acaactacca attgttttg tacataatag attggatggt tgacatccat     111060
ggtggaataa actactcgaa cagatagttt atctttcccc ctagatacat agccgtaat      111120 agttgtcggc ctaaagaata tctttggtgt aaagttaaaa gttagggttc ttgttccatt    111180
attgcttttt gtcagtagtt cattataaat tctcgagatg ggtccgttct ctgaatatag    111240
aacatcattt ccaaatctaa cttctagtct agaaataata tcggtcttat tcttaaaatc    111300
tattcccttg atgaagggat cgttaatgaa caaatccttg gcctttgatt cggctgatct    111360
attatctccg ttatagacgt tacgttgact agtccaaaga cttacaggaa tagatgtatc     111420
gatgatgttg atactatgtg atatgtgagc aaagattgtt ctcttagtgg catcactata      111480
tgttccagta atggcggaaa acttttttaga aatgttatat ataaaagaat tttttcgtgt    111540
tccaaacatt agcagattag tatgaagata aacactcata ttatcaggaa cattatcaat    111600
ttttacatac acatcagcat cttgaataga aacgatacca tcttctggaa cctctacgat   111660
ctcggcagac tccggataac cagtcggtgg accatcgcta acaataacta gatcatccaa   111720
```

```
caatctactc acatatgcat ctatataatc tttttcatct tgtgagtacc ctggatacga   111780
aataaattta ttatccgtat ttccataata aggtttagta taaacagaga gagatgttgc   111840
cgcatgaact tcagttacag tcgccgttgg ttggtttatt tgacctatta ctctcctagg   111900
tttctctata aacgatggtt taatttgtac attcttaacc atatatccaa taaagctcaa   111960
ttcaggaaca taaacaaatt ctttgttgaa cgtttcaaag tcgaacgaag agtcacgaat   112020
aacgatatcg gatactggat tgaaggttac cgttacggta attttttgaat cggatagttt   112080
aagactgctg aatgtatctt ccacatcaaa cggagtttta atataaacgt atactgtaga   112140
tggttcttta atagtgtcat taggagttag gccaatagaa atatcattaa gttcactaga   112200
atatccagag tgtttcaaag caattgtatt attgatacaa ttattatata attcttcgcc   112260
ctcaatttcc caaataacac cgttacacga agagatagat acgtgattaa tacatttata   112320
tccaacatat ggtacgtaac cgaatcttcc catacctttta acttctggaa gttccaaact   112380
cagaaccaaa tgattaagcg cagtaatata ctgatcccta atttcgaagc tagcgatagc   112440
ctgattgtct ggaccatcgt tgtcataac tccggataga gaaatatatt gcggcatata   112500
taaagttgga atttgactat cgactgcgaa gacattagac cgtttaatag agtcatcccc   112560
accgatcaaa gaattaatga tagtattatt cattttctat ttaaaatgga aaaagcttac   112620
aataaactcc gtagagaaat atctataatt tgtgagtttt ccttaaagta acagcttccg   112680
taaacgccgt ctttatctct tagtaggttt attgtattta tgaccttttc cttatcttca   112740
tagaatacta aaggcaacaa agaaattttt ggttcttctc taagagctac gtgagactta   112800
accatagaag ccaacgaatc cctacatatt ttagaacaga aatacctac ttcaccaccc   112860
ttgtatgtct caatactaat aggtctaaaa accaaatctt gattacaaaa ccaacactta   112920
tcaattacac tatttgtctt aatagacaca tctgccatag atttataata ctttggtagt   112980
atacaagcga gtgcttcttc tttagcgggc ttaaagactg ctttaggtgc tgaaataacc   113040
acatctggaa ggcttactcg cttagccatt taattacgga actatttttt tatacttcta   113100
atgagcaagt agaaaacctc tcatctacaa aaacgtactc gtgtccataa tcctctacca   113160
tagtaacacg tttttttagat ctcatatgtg ctaaaaagtt ttcccatact aattggttac   113220
tattattttt cgtataattt ttaacagttt gaggttttag atttttagtt acagaagtga   113280
tatcgaatat tttatccaaa aagaatgaat aattaattgt cttagaagga gtgttttctt   113340
ggcaaaagaa taccaagtgc ttaaatattt ctactacttc attaatcttt tctgtactca   113400
gattcagttt ctcatctttt acttgattga ttatttcaaa gactaactta taatccttt   113460
tatttattct ctcgttagcc ttaagaaaac tagatacaaa atttgcatct acatcatccg   113520
tggatatttg attttttttcc atgatatcca agagttccga gataatttct ccagaacatt   113580
gatgagacaa taatctccgc aatacatttc tcaaatgaat aagtttatta gacacgtgga   113640
agtttgactt tttttgtacc tttgtacatt tttgaaatac cgactcgcaa aaaatacaat   113700
attcatatcc ttgttcagat actataccgt tgtgtctaca accgctacat aatcgtagat   113760
tcatgttaac actctacgta tctcgtcgtc caatatttta tataaaaaca ttttatttct   113820
agacgttgcc agaaaatcct gtaatatttt tagttttttg ggctgtgaat aaagtatcgc   113880
cctaatatgg ttaccgtctt ccgccaatat agtagttaaa ttatccgcac atgcagaaga   113940
acaccgctta ggcggattca gtacaatgtt atatttttcg taccaactca tttaaatatc   114000
ataatctaaa atagttctgt aatatgtcta gcgctaatat attgatcata atcctgtgca   114060
taaattaaga tacaacaatg tctcgaaatc atcgacatgg cttcttccat agttagaaga   114120
```

```
tcgtcgtcaa agttagcaac gtgattcatc aacatttgct gttttgaggc agcaaatact   114180
gaaccgtcgc cattcaacca ttcataaaaa ccatcgtctg aatccattga taatttcttg   114240
tactggtttt tgagagctcg catcaatcta gcatttctag ctcccggatt gaaaacagaa   114300
agaggatcgt acatccaggg tccatttcct gtaaatagaa tcgtataatg tcccttcaag   114360
aagatatcag acgatccaca atcaaagaat tggtctccga gtttgtaaca acagcggac    114420
tttaacctat acatgatacc gtttagcata atttctggtg atacgtcaat cggagtatca   114480
tctattagag atctaaagcc ggtgtaacat tctccaccaa acatattctt attctgacgt   114540
cgttctacat aaaacatcat tgctccatta acgataacag gggaatgaac agcactaccc   114600
atcacattag ttcccaatgg atcaatgtgt gtaactccag aacatcttcc atagcctatg   114660
ttaggaggag cgaacaccac tcttccacta ttgccatcga atgccataga ataaatatcc   114720
ttggaattga tagaaatcgg actgtcggat gttgtgatca tcttcatagg attaacaact   114780
atgtatggtg ccgcctgaag tttcatatcg taactgatgc cgtttatagg tctagccaca   114840
gaaaccaacg taggtctaaa tccaactata gacaaaatag aagccaatat ctgttcctca   114900
tctgtcataa cttgagagca tccagtatga ataatcttca ttagatgggg atctaccgca   114960
tcatcatcgt tacaataaaa aattcccatt ctaatgttca taattgcttt tctaatcatg   115020
gtatgcatgt ttgctctctg aatctctgtg gaaattagat ctgatacacc tgtaatcact   115080
atcggattat cctccgtaag acgattaacc aacaacatat aattataaga ctttactttt   115140
ctaaattcat aaagttgctg gattaggcta taggtgtctc catgtacata cgcgttctcg   115200
agcgcaggaa gtttaatacc gaatagtgcc atcagaatag gatgaatata gtaattagtt   115260
tctggttttc tataaataaa agacaaatct tgtgaactag acatatcggt aaaatgcatg   115320
gattggaatc gtgtagtcga cagaagaata tgatgattag atggagagta tattttatct   115380
aactctttga gttggtcacc gattctagga ctagctcgag aatgaataag tactaaagga   115440
tgagtacatt tcacagaaac actagcattg ttcaatgtgc tctttacatg ggtaaggagt   115500
tgaaatagct cgtttctatt tgttctgaca atatttagtt tattcataat gttaagcata   115560
tcctgaatag taaagttaga tgtgtcatac ttgttagtag ttagatattt agcaattgca   115620
ttcccatcat ttctcaatct cgtactccaa tcatgcgtag atgctacttc atctatagaa   115680
accatacaat ccttttgat aggctgttga gattgattat ttcctgcacg tttaggtttg    115740
gtacgttgat ttctagcccc tgcggatata aagtcatcgt ctacaatttg ggacaatgaa   115800
ttgcatacac tacaagacaa agattatcaa gaagtgtgaa tatgatcttc atctactaaa   115860
gaaagagttt gattagtata actagatttt agtcctgcgt tagatgttaa aaaaacatcg   115920
ctattgacca cggcttccat tatttatatt cgtagttttt actcgaaagc gtgattttaa   115980
tatccaatct tattacttt ggaatcgttc aaaacctttg actaattgta gaatttgatc    116040
tattgcccta cgcgtatact cccttgcatc atatacgttc gtcaccagat cgtttgtttc   116100
ggcctgaagt tggtgcatat ctctttcaac attcgacatg agatccttaa gggccatatc   116160
gtctagattt tgttgagatg ctgctcctgg atttggattt tgttgtgctg ttgtacatac   116220
tgtaccacca gtaggtgtag gagtacatac agtggccaca ataggaggtt gaggaggtgt   116280
aaccgttgga gtagtacaag aaatacttcc atccgattgt tgtgtacatg tagttgttgg   116340
taacgtctga gaaggttggg tagatggcgg tgtcgtcgtc ttttgatctt tattaaattt   116400
agagataata tcctgaacag cattgctcgg cgtcaacgct ggaaggagtg aactcgccgg   116460
cgcatcagta tctgcagaca gccaatcaaa aagattagac atatcagatg atgtattagt   116520
```

```
ttgttgtcgt ggttttggtg taggagcagt actactaggt agaagaatag gagccggtgt   116580
agctgttgga accggctgtg gagttatatg aatagttggt tgtagcggtt ggataggctg   116640
tctgctggcg gccatcatat tatctctagc tagttgttct cgcaactgtc tttgataata   116700
cgactcttga gactttagtc ctatttcaat cgcttcatcc tttttcgtat ccggatcctt   116760
ttcttcagaa taatagattg acgactttgg tgtagaggat tctgccagcc tctgtgagaa   116820
cttgttaaag aagtccattt aaggctttaa aattgaattg cgattataag attaaatggc   116880
agacacagac gatattatcg actatgaatc cgatgatctc accgaatacg aggatgatga   116940
agaagaggaa gaagatggag agtcactaga aactagtgat atagatccca aatcttctta   117000
taagattgta gaatcagcat ccactcatat agaagatgcg cattccaatc ttaaacatat   117060
agggaatcat atatctgctc ttaaacgacg ctatactaga cgtataagtc tatttgaaat   117120
agcgggtata atagcagaaa gctataactt gcttcaacga ggaagattac ctctagtttc   117180
agaattttct gacgaaacga tgaagcaaaa tatgctacat gtaattatac aagagataga   117240
ggagggttct tgtcctatag tcatcgaaaa gaacggagaa ttgttgtcgg taaacgattt   117300
tgacaaagat ggtctaaaat tccatctaga ctatattatc aaaatttgga aacttcaaaa   117360
acgatattag aatttatacg aatatcgttc tctaaatgtc acaatcaagt ctcgcatgtt   117420
cagcaattta ttgtcgtact ttatatcgtg ttcattaacg atatcttgca aaatagtaat   117480
gattctatct tccttcgata gatattcttc agagattatt gtcttatatt ctttcttgtt   117540
atcagatatg aatttgataa gactttgaac attattgata cccgtctgtt taatttttttc   117600 tacagatatt ttagttttgg cagattctat cgtatctgtc aatagacatc caacatcgac   117660
attcgacgtc aattgtctat aaatcaacgt ataaattta gaataacat tagcgaattg   117720 ttgtgcgttg atgtcgttat tttgaaacag tatgatttta ggtagcatt tcttaacaaa   117780 gagaacgtat ttattgttac tcagttgaac agatgatata tccagattac taacgcatct   117840
gattccgtat accaaacttt cagaagaaat ggtatacaat tgtttgtatt cattcaatgt   117900 ctcttttttca gaaattagtt tagagtcgaa tactgcaata attttcaaga gatagttttc   117960
atcagataag atttttattta gtgtagatat gataaaacta ttgttttgtt ggagaacttg   118020
atacgccgcg ttctctgtag tcgacgctct caaatgggaa acaatctcca ttatttttt   118080 ggaatcggat acaatatctt cggtatcttg acgcagtcta gtatacatag agttaagaga   118140
gattagagtt tgtacattaa gcaacatgtc tctaaatgtg gctacaaact tttccttttt   118200
cacatcatct agtttattat ataccgattt cacaacggca ccagatttaa ggaaccagaa   118260
tgaaaaactc tgataactac aatatttcat catagttacg attttatcat cttctatagt   118320
tggtgtaata gcgcataccct ttttctccaa gactggaacc aacgtcataa aaatgtttaa   118380
atcaaaatcc atatcaacat ctgatgcgct aagaccagtc tcgcgttcaa gattatcttt   118440
actaatggtg acgaactcat cgtatagaac tctaagtttg tccattattt atttacagat   118500
ttagttgttt aatttatttg tgctcttcca gagttgggat agtattttttc taacgtcggt   118560 attatatttat taggatctac gttcatatgt atcataatat taatcatcca cgttttgata   118620
aatctatctt tagcttctga aataacgtat ttaaacaaag gagaaaaata tttagctacg   118680
gcatcagacg caataacatt ttttgtaaat gtaacgtatt tagacgacag atcttcgtta   118740
aaaagttttc catctatgta gaatccatcg gttgttaaca ccattcccgc gtcagattga   118800
ataggagttt gaatagtttg ttttggaaat agatccttca ataacttata gttgggtggg   118860
aaaaaatcga ttttatcact agactctttc ttttttacta tcattacctc atgaactatt   118920
```

```
tcttgaatga gtatatgtat tttctttcct atatcggacg cgttcattgg aaaatatacc    118980
atgtcgttaa ctataagaat attttttatcc tcgtttacaa actgaataat atcagatgta   119040
gttcgtaaac gaactatatc atcaccagca caacatctaa ctatatgata tccactagtt   119100
tcctttagtc gtttattatc ttgttccata ttagcagtca ttccatcatt taagaaggcg   119160
tcaaagataa tagggagaaa tgacattttg gattctgtta cgactttacc aaaattaagg   119220
atatacggac ttactatctt tttctcaacg tcgatttgat gaacacacga tgaaaatgtg   119280
cttctatgag attgatcatg tagaaaacaa caagggatac aatatttccg catatcatga   119340
aatatattaa gaaatcccac cttattatat ttccccaaag gatccatgca cgtaaacatt   119400
atgccgttat cattaataaa gacttctttc tcatcggatc tgtaaaagtt gttactgatt   119460
tttttcattc caggatctag ataattaata atgatgggtt ttctattctt attctttgta   119520
ttttggcata tcctagacca gtaaacagtt tccactttgg taaaatcagc agacttttga   119580
acgctattaa acatggcatt aatggcaata actaaaaatg taaatatttt ttctatgtta   119640
ggaatatggt ttttcacttt aatagatata tggttttttgg ccaaaatgat agatattttt   119700
ttatccgagg atagtaaaat attattagtc gccgtctcta taaaaatgaa gctagtctcg   119760
atatccaatt ttattctaga attgatagga gtcgccaaat gtaccttata cgttatatct   119820
cccttgatgc gttccatttg tgtatctata tcggacacaa gatctgtaaa tagtttttacg  119880 ttattaatca tcacggtatc gccgtcgcta gataacgcta atgtaccatc caagtcccaa   119940
atggagagat ttaactgttc atcgtttaga ataaaatgat taccggtcat attaataaag   120000
tgttcatcgt atctagataa caacgactta taattaatgt ccaagtcttg aactcgctga   120060
atgatctttt ttaacccagt tagttttaga ttggtacgaa atatattgtt aaactttgat   120120
tctacagtaa tgtccaaatc tagttgtgga aatacttcca tcaacattgt ttcaaacttg   120180
ataatattat tatctacatc ttcgtacgat ccaaattccg gaatagatgt atcgcacgct   120240
ctggccaccc agataaccaa aaagtcacac gctccaggat atacattgta taaaaagcta   120300
tcgtttttta gtagggtttt tttctgcgtg tatacgaagg gattaaaaat agtattatca   120360
acgtaactat attccaaatt attcttatga gaatagataa taatatcgtc cttaatatct   120420
aacaaatttc ctaaatatcc ctttaattga gtcattcgaa gcgtcaatag aatatgtctc   120480
ttaactattt ccggctgttg tatatttaaa tgacttcgta aaaaataata tatgggcgac   120540
ttctcatcta tgtaatcata tggagtgaga tatagggctc gttctacctc ctgcccctta   120600
cccacctgta ataccaattg cggacttact atatatcgca tatttatatc gtggggtaaa   120660
gtgaaaatct actaccgatg atgtaagtct tacaatgttc gaaccagtac cagatcttaa   120720
tttggaggcc tccgtagaac tagggggaggt aaatatagat caaacaacac ctatgataaa  120780
ggagaatagc ggttttatat cccgcagtag acgtctattc gcccatagat ctaaggatga   120840
tgagagaaaa ctagcactac gattcttttt acaaagactt tatttttttag atcatagaga  120900 gattcattat ttgttcagat gcgttgacgc tgtaaaagac gtcactatta ccaaaaaaaa   120960
taacattata gtggcgccct atatagcact tttaactatc gcatcaaaag gatgcaaact   121020
tacagaaaca atgattgaag cattcttttcc agaactatat aatgaacata gtaagaaatt   121080
taaattcaac tctcaagtat ccatcatcca agaaaaactc ggataccagt ttggaaacta   121140
tcacgtttat gattttgaac cgtattactc tacagtagct ctggctattc gagatgaaca   121200
ttcatctggc attttttaata tccgtcaaga gagtttatctg gtaagttcat tatctgaaat   121260
aacatataga ttttatctaa ttaatctaaa atctgatctt gttcaatgga gtgctagtac   121320
```

```
gggcgctgta attaatcaaa tggtaaatac tgtattgatt acagtgtatg aaaagttaca   121380
actggtcata gaaaatgatt cacaatttac atgttcattg gctgtggaat caaaacttcc   121440
aataaaatta cttaaagata gaaatgaatt atttacaaaa ttcattaacg agttaaaaaa   121500
gaccagttca ttcaagataa gcaaacgcga taaggatacg ctattaaaat attttactta   121560
ggactggagt tagaatttat agacgactca tttcgtttat cattgttact accatcatta   121620
ttagtattct tcttgtcatc ttgttcagaa atatacagca atgctatacc taatactaaa   121680
tacattatca tgctcgcaat ggctctaaca acaacgaacc aaaatgaatt tggtcgtagc   121740
ttttgttcac aaaaatacat aaagaaatgt ctacataaat ctatggcgcc attggctact   121800
tgaaatagcg ccagtcctcc tacagatttt aatatagctg tataacatga catttattca   121860
tcatcaaaag agacagagtc accatctgtc atatttagat ttttttttcat gtgttcaaag   121920 tatcctctac tcatttcatt ataatagttt atcatactta gaattttagg acggatcaat   121980
gagtaagact tgactagatc gtcagtagta atttgtgcat cgtctattct gcatccgctt   122040
cgtcgaataa tgtatagcat cgctttgaga ttctccatag ctatcaagtc tttatacaat   122100
gacatggaaa tatctgtgaa tactttatac ttctccaaca tcgatgcctt aacatcatcg   122160
cctactttag cattgaaaat acgttctatt gtgtagatgg atgtagcaag attttttaaac  122220 aacaatgcca tcttacacga tgattgcctc aagtctccaa tcgtttgttt agaacgatta   122280
gctacagagt ccaatgcttg gctgactagc atattattat ctttagaaat tgtattcttc   122340
aatgaggcgt ttatcatatc tgtgatttcg ttagtcatat tacagtctga ctgggttgta   122400
atgttatcca acatatcacc tatggatacg gtacacgtac cagcatttgt aataatccta   122460
tctaagatgt tgtatggcat tgcgcagaaa atatcttctc ctgtaatatc tccactctcg   122520
ataaatctac tcagattatt cttaaatgcc ttattctctg gagaaaagat atcagtgtcc   122580
atcatttcat taatagtata cgcagaaaag ataccacgag tatcaattct atccaagata   122640
cttatcggtt ccgagtcaca gataatggtt tcctctcctt cgggagatcc tgcatagaaa   122700
tatctaggac aatagtttct atactgtctg taactctgat aatctctaaa gtcactaact   122760
gataccatga aattgagaag atcaaacgct gaagtaatta attttttctgc ctcgttttta   122820 ctacaactag ttttcatcaa tgtagtgacg atgtattgtt tagttacttt tggtctaata   122880
ctgatgatag agatattatt acttcccata atggatcttc tagtagtcac cttaaagccc   122940
attgatgcga atagcagata gataaagtct tggtatgact cctttctaat atagtacgga   123000
ctacctttgt cacccaactt tatcccaca taagccataa caacctcttt aatagccgtt   123060
tcatgaggtt tatcagccat gagcctgagt agttggaaga atctcatgaa tcccgtctca   123120
gaaagtccta tatgcatgat agatttatct ttcctgggaa actctcgtat agtcatagat   123180
gaaatactct tcaaagtttc tgaaataaga ttagtaacag tcttacctcc gactactcta   123240
ggtaacaaac aaactctaat aggtgttttc tctgcggaga taatatcaga aaggatagag   123300
caataagtag tattattgtg attataaaga ccgaatacat aacaggtaga atttataaac   123360
atcatgtcct gaaggttttt agacttgtat tcctcgtaat ccataccgtc caaaacatg    123420 gatttggtaa cttttgatagc cgtagatctt tgttccttcg ccaacaggtt aaagaaatta   123480
ataaagaatt tgttgtttct atttatgtcc acaaattgca cgtttggaag cgccacggtt   123540
acattcactg cagcattttg aggatcgcga gtatgaagta cgatgttatt gtttactggt   123600
atatctggaa agaaatctac cagtctagga ataagagatt gatatcgcat agaaatagta   123660
aagtttataa tctcatcatc gaagagcatt ttgttaccat tgtaataaat atccactctg   123720
```

```
tcatatgtat aaatgaagta ctgttcaaac atgatgagat gtttatatgt tggcatagta   123780
gtgagatcga cgtttggtaa tggcaatgta ttaagattaa ctccataatg tctagcagca   123840
tctgcgatgt tataagcgtc gtcaaagcgg ggtcgatctt gtattgttat atattgtcta   123900
acacctataa gattatcaaa atcttgtctg cttaatacac cgttaacaat ttttgccttg   123960
aattctttta ttggtgcatt aataacatcc ttatagagga tgttaaacaa ataagtgtta   124020
tcaaagttaa gatctggata tttcttttct gctagaacat ccattgagtc ggagccatct   124080
ggtttaatat aaccaccgat aaatctagct ctgtattctg tatccgtcaa tctaatatta   124140
agaaggtgtt gagtgaaagg tggaagatcg taaaagctgt gagtattaat gataggatta   124200
gtttccgaac taatgttaat tggggtatta ataatatcta tatttccagc gttaagtgta   124260
acattaaaca gttttaattc acgtgacgtg gtatcaatta ataattaat gcccaatttg    124320 gatatagcag cctgaagctc atcttgttta gttacggatc ctaatgagtt attaagcaat   124380
atatcgaacg gatgaacgaa ggttgtttta agttggtcgc atactttgta atctagacat   124440
agatgcggaa gaacggtaga aactatacga aataaatatt cagagtcctc taattgatca   124500
agagtaacta ttgacttaat aggcatcatt tatttagtat taaatgacga ccgtaccagt   124560
gacggatata caaaacgatt taattacaga gttttcagaa gataattatc catctaacaa   124620
aaattatgaa ataactcttc gtcaaatgtc tattctaact cacgttaaca acgtggtaga   124680
tagagaacat aatgccgccg tagtgtcatc tccagaggaa atatcctcac aacttaatga   124740
agatctattt ccagatgatg attcaccggc cactattatc gaacgagtac aacctcatac   124800
tactattatt gacaatactc cacctcctac gtttcgtaga gagttattaa tatcggaaca   124860
acgtcaacaa cgagaaaaaa gatttaatat tacagtatcg aaaaatgctg aagcaataat   124920
ggaatctaga tctatgataa cttctatgcc aacacaaaca ccatccttgg gagtagttta   124980
tgataaagat aaaagaattc agatgttaga ggatgaagtg gttaatctta gaaatcaacg   125040
atctaataca aaatcatctg ataatttaga taatttttacc aaaatactat ttggtaagac   125100
tccgtataaa tcaacagaag ttaataagcg tatagccatc gttaattatg caaatttgaa   125160
cgggtctccc ttatcagtcg aggacttgga tgtttgttca gaggatgaaa tagatagaat   125220
ctataaaacg attaaacaat atcacgaaag tagaaaacga aaaattatcg tcactaacgt   125280
gattattatt gtcataaaca ttatcgagca ggcattgcta aaactcggat ttgaagaaat   125340
caaaggactg agtaccgata tcacttcaga aattatcgat gtggagatcg gagatgactg   125400
cgatgctgta gcatcaaaac taggaatcgg taacagtccg gttcttaata ttgtattgtt   125460
tatactcaag atattcgtta aacgaattaa aattatttaa tttaatacat tcccatatcc   125520
agacaacaat cgtctggatt aatctgttcc tgtcgtctca taccggacga catattaatc   125580
tttttattag tgggcatctt tttagatggt ttcttttttcc cagcattaac tgattcgata   125640
cctagaagat cgtgattgat ctctccgacc attccacgaa cttctaattg gccgtctctg   125700
acggtaccat aaactatttt accagcatta gtaacagctt ggacaatctg accatccatc   125760
gcattgtacg atgtagtagt aactgttgtt ctacgtctag gagcaccaga gtattttttg   125820
gagcccttgg atgttgatgt agaagaagac gaggattttg attttggttt acatgtaata   125880
cattttgaac tctttgattt tgtatcacat gcgccggcag tcacatctgt ttgagaatta   125940
agattattgt tgcctccttt gacggctgca tctccaccga tttgcgctag tagatttta   126000 agctgtggtg taatcttatt aactgttcg atataatcat cgtaactgct tctaacggct    126060 aaatttttt tatccgccat ttagaagcta aaaatatttt tatttatgca gaagatttaa    126120
```

```
ctagattata caatgaacta atatgatcct tttccagatt atttacaaac ttggtatttt   126180
ttggttctgg aggaggcgaa tttaaattcg gacttggatt cggattttgt aagttcttga   126240
tcttattata catcgagtat aggatggcga cagtaactgc tacacaaata ccgatcaaaa   126300
gaagaatacc aatcatttat tgacaataac ttcactattg atcaagtatg caatatatca   126360
tcttttcact aaataagtag taataatgat tcaacaatgt cgagatatat ggacgataat   126420
aatttagttc atggaaatat cgctatgatt ggtgtgaatg actccgctaa ctctgtgggg   126480
tgcgcagtgc tttccccaca tagaataaat tagcattccg actgtgataa taataccaag   126540
tataaacgcc ataatactca atactttcca tgtacgagtg ggactggtag acttactaaa   126600
gtcaataaag gcgaagatac acgaagaat caaagaatg attccagcga ttagcacgcc     126660
ggaaaaataa tttccaatca taagcatcat gtccatttaa ctaataaaaa ttttaaatcg   126720
ccgaatgaac aaagtggaat ataaaccata taaaaacaat agtttgtact gcaaaaataa   126780
tatctatttt tgttttcgaa gatatggtaa aattaaatag tagtacacag catgttataa   126840
ctaacagcag caacggctcg taattactta tcatttacta gacgaaaagg tggtgggata   126900
ttttcttgct caaataatac gaatatatca cccatccatt ttatgcgatg tttatatact   126960
ctaatcttta atagatctat agacgacggg tttaccaaca atatagattt tatcgattca   127020
tctaatttaa acccttcctt aaacgtgaat gatctattat ctggcataac gatgacccta   127080
cctgatgaat cggacaatgt actgggccat gtagaataaa ttatcaacga attatcgtct   127140
acgaacattt atatcatttg ttttaatttt aggacgcgaa taaatggata taaaatagaa   127200
aataacagat attacaacca gtgttatggc cgcgcccaac caggtaggca gttttatttt   127260
atcttttact acaggttctc ctggatgtac gtcaccaacg gcggacgtag ttctagtaca   127320
attagacgta agttccgctt gggaattttt taacgctaaa gagttaacgt taatcgtaca   127380
cccaacgtat ttcatctag ttctttgaac atcttgatta taatataacc attttctatc    127440
tctagattcg tcggtgcact catgtaacca acatacccta ggtcctaaat atttatctcc   127500
ggaattagat tttggataat tcgcgcacca acaatttcta tttcctttat gatcgttaca   127560
aaagacgtat aatgccgtat ccccaaaagt aaaataatca ggacgaataa ttctaataaa   127620
ctcagaacaa tatctcgcat ccatatgttt ggagcaaata tcggaataag tagacatagc   127680
cggtttccgt tttgcacgta accattctaa acaattgggg tttccaggat cgttctaca    127740
aaatccagtc atgaaatcgt cacaatgttc tgtcttgtaa ttattattaa atattttgg     127800
acagtgtttg gtatttgtct tagaacaaca ttttgccacg ctatcactat cgcccaggag   127860
ataatccttt tttataaaat gacatcgttg cccggatgct atataatcag tggcgtgttt   127920
taaatcctta atatattcag gagttacctc gttctgataa tagattaatg atccaggacg   127980
aaatttgaaa gaactacatg gttctccatg aattaataca tattgtttag caaattcagg   128040
aactataaaa ctactacaat gatctatcga cataccatct atcaaacaaa acttgggttt   128100
aatttctccc ggagatgttt cataatagta cgtataactt tcttctgcaa acttaacagc   128160
tctattatat tcaggataat taaaacctaa ttccatatat ttgtctcgta tatctgctat   128220
tcctggtgct attttgattc tattaagagt aacagctgcc cccattctta ataatcgtca   128280
gtatttaaac tgttaaatgt tggtatatca acatctacct tatttcccgc agtataaggt   128340
ttgttgcagg tatactgttc aggaatggtt acatttatac ttcttctata gtcctgtctt   128400
tcgatgttca tcacatatgc aaagaacaga ataaacaaaa taatgtaaga aataatatta   128460
aatatctgtg aattcgtaaa tacattgatt gccataataa ttacagcagc tacaatacac   128520
```

```
acaatagaca ttcccacagt gttgccatta cctccacgat acatttgagt tactaagcaa    128580
taggtaataa ctaagctagt aagaggcaat agaaaagatg agataaatat catcaatata    128640
gagattagag gagggctata tagagccaag acgaacaaaa tcaaaccgag taacgttcta    128700
acatcattat ttttgaagat tcccaaataa tcattcattc ctccataatc gttttgcatc    128760
atacctccat cttaggcat  aaacgattgc tgctgttcct ctgtaaataa atctttatca    128820
agcactccag cacccgcaga gaagtcgtca agcatattgt aatatcttaa ataactcatt    128880
tatatattaa aaaatgtcac tattaaagat ggagtataat ctttatgccg aactaaaaaa    128940
aatgacttgt ggtcaacccc taagtctttt taacgaagac ggggatttcg tagaagttga    129000
accgggatca tcctttaagt ttctgatacc taagggattt tacgcctctc cttccgtaaa    129060
gacgagtcta gtattcgaga cattaacaac gaccgataat aaaatcacta gtatcaatcc    129120
aacaaatgcg ccaaagttat atcctcttca acgcaaagtc gtatctgaag tagtttctaa    129180
tatgaggaaa atgatcgaat caaaacgtcc tctatacatt actcttcact tggcgtgtgg    129240
atttggtaag actattacca cgtgttatct tatggctaca cacggtagaa aaaccgtcat    129300
ttgcgtaccc aataaaatgt taatacatca atggaagaca caggtagagg cagtcggatt    129360
ggaacataag atatccatag atggagtaag tagtctatta aaggaactaa agactcaaag    129420
tccggatgta ttaatagtag tcagtagaca tctgacaaac gatgccttt  gtaaatatat    129480 caataagcat tatgatttgt tcatcttgga tgaatcacat acgtataatc tgatgaacaa    129540
tacagcagtt acaagatttt tagcgtatta tcctccgatg atgtgttatt ttttaactgc    129600
tacacctaga ccatctaacc gaatttattg taacagtatt attaatattg ccaagttatc    129660
cgatctaaaa aaaactatct atgcggtaga tagttttttt gagccatatt ccacagacaa    129720
tattagacat atgataaaac gattagatgg accatctaat aaatatcata tatatactga    129780
gaagttatta tctgtagacg agcctagaaa tcaacttatt cttaataccc tggtagaaga    129840
attcaagtca ggaactatta atcgcatttt agttattact aaactacgtg aacatatggt    129900
attcttctac aaacgattat tagatctttt cggaccagag gttgtattta taggagacgc    129960
ccaaaataga cgtactccag atatggtcaa atcaatcaag gaactaaata gatttatatt    130020
cgtatccacc ttatttttatt ccggtactgg tttagatatt cctagtttgg attcgttgtt    130080
catttgctcg gcagtaatca acaatatgca aatagagcaa ttactaggga gggtatgtcg    130140
agaaacagaa ctattagata ggacggtata tgtatttcct aacacatcca tcaaagaaat    130200
aaagtacatg ataggaaatt tcatgcaacg aattattagt ctgtctgtag ataaactagg    130260
atttaaacaa aaaagttatc ggaaacatca agaatccgat cccacttctg tatgtacaac    130320
atcctccaga gaagaacgtg tattaaatag aatatttaac tcgcaaaatc gttaagaagt    130380
ttaagcgacg atccgcatgc tgcgcaggcc agtgtattac ccctcatagt attaatataa    130440
tccaatgata cttttgtgat gtcggaaatc ttaaccaatt tagactgaca ggcagaacac    130500
gtcatgcaat catcatcgtc atcgataact gtagtcttgg gcttcttttt gcggctcttc    130560
attccggaac gcacattggt gctatccatt taggtagtaa aaaataagtc agaatatgcc    130620
ctataacacg atcgtgcaaa acctggtata tcgtctctat ctttatcaca atatagtgta    130680
tcgacatttt tattattatt gacctcgttt atccttggaac atggaatggg aacatttttg    130740
ttatcaacgg ccacctttgc cttaattcca gatgttgtaa aattataact aaacagtcta    130800
tcatcgacac aaatgaaatt cttgtttaga cgtttgtagt ttacgtatgc ggctcgttcg    130860
cgtctcattt tttcagatat tgcaggtact ataatattaa aaataagaat gaaataacat    130920
```

```
aggattaaaa ataaagttat catgacttct agcgctgatt taactaactt aaaagaatta    130980
cttagtctgt acaaaagttt gagattttca gattctgcgg ctatagaaaa gtataattct    131040
ttggtagaat ggggaacatc tacttactgg aaaataggcg tgcaaaaggt agctaatgtc    131100
gagacgtcaa tatctgatta ttatgatgag gtaaaaaata aaccgtttaa tattgatccg    131160
ggctattaca ttttcttacc ggtatatttt gggagcgtct ttatttattc gaagggtaaa    131220
aatatggtag aacttggatc tggaaactct tttcaaatac cagatgatat gcgaagtgcg    131280
tgtaacaaag tattagacag cgataacgga atagactttc tgagatttgt tttgttaaac    131340
aatagatgga taatggaaga tgctatatca aaatatcagt ctccagttaa tatatttaaa    131400
ctagctagtg agtacggatt aaacataccc aaatatttag aaattgaaat agaggaagac    131460
acattatttg acgacgagtt atactctatt atagaacgct cttttgatga taaatttcca    131520
aaaatatcca tatcgtatat taagttggga gaacttagac ggcaagttgt agacttttc    131580
aaattctcat tcatgtatat tgagtccatc aaggtagatc gtataggaga taatatttt    131640
attcctagcg ttataacaaa atcaggaaaa aagatattag taaaagatgt agaccattta    131700
atacgatcta aggttagaga acatacattt gtaaaagtaa aaaagaaaaa cacattttcc    131760
attttatacg actatgatgg gaacggaaca gaaactagag gagaagtaat aaaacgaatt    131820
atagacacta taggacgaga ctattatgtt aacggaaagt atttctctaa ggttggtagt    131880
gcaggcttaa agcaattgac taataaatta gatattaatg agtgcgcaac tgtcgatgag    131940
ttagttgatg agattaataa atccggaact gtaaaacgaa aaataaaaaa ccaatcagca    132000
tttgatttaa gcagagaatg tttgggatat ccagaagcgg attttataac gttagttaat    132060
aacatgcggt tcaaaataga aaattgtaag gttgtaaatt tcaatattga aaatactaat    132120
tgtttaaata acccgagtat tgaaactata tatggaaact ttaaccagtt cgtctcaatc    132180
tttaatgtcg tcaccgatgt caaaaaaaga ttattcgagt gaaataatat gcgccttga    132240
tataggtgca aaaaatcctg ccagaactgt tttagaagtc aaggataact ccgttagggt    132300
attggatata tcaaaattag actggagttc tgattgggaa aggcgcatag ctaaagattt    132360
gtcacaatat gaatacacta cagttcttct agaacgtcag cctagaaggt cgccgtatgt    132420
taaatttatc tattttatta aaggcttttt atatcataca tcggctgcca aagttatttg    132480
cgtctcgcct gtcatgtctg gtaattcata tagagatcga aaaaagagat cggtcgaagc    132540
atttcttgat tggatggaca cattcggatt gcgagactcc gttccggata gacgcaaatt    132600
agacgatgta gcggatagtt tcaatttggc tatgagatac gtattagata aatgaatac    132660
taattataca ccttataata ggtgtaaatc tagaaattac ataaaaaaaa tgtaataacg    132720
ttagtaacgc cattatggat aatctatta cctttctaca tgaaatagaa gatagatatg    132780
ccagaactat ttttaacttt catctaataa gttgcgatga aataggagat atatatggtc    132840
ttatgaaaga acgcatttcc tcagaggata tgtttgataa tatagtgtat aataaagata    132900
tacatcctgc cattaagaaa ctagtgtatt gcgacatcca acttactaaa cacattatta    132960
atcagaatac gtatccggta tttaacgatt cttcacaagt gaaatgttgt cattatttcg    133020
acataaactc agataatagc aatattagct ctcgtacagt agagatattt gagagggaaa    133080
agtcatctct tgtatcatat attaaaaacta ccaataagaa gagaaaggtc aattacggcg    133140
aaataaagaa aactgttcat ggaggcacta atgcaaatta cttttccggt aaaaagtctg    133200
acgagtatct gagtactaca gttagatcca acattaatca accttggatc aaaaccattt    133260
ctaagagaat gagagtagat atcattaatc actctatagt aacgcgtgga aaaagctcta    133320
```

```
tattacaaac tatagaaatt attttttacta atagaacatg tgtgaaaata ttcaaggatt    133380
ctactatgca cattattcta tccaaggaca aggatgaaaa ggggtgtata cacatgattg    133440
acaaattatt ctatgtctat tataatttat ttctgttgtt cgaagatatc atccaaaacg    133500
agtactttaa agaagtagct aatgttgtaa accacgtact cacggctacg gcattagatg    133560
agaaattatt cctaattaag aaaatggctg aacacgatgt ttatggagtt agcaatttca    133620
aaatagggat gtttaacctg acatttatta agtcgttgga tcataccgtt ttcccctctc    133680
tgttagatga ggatagcaaa ataaagtttt taaggggaa aaagctcaat attgtagcat     133740
tacgatctct ggaggattgt ataaattacg tgactaaatc cgagaatatg atagaaatga    133800
tgaaggaaag atcgactatt ttaaatagca tagatataga aacggaatcg gtagatcgtc    133860
taaaagaatt gcttctaaaa tgaaaaaaaa cactgattca gaaatggatc aacgactcgg    133920
atataagttt ttggtgcctg atcctaaagc cggagttttt tatagaccgt tacatttcca    133980
atatgtatcg tattctaatt ttatattgca tcgattgcat gaaatcttga ccgtcaagcg    134040
gccactctta tcgtttaaga ataatacaga acgaattatg atagaaatta gcaatgttaa    134100
agtgactcct ccagattact cacctataat cgcgagtatt aaaggtaaga gttatgacgc    134160
attagccacg ttcactgtaa atatctttaa agaggtaatg accaagagg gtatatccat     134220
cactaaaata agtagttatg agggaaaaga ttctcatttg ataaaaattc cgctactaat    134280
aggatacggg aataaaaatc cacttgatac agccaagtat cttgttccta atgtcatagg    134340
tggagtctttt atcaataaac aatctgtcga aaaagtagga attaatctag tagaaaagat   134400
tacaacatgg ccaaaattta gggttgttaa gccaaactca ttcactttct cgttttcctc    134460
cgtatcccct cctaatgtat taccgacaag atatcgccat tacaagatat ctctggatat    134520
atcacaattg gaagcgttga atatatcatc gacaaagaca tttataacgg tcaatattgt    134580
tttgctgtct caatatttat ctagagtgag tctagaattc attagacgta gtttatcata    134640
cgatatgcct ccagaagttg tctatctagt aaacgcgata atagatagtg ctaaacgaat    134700
tactgaatct attactgact ttaatattga tacatacatt aatgacctgg tggaagctga    134760
acacattaaa caaaaatctc agttaacgat taacgagttc aaatatgaaa tgctgcataa    134820
cttttttacct catatgaact atacacccga tcaactaaag ggattttata tgatatcttt   134880
actaagaaag tttctctact gtatcttcca cacttctaga tatccagata gagattcgat    134940
ggtttgtcat cgcatcctaa cgtacggcaa atattttgag acgttggcac atgatgaatt    135000
agagaattac ataggcaaca tccgaaacga tatcatgaac aatcacaaga acagaggcac    135060
ttacgcggta acattcatg tactaacaac tcccggactt aatcatgcat tttctagtct     135120
attgagtgga aagttcaaaa agtcagacgg tagttatcga acacatcctc actattcatg    135180
gatgcagaat atttctattc ctaggagtgt tggattttat ccggatcaag taaagatttc    135240
aaagatgttt tctgtcagaa aataccatcc aagtcaatat ctttacttttt gttcatcaga   135300
cgttccggaa agaggtcctc aggtaggttt agtatctcaa ttgtctgtct tgagttccat    135360
tacaaatata ctaacgtctg agtatttgga tttggaaaag aaaatttgtg agtatatcag    135420
atcatattat aaagatgata taagttactt tgaaacagga tttccaatca ctatagaaaa    135480
tgctctagtc gcatctctta atccaaatat gatatgtgat tttgtaactg actttagacg    135540
tagaaaacgg atgggatttt tcggtaactt ggaggtaggt attactttag ttagggatca    135600
catgaatgaa attcgcatta atattggagc gggaagatta gtcagaccat tcttggttgt    135660
ggataacgga gagctcatga tggatgtgtg tccggagtta gaaagcagat tagacgacat    135720
```

```
gacattctct gacattcaga aagagtttcc gcatgtcatc gaaatggtag atatagaaca    135780
atttactttt agtaacgtat gtgaatcggt tcaaaaattt agaatgatgt caaaggatga    135840
aagaaagcaa tacgatttat gtgactttcc tgccgaattt agagatggat atgtggcatc    135900
ttcattagtg ggaatcaatc acaattctgg acccagagct attcttggat gtgctcaagc    135960
taaacaagct atctcttgtc tgagctcgga tatacgaaat aaaatagaca atggaattca    136020
tttgatgtat ccagagaggc caattgtcat tagtaaggct ttagaaactt caaagattgc    136080
ggctaattgc ttcggccaac atgttactat agcattaatg tcgtacaaag gtatcaatca    136140
agaggatgga attatcatca aaaacaatt tattcagaga ggcggtctcg atatagttac    136200
cgcaaagaaa catcaagtag aaattccatt ggaaaacttt aataacaaag aaagagatag    136260
gtctaacgcc tattcaaaat tagaaagtaa tggattagtt agactgaatg ctttcttgga    136320
atccggagac gctatagcac gaaatatctc atcaagaact cttgaagatg attttgctag    136380
agataatcag attagcttcg atgtttccga gaaatatacc gatatgtaca aatctcgcgt    136440
tgaacgagta caagtagaac ttactgacaa agttaaggta cgagtattaa ccatgaaaga    136500
aagaagaccc attctaggag acaaatttac cactagaacg agtcaaaagg gaacagtcgc    136560
gtatgtcgcg gatgaaacgg aacttccata cgacgaaaat ggtatcacac cagatgtcat    136620
tattaattct acatccatct tctctagaaa aactatatct atgttgatag aggttatttt    136680
aacagccgca tattctgcta agccgtacaa caataaggga gaaaaccgac ctgtctgttt    136740
tcctagtagt aacgaaacat ccatcgatac atatatgcaa ttcgctaaac aatgttatga    136800
gcattcaaat ccgaaattgt ctgatgaaga attatcggat aaaatctttt gtgaaaagat    136860
tctctatgat cctgaaacgg ataagcctta tgcatccaaa gtattttttg gaccaattta    136920
ttacttgcgt ctgaggcatt taactcagga caaggcaacc gttagatgta gaggtaaaaa    136980
gacgaagctc attagacagg cgaatgaggg acgaaaacgt ggaggaggta tcaagttcgg    137040
agaaatggag agagactgtt taatagcgca tggtgcagcc aatactatta cagaagtttt    137100
gaaagattcg gaagaagatt atcaagatgt gtatgtttgt gaaaattgtg gagacatagc    137160
agcacaaatc aaaagtatta atacatgtct tagatgttca aaacttaatc tctctcctct    137220
cttaacaaaa attgatacca cgcacgtatc taaagtattt cttactcaaa tgaacgccag    137280
aggcgtaaaa gtcaaattag atttcgaacg aagacctcct tcgttttata accattaga    137340 taaagttgat ctcaagccgt cttttctggt gtaatattct agtttggtag tagatacata    137400
tcaatatcat caaattcgag atccgaatta taaaatgggc gtggattgtt aactatagaa    137460
tcggacgtct gatattcgaa aatctgtgga gtttcaggtt ttggtggagg tgtaactgct    137520
acttgggata ctgaagtctg atattcagaa agctggggga tgttctggtt cggcatccac    137580
cgatggtgtc acatcactaa tcggttcggt aacgtctgtg gatggaggtg ctacttctac    137640
agaacctgta gcctcagttg tcaacggagc tacttcaatg cgaggaaatg tataatttgg    137700
taatggtttc tcatgtggat ctgaagaaga ggtaagatat ctactagaaa gataccgatc    137760
acgttctagt tctcttttgt aaaacttaac ttttctcttc tcagcatcta gttgatattc    137820
caacctcttc acgttactac gttcagattc caattcacgt tcgcatgggt tacctccgca    137880 gttttttacga gcgatttcac gttcagcctt catgcgtctc tccctctctc tatcgagttt    137940
atcagagcag tctttctgaa ggcgatcgaa ctccataaat ttctccaacg ctttgattgt    138000
ttccatagat ttccgaagtt cagcttttag gactgtgatt cttttctttt cgaattcaca    138060
gctggatgta caaccgtttc cattaccgcc atctctaagt ttcttttcta gatcggcaac    138120
```

```
atttcatccc catgcctttt acattcctcg agtctactgt cgtcgaaata tcgttccagc   138180 tcctttcga catcaataac tttagcacgt tgtctctcaa gctctctttt gtagttatct   138240
gattccctgg cacgtttaag atcttcatgc aattgagtca gctcttaact tcctctcttg   138300
cttcttcgtc atagtactta caatcactat gggatccatt gttaccacgt ctacactcgg   138360
cgagctcgcg tttaagagat tcaatttccc gtttgtattg gtccatgttt ccattgctac   138420
caccattaga tttacaggct gctagttgtc gttcgagatc agaaatacgg gttttcttgg   138480
aattgatttc gtcgatgtac ttggcatcga aacacttatt aagttctttt tccaattcta   138540
cgattttatt tctttcgcga gtcaattccc tcctgtagta actatctgtt ttgtcagatt   138600
cacgctctct acgtagactt tcttgcaagt tactaatttg ttccctagca cgtccgagtt   138660
tagttttata tgctgaatag agttctgatt catcctttga gcagatctct agcgatcgtt   138720
taagattcct gattctagtc tttagcctat ttacctcctc agaagatgtt ccgttaccgt   138780
tgcgtttaca ctcgttaagc tgtctatcaa gatccatgat tctatctcta agacgttgca   138840
tctctctttc catatcagca ttgctttcat tattacgtct gcagtcactc aactgtcttt   138900
caatatctga gattctatct ctaagacgtc gcatctctct ctgtttcggc attggtttca   138960
ttattacgtc tacagtcgtt caactgtctt tcaagatctg atattctaga ttggagtctg   139020
ctaatctctg tagcattttc acggcattca ctcagttgtc tttcaagatc tgagatttta   139080
gattggagtc tgctaatctc tgtaagattt cctcctccgc tctcgatgca gtcggtcaac   139140
ttattctcta gttctctaat acgcgaacgc agtgcatcaa cttcttgcgt gtcttcctgg   139200
ttgcgtgtac attcatcgag tctagattcg agatctctaa cgcgtcgtcg ttcttcctca   139260
agttctctgc gtactacaga aagcgtgtcc ctatcttgtt gatatttagc aatttctgat   139320
tctagagtac tgattttgct tacgtagtta ctaatagttg tcttggcctt atcaagatcc   139380
tccttgtatt tgtcgcattc cttgatatcc ctacgaagtc tggacagttc ccattcgaca   139440
ttacgacgtt tatcgatttc agctcggaga tcgtcatcgc gttgttttag ccacatacga   139500
ctgagttcaa gttctcgttg acaagatcca tctacttttc cattcctaat agtatccagt   139560
tccttttcta gttctgaacg catttctcgt tccctatcaa gcgattctct caattctcgg   139620
atagtcttct tatcaatttc taataaatct gaaccatcat ctgtcccatt ttgaatatcc   139680
ctgtgttctt tgatctcttt tgtaagtcgg tcgattcttt cggttttata aacagaatcc   139740
ctttccaaag tcctaatctt actgagttta tcactaagtt ctgcattcaa ttcggtgagt   139800
tttctcttgg cttcttccaa ctctgtttta aactctccac tatttccgca ttcttcctcg   139860
catttatcta accattcaat tagtttatta ataactagtt ggtaatcagc gattcctata   139920
gccgttcttg taattgtggg aacataatta ggatcttcta atggattgta tggcttgata   139980
gcatcatctt tatcattatt aggggatgg acaaccttaa ttggttggtc ctcatctcct   140040
ccagtagcgt gtggttcttc aataccagtg ttagtaatag gcttaggcaa atgcttgtcg   140100
tacgcgggca cttcctcatc catcaagtat ttataatcgg gttctacttc agaatattct   140160
tttctaagag acgcgacttc gggagttagt agaagaactc tgtttctgta tctatcaacg   140220
ctggaatcaa tactcaagtt aaggatagcg aatacctcat cgtcatcatc cgtatcttct   140280
gaaacaccat catatgacat ttcatgaagt ctaacgtatt gataaataga atcagattta   140340
gtattaaaca gatccttaac cttttttagta aacgcatatg tatattttag atctccagat   140400
ttcataatat gatcacatgc cttaaatgtc agtgcttcca tgatataatc tggaacacta   140460
atgggtgacg aaaaagatac agcaccatat gctacgttga taaataaatc tgaaccacta   140520
```

```
agtagataat gattaatgtt aaggaaaaga aaatattcag tgtataggta tgtcttggcg   140580
tcatatcttg tactaaacac gctaaacagt ttgttaatgt gatcaatttc caatagatta   140640
attagagcag caggaatacc aacaaacata ttaccacatc cgtattttct atgaatatca   140700
catatcatgt taaaaaatct tgatagaaga gcgaatatct cgtctgactt aatgagtcgt   140760
agttcagcag caacataagt cataactgta aatagaacat actttcctgt agtgttgatt   140820
ctagactcca catcaacacc attattaaaa atagttttat atacatcttt aatctgctct   140880
ccgttaatcg tcgaacgttc tagtatacgg aaacactttg atttcttatc tgtagttaat   140940
gacttagtga tatcacgaag aatattacga attacatttc ttgttttttct tgagagacct   141000
gattcagaac tcaactcatc gttccatagt ttttctacct cagtggcgaa atctttggag   141060
tgcttggtac atttttcaat aaggttcgtg acctccattt attataaaaa atttattcaa   141120
aacttaacta caatcgggta attataagat cgtagatctc ccatgtggcg gaatactacc   141180
atctatcgca tgtggatgga cagtaggtaa tggccatggg aacagtaatg attgcatatt   141240
tatcttttctt gccagtatta ctgcatattg tcccaatgtt tcgatgtgat gttctaacct   141300
atcaactgcc gctgtatcac aacaatagtg tccgatgaaa ttaagattat gatccaatgt   141360
gtttaatata tgattatcaa gtcttatacg atccgcgtct tttttgacag gatcaggttc   141420
ttctacagga agaagtttcg gcctcttatg atattcatgt ctgggaaacg gtggtctagg   141480
gtgaggctcc ggtatcggag tgggttttgg attataatca tcatcgtcta tgacatcatc   141540
atcatcttcg acttcgatat ttattttgct atcttgatga tgtcctgtat cagttgcatt   141600
ttcagcactc gactgaatat tagcgcattc attgtctatt attaccatat ttctaaaccc   141660
aaaatgtatg tgttgaacat cagtactatc gttgatgagt cttatagcat gaattcgctt   141720
atcgttatcg ggtttatctt ctgtcacctt agcaattcct tttttattaa actctacata   141780
atcatatcca tttctattgt ttgttctaat ataaacgagt atagcatcat tgctaaattt   141840
ttcaatagta tcgaaaacag aatatcctaa accatataat atatattcag gaacactcaa   141900
actaaatgtc caggattctc ctaaatacgt aaactttaat agtgcgaaat cattcaaaaa   141960
tctaccactt atagatagat agtacataaa tgcgtatagt agtctaccta tctctttatt   142020
atgaaaaccg gcattacgat catatatgtc gtgatatacc tgtgatccgt ttacgttaaa   142080
ccataaaatac atgggtgatc ctataaacat gaatttattt ctaattctca gagctatagt   142140
taattgaccg tgtaatattt gcttacatgc atacttgata cgctcattaa taagattttt   142200
atcattgctc gttatttcag aatcgtatat ataaggagta ccatcgtgat tcttaccaga   142260
tattatacaa aatactatat ataaaatata ttgacccacg ttagtaatca tataaatgtt   142320
taacgtttta aattttgtat tcaatgatcc attatcatac gctatcatgg tcttgtaata   142380
ttcattcttt aaaatataat attgtgttag ccattgcatt ggggctccta atggagattt   142440
tttattctca tccattttag gataggcttt cataaagtcc ctaataactt cgtgaataat   142500
gtttctatgt tttctactga tgcatgtatt tgcttcgatt tttttatccc atgtttcatc   142560
tatcatagat ttaaacgcag taatgctcgc aacattaaca tcttgaaccg ttggtacaat   142620
tccgttccat aaatttataa tgttcgccat ttatataact cattttttga atatactttt   142680
aattaacaaa agagttaagt tactcatatg gacgccgtcc agtctgaaca tcaatctttt   142740
tagccagaga tatcatagcc gctcttagag tttcagcgtg attttccaac ctaaatagaa   142800
cttcatcgtt gcgtttacaa cacttttcta tttgttcaaa ctttgttgtt acattagtaa   142860
tctttttttc caaattagtt agccgttgtt tgagagtttc ctcattgtcg tcttcatcgg   142920
```

```
ctttaacaat tgcttcgcgt ttagcctctg gcttttttagc agcctttgta gaaaaaaatt    142980
cagttgctgg aattgcaaga tcgtcatctc cggggaaaag agttccgtcc atttaaagta    143040
cagattttag aaactgacac tctgcgttat ttatatttgg tacaacacat ggattataaa    143100
tattgatgtt aataacatca gaaaatgtaa agtctataca ttgttgcatc gtgttaaatt    143160
ttctaatgga tctagtatta ttgggtccaa cttctgcctg aaatccaaat atggaagcgg    143220
atacaaaacc gtttcctgga taaccacac atctccactt ttgctttaca tcagaaattg    143280
tgtcgttgac atcttgaact ctcctatcta atgccggtgt tccacctata gattttgaat    143340
attcgaatgc tgcatgagta gcattaaatt ccttaatatt gccataattt tcatatattg    143400
agtaaccctg gataaaaagt aaacacaccg cagccgtcgc taccacaata aaaaaaattg    143460
atagagagtt catttataat ctattagaag ctgacaaaat ttttttacac gcatcagaca    143520
atgctttaat aaatagttca acatctactt ttgtcatatc gaaccgatgg tatgattcta    143580
acctagaatt acatccgaaa aagttgacta tgttcatagt cattaagtca ttaacaaaca    143640
acattccaga ctctggatta taagacgata ctgtttcgtc acaattaccct accttaatca    143700
tgtgattatg aatattggct attagagcac cttctaagaa atctataata tctttgaaac    143760
acgatttaaa atcaaaccac gaatatactt ctacgaagaa agttagttta cccataggag    143820
aaataactat aaatggagat ctaaatacaa aatccggatc tatgatagtt ttaacattat    143880
tatattctct attaaatacc tccacatcta aaaatgttaa ttttgaaact atgtcttcgt    143940
ttattaccgt acctgaacta aacgctataa gctctattgt ttgagaactc tttaaacgat    144000
attcttgaaa tacatgtaac aaagtttcct ttaactcggt cggtttatct accatagtta    144060
cagaatttgt atccttatct ataatataat aatcaaaatc gtaaaagtt atataattat    144120
cgcgttcaga ttgggatctt ttcaaataga ctaaaaaccc catttctcta gtaagtatct    144180
tatgtatatg tttgtaaaat atcttcatgg tgggaatatg ctctaccgca gttagccatt    144240
cctcattgac agcggtagat gtattagaca aaactattcc aatgtttaac aagggccatt    144300
ttacgagatt attaaatcct tgtttgataa atgtagccaa tgagggttcg agttcaacga    144360
cgattgaatt ctcttcccgc ggatgctgca tgatgaacga cgggatgttg ttcgattgat    144420
ttggaattct ttttcgactt tttgtttata ttaaatattt taaaatttat agcggatagc    144480
aattcatgta ccacggataa tgtagacgcg tattgcgcat cgatatcttt attattagat    144540
aaatttatca ataaatgtga gaagtttgcc tcgttaaggt cttccattta aatattatat    144600
aaacatttgt gtttgtatct tattcgtctt ttatggaata gttttttact agtaaagctg    144660
caattacaca ctttgtccgt aaaacataaa tataaacacc agcttttatc aatcgttcca    144720
aaaagtcgac ggcggacatt tttaacatgg catctatttt aaatacactt aggtttttgg    144780
aaaaaacatc attttataat tgtaacgatt caataactaa agaaaagatt aagattaaac    144840
ataagggaat gtcatttgta ttttataagc caaagcattc taccgttgtt aaatacttgt    144900
ctggaggagg tatatatcat gatgatttgg ttgtattggg gaaggtaaca attaatgatc    144960
taaagatgat gctatttac atggatttat catatcatgg agtgacaagt agtggagcaa    145020
tttacaaatt gggatcgtct atcgatagac tttctctaaa taggactatt gttacaaaag    145080
ttaataatta tgatgataca ttttttgacg acgatgattg atcgctattg cacaattttg    145140
ttttttttact ttctaatata gcgtttagat tcttttttcat gtgcgaatat tgatttacta    145200
aaatatctat gtttaacttt tgttctataa cgtccttatc ggcggtatcg gtacatatac    145260
gtaattcacc ttcacaaaat acggagtctt cgataataat agccaatcga ttattggatc    145320
```

```
tagctgtctg tatcatattc aacatgttta atatatcctt tcgtttcccc tttacaggca   145380
tcgatcgtag catattttcc gcgtctgaga tggaaatgtt aaaactacaa aaatgcgtaa   145440
tgttagcccg tcctaatatt ggtacgtgtc tataagtttg gcatagtaga ataatagacg   145500
tgtttaaatg ccttccaaag tttaagaatt ctattagagt attgcatttt gatagtttat   145560
cgcctacatc atcaaaaata agtaaaaagt gtgctgattt tttatgattt tgtgcgacag   145620
caatacattt ttctatgtta cttttagttc gtatcagatt atattctaga gattcctgac   145680
tactaacgaa attaatatga tttggccaaa tgtatccatc ataatctggg ttataaacgg   145740
gtgtaaacaa gaatatatgt ttatatttt taactagtgt agaaaacaga gatagtaaat    145800
agatagtttt tccagatcca gatcctcccg ttaaaaccat tctaaacggc attttaata    145860 aattttctct tgaaaattgt ttttcttgga aacaattcat aattatattt acagttacta   145920
aattaatttg ataataaatc aaaatatgga aaactaaggt tgttagtagg gaggagaaca   145980
aagaaggcac atcgtgacat aaataacatt tattatcatg atgacaccag aaaacgacga   146040
agagcagaca tctgtgttct ccgctactgt ttacggagac aaaattcagg gaaagaataa   146100
acgcaaacgc gtgattggtc tatgtattag aatatctatg gttatttcac tactatctat   146160
gattaccatg tccgcgtttc tcatagtgcg cctaaatcaa tgcatgtctg ctaacgaggc   146220
tgctattact gacgccgctg ttgccgttgc tgctgcatca tctactcata gaaaggttgc   146280
gtctagcact acacaatatg atcacaaaga aagctgtaat ggtttatatt accagggttc   146340
ttgttatata ttcattcag actaccagtt attctcggat gctaaagcaa attgcactgc    146400
ggaatcatca acactaccca ataaatccga tgtcttgact acctggctca ttgattatgt   146460
tgaggataca tggggatctg atggtaatcc aattacaaaa actacatccg attatcaaga   146520
ttctgatgta tcacaagaag ttagaaagta ttttttgtgtt aaaacaatga actaatattt   146580
atttttgtac attaataaat gaaatcgctt aatagacaaa ctgtaagtag gtttaagaag   146640
ttgtcggtgc cggccgctat aatgatgata ctctcaacca ttattagtgg cataggaaca   146700
tttctgcatt acaaagaaga actgatgcct agtgcttgcg ccaatggatg gatacaatac   146760
gataaacatt gttatttaga tactaacatt aaaatgtcta cagataatgc ggtttatcag   146820
tgtcgtaaat tacgagccag attgcctaga cctgatacta gacatctgag agtattgttt   146880
agtatttttt ataagatta ttgggtaagt ttaaaaaaga ccaataataa atggttagat    146940
attaataatg ataaagatat agatattagt aaattaacaa attttaaaca actaaacagt   147000
acgacggatg ctgaagcgtg ttatatatac aagtctggaa aactggttaa aacagtatgt   147060
aaaagtactc aatctgtact atgtgttaaa aaattctaca agtgacaaca aaaaatgaat   147120
taataataag tcgttaacgt acgccgccat ggacgccgcg tttgttatta ctccaatggg   147180
tgtgttgact ataacagata cattgtatga tgatctcgat atctcaatca tggactttat   147240
aggaccatac attataggta acataaaaac tgtccaaata gatgtacggg atataaaata   147300
ttccgacatg caaaaatgct actttagcta aagggtaaa atagttcctc aggattctaa    147360
tgatttggct agattcaaca tttatagcat ttgtgccgca tacagatcaa aaaataccat   147420
catcatagca tgcgactatg atatcatgtt agatatagaa gataaacatc agccatttta   147480
tctattccca tctattgatg tttttaacgc tacaatcata gaagcgtata acctgtatac   147540
agctggagat tatcatctaa tcatcaatcc ttcagataat ctgaaaatga aattgtcgtt   147600
taattcttca ttctgcatat cagacggcaa tggatggatc ataattgatg ggaaatgcaa   147660
tagtaatttt ttatcataaa agttgtaaag taaataataa aacaataaat attgaactag   147720
```

```
tagtacgtat attgagcaat cagaaatgat gctggtacct cttatcacgg tgaccgtagt   147780
tgcgggaaca atattagtat gttatatatt atatatttgt aggaaaaaga tacgtactgt   147840
ctataatgac aataaaatta tcatgacaaa attaaaaaag ataaagagtt ctaattccag   147900
caaatctagt aaatcaactg atagcgaatc agactgggag gatcactgta gtgctatgga   147960
acaaaacaat aacgtagata atatttctag gaatgagata ttggacgatg atagcttcgc   148020
tggtagttta atatgggata acgaatccaa tgttatggcg cctagcacag aacacattta   148080
cgatagtgtt gctggaagca cgctgctaat aaataatgat cgtaatgaac agactattta   148140
tcagaacact acagtagtaa ttaatgaaac ggagactgtt aaagtactta atgaagatac   148200
caaacagaat cctaactatt catccaatcc tttcgtaaat tataataaaa ccagtatttg   148260
tagcaagtca aatccgttta ttacagaact taacaataaa tttagtgaga ataatccgtt   148320
tagacgagca catagcgatg attatcttaa taagcaagaa caagatcatg aacacgatga   148380
tatagaatca tcggtcgtat cattggtgtg attagtttcc tttttataaa attgaagtaa   148440
tatttagtat tattgctgcc gtcacgttgt acaaatggag atattccctg tattcggcat   148500
ttctaaaatt agcaatttta ttgctaataa tgactgtaga tattatatag atacagaaca   148560
tcaaaaaatt atatctgatg agatcaatag acagatggat gaaacggtac ttcttaccaa   148620
catcttaagc gtagaagttg taaatgacaa tgagatgtac catcttattc ctcatagatt   148680
atcgacgatt atactctgta ttagttctgt cggaggatgt gttatctcta tagataatga   148740
catcaatgac aaaaatattc taacctttcc cattgatcat gctgtaatca tatccccact   148800
gagtaaatgt gtcgtagtta gcaagggtcc tacaaccata ttggttgtta aagcggatat   148860
acctagcaaa cgattggtaa catcgtttac aaacgacata ctatatgtaa acaatctgtc   148920
actgattaat tatttgccgt tgtctgtatt cattattaga cgagtcaccg actatttgga   148980
tagacacata tgcgatcaga tatttgctaa taataagtgg tattccctta taaccatcga   149040
cgataagcaa tatcctattc catcaaactg tataggtatg tcctctgcca agtacataaa   149100
ttctagcatc gagcaagata cttttaatcca tgtttgtaac ctcgagcatc cgttcgactc   149160
agtatacaaa aaaatgcagt cgtacaattc tctacctatc aaggaacaaa tattgtacgg   149220
tagaattgat aatataaata tgagcattag tatttctgtg gattaataga tttctagtat   149280
ggggatcatt aatcatctct aatctctaaa tacctcataa aacgaaaaaa aagctattat   149340
caaatactgt acggaatgga ttcattctct tctcttttta tgaaactctg ttgtatatct   149400
actgataaaa ctggaagcaa aaaatctgat aaaagaata agaataagat caaggattat   149460
atggaacacg attattataa aataacaata gttcctggtt cctcttccac gtctactagc   149520
tcgtggtatt atacacatgc ctagtaatag tctctttgcg ttgacggaaa gcagactaga   149580
aataacaggc taaatgttc agacaccata atagttccca acccagataa taacagagtt   149640
ccatcaacac attcctttaa actcaatccc aaacccaaaa ccgttaaaat gtatccggcc   149700
aattgatagt agataatgag gtgtacagcg catgataatt tacacagtaa ccaaaatgaa   149760
aacactttag taattataag aaatatagac ggtaatgtca tcatcaacaa tccgataata   149820
tgcctgagag taaacattga tggataaaac aaaaatgctc cgcataactc tatcatggca   149880
ataacacaac caaacacttg taaaattcct aaattagtag aaaatacaac ggatatcgat   149940
gtataagtga tctcgagaaa taataagaat aaagtaatgc ccgtaaagat aaacatcaac   150000
attgtttggt aatcattaaa ccaattagta tgaagttgaa ctaatttcac agtagatttt   150060
attccagtat tatccccgca tgtatacgta cctggtaaga tatctttata ttccataatc   150120
```

```
aatgagacat cactatctga taacgaatga agtctagcac tagtatgcca tttacttaat   150180
attgtcgtct tggaagtttt attataagtt aaaatatcat ggttatccaa tttccatcta   150240
atatactttg tcggattatc tatagtacac ggaataatga tggtatcatt acatgctgta   150300
tactctatgg tctttgtagt tgttataaca accaacgtat agaggtatat caacgatatt   150360
ctaactcttg acattttta tttatttaaa atgatacctt tgttatttat tttattctat   150420
tttgctaacg gtattgaatg gcataagttt gaaacgagtg aagaaataat ttctacttac   150480
ttattagacg acgtattata cacgggtgtt aatggggcgg tatacacatt ttcaaataat   150540
aaactaaaca aaactggttt aactaataat aattatataa caacatctat aaaagtagag   150600
gatgcggata aggatacatt agtatgcgga accaataacg gaaatcccaa atgttggaaa   150660
atagacggtt cagacgaccc aaaacataga ggtagaggat acgctcctta tcaaaatagc   150720
aaagtaacga taatcagtca caacggatgt gtactatctg acataaacat atcaaaagaa   150780
ggaattaaac gatggagaag atttgacgga ccatgtggtt atgatttatt cacggcggat   150840
aacgtaattc caaaagatgg tttacgagga gcattcgtcg ataaagacgg tacttatgac   150900
aaagtttaca ttcttttcac tgatactatc ggctcaaaga gaattgtcaa aattccgtat   150960
atagcacaaa tgtgcttaaa cgacgaaggt ggtccatcat cgttgtctag tcatagatgg   151020
tcgacgtttc tcaaagtcga attagaatgt gatatcgacg gaagaagtta tagacaaatt   151080
attcattcta gaactataaa aacagataat gatacgatac tatatgtatt cttcgatagt   151140
ccttattcca gtccgcatt atgtacctat tctatgaata ccattaaaca atcttttct     151200
acgtcaaaat tggaaggata tacaaagcaa ttgccgtctc cagctcctgg tatatgttta   151260
ccagctggaa aagttgttcc acataccacg tttgaagtca tagaaaaata taatgtacta   151320
gatgatatta taaagccttt atctaaccaa cctatcttcg aaggaccgtc tggtgttaaa   151380
tggttcgata taaggagaa ggaaaatgaa catcgggaat atagaatata cttcataaaa    151440
gaaaattcta tatattcgtt cgatacaaaa tctaaacaaa ctcgtagctc gcaagtcgat   151500
gcgcgactat tttcagtaat ggtaacttcg aaaccgttat ttatagcaga tagggata    151560
ggagtaggaa tgccacaaat gaaaaaaata cttaaaatgt aatcttaatc gagtacacca   151620
cacgacaatg aacaaacata agacagatta tgctggttat gcttgctgcg taatatgcgg   151680
tctaattgtc ggaattattt ttacagcgac actattaaaa gttgtagaac gtaaattagt   151740
tcatacacca tcaatagata aaacgataaa agatgcatat attagagaag attgtcctac   151800
tgactggata agctataata ataaatgtat ccatttatct actgatcgaa aaacctggga   151860
ggaaggacgt aatgcatgca aagctctaaa tccaaattcg gatctaatta agatagagac   151920
tccaaacgag ttaagttttt taagaagcct tagacgcgga tattgggtag gagaatccga   151980
aatattaaac cagacaaccc catataattt tatagctaag aatgccacga agaatggaac   152040
taaaaacgg aaatatattt gtagcacaac gaatactccc aaactgcatt cgtgttacac    152100
tatataacaa ttcactaca ttttatcat accactactt cggttagatg ttttagaaaa    152160
aaataaatat cgccgtaccg ttcttgtttt tataaaaata acaattaaca attatcaaat   152220
ttttctttta atattttacg tggttgacca ttcttggtgg taaaataatc tcttagtgtt   152280
ggaatggaat gctgtttaat gtttccacac tcatcgtata ttttgacgta tgtagtcaca   152340
tcgtttacgc aatagtcaga ctgtagttct atcatgcttc ctacatcaga aggaggaaca   152400
gttttaaagt ctcttggttt taatctatta ccgttagttt tcatgaaatc ctttgtttta   152460
tccacttcac attttaaata aatgtccact atacattctt ttgttaattt tactagatcg   152520
```

```
tcatgggtca tagaatttat aggttccgta gtccatggat ccaaactagc aaacttcgcg   152580
tatacggtat cgcgattagt gtatacacca actgtatgaa aattaagaaa acagtttaat   152640
agatcaacag aaatatttaa tcctccgttt gatacagatg cgccatattt atggatttcg   152700
gattcacacg ttgtttgtct gaggtgttcg tctagtgttg cttctacgta aacttcgatt   152760
cccatatatt ctttattgtc agaatcgcat accgatttat catcatacac tgtttgaaaa   152820
ctaaatggta tacacatcaa aataataaat aataacgagt acattctgca atattgttat   152880
cgtaattgga aaaatagtgt tcgagtgagt tggattatgt gagtattgga ttgtatattt   152940
tattttatat tttgtaataa gaataaaatg ctaatgtcaa gtttattcca atagatgtct   153000
tattaaaaac atatataata aataacaatg gctgaatggc ataaaattat cgaggatatc   153060
tcaaaaaata ataagttcga ggatgccgcc atcgttgatt acaagactac aaagaatgtt   153120
ctagctgcta ttcctaacag aacatttgcc aagattaatc cgggtgaaat tattcctctc   153180
atcactaatc gtaatattct aaaacctctt attggtcaga aatattgtat tgtatatact   153240
aactctctaa tggatgagaa cacgtatgct atggagttgc ttactgggta cgcccctgta   153300
tctccgatcg ttatagcgag aactcatacc gcacttatat ttttgatggg taagccaaca   153360
acatccagac gtgacgtgta tagaacgtgt agagatcacg ctacccgtgt acgtgcaact   153420
ggtaattaaa ataaaagta atattcatat gtagtgtcaa ttttaaatga tgatgatgaa   153480
atggataata tccatattga cgatgtcaat aatgccggta ttggcataca gttcatcgat   153540
ttttagattt cattcagagg atgtggaatt atgttatggg catttgtatt ttgataggat   153600
ctataatgta gtaaatataa aatataatcc gcatattcca tatagatata attttattaa   153660
tcgcacgtta accgtagatg aactagacga taatgtctttt tttacacatg gttattttt   153720 aaaacacaaa tatggttcac ttaatcctag tttgattgtc tcattatcag gaaacttaaa   153780
atataatgat atacaatgct cagtaaatgt atcgtgtctc attaaaaatt tggcaacgag   153840
tacatctact atattaacat ctaaacataa gacttattct ctacatcggt ccacgtgtat   153900
tactataata ggatacgatt ctattatatg gtataaagat ataaatgaca agtataatga   153960
catctatgat tttactgcaa tatgtatgct aatagcgtct acattgatag tgaccatata   154020 cgtgttttaaa aaaataaaaa tgaactctta attatgctat gctattagaa atggataaaa   154080
tcaaaattac ggttgattca aaaattggta atgttgttac catatcgtat aacttggaaa   154140
agataactat tgatgtcaca cctaaaaaga aaaagaaaa ggatgtatta ttagcgcaat   154200
cagttgctgt cgaagaggca aaagatgtca aggtagaaga aaaaaatatt atcgatattg   154260
aagatgacga tgatatggat gtagaaagcg cataatacga tctataaaaa taagtatata   154320 aatactttt atttactgta ctcttactgt gtagtggtga tacccctactc aattattttt   154380 ttaaaaaaat acttattctg attcttctaa ccatttccgt gttcgttcga atgccacatc   154440
gacgtcaaag ataggggagt agttgaaatc tagttctgca ttgttggtac gcacctcaaa   154500
tgtagtgttg gatatcttca acgtatagtt gttgagtagt gatggttttc taaatagaat   154560
tctcttcata tcattcttgc acgcgtacat ttttagcatc catcttggaa ttctagatcc   154620
ttgttctatt cccaatggtt tcatcaatag aagattaaac atatcgtacg aacacgatgg   154680
agagtaatcg tagcaaaagt aagcatttcc tttaatctca gatcccggat actgagatata   154740 ttttgcagcc aacacgtgca tccatgcaac atttcctaca tatacccggc tatgcaccgc   154800
gtcatcatcg actgtacgat acataatgtt accgtgttgc ttacattgct cgtaaaagac   154860
tttcgtcaat ttgtctcctt ctccgtaaat tccagtgggt cttaggcaac aagtatacaa   154920
```

```
ttttgctcca ttcatgatta cggaattatt ggctttcata accagttgct cggccatacg   154980 tttactttt  gcgtatacat gtcctggtga tatatcataa agggtatgct catggccgat   155040
gaatggatca ccgtgtttat tgggtcctat tgcttccatg ctactagtat agatcaaata   155100
cttgattcct aggtccacac aagctgccaa aatagtctgt gttccataat agtttacttt   155160
catgatttca ttatcggtgt attttccaaa tacatccact agagcagccg tatgaataat   155220
cagatttacc ccatctagcg cttctctcac cttatcaaag tcgtttatat cacattgtat   155280
atagtttata accttaactt tcgaggttat tggttgtgga tcttctacaa tatctatgac   155340
tctgatttct tgaacatcat ctgcactaat taacagtttt actatatacc tgcctagaaa   155400
tccggcacca ccagtaaccg cgtacacggc cattgctgcc actcataata tcagactact   155460
tattctattt tactaaataa tggctgtttg tataatagac cacgataata tcagaggagt   155520
tatttacttt gaaccagtcc atggaaaaga taaagtttta ggatcagtta ttggattaaa   155580
atccggaacg tatagtttga taattcatcg ttacggagat attagtcaag gatgtgattc   155640
cataggcagt ccagaaatat ttatcggtaa catctttgta aacagatatg gtgtagcata   155700
tgtttattta gatacagatg taaatatatc tacaattatt ggaaaggcgt tatctatttc   155760
aaaaaatgat cagagattag cgtgtggagt tattggtatt tcttacataa atgaaaagat   155820
aatacatttt cttacaatta acgagaatgg cgtttgatat atcagttaat gcgtctaaaa   155880
caataaatgc attagtttac ttttctactc agcaaaataa attagtcata cgtaatgaag   155940
ttaatgatac acactacact gtcgaatttg atagggacaa agtagttgac acgtttattt   156000
catataataa acataatgac accatagaga taagaggggt gcttccagag gaaactaata   156060
ttggttgcgc ggttaatacg ccggttagta tgacttactt gtataataag tatagtttta   156120
aactgatttt agcagaatat ataagacaca gaaatactat atccggcaat atttattcgg   156180
cattgatgac actagatgat ttggctatta aacagtatgg agacattgat ctattattta   156240
atgagaaact taaagtagac tccgattcgg gactatttga ctttgtcaac tttgtaaagg   156300
atatgatatg ttgtgattct agaatagtag tagctctatc tagtctagta tctaaacatt   156360
gggaattgac aaataaaaaa tataggtgta tggcattagc cgaacatata tctgatagta   156420
ttccaatatc tgagctatct agactacgat acaatctatg taagtatcta cgcggacaca   156480
ctgagagcat agaggataaa tttgattatt ttgaagacga tgattcgtct acatgttctg   156540
ccgtaaccga cagggaaacg gatgtataat tttttttata gcgtgaagga tatgataaaa   156600
aatataattg ttgtatttat cccattctaa tcacctttata tgattctgta acacaataaa   156660
ggagtctcat agatgtatag aggtcagata ctggtttgat aaactgttta ttccacataa   156720
gtatgtttga ctttatggtt agacccgcat actttaacaa atcactgaaa attggagtta   156780
ggtattgacc tctcagaatc agttgccgtt ctggaacatt aaatgtattt tttatgatat   156840
actccaacgc atttatgtgg gcatacaaca agtcattact aatggagtat tccaagagtt   156900
ttagttgtct agtatttaac aagagaagag atttcaacag actgtttatg aactcgaatg   156960
ccgcctcatt gtcgcttata ttgatgatgt cgaattctcc caatatcatc actgatgagt   157020
agctcatctt gttatcggga tccaagtttt ctaaagatgt cattaaaccc tcgatcatga   157080
atggatttat catcatcgtt tttatgttgg acatgagctt agtccgtttg tccacatcta   157140
tagacgacga tttctgaatt atttcatata tccctctctt taactccagg aacttgtcag   157200
gatggtctac tttaatatgt tctcgtctaa gagatgaaaa tctttggatg gttgcacgcg   157260
acttttctct aaaggatgac gttgcccaag atcctctctt aaatgaatcc atcttatcct   157320
```

```
tggacaagat ggacagtcta tttccttag atggtttaat attttgttta ccatgatct    157380 ataaaggtag acctaatcgt ctcggatgac ctatatattt attttcagtt ttattatacg   157440
cataaattgt aaaaaatatg ttaggtttac aaaaatgtct cgtggggcat taatcgtttt   157500
tgaaggattg gacaaatctg gaaaacaac acaatgtatg aacatcatgg aatctatacc    157560
ggcaaacacg ataaaatatc ttaactttcc tcagagatcc actgtcactg gaaagatgat   157620
agatgactat ctaactcgta aaaaaaccta taatgatcat atagttaatc tattatttg    157680 tgcaaataga tgggagtttg catcttttat acaagaacaa ctagaacagg gaattacttt   157740
aatagttgat agatacgcat tttctggagt agcgtatgcc gccgctaaag gcgcgtcaat   157800
gactctcagt aagagttatg aatctggatt gcctaaaccc gacttagtta tattcttgga   157860
atctggtagc aaagaaatta atagaaacgt cggcgaggaa atttatgaag atgttacatt   157920
ccaacaaaag gtattacaag aatataaaaa aatgattgaa gaggagata ttcattggca     157980 aattatttct tctgaattcg aggaagatgt aagaaggag ttgattaaga atatagttat     158040
agaggctata cacacggtta ctggaccagt ggggcaactg tggatgtaat agtgaaatta   158100
cattttttat aaatagatgt tagtacagtg ttataaatgg atgaagcata ttactctggc   158160
aacttggaat cagtactcgg atacgtgtcc gatatgcata ccgaactcgc atcaatatct   158220
caattagtta ttgccaagat agaaactata gataatgata tattaaacaa ggacattgta   158280
aattttatca tgtgtagatc aaacttggat aatccattta tctctttcct agatactgta   158340
tatactatta tagatcaaga gaactatcag actgagttga ttaattcatt agacgacaat   158400
gaaattatcg attgtatagt taataagttt atgagctttt ataaggataa cctagaaaat   158460
atagtagatg ctatcattac tctaaaatat ataatgaata atccagattt taaaactacg   158520
tatgccgaag tactcggttc cagaatagcc gatatagata ttaaacaagt gatacgtaag   158580
aatatactac aattgtctaa tgatatccgc gaacgatatt tgtgaaaaat attaaaaaaa   158640 aatactttt ttattaaatg acgtcgcttc gcgaatttag aaaattatgc tgtgatatat    158700
atcacgcatc aggatataaa gaaaaatcta aattaattag agactttata acagataggg   158760
atgataaata tttgatcatt aagctattgc ttcccggatt agacgataga atttataaca   158820
tgaacgataa acaaattata aaattatata gtataatatt taaacaatct caggaagata   158880
tgctacaaga tttaggatac ggatatatag gagacactat taggactttc ttcaaagaga   158940
acacagaaat ccgtccacga gataaaagca ttttaacttt agaagaagtg gatagttttt   159000
taactacgtt atcatccgta actaaagaat cgcatcaaat aaaattattg actgatgtag   159060
catctgtttg tacatgtaat gatttaaaat gtgtagtcat gcttattgat aaagatctaa   159120
aaattaaagc gggtcctcgg tacgtactta acgctattag tcctcatgcc tatgatgtgt   159180
ttagaaaatc taataacttg aaagagataa tagaaaattc atctaaacaa aatctagact   159240
ctatatctat ttctgttatg actccaatta atcccatgtt agcggaatcg tgtgattctg   159300
tcaataaggc gtttaaaaaa tttccatcag gaatgtttgc ggaagtcaaa tacgatggtg   159360
aaagagtaca agttcataaa aataataacg agtttgcctt ctttagtaga aacatgaaac   159420
cagtactctc tcataaagtg gattatctca agaatacat accgaaagca tttaaaaaag    159480
ctacgtctat cgtattggat tctgaaattg ttcttgtaga cgaacataat gtaccgctcc   159540
cgtttggaag tttaggtata cacaaaaaga aagaatataa aaactctaac atgtgtttgt   159600
tcgtgtttga ctgtttgtac tttgatggat tcgatatgac ggacattcca ttgtacgaac   159660
gaagatcttt tctcaaagat gttatggttg aaataccccaa tagaatagta ttctcagagt   159720
```

```
tgacgaatat tagtaacgag tctcagttaa ctgacgtatt ggatgatgca ctaacgagaa   159780
aattagaagg attggtctta aaagatatta atggagtata cgaaccggga aagagaagat   159840
ggttaaaaat aaagcgagac tatttgaacg agggttccat ggcagattct gccgatttag   159900
tagtactagg tgcttactat ggtaaaggag caaagggtgg tatcatggca gtctttctaa   159960
tgggttgtta cgacgatgaa tccggtaaat ggaagacggt taccaagtgt tcaggacacg   160020
atgataatac gttaagggag ttgcaagacc aattaaagat gattaaaatt aacaaggatc   160080
ccaaaaaaat tccagagtgg ttagtagtta ataaaatcta tattcccgat tttgtagtag   160140
aggatccaaa acaatctcag atatgggaaa tttcaggagc agagtttaca tcttccaagt   160200
cccataccgc aaatggaata tccattagat ttcctagatt tactaggata agagaggata   160260
aaacgtggaa agaatctact catctaaacg atttagtaaa cttgactaaa tcttaatagt   160320
tacatacaaa ctaaaaatta aaataacact atttagttgg tggtcgccat ggatggtgtt   160380
attgtatact gtctaaacgc gctagtaaaa catggcgagg aaataaatca tataaaaaat   160440
gatttcatga ttaaaccatg ttgtgaaaga gtttgtgaaa aagtcaagaa cgttcacatc   160500
gacggacaat ctaaaaacaa tacagtgatt gcagatttgc catatctgga taatgctgta   160560
tccgatgtat gcaaatcgat atatatatag tatcaagaat atccagattt gctaatttga   160620
taaagataga tgacgatgac aagactccta ctggtgtata taattatttt aaacctaaag   160680
atgttattcc tgttatcata tctataggaa aggataaaga tgtctgtgaa ctattaatct   160740
catcagacat atcgtgtgca tgcgtggagt taaattcata tcacgtagcc attcttccca   160800
tggatgtttc ctttttttacc aaaggaaatg catcattgat tattctcctg tttgatttct   160860
ctatcgatgc ggcacctctc ttaagaagtg taaccgataa taatgttatt atatctagac   160920
accagcgtat acatgacgag cttccgagtt ccaattggtt caagttttac ataagtataa   160980
agtccgacta ttgttctata ttatatatgg ttgttgatgg atctgtgatg catgcgatag   161040
ctgataatag aactcacgca attattagca aaaatatatt agacaatact acgattaacg   161100
atgagtgtag atgctgttat tttgaaccac agattaggat tcttgataga atgagatgc    161160 tcaatggatc atcgtgtgat atgaacagac attgtattat gatgaattta cctgatgtag   161220
gcgaatttgg atctagtatg ttggggaaat atgaacctga catgattaag attgctcttt   161280
cggtggctgg taatttaata agaaatcgag actacattcc cgggagacga ggatatagct   161340
actacgttta cggtatagcc tctagataat tttttttaagc acgaaataaa aaacataatt   161400
ttaaaccaat ctatttcata ctattttgtg tgatcaccat ggacataaag atagatatta   161460
gtatttctgg tgataaattt acggtgacta ctaggaggga aaatgaagaa agaaaaaaat   161520
atctacctct ccaaaaagaa aaaactactg atgttatcaa acctgattat cttgagtacg   161580
atgacttgtt agatagagat gagatgttta ctattctaga ggaatatttt atgtacagag   161640
gtctattagg cctcagaata aaatatggac gactctttaa cgaaattaaa aaattcgaca   161700
atgatgcgga agaacaattc ggtactatag aagaactcaa gcagaaactt agattaaatt   161760
ctgaagaggg agcagataac tttatagatt atataaaggt acaaaaacag gatatcgtca   161820
aacttactgt atacgattgc atatctatga taggattgtg tgcatgcgtg gtagatgttt   161880
ggagaaatga gaaactgttt tctagatgga atattgtttt acgagcgatt aaactgttta   161940
ttgatgatca catgcttgat aagataaaat ctatactgca gaatagacta gtgtatgtgg   162000
aaatgtcata gaaagttaaa agttaatgag agcaaaaata tataaggttg tattccatat   162060
ttgttatttt tttctgtaat agttagaaaa atacattcga tggtctatct atcagattat   162120
```

```
tatgtgttat aaggtacttt ttctcataat aaactagagt atgagtaaga tagtgttttt   162180
caaaacatat aaatctaaaa ttgatggatg agatatacag ctattaattt cgaaaatata   162240
ttttaatctg ataactttaa acatggattt ttgatggtgg tttaacgttt taaaaaaaga   162300
ttttgttatt gtagtatatg ataatattaa aagatggata taaagaattt gctgactgta   162360
tgtactattt tttacattac tacattggct acggcagata tacctacttc gtcactgcca   162420
cacgctccgg taaacggggc atgtgacgag ggagaatatc ttgataagag gcataatcaa   162480
tgttgtaatc ggtgtccacc tggagaattt gccaaggtta gatgtaatgg taacgataac   162540
acaaaatgtg aacgctgccc acctcataca tataccgcaa tccccaatta ctctaatgga   162600
tgtcatcaat gtagaaaatg cccaacagga tcatttgata aggtaaagtg taccggaaca   162660
cagaacagta aatgttcgtg tcttcctggt tggtattgcg ctactgattc ttcacagact   162720
gaagattgtc gagattgtat accaaaaagg agatgtccat gcggatactt tggtggaata   162780
gatgaacaag gaaatcctat ttgtaaatcg tgttgtgttg gtgaatattg cgactaccta   162840
cgtaattata gacttgatcc atttcctcca tgcaaactat ctaaatgtaa ttaattatga   162900
ttttgatgat aatgttacca tacattatat cgctacttgg ttagtgtatt attcagtatg   162960
aagacctatt aataattact tatcttttga cgatcttgtt ataattataa tataaaaact   163020
tatggcatag taacttataa ttgctgacgc gataaattcg taataatctg ttttgttcaa   163080
aggaatctac aggcataaaa ataaaaatat aatttataat atactcttac agcgcgccat   163140
catgaataac agcagtgaat tgattgctgt tattaatgga tttagaaata gtggacgatt   163200
ttgtgatatt agtatagtta ttaatgatga aaggataaac gctcataaac tcatcctatc   163260
tggagcctcc gaatattttt ccattctgtt ttccaataat tttatcgatt ctaatgaata   163320
cgaagttaat ctaagtcatt tagattatca aagtgttaac gatttgatcg attatatttc   163380
tgggataccc ttgagcctaa ctaacgataa cgtgaaatat attctttcaa ccgctgatt   163440
tttacaaatt ggatctgcta ttacggagtg tgaaaattac atacttaaaa atctttgttc   163500
tagaaactgt atcgatttct acatatacgc tgataaatat aataacaaga aaatagaatc   163560
agcgtcgttt aacacaatat tacaaaatat tttgagactc atcaacgatg aaaacttaa   163620
atacttaaca gaggaatcaa tgataaaaat tttaagcgat gatatgttaa atataaaaaa   163680
tgaggatttc gccccactaa ttctcattaa atggttagag agtactcaac aaccatgcac   163740
cgtcgagtta cttaaatgcc tcagaatatc attgcttttcc ccacaagtta taaaatcact   163800
ttatagtcat cgactggtta gttcaatcta cgaatgtata acattcttaa acaatatagc   163860
attcttggat gaatcatttc ctagatacca tagcatcgag ttgatatcta tcggtataag   163920
taattcgcat gataagattt ccataaactg ctacaatcat aaaaaaaata catgggaaat   163980
gatatcttca cgtagatata ggtgtagttt cgcagtggcc gtcctggata atattattta   164040
tatgatgggt ggatatgatc agtccccgta tagaagttca aaggttatag cgtacaaatac   164100
atgtacaaat tcttggatat atgatatacc agagctaaaa tatcctcgtt ctaattgtgg   164160
gggactggct gatgacgaat acatttattg tataggcggc atacgcgatc aggattcatc   164220
gttgacatct agtattgata aatggaagcc atcaaaacca tattggcaga agtatgctaa   164280
aatgcgcgaa ccaaaatgtg atatgggggt tgcgatgtta aacggattaa tatatgttat   164340
aggtggaatc gttaaaggtg acacgtgtac cgacgcacta gagagtttat cagaagatgg   164400
atggatgaag catcaacgtc ttccaataaa aatgtccaat atgtcgacga ttgttcatga   164460
tggcaagatt tatatatctg gaggttacaa caatagtagt gtagttaatg taatatcgaa   164520
```

```
tctagtcctt agctataatt cgatatatga tgaatggacc aaattatcat cattaaacat   164580
tcctagaatt aatcccgctc tatggtcagc gcataataaa ttatatgtag gaggaggaat   164640
atctgatgat gttcgaacta atacatctga aacatacgat aaagaaaaag attgttggac   164700
attggataat ggtcacgtgt taccacgcaa ttatataatg tataaatgcg aaccgattaa   164760
acataaatat ccattggaaa aaacacagta cacgaatgat tttctaaagt atttggaaag   164820
ttttataggt agttgataga acaaaataca taattttgta aaaataaatc acttttata    164880 ctaatatgac acgattacca atactttttgt tactaatatc attagtatac gctacacctt  164940
ttcctcagac atctaaaaaa ataggtgatg atgcaactct atcatgtaat cgaaataata   165000
caaatgacta cgttgttatg agtgcttggt ataaggagcc caattccatt attcttttag   165060
ctgctaaaag tgacgtcttg tattttgata attataccaa ggataaaata tcttacgact   165120
ctccatacga tgatctagtt acaactatca caattaaatc attgactgct agagatgccg   165180
gtacttatgt atgtgcattc tttatgacat cgcctacaaa tgacactgat aaagtagatt   165240
atgaagaata ctccacagag ttgattgtaa atacagatag tgaatcgact atagacataa   165300
tactatctgg atctacacat tcaccggaaa ctagttctga gaaacctgat tatatagata   165360
attctaattg ctcgtcggta ttcgaaatcg cgactccgga accaattact gataatgtag   165420
aagatcatac agacaccgtc acatacacta gtgatagcat taatacagta agtgcatcat   165480
ctggagaatc cacaacagac gagactccgg aaccaattac tgataaagaa gaagatcata   165540
cagtcacaga cactgtctca tacactacag taagtcatc atctggaatt gtcactacta    165600
aatcaaccac cgatgatgcg gatcttcatg atacgtacaa tgatacagta ccatcaacta   165660
ctgtaggcgg tagtacaacc tctattagca attataaaac caaggactttt gtagaaatat   165720 ttggtattac cgcattaatt atattgtcgg ccgtggcaat tttctgtatt acgtattata   165780
tatgtaataa acgttcacgt aaatacaaaa cagagaacaa agtctagatt tttgacttac   165840
ataaatgtct gggatagtaa aatctatcat attgagcgga ccatctggtt taggaaagac   165900
agccatagcc aaaagactat gggaatatat ttggatttgt ggtgtcccat accactagat   165960
ttcctcgtcc tatggaacga gaaggtgtcg attaccatta cgttaacaga gaggccatct   166020
ggaagggaat agccgccgga aactttctag aacatactga gttttttagga aatatttacg   166080 gaacttctaa aactgctgtg aatacagcgg ctattaataa tcgtatttgt gtgatggatc   166140
taaacatcga tggcgttaga agtcttaaaa atacgtacct aatgccttac tcggtgtata   166200
taagacctac ctctcttaaa atggttgaga ccaagcttcg ttgtagaaac actgaagcta   166260
acgatgagat tcatcgtcgt gtgatgttgg caaaaactga catggatgag gcaggtgaag   166320
ccggtctatt cgacactatt attattgaag atgatgtgaa tttagcatat agtaagttaa   166380
ttcagatact acaggaccgt attagaatgt atttttaacac taattagaga cttaagactt   166440
aaaacttgat aattaataat ataactcgtt tttatatgtg tctatttcaa cgtctaatgt   166500
attagttaaa tattaaaact taccacgtaa aacttaaaat ttaaaatgat atttcattga   166560
cagatagatc acacattatg aactttcaag gacttgtgtt aactgacaat tgcaaaaatc   166620
aatgggtcgt tggaccatta ataggaaaag gtggatttgg tagtatttat actactaatg   166680
acaataatta tgtagtaaaa atagagccca aagctaacgg atcattattt accgaacagg   166740
cattttatac tagagtactt aaaccatccg ttatcgaaga atggaaaaaa tctcacaata   166800
taaagcacgt aggtcttatc acgtgcaagg catttggtct atacaaatcc attaatgtgg   166860
aatatcgatt cttggtaatt aatagattag gtgcagatct agatgcggtg atcagagcca   166920
```

```
ataataatag actaccaaaa aggtcggtga tgttgatcgg aatcgaaatc ttaaatacca    166980
tacaatttat gcacgagcaa ggatattctc acggagatat taaagcgagt aatatagtct    167040
tggatcaaat agataagaat aaattatatc tagtggatta cggattggtt tctaaattca    167100
tgtctaatgg cgaacatgtt ccatttataa gaaatccaaa taaaatggat aacggtactc    167160
tagaatttac acctatagat tcgcataaag gatacgttgt atctagacgt ggagatctag    167220
aaacacttgg atattgtatg attagatggt tgggaggtat cttgccatgg actaagatat    167280
ctgaaacaaa gaattgtgca ttagtaagtg ccacaaaaca gaaatatgtt aacaatactg    167340
cgactttgtt aatgaccagt ttgcaatatg aacctagaga attgctgcaa tatattacca    167400
tggtaaactc tttgacatat tttgaggaac ccaattacga caagtttcgg cacatattaa    167460
tgcagggtgt atattattaa gtgtggtgtt tggtcgatgt aaaattttttg tcgataaaaa    167520 ttaaaaaata acttaatttta ttattgatct cgtgtgtaca accgaaatca tggcgatgtt    167580
ttacgcacac gctctcggtg ggtacgacga gaatcttcat gcctttcctg gaatatcatc    167640
gactgttgcc aatgatgtca ggaaatattc tgttgtgtta gtttataata acaagtatga    167700
cattgtaaaa gacaaatata tgtggtgtta cagtcaggtg aacaagagat atattggagc    167760
actgctgcct atgtttgagt gcaatgaata tctacaaatt ggagatccga tccatgatca    167820
agaaggaaat caaatctcta tcatcacata tcgccacaaa aactactatg ctctaagcgg    167880
aatcgggtac gagagtctag acttgtgttt ggaaggagta gggattcatc atcacgtact    167940
tgaaacagga aacgctgtat atggaaaagt tcaacatgat tattctacta tcaaagagaa    168000
ggccaaagaa atgaatgcac ttagtccagg acctatcatc gattaccacg tctggatagg    168060
agattgtatc tgtcaagtta ctgctgtgga cgtacatgga aaggaaatta tgaaaatgag    168120
attcaaaaag ggtgcggtgc ttccgatccc aaatctggta aaagttaaac ttggggagaa    168180
tgatacagaa aatctttctt ctactatatc ggcggcacca tcgaggtaac cacctctctg    168240
gaagacagcg tgaataatgt actcatgaaa cgtttggaaa ctatacgcca tatgtggtct    168300
gttgtatatg atcattttga tattgtgaat ggtaaagaat gctgttatgt gcatacgcat    168360
ttgtctaatc aaaatcctat accgagtact gtaaaaacaa atttgtacat gaagactatg    168420
ggatcatgca ttcaaatgga ttccatggaa gctctagagt atcttagcga actgaaggaa    168480
tcaggtggat ggagtcccag accagaaatg caggaatttg aatatccaga tggagtggaa    168540
gacactgaat caattgagag attggtagag gagttcttca atagatcaga acttcaggct    168600
ggtgaatcag tcaaatttgg taattctatt aattgttaaa catacatctg tttcagctaa    168660
gcaactaaga acacgtatac ggcagcagct tccttttata ctctcatctt ttaccaacac    168720
aaagggtgga tatttgttca ttggagttga taataataca cacaaagtat ttggattcac    168780
ggtgggttac gactacctca gactggtaga gaatgatata gaaaagcata tcaaaagact    168840
ttgtgttgtg tatttctgtg agaagaaaga ggacatcaag tacgcgtgtc gattcatcaa    168900
ggtatataaa cctggggatg aggctacctc gacatacgtg tgcgctatca aagtggaaag    168960
atgctgttgt gctgtgtttg cagattggcc agaatcatgg tatatggata ctaatggtat    169020
caagaagtat tctccagatg aatgggtgtc acatataaaa ttttaattaa tgtaatagag    169080
aacaaataat aaggttgtaa tatcatatag acaataacta acaattaatt agtaactgtt    169140
atctcttttt taactaacca actaactata tacctattaa tacatcgtaa ttatagttct    169200
taacatctat taatcattaa ttcgcttcct taatttttta taaactaaca ttgttaattg    169260
aaaagggata acatgttaca gaatataaat tatatatgga tttttttaaa aaggaaatac    169320
```

```
ttgactggag tatatattta tctcttcatt atatagcacg cgtgttttcc aattttttcca    169380
catcccatat aatacaggat tataatctcg ttcgaacata cgagaaagtg gataaaacaa    169440
tagttgattt tttatctagg ttgccaaatt tattccatat tttagaatat ggggaaaata    169500
ttctacatat ttattctatg gatgatgcta atacgaatat tataattttt tttctagata    169560
gagtattaaa tattaataag aacgggtcat ttatacacaa tctcgggtta tcatcatcca    169620
ttaatataaa agaatatgta tatcaattag ttaataatga tcatccagat aataggataa    169680
gactaatgct tgaaaatgga cgtagaacaa gacatttttt gtcctatata tcagatacag    169740
ttaatatcta tatatgtatt ttaataaatc atggatttta tatagatgcc gaagacagtt    169800
acggttgtac attattacat agatgtatat atcactataa gaaatcagaa tcagaatcat    169860
acaatgaatt aattaagata ttgttaaata atggatcaga tgtagataaa aaagatacgt    169920
acggaaacac accttttatc ctattatgta aacacgatat caacaacgtg gaattgtttg    169980
agatatgttt agagaatgct aatatagact ctgtagactt taatagatat acacctcttc    170040
attatgtctc atgtcgtaat aaatatgatt ttgtaaagtt attaatttct aaaggagcaa    170100
atgttaatgc gcgtaataaa ttcggaacta ctccatttta ttgtggaatt atacacggta    170160
tctcgcttat aaaactatat ttggaatcag acacagagtt agaaatagat aatgaacata    170220
tagttcgtca tttaataatt tttgatgctg ttgaatcttt agattatcta ttatccagag    170280
gagttattga tattaactat cgtactatat acaacgaaac atctatttac gacgctgtca    170340
gttataatgc gtataatacg ttggtctatc tattaaacag aaatggtgat tttgagacga    170400
ttactactag tggatgtaca tgtatttcgg aagcagtcgc aaacaacaac aaaataataa    170460
tggaagtact attgtctaaa cgaccatctt tgaaaattat gatacagtct atgatagcaa    170520
ttactaaaca taaacagcat aatgcagatt tattgaaaat gtgtataaaa tatactgcgt    170580
gtatgaccga ttatgatact cttatagatg tacagtcgct acagcaatat aaatggtata    170640
ttttaaaatg tttcgatgaa atagatatca tgaagagatg ttatataaaa aataaaactg    170700
tattccaatt agttttttgt atcaaagaca ttaatacttt aatgagatac ggtaaacatc    170760
cttctttcgt gaaatgcact agtctcgacg tatacggaag tcgtgtacgt aatatcatag    170820
catctattag atatcgtcag agattaatta gtctattatc caagaagctg gatcctggag    170880
ataaatggtc gtgttttcct aacgaaataa aatataaaat attggaaaac tttaacgata    170940
acgaactatc cacatatcta aaaatcttat aaacactatt aaaatataaa atctaagtag    171000
gataaaatca cactacatca ttgtttcctt ttagtgctcg acagtgtata ctatttttaa    171060
cgctcataaa taaaaatgaa aacgatttcc gttgttacgt tgttatgcgt actacctgct    171120
gttgtttatt caacatgtac tgtacccact atgaataacg ctaaattaac gtctaccgaa    171180
acatcgttta atgataaaca gaaagttaca tttacatgtg atcagggata tcattcttcg    171240
gatccaaatg ctgtctgcga aacagataaa tggaaatacg aaaatccatg caagaaaatg    171300
tgcacagttt ctgattacat ctctgaacta tataataaac cgctatacga agtgaattcc    171360
accatgacac taagttgcaa cggcgaaaca aaatattttc gttgcgaaga aaaaaatgga    171420
aatacttctt ggaatgatac tgttacgtgt cctaatgcgg aatgtcaacc tcttcaatta    171480
gaacacggat cgtgtcaacc agttaaagaa aaatactcat ttggggaata tatgactatc    171540
aactgtgatg ttggatatga ggttattggt gcttcgtaca taagttgtac agctaattct    171600
tggaatgtta ttccatcatg tcaacaaaaa tgtgatatgc cgtctctatc taacggatta    171660
atttccggat ctacatttttc tatcggtggc gttatacatc ttagttgtaa aagtggtttt    171720
```

```
acactaacgg ggtctccatc atccacatgt atcgacggta aatggaatcc cgtactccca   171780
acatgtgtac gaactaacga aaaatttgat ccagtggatg atggtcccga cgatgagaca   171840
gatttgagca aactctcgaa agacgttgta caatatgaac aagaaataga atcgttagaa   171900
gcaacttatc atataatcat agtggcgttg acaattatgg gcgtcatatt tttaatctcc   171960
gttatagtat tagtttgttc ctgtgacaaa ataatgacc aatataagtt ccataaattg    172020
ctaccgtgaa tataaatccg ttaaaataat taataattta ataacaaaca agtatcaaaa   172080
gattaaagac ttatagctag aatcaattga gatgtcttct tcagtggatg ttgatatcta   172140
cgatgccgtt agagcatttt tactcaggca ctattataac aagagattta ttgtgtatgg   172200
aagaagtaac gccatattac ataatatata caggctattt acaagatgcg ccgttatacc   172260
gttcgatgat atagtacgta ctatgccaaa tgaatcacgt gttaaacaat gggtgatgga   172320
tacacttaat ggtataatga tgaatgaacg cgatgtttct gtaagcgttg gcaccggaat   172380
actattcatg gaaatgtttt tcgattacaa taaaaatagt atcaacaatc aactaatgta   172440
tgatataatt aatagcgtat ctataattct agctaatgag agatatagaa gcgcttttaa   172500
cgacgatggt atatacatcc gtagaaatat gattaacaag ttgtacggat acgcatctct   172560
aactactatt ggcacgatcg ctggaggtgt ttgttattat ctgttgatgc atctagttag   172620
tttgtataaa taattatttc aatatactag ttaaaatttt aagattttaa atgtataaaa   172680
aactaataac gttttatttt gtaataggtg cattagcatc ctattcgaat aatgagtaca   172740
ctccgtttaa taaactgagt gtaaaactct atatagatgg agtagataat atagaaaatt   172800
catatactga tgataataat gaattggtgt taaatttta agagtacaca atttctatta    172860
ttacagagtc atgcgacgtc ggatttgatt ccatagatat agatgttata aacgactata   172920
aaattattga tatgtatacc attgactcgt ctactattca acgcagaggt cacacgtgta   172980
gaatatctac caaattatca tgccattatg ataagtaccc ttatattcac aaatatgatg   173040
gtgatgagcg acaatattct attactgcag agggaaaatg ctataaagga ataaaatatg   173100
aaataagtat gatcaacgat gatactctat tgagaaaaca tactcttaaa attggatcta   173160
cttatatatt tgatcgtcat ggacatagta atacatatta ttcaaaatat gatttttaaa   173220
aatttaaaat atattatcac ttcagtgaca gtagtcaaat aacaaacaac accatgagat   173280
atattataat tctcgcagtt ttgttcatta atagtataca tgctaaaata actagttata   173340
agtttgaatc cgtcaatttt gattccaaaa ttgaatggac tggggatggt ctatacaata   173400
tatcccttaa aaattatggc atcaagacgt ggcaaacaat gtatacaaat gtaccagaag   173460
gaacatacga catatccgca tttccaaaga atgatttcgt atctttctgg gttaaatttg   173520
aacaaggcga ttataaagtg gaagagtatt gtacgggact atgcgtcgaa gtaaaaattg   173580
gaccaccgac tgtaacatta actgaatacg acgaccatat caatttgtac atcgagcatc   173640
cgtatgctac tagaggtagc aaaaagattc ctatttacaa acgcggtgac atgtgtgata   173700
tctacttgtt gtatacggct aacttcacat tcggagattc taaagaacca gtaccatatg   173760
atatcgatga ctacgattgc acgtctacag gttgcagcat agactttgtc acaacagaaa   173820
aagtgtgcgt gacagcacag ggagccacag aagggtttct cgaaaaaatt actccatgga   173880
gttcgaaagt atgtctgaca cctaaaaaga gtgtatatac atgcgcaatt agatccaaag   173940
aagatgttcc caatttcaag gacaaaatgg ccagagttat caagagaaaa tttaataaac   174000
agtctcaatc ttatttaact aaaatttctcg gtagcacatc aaatgatgtt accactttc    174060
ttagcatgct taacttgact aaaatattcat aactaatttt tattaatgat acaaaaacga   174120
```

```
aataaaactg catattatac actggttaac gcccttatag gctctaacca ttttcaagat   174180
gaggtccctg attatagtcc ttctgttccc ctctatcatc tactccatgt ctattagacg   174240
atgtgagaag actgaagagg aaacatgggg attgaaaata gggttgtgta taattgccaa   174300
agatttctat cccgaaagaa ctgattgcag tgttcatctc ccaactgcaa gtgaaggatt   174360
gataactgaa ggcaatggat tcagggatat acgaaacacc gataaattat aaaaaaagca   174420
atgtgtccgc tgtttccgtt aataatacta tttttgtaac tggcgaatta ttcataaata   174480
actctaatag cacgatcgtg gttaacaata tggaaaaact tgacatttat aaagacaaac   174540
aatggtcgat tatagaaatg cctatggcta gggtatatca cggcatcgac tcgacatttg   174600
gaatgttata ttttgccgga ggtctatccg ttaccgaaca atatggtaat ttagagaaaa   174660
acaacgagat atcttgttac aatcctagaa cgaataagtg gtttgatatt tcatatacta   174720
tttataagat atccatatca tcattgtgta aactaaataa cgtcttctat gtatttagta   174780
aggacattgg atatgtggaa aagtatgatg gtgcacggaa gttagtacat gatcgtctcc   174840
ccgctataaa ggcattatca acttctcctt attgattgaa aatgaaaata taaatagttt   174900
ttatgcatag cagtattacc ctatagtttt attgcttact actaacatgg atacagatgt   174960
tacaaatgta gaagatatca taaatgaaat agatagagag aaagaagaaa tactaaaaaa   175020
tgtagaaatt gaaataaata aaaacattaa caagaatcat ccaagtggat atattagaga   175080
agcactcgtt attaatacca gtagtaatag tgattccatt gataaagaag ttatagaatg   175140
tatcagtcac gatgtaggaa tatagatcat atctactaat ttttataatc gatacaaaac   175200
ataaaaaaca actcgttatt acatagcagg catggaatcc ttcaagtatt gttttgataa   175260
cgatggcaag aaatggatta tcggaaatac tttatattct ggtaattcaa tactctataa   175320
ggtcagaaaa aatttcacta gttcgttcta caattacgta atgaagatag atcacaaatc   175380
acacaagcca ttgttgtctg aaatacgatt ctatatatct gtattggatc ctttgactat   175440
cgacaactgg acacgggaac gtggtataaa gtatttggct attccagatc tgtatggaat   175500
tggagaaacc gatgattata tgttcttcgt tataaagaat ttgggaagag tattcgcccc   175560
aaaggatact gaatcagtct tcgaagcatg cgtcactatg ataaacacgt tagagtttat   175620
acactctcaa ggatttaccc atggaaaaat agaaccgagg aatatactga ttagaaataa   175680
acgtcttttca ctaattgact attctagaac taacaaacta tacaagagtg gaaactcaca   175740
tatagattac aacgaggaca tgataacttc aggaaatatc aattatatgt gtgtagacaa   175800
tcatcttgga gcaacagttt caagacgagg agatttagaa atgttgggat attgcatgat   175860
agaatggttc ggtggcaaac ttccatggaa aaacgaaagt agtataaaag taataaaaca   175920
aaaaaaagaa tataaaaaat ttatagctac tttctttgag gactgttttc ctgaaggaaa   175980
tgaacctctg gaattagtta gatatataga attagtatac acgttagatt attctcaaac   176040
tcctaattat gacagactac gtaaactgtt tatacaagat tgaaattata ttcttttttt   176100
tatagagtgt ggtagtgtta cggatattta atattagact atctctatcg cgctacacga   176160
ccaatatcga ttactatgga tatcttctat gaaaggagag aatgtattca tttctccagc   176220
gtcaatctcg tcagtattga caatactgta ttatggagct aatggatcca ctgctgaaca   176280
gctatcgaaa tatgtagaaa aggaggagaa cacggataag gttagcgctc aaaatatctc   176340
attcaaatcc ataaataaag tatatgggcg atattctgcc gtgtttaaag atttcttttt   176400
gggaaaaatt ggcgataagt ttcaaactgt tgacttcact gattgtcgca ctatagatgc   176460
aatcaacaag tgtgtagata tctttactga ggggaaaatc aatccactat tggatgaacc   176520
```

```
attgtctcct agcaattagt gccgtatact ttaaagcaaa atggttgacg ccattcgaaa    176580
aggaatttac cagtgattat ccctttacg tatctccgac ggaaatggta gatgtaagta    176640
tgatgtctat gtacggcgag ctatttaatc acgcatctgt aaaagaatca ttcggcaact   176700
tttcaatcat agaactgcca tatgttggag atactagtat gatggtcatt cttccagaca   176760
agattgatgg attagaatcc atagaacaaa atctaacaga tacaaatttt aagaaatggt   176820
gtgactttat ggatgctatg tttatagatg ttcacattcc caagtttaag gtaacaggtt   176880
cgtataatct ggtggatact ctagtaaagt caggactgac agaggtgttc ggttcaactg   176940
gagattatag caatatgtgt aatttagatg tgagtgtcga cgctatgatc cacaaaacgt   177000
atatagatgt caatgaagag tatacagaag cagctgcagc aacttctgta ctagtggcag   177060
actgtgcatc aacagttaca aatgagttct gtgcagatca tccgttcatc tatgtgatta   177120
ggcatgttga tggcaaaatt cttttcgttg gtagatattg ctctccaaca actaattgtt   177180
aaccatttt tttaaaaaaa tagaaaaaac atgtggtatt agtgcaggtc gttgttcttc    177240
caattgcaat tggtaagatg acggccaact ttagtaccca cgtcttttca ccacagcact   177300
gtggatgtga cagactgacc agtattgatg acgtcaaaca atgtttgact gaatatattt   177360
attggtcgtc ctatgcatac cgcaacaggc aatgcgctgg acaattgtat tccacactcc   177420
tctcttttag agatgatgcg gaattagtgt tcatcgacat tcgcgagctg gtaaaaaata   177480
tgccgtggga tgatgtcaaa gattgtacag aaatcatccg ttgttatata ccggatgagc   177540
aaaaaaccat cagagagatt tcggccatca tcggactttg tgcatatgct gctacttact   177600
ggggaggtga agaccatccc actagtaaca gtctgaacgc attgtttgtg atgcttgaga   177660
tgctaaatta cgtggattat aacatcatat tccggcgtat gaattgatga gttgtacatc   177720
ttgacatttt ctttcttctc ttctcccttt cttctcttct cccttcctcc ctcttctccc   177780
tttcccagaa acaaactttt ttacccacta taaaataaaa tgagtatact acctgttata   177840
tttcttccta tattttttta ttcttcattc gttcagactt taacgcgcc tgaatgtatc    177900
gacaaagggc aatattttgc atcattcatg gagttagaaa acgagccagt aatcttacca   177960
tgtcctcaaa taaatacgct atcatccgga tataatatat tagatatttt atgggaaaaa   178020
cgaggagcgg ataatgatag aattataccg atagataatg gtagcaatat gctaattctg   178080
aacccgacac aatcagactc tggtatttat atatgcatta ccacgaacga aacctactgt   178140
gacatgatgt cgttaaattt gacaatcgtg tctgtctcag aatcaaatat agatcttatc   178200
tcgtatccac aaatagtaaa tgagagatct actggcgaaa tggtatgtcc caatattaat   178260
gcatttattg ctagtaacgt aaacgcagat attatatgga gcggacatcg acgccttaga   178320
aataagagac ttaaacaacg gacacctgga attattacca tagaagatgt tagaaaaaat   178380
gatgctggtt attatacatg tgttttagaa tatatataca gaggtaaaac atataacgta   178440
accagaattg taaaattaga ggtacgggat aaaataatac cttctactat gcaattacca   178500
gatggcattg taacttcaat aggtagtaat ttgactattg cgtgtagagt atcgttgaga   178560
cctcccacaa cggatgcaga cgtcttttgg ataagtaatg gtatgtatta cgaagaagat   178620
gatggggacg gaaacggtag aataagtgta gcaaataaaa tctatatgac cgataagaga   178680
cgtgttatta catcccggtt aaacattaat cctgtcaagg aagaagatgc tacaacgttt   178740
acgtgtatgg cgtttactat tcctagcatc agcaaaacag ttactgttag tataacgtga   178800
atgtatgttg ttcatttcc atgtcaattg agttttataag aatttttata cattatcttc   178860
caacaaacaa ttgacgaacg tattgctatg attaactccc acgatactat gcatattatt   178920
```

```
aatcattaac ttgcagacta tacctagtgc tattttgaca tactcatgtt cttgtgtaat   178980
tgcggtatct atattattaa agtacgtaaa tctagctata gttttattat ttaattttag   179040
ataatatacc gtctccttat ttttaaaaat tgccacatcc tttattaaat catgaatggg   179100
aatttctatg tcatcgttag tatattgtga acaacaagag cagatatcta taggaaaggg   179160
tggaatgcga tacattgatc tatgtagttt taaaacacac gcgaactttg aagaatttat   179220
ataaatcatt ccatcgatac atccttctat gttgacatgt atatatccag gaattctttt   179280
attaatgtca ggaaatgtat aaactaaaac attgcccgaa agcggtgcct ctatctgcgt   179340
tatatccgtt cttaacttac aaaatgtaac caatacttt gcatgacttg ttttgttcgg   179400
caacgttagt ttaaacttga cgaatggatt aattacaata gcatgatccg cgcatctatt   179460
aagttttttt actttaacgc ccttgtatgt ttttacagag actttatcta aatttctagt   179520
gcttgtatgt gttataaata taacgggata tagaactgaa tcacctacct tagatacccca  179580 attcatttt atcagatcca gataataaac aaattttgtc gccctaacta attctatatt   179640
gttatatatt ttacaattgg ttatgatatc atgtaataac ttggagtcta acgcgcatcg   179700
tcgtacgttt atacaattgt gatttagtgt agtatatcta cacatgtatt tttccgcact   179760
atagtattct ggactagtga taaaactatc gttatatctg tcttcaatga actcatcgag   179820
atattgctct ctgtcatatt catacacctg cataaacttt ctagacatct tacaatccgt   179880
gttattttag gatcatattt acatatttac gggtatatca aagatgttag attagttaat   179940
gggaatcgtc tataataatg aatattaaac aattatatga ggactttac cacaaagcat    180000 cataaaaatg agtcgtcgtc tgatttatgt tttaaatatc aaccgcgaat caactcataa   180060
aatacaagag aatgaaatat atacatattt tagtcattgc aatatagacc atacttctac   180120
agaacttgat tttgtagtta aaaactatga tctaaacaga cgacaacctg taactgggta   180180
tactgcacta cactgctatt tgtataataa ttactttaca aacgatgtac tgaagatatt   180240
attaaatcat ggagtggatg taacgatgaa aaccagtagc ggacgtatgc ctgtttatat   180300
attgcttact agatgttgca atatttcaca tgatgtagtg atagatatga tagacaaaga   180360
taaaaaccac ttattacata gagactattc caacctatta ctagagtata aaaatctcg   180420 ttacatgtta ttaaggaag aggatatcga tgagaacata gtatccactt tattagataa   180480
gggaatcgat cctaacttta aacaagacgg atatacagcg ttacattatt attatttgtg   180540
tctcgcacac gtttataaac caggtgagtg tagaaaaccg ataacgataa aaaaggccaa   180600
gcgaattatt tctttgttta tacaacatgg agctaatcta aacgcgttag ataattgtgg   180660
taatacacca ttccatttgt atcttagtat tgaaatgtgt aataatattc atatgactaa   180720
aatgctgttg acttttaatc cgaatttcga aatatgtaat aatcatggat taacgcctat   180780
actatgttat ataacttccg actacataca acacgatatt cttgttatgt taatacatca   180840
ctatgaaaca aatgttggag aaatgccgat agatgagcgt cgtatgatcg tattcgagtt   180900
tatcaaaaca tattctacac gtccggcaga ttcgataact tatttgatga ataggtttaa   180960 aaatatat atttataccc gctatgaagg aaagacatta ttacacgtag catgtgaata    181020
taataataca cacgtaatag attatcttat acgtatcaac ggagatataa atgcgttaac   181080
cgacaataac aaaacacgcta cacaactcat tatagataac aaagaaaatt ccccatatac   181140
cattaattgt ttactgtata tacttagata tattgtagat aagaatgtga taagatcgtt   181200
ggtggatcaa cttccatctc taccctatctt tcgtcgctta tcatactagt catatcctaa   181260
atgttgatca tattccacca aatgattgtg aaagagattg agattaaatc gtctaacaaa   181320
```

-continued

```
caattagttt ttatgacatt aacatataat aaataaatta atcattattg acttaacgat  181380
gacgaaagtt atcatcatct taggattctt gattattaat acaaattcat tgtctatgaa  181440
atgtgaacaa ggtgtctcat attataattc acaagaatta aagtgttgta aactatgtaa  181500
gccaggaaca tattcagatc atcgatgtga taaatacagc gataccattt gtggacattg  181560
tccgagtgac acattcacgt caatatataa tcgttctcct tggtgtcata gttgtagagg  181620
tccatgtggt actaatcgag tagaggtcac accttgtaca cctaccacaa atagaatctg  181680
tcattgtgac tcgaatagtt attgtctcct taaagcttct gatggtaact gtgttacatg  181740
tgctcctaaa acaaaatgtg gtcgtgggta tggaaaaaaa ggagaagatg aaatgggtaa  181800
taccatttgt aagaaatgtc ggaagggtac ttattcagat attgtatctg actctgatca  181860
atgtaaacca atgacaagat aagacttact cgcatctact ggatagacat aaaatatcct  181920
cctcgtaata atgaaatata aatatacact aattattaat atcaataaca atcgagtatt  181980
aatatatagg tcatttttaa atcccttttg ggttccgtcc caaacggcgt ttcggtctgc  182040
gtcgccgcca tggccatgcc gagcctctcc gcgtgctcct ccatcgagga cgacttcaac  182100
tatggcagct cggtggcgtc tgccagcgtg cacatacgaa tggcatttct aagaaaagtc  182160
tacggtatcc tttgtctaca atttctttta acaacggcaa caactgcagt attttatac   182220 tttgactgca tgcggacatt tatacaaggg agtcctgttc taatattggc atcaatgttc  182280
ggatctatag gcttgatttt cgcattgact ttacacagac ataaacatcc cctgaatctg  182340
tacctgcttt gtggatttac actgtcggaa tctctaacgc tggcctctgt tgttactttc  182400
tatgatgtgc atgtcgttat gcaagctttc atgctgacta ctgcagcgtt tcttgctctg  182460
actacatata ctctacaatc aaagagagat ttcagtaaac ttggagcagg attgtttgct  182520
gctttgtgga ttttaatttt gtcaggactc ttggggatat ttgtgcaaaa tgagacagtg  182580
aagctggtcc tgtctgcttt tggggcccTt gtattctgtg gattcattat ctatgacacg  182640
cactcactaa tacataagct ctcgcctgaa gagtatgtgt tagcctctat caatctctac  182700
ttggatatca tcaatctgtt cttgcatctg ttgcagcttt tggaagtatc taataagaaa  182760
taaagtttaa aatagaatta ataaaaacat ataggtcatt ttttaaacat ggattggaaa  182820
ccaaggtagt tagttaatac acacaagata tattttttc acatcatcca cccatgggta   182880
acaccaaggt tgttagttaa taatatacaa gatattttt ctcactctga tccatgtaaa   182940
ccaaggacga gataagacac tctcattcct catccacaac ccattaaaaa aatggaaatt  183000
aaagccctct attagcataa acggctacag gtctaccatc aggttaacct tcgtctacct  183060
tcacaatggc ctctccttgt gccaagttca gaccctgtca ttgccacgct actaaggact  183120
ccctgaatac cgtggccgac gtcagacatt gtctgactga atacatcctg tgggtttctc  183180
atagatggac ccatagagaa agcgcagggt ctctctacag gcttctcatc tctttcagaa  183240
ctgatgcaac ggagctcttt ggtggtgagt tgaaggattc acttccgtgg gacaattgcg  183300
tggagatcat taaatgtttc atcagaaatg actccatgaa aaccgccgaa gaacttcgtg  183360
caatcattgg actttgtact caatcagcta tcgtctctgg aagagtcttc aacgataagt  183420
atatcgacat actacttatg ctgcgaaaga ttctgaacga gaacgactat ctcaccctct  183480
tggatcatat ccgcactgct aaatactaaa tctccttcat gctctctcac tacactttt   183540 atcatcttat gaggaatgat tgccttcgtg aaataggaat aattagcacc agaatagcta  183600
tggattattg tggtagagag tgcactattt tatgtcgtct actggatgaa gatgtgacgt  183660
acaaaaaaat aaaaccagag attgaaacgt gtcacaactt atcaaaacat atagatagac  183720
```

```
gaggaaacaa tgcgctacat tgttacgtct tcaataaatg cgatacagac attaagattg   183780
ttcggctgtt actctctcgc ggagtcgaga gactttgtag aaacaacgaa ggattaactc   183840
cgctaggagc atacagtaag catagatacg tcaaatctca gattgtgcat ctactgatat   183900
ccagctattc gaattcctct aacgaactca agtcgaatat aaatgatttc gatctgtatt   183960
cggataatat cgacttacgt ctgctaaaat acctaattgt ggataaacgg atacgtccgt   184020 ccaagaaatac gaattatgca atcaatggtc tcggattggt ggatatatac gtaacgacgc   184080
ctaatccgag accagaagta ttgctatggc ttcttaaatc agaatgttac agcaccggtt   184140
acgtatttcg tacctgtatg tacgacagtg atatgtgtaa gaactctctt cattactata   184200
tatcgtctca tagagaatct caatctctat ccaaggatgt aattaaatgt ttgatcgata   184260
acaatgtttc catccatggc agagacgaag gaggatcttt acccatccaa tactactggt   184320
cttgctcaac catagatata gagattgtta aattattaat aaaggatgtg gacacgtgta   184380
gagtatacga cgtcagccct atattagagg cgtattatct aaacaagcga tttagagtaa   184440
ccccatataa tgtagacatg gaaatcgtta atcttcttat tgagagacgt catactcttg   184500
tcgacgtaat gcgtagtatt acttcgtacg attccagaga atataaccac tacatcatcg   184560
ataacattct aaagagattt agacaacagg atgtacaagc catgttgata aactacttac   184620
attacggcga tatggtaagt atacctatca ttcaatgcat gttggataac ggagcaacca   184680
tggataagac gacggacaac aactatcctc tgcacgacta ctttgttaat aataatctcg   184740
tcgatgtaaa cgtcgtaagg tttatcgtgg aaaatatgga cacgcggctg taaatcacat   184800
atcgaacaat ggccgtctat gtatgtacgg tctgatatta tcgagattta ataattgcgg   184860
gtatcactgt tatgaaacca tactgataga tgtatttgat atactaagca agtcatgga   184920 tgatatagat atgatcgata actctactat attacgcggt cgatgtcaat aatatacaat   184980
ttgcaaagcg gttattggaa tatggagcga gtgtcacgct cgataatcaa tacggccatc   185040
cagaaaagca gttacagaag agaaaacaaa acgaagctag ttgatttatt actgagttac   185100
catcccactc tagagactat gattgacgca tttaatagag atatacgcta tctatatcct   185160
gaaccattat tcgcctgtat cagatacgcc ttaatcctag atgatgattt tccttctaaa   185220
gtaaagtatg atatcgccgg tcgtcataag gaactaaagc gctatagagc agacattaat   185280
agaatgaaga atgtctacat atcaggcgtc tccatgtttg atatattatt taaacgaagc   185340
aaacgccaca gattgagata cgcaaagaat ccgacatcaa atggtacaaa aaagaactaa   185400
cgtccatcat tacagaaact gtaaagaaca atgagaggat cgactccata gtggacaaca   185460
ttaatacaga cgataacttg atttcgaaat tacccatgga gatactttat tactccatta   185520
aataatttat catggagcga taatgtcctg tttcatttgt ttccatgaca tattacaaaa   185580
tcgattccgt ccaagatgat aaaaacattt accggcatca taaacacgga gtttatttta   185640
tatgtctcgc ataaacatta ctaaaaaaat atattgttct gttttcttt tcttttttct   185700 ttttctttcg tacatctcta attatgaaaa agtaaatcat tatgagatgg acgagattgt   185760
acgcatcgtt cgcgatagta tgtggtttat acctaacgta tttatggacg acggtaagaa   185820
tgaaggtcac gtttctgtca acaatgtctg tcatatgtat ttcacgttct ttgatgtgga   185880
tacatcgtct catctgtttta agctagttat taaacactgc gatctgaata acgaggtaa   185940 ctctccatta cattgctata cgatgaatac acgatttaat ccatctgtat taaagatatt   186000
gttacaccac ggcatgcgta actttgatag caaggatgac cactatcaat cgataacaag   186060
atctttgata tactaacgga caccattgat gactttagta aatcatccga tctattgctg   186120
```

```
tgttatctta gatataaatt caatgggagc ttaaactatt acgttctgta caaggatcc   186180
gaccctaatt gcgccgacga ggatgaactc acttctcttc attactactg taaacacata  186240
tccacgttct acgaaagcaa ttattacaag ttaagtcaca ctaagatgcg agccgagaag  186300
cgattcatct acgcgataat agattatgga gcaaacatta acgcggttac acacttacct  186360
tcaacagtat accaaacata gtcctcgtgt ggtgtatgct cttttatctc gaggatacgt  186420
aataatcttg attgtacacc catcatggaa cgattgtgca acaggtcata ttctcataat  186480
gttactcaat tggcacgaac aaaaggaaga aggacaacat ctactttatc tattcataaa  186540
acataatcaa ggatacactc tcaatatact acggtatcta ctagataggt tcgacattca  186600
gaaagacgaa tactataata ccgcctttca aaattgtaac aacaatgttg cctcatacat  186660
cggatacgac atcaaccttc cgactaaaga cggtattcga cttggtgttt gaaaacagaa  186720
acatcatata caaggcggat gttgtgaatg acatcatcca ccacagactg aaagtatctc  186780
tacctatgat taaatcgttg ttctacaaga tgtctctccc tacgacgatt actacgtaaa  186840
aaagatacta gcctactgcc tattaaggga cgagtcattc gcggaactac atagtaaatt  186900
ctgtttaaac gaggactata aaagtgtatt tatgaaaaat atatcattcg ataagataga  186960
ttccatcatc gtgacataag tcgccttaaa gagattcgaa tctccgacac cgacctgtat  187020
acggtatcac agctatctta aagccataca ttcggacaga cacatttcat ttcccatgta  187080
cgacgatctc atagaacagt gccatctatc gatggagcgt aaaagtaaac tcgtcgacaa  187140
agcactcaat aaattagagt ctaccatcgg tcaatctaga ctatcgtatt tgcctccgga  187200
aattatgcgc aatatcatct aaacagtatg ttgtacggaa agaaccatta caaatattat  187260
ccatgataga aagaaaatat ctatatgatt ggagaagtag gaaacaggaa caagacgacg  187320
attactacat tattaaatca tgaagtccgt attatactcg tatatattgt ttctctcatg  187380
tataataata aacggaagag atatagcacc gcatgcacca tccgatggaa agtgtaaaga  187440
caacgaatac aaacgccata atttgtgtcc gggaacatac gcttccagat tatgcgatag  187500
caagactaac acacaatgta cgccgtgtgg ttcgggtacc ttcacatctc gcaataatca  187560
tttacccgct tgtctaagtt gtaacggaag acgcgatcgt gtaacacgac tcacaataga  187620
atctgtgaat gctctcccgg atattattgt cttctcaaag gatcatccgg atgcaaggca  187680
tgtgttccc aaacaaaatg tggaatagga tacgagtat ccggagacgt catctgttct   187740
ccgtgtggtc tcggaacata ttctcacacc gtctcttccg cagataaatg cgaacccgta  187800
cccagaaata cctttaacta tatcgatgtg gaaattaacc tgtatccagt taacgacaca  187860
tcgtgtactc ggacgaccac taccggtctc agcgaatcca tctcaacgtc ggaactaact  187920
attactatga atcataaaga ctgtaatccc gtctttcgtg aggaatactt ctccgtcctt  187980
aataaggtag caacttcagg tttctttaca ggagaaaggt gtgcactctg aatttcgaga  188040
ttaaatgcaa taacaaagat tcttcctcca aacagttaac gaaagcaaag aatgatacta  188100
tcatgccgca ttcggagaca gtaactctag tgggcgacat ctatatacta tatagtaata  188160
ccaatactca agactacgaa actgatacaa tctcttatca tgtgggtaat gttctcgatg  188220
tcgatagcca tatgcccggt agttgcgata tacataaact gatcactaat tccaaaccca  188280
cccactttt atagtaagtt tttcacccat aaataataaa tacaataatt aatttctcgt   188340
aaaagtagaa aatatattct aatttattgc acggtaagga agtagaatca taaagaacag  188400
tactcaatca atagcaatta tgaaacaata tatcgtcctg gcatgcatgt gcctggcggc  188460
agctgctatg cctgccagtc ttcagcaatc atcctcatcc tcctcctcgt gtacggaaga  188520
```

```
agaaaacaaa catcatatgg gaatcgatgt tattatcaaa gtcacaaagc aagaccaaac    188580
accgaccaat gataagattt gccaatccgt aacggaaatt acagagtccg agtcagatcc    188640
agatcccgag gtggaatcag aagatgattc cacatcagtc gaggatgtag atcctcctac    188700
cacttattac tccatcatcg gtggaggtct gagaatgaac tttggattca ccaaatgtcc    188760
tcagattaaa tccatctcag aatccgctga tggaaacaca gtgaatgcta gattgtccag    188820
cgtgtcccca ggacaaggta aggactctcc cgcgatcact catgaagaag ctcttgctat    188880
gatcaaagac tgtgaggtgt ctatcgacat cagatgtagc gaagaagaga aagacagcga    188940
catcaagacc catccagtac tcgggtctaa catctctcat aagaaagtga gttacgaaga    189000
tatcatcggt tcaacgatcg tcgatacaaa atgcgtcaaa aatctagagt ttagcgttcg    189060
tatcggagac atgtgcaagg aatcatctga acttgaggtc aaggatggat tcaagtatgt    189120
cgacggatcg gcatctgaag gtgcaaccga tgatacttca ctcatcgatt caacaaaact    189180
caaagcgtgt gtctgaatcg ataactctat tcatctgaaa ttggatgagt agggttaatc    189240
gaacgattca ggcacaccac gaattaaaaa agtgtaccgg acactatatt ccggtttgca    189300
aaacaaaaat gttcttaact acattcacaa aaagttacct ctcgcgactt cttcttttc    189360 tgtctcaata gtgtgatacg attatgacac tattcctatt cctattccta tttcctttca    189420
g                                                                    189421

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
gcgctcgaga taaagtagcc attcttcc                                         28

<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3
gcgggatcct accagccacc gaaagag                                          27

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
cgcggatcct ttggaaagtt ttataggtag                                       30

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
cgcgagctca tgtcataaag aatgcacat                                        29
```

```
<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
gcggagctcc atggagctaa tctaaacg                                          28

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
gcgggatcca agataggtag agatggaag                                         29

<210> SEQ ID NO 8
<211> LENGTH: 27
<212> TYPE: DNA
<213> ORGANISM: Artificial
<220> FEATURE:
<223> OTHER INFORMATION: primer

<400> SEQUENCE: 8
gcgctcgagg agagtaacag tcgaaca                                           27

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
gcgggatccg atcattaaat gtttcatcag                                        30

<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10
gcgctcgagg agagtaacag tcgaaca                                           27

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
gcgggatccg atcattaaat gtttcatcag                                        30

<210> SEQ ID NO 12
<211> LENGTH: 30
<212> TYPE: DNA
<213> ORGANISM: Artificial
<220> FEATURE:
<223> OTHER INFORMATION: primer
```

-continued

```
<400> SEQUENCE: 12
cgcggatcct aaatttcagt ttatgtttgt                                  30

<210> SEQ ID NO 13
<211> LENGTH: 28
<212> TYPE: DNA
<213> ORGANISM: Artificial
<220> FEATURE:
<223> OTHER INFORMATION: primer

<400> SEQUENCE: 13
ggcgagctct agcgtttgta atttctgg                                    28

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
gcgctcgagt cgaaattcag agtgcac                                     27

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
gcgggatccg acgcgatcgt gtaaca                                      26

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cgcggatcca cattgttgac agaaacg                                     27

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
cgcgagctca cagactgaga tacgcaa                                     27

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
tcgagaactt gatattggat atatcac                                     27

<210> SEQ ID NO 19
<211> LENGTH: 23
<212> TYPE: DNA
```

```
<213> ORGANISM: Artificial
<220> FEATURE:
<223> OTHER INFORMATION: primer

<400> SEQUENCE: 19
gaacttgata ttggatatat cac                                    23

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
gatccataga gaaaatagct ccagaata                               28

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
catagagaaa atagctccag aata                                   24

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
gatccgaatc atccattcca ctgaata                                27

<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23
cgaatcatcc attccactga ata                                    23

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
ccatggtagc tacggcgaga t                                      21

<210> SEQ ID NO 25
<211> LENGTH: 25
<212> TYPE: DNA
<213> ORGANISM: Artificial
<220> FEATURE:
<223> OTHER INFORMATION: primer

<400> SEQUENCE: 25
agctccatgg tagctacggc gagat                                  25
```

-continued

```
<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
gatagaatca gactctaaag                                               20

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
tagaacatca gtctccaa                                                 18

<210> SEQ ID NO 28
<211> LENGTH: 18
<212> TYPE: DNA
<213> ORGANISM: Artificial
<220> FEATURE:
<223> OTHER INFORMATION: primer

<400> SEQUENCE: 28
atggatctgt cacgaatt                                                 18

<210> SEQ ID NO 29
<211> LENGTH: 19
<212> TYPE: DNA
<213> ORGANISM: Artificial
<220> FEATURE:
<223> OTHER INFORMATION: primer

<400> SEQUENCE: 29
gctgataata gaactcacg                                                19

<210> SEQ ID NO 30
<211> LENGTH: 18
<212> TYPE: DNA
<213> ORGANISM: Artificial
<220> FEATURE:
<223> OTHER INFORMATION: primer

<400> SEQUENCE: 30
gataatggtc acgtgtta                                                 18

<210> SEQ ID NO 31
<211> LENGTH: 18
<212> TYPE: DNA
<213> ORGANISM: Artificial
<220> FEATURE:
<223> OTHER INFORMATION: primer

<400> SEQUENCE: 31
aagacgtcgc ttttagca                                                 18

<210> SEQ ID NO 32
<211> LENGTH: 18
<212> TYPE: DNA
<213> ORGANISM: Artificial
<220> FEATURE:
<223> OTHER INFORMATION: primer
```

-continued

```
<400> SEQUENCE: 32
gctatgaagg aaagacat                                                 18

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
gtctctctac aggcttct                                                 18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
gcaatcattc ctcataag                                                 18

<210> SEQ ID NO 35
<211> LENGTH: 19
<212> TYPE: DNA
<213> ORGANISM: Artificial
<220> FEATURE:
<223> OTHER INFORMATION: primer

<400> SEQUENCE: 35
gcaatcattc ctcataaga                                                19

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
atagaaactg gagaaatcaa                                               20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
caatattgaa tgtgttgctg                                               20
```

VIRAL STRAINS DERIVED FROM THE VACCINIA VIRUS LISTER VACV-107 AND USES THEREOF

FIELD OF THE INVENTION

Figure 1A:
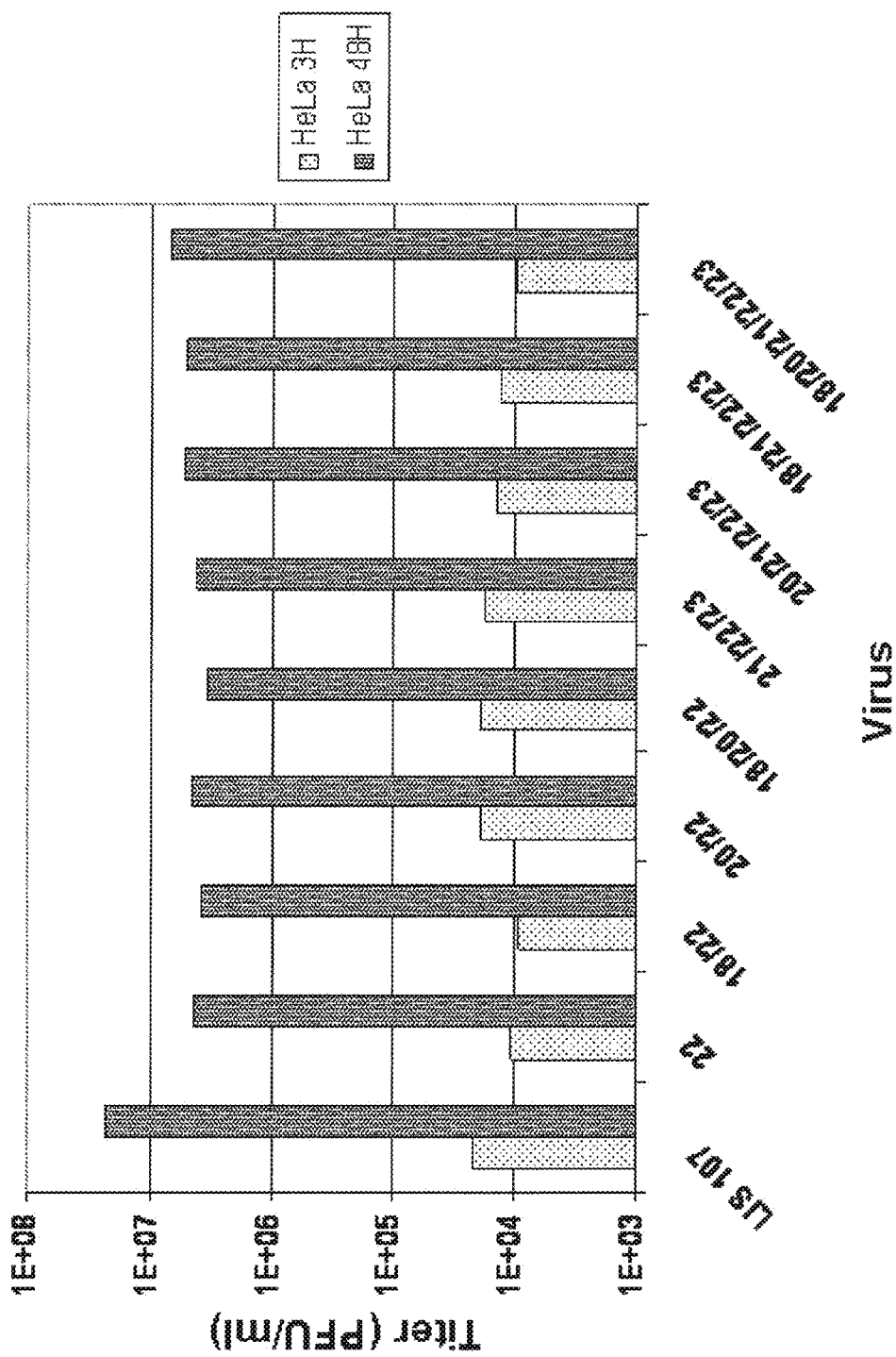

The invention relates to viral strains derived from the first generation vaccinia virus Lister smallpox vaccine and particularly a viral clone of this traditional vaccine called "Lister VACV-107" and to pharmaceutical composition containing thereof.

BACKGROUND OF THE INVENTION

Smallpox was eradicated through a worldwide effort coordinated by the World Health Organization (WHO) global vaccination campaign in the second half of the last century (Fenner F. et Al., 1988). This disease was "the most dreadful scourge of the human species" (Fenner F., 1984) and claimed hundreds of millions of victims for centuries (Fenner F. et AL., 1988). Variola virus (VARV), its causative agent, spreads easily and exclusively from human to human by the respiratory route. It causes fever, severe rash and in about 30% of cases, death (Fenner F., et Al., 1984).

The fear of the release of VARV through bioterrorism has generated renewed interest in the prevention of smallpox because of the high proportion of unimmunised people in the global population and because vaccination is the only currently effective means to curtail a smallpox epidemic. Live vaccinia virus (VACV) is the active ingredient of the smallpox vaccine administered by scarification. VACV and VARV belong to the Orthopoxvirus genus within the family Poxyiridae and both these viruses display considerable serological cross-reactivity, allowing VACV to provide protection from VARV infection, the accepted basis of its use as a smallpox vaccine. In view of the smallpox threat, a number of countries have maintained stockpiles of the first-generation smallpox vaccine. Inevitably, there will be a need to replace or to increase the stockpiles, but the historical manufacturing process, in the skin of live animals is no longer acceptable. This has stimulated interest in developing second-generation vaccines made of live, replicative, vaccinia virus, but manufactured by virus replication in cell cultures.

Several new second-generation smallpox vaccines have been developed using tissue culture-adapted virus: one such vaccine (ACAM2000™, a live vaccinia virus smallpox vaccine) is derived from a New York City Board of Health (NY-CBH) strain first-generation vaccine through cloning and propagation in MRC-5 and Vero cell cultures (Monath T P, et Al., 2004) (Weltzin R, et Al., 2003), and others are derived from a Lister/Elstree first-generation vaccine without cloning.

Second-generation vaccines have the advantage over first-generation vaccines of being produced and controlled according to Good Manufacturing Practices (GMP), thus being more standardised and free of adventitious agents. Nevertheless, these second-generation vaccines are unsatisfactory because they may still induce the same vaccine complications as those induced by the first generation vaccines.

H. Mahnel and colleagues passaged the vaccinia virus Ankara strain (CVA) more than 500 times in chicken embryo cells and isolated a highly attenuated vaccine named MVA (Mahnel, H. and Mayr, A., 1994). During the multiple passages of the CVA virus in tissue culture that ultimately led to the MVA virus, 6 main regions of the viral genome were deleted and numerous point mutations and smaller deletions occurred (Antoine, G., F. et Al., 1998 and Meyer, H., et Al., 1991; Meisinger-Henschel et AL., 2007)

The MVA strain has been extensively characterised and has been found to be efficacious in protecting animals from challenge infections mimicking smallpox and to display a very promising profile as a smallpox vaccine in clinical trials. Nevertheless, potential drawbacks of the MVA smallpox vaccine lie in the fact that it must be employed at very high doses ($10^8$ PFU/injection intramuscularly or intradermally, a dose more than 100 fold higher than the dose used with the first generation smallpox vaccine) because it does not replicate in human cells and a booster vaccination is recommended to achieve long-lasting immunity. Furthermore, the MVA vaccine produces no visual take at the site of inoculation as produced by the traditional smallpox vaccine.

Therefore, there is still an important need for new viral strains derived from the vaccinia virus which have better vaccine potency at a lower dose than the MVA strain dose.

SUMMARY OF THE INVENTION

A first object of the invention relates to a viral strain derived from the vaccinia virus Lister VACV-107 wherein strain contains in its genomic sequence (SEQ ID N°1) at least one deletion selected from the group consisting of: deletion of the nucleotides 19758 to 28309 in the sequence ID NO°1 ($\Delta$18), deletion of the nucleotides 161293 to 164811 in the sequence ID NO°1 ($\Delta$20), deletion of the nucleotides 181231 to 183304 in the sequence ID NO°1 ($\Delta$21), deletion of the nucleotides 6118 to 9677 in the sequence ID NO°1 ($\Delta$22) and deletion of the nucleotides 1833 to 3574 and 185848 to 187589 in the sequence ID NO°1 ($\Delta$23).

Another object of the invention relates to a viral strain according to the invention comprising at least one homologous and/or heterologous nucleic acid sequence.

Another object of the invention relates to a pharmaceutical composition comprising the viral strain according to the invention.

DETAILED DESCRIPTION OF THE INVENTION

Viral Strains and Applications Thereof

To investigate if a vaccinia virus strain with fewer alterations than those found in the MVA strain may display satisfactory attenuation while maintaining total vaccine efficacy, the inventors have now constructed a series of new strains derived from the Lister VACV 107 strain (a viral clone selected from the vaccinia virus Lister first generation smallpox vaccine) which are multiply deleted in the six major regions deleted in the MVA strain so as to create all of the possible combinations of the six major deletions. This led to the creation of 17 distinct viral mutants which multiplied well in tissue culture cells. The inventors show that deletion of several regions of the Lister genome does not entail a significant loss of vaccine potency when compared to the parental Lister VACV-107 strain. In fact, for most of the deletion mutants, vaccination against a challenge infection that mimics smallpox (intranasal infection of mice with cowpox virus) is as efficient as vaccination with the parental Lister strain. The inventors show that most of the deletion mutants were more attenuated than the parental Lister strain as demonstrated by experimental infection of immunocompromised mice (athymic Nude mice) concomitantly with unaltered vaccine potency. Thus, the inventors have now produced viral strains derived from the vaccinia virus Lister VACV-107 which provide good protection against cowpox virus infection (a model infection for smallpox) and which can be used as efficient vaccines at a low viral dose. Moreover, the usefulness of the new virus strains as new vectors for heterologous vaccination is pointed out.

As used herein the term "Smallpox" denotes an infectious disease unique to humans, caused by either Variola major or Variola minor.

As used herein the term "vaccinia virus" or "VACV" denotes a large, complex, enveloped virus belonging to the poxvirus family. It has a linear, double-stranded DNA genome approximately 190 kbp in length, and which encodes approximately 200 proteins. The dimensions of the virion are roughly 360×270×250 nm.

As used herein the terms "vaccinia virus Lister VACV-107" or "Lister VACV-107" denote a strain of vaccinia virus. As used in the invention, this vaccinia virus Lister VACV-107 has been cloned from the original live vaccinia virus Lister strain (production lot X5533 obtained from the Sanofi-Pasteur Company). The GenBank/EMBL/DDBJ accession number for its nucleic acid sequence is DQ121394 (SEQ ID N: °1).

The deletions obtained in the genomic sequence ID NO°1 are described in the table A below.

TABLE A deletions in the genomic sequence of Lister VACV-107 (SEQ ID NO: 1).

| Deletion code | Deletions in the genomic sequence ID NO°1 |
| --- | --- |
| Δ18 | deletion of the nucleotides 19758 to 28309 in the sequence ID NO°1 |
| Δ20 | deletion of the nucleotides 161293 to 164811 in the sequence ID NO°1 |
| Δ21 | deletion of the nucleotides 181231 to 183304 in the sequence ID NO°1 |
| Δ22 | deletion of the nucleotides 6118 to 9677 in the sequence ID NO°1 |
| Δ23 | deletion of the nucleotides 1833 to 3574 and 185848 to 187589 in the sequence ID NO°1 |

So a first object of the invention relates to a viral strain derived from the vaccinia virus Lister VACV-107 wherein strain contains in its genomic sequence (SEQ ID N°1) at least one deletion selected from the group consisting of: deletion of the nucleotides 19758 to 28309 in the sequence ID NO°1 (Δ18), deletion of the nucleotides 161293 to 164811 in the sequence ID NO°1 (Δ20), deletion of the nucleotides 181231 to 183304 in the sequence ID NO°1 (Δ21), deletion of the nucleotides acid 6118 to 9677 in the sequence ID NO°1 (Δ22), deletion of the nucleotides 1833 to 3574 and 185848 to 187589 in the sequence ID NO°1 (Δ23).

The inventors have demonstrated that particular viral strains of this kind:
- display significantly reduced pathogenicity in mice in particular no mortality in immunocompromised Nude mice as compared to a standard smallpox vaccine;
- induce a similar level of protection against a lethal poxvirus challenge as the standard smallpox first generation vaccine when both viruses are employed at similar doses.
- induce vaccinia virus neutralizing antibodies and vaccinia virus specific T lymphocyte responses of a similar magnitude as those induced by the standard smallpox vaccine
- replicate in both avian and mammalian cells including human cells.

In a preferred embodiment, the viral strain according to the invention contains in its genomic sequence (SEQ ID N°1) at least two deletions selected from the group defined above.

In another embodiment, the viral strain according to the invention contains in its genomic sequence (SEQ ID N°1) the deletion of the nucleotides 19758 to 28309 in the sequence ID NO°1 (Δ18) and the deletion of the nucleotides 6118 to 9677 in the sequence ID NO°1 (Δ22). According to the invention, said viral strain is named: VACV-107Δ18/22 deletion mutant.

In another embodiment, the viral strain according to the invention contains in its genomic sequence (SEQ ID N°1) the deletion of the nucleotides 19758 to 28309 in the sequence ID NO°1 (Δ18) and the deletion of the nucleotides 161293 to 164811 in the sequence ID NO°1 (Δ20). According to the invention said viral strain is named: VACV-107Δ18/20 deletion mutant.

In another embodiment, the viral strain according to the invention contains in its genomic sequence (SEQ ID N°1) the deletion of the nucleotides 161293 to 164811 in the sequence ID NO°1 (Δ20) and the deletion of the nucleotides 6118 to 9677 in the sequence ID NO°1 (Δ22). According to the invention said viral strain is named VACV-107Δ20/22 deletion mutant.

In another embodiment, the viral strain according to the invention contains in its genomic sequence (SEQ ID N°1) the deletion of the nucleotides 181231 to 183304 in the sequence ID NO°1 (Δ21) and the deletion of the nucleotides 1833 to 3574 and 185848 to 187589 in the sequence ID NO°1 (Δ23). According to the invention said viral strain is named: VACV-107Δ21/23 deletion mutant.

In another embodiment, the viral strain according to the invention contains in its genomic sequence (SEQ ID N°1) the deletion of the nucleotides 19758 to 28309 in the sequence ID NO°1 (Δ18), the deletion of the nucleotides 161293 to 164811 in the sequence ID NO°1 (Δ20) and the deletion of the nucleotides 6118 to 9677 in the sequence ID NO°1 (Δ22). According to the invention said viral strain is named: VACV-107Δ18/20/22 deletion mutant.

In another embodiment, the viral strain according to the invention contains in its genomic sequence (SEQ ID N°1) the deletion of the nucleotides 19758 to 28309 in the sequence ID NO°1 (Δ18), the deletion of the nucleotides 181231 to 183304 in the sequence ID NO°1 (Δ21) and the deletion of the nucleotides 1833 to 3574 and 185848 to 187589 in the sequence ID NO°1 (Δ23). According to the invention said viral strain is named: VACV-107Δ18/21/23 deletion mutant.

In another embodiment, the viral strain according to the invention contains in its genomic sequence (SEQ ID N°1) the deletion of the nucleotides 181231 to 183304 in the sequence ID NO°1 (Δ21), the deletion of the nucleotides 6118 to 9677 in the sequence ID NO°1 (Δ22) and the deletion of the nucleotides 1833 to 3574 and 185848 to 187589 in the sequence ID NO°1 (Δ23). According to the invention said viral strain is named: VACV-107Δ21/22/23 deletion mutant.

In another embodiment, the viral strain according to the invention contains in its genomic sequence (SEQ ID N°1) the deletion of the nucleotides 161293 to 164811 in the sequence ID NO°1 (Δ20), the deletion of the nucleotides 181231 to 183304 in the sequence ID NO°1 (Δ21) and the deletion of the nucleotides 1833 to 3574 and 185848 to 187589 in the sequence ID NO°1 (Δ23). According to the invention said viral strain is named: VACV-107Δ20/21/23 deletion mutant.

In another embodiment, the viral strain according to the invention contains in its genomic sequence (SEQ ID N°1) the deletion of the nucleotides 19758 to 28309 in the sequence ID NO°1 (Δ18), the deletion of the nucleotides 181231 to 183304 in the sequence ID NO°1 (Δ21), the deletion of the nucleotides 6118 to 9677 in the sequence ID NO°1 (Δ22) and the deletion of the nucleotides 1833 to 3574 and 185848 to 187589 in the sequence ID N°1 (Δ23). According to the invention said viral strain is named: VACV-107Δ18/21/22/23 deletion mutant.

In another embodiment, the viral strain according to the invention contains in its genomic sequence (SEQ ID N°1) the deletion of the nucleotides 19758 to 28309 in the sequence ID NO°1 (Δ18), the deletion of the nucleotides 161293 to 164811 in the sequence ID N°1 (Δ20), the deletion of the nucleotides 181231 to 183304 in the sequence ID NO°1 (Δ21) and the deletion of the nucleotides 1833 to 3574 and 185848 to 187589 in the sequence ID NO°1 (Δ23). According to the invention said viral strain is named: VACV-107Δ18/20//21/23 deletion mutant.

In another embodiment, the viral strain according to the invention contains in its genomic sequence (SEQ ID N°1) the deletion of the nucleotides 161293 to 164811 in the sequence ID NO°1 (Δ20), the deletion of the nucleotides 181231 to 183304 in the sequence ID NO°1 (Δ21), the deletion of the nucleotides 6118 to 9677 in the sequence ID NO°1 (Δ22) and the deletion of the nucleotides 1833 to 3574 and 185848 to 187589 in the sequence ID N°1 (Δ23). According to the invention said viral strain is named: VACV-107Δ20/21/22/23 deletion mutant.

In another embodiment, the viral strain according to the invention contains in its genomic sequence (SEQ ID N°1) the deletion of the nucleotides 19758 to 28309 in the sequence ID NO°1 (Δ18), the deletion of the nucleotides 161293 to 164811 in the sequence ID NO°1 (Δ20), the deletion of the nucleotides 181231 to 183304 in the sequence ID NO°1 (Δ21), the deletion of the nucleotides 6118 to 9677 in the sequence ID NO°1 (Δ22) and the deletion of the nucleotides 1833 to 3574 and 185848 to 187589 in the sequence ID NO°1 (Δ23). According to the invention said viral strain is named: VACV-107Δ18/20/21/22/23 deletion mutant.

In another embodiment, the invention relates to the genomic sequence SEQ ID NO°1 with at least one deletion as defined above.

In a further embodiment of the invention, the viral strain according to the invention may comprise at least one heterologous nucleic acid sequence.

As used herein, the term "heterologous" denotes any combination of nucleic acid sequences that is not normally found intimately associated with the viral strain in nature, such viral strain is also called "recombinant viral strain". Furthermore, the genomic sequence of the virus with the heterologous nucleic acid sequence is called "recombinant genomic sequence".

Accordingly, recombinant viral strains according to the invention may be used as vectors for introducing a homologous and/or heterologous nucleic acid sequence into a host cell.

The term "vector" means the vehicle by which a nucleic acid sequence can be introduced into a host cell, so as to transform the host and promote expression (e.g. transcription and translation) of the introduced sequence.

For example, the introduction of such a heterologous nucleic acid sequence into a target cell may be used to produce in vitro heterologous peptides or polypeptides and/or complete viruses encoded by said sequence. This method comprises the infection of a host cell with the recombinant viral strain, cultivation of the infected host cell under suitable conditions, and isolation and/or enrichment of the peptide, protein and/or virus produced by said host cell.

So the invention relates to a host cell infected with the viral strains according to the present invention.

According to another embodiment, the recombinant viral strain can be used in gene therapy. Indeed, the viral strain may be used to insert in cells or animal (including humans) any nucleic acid sequence of therapeutic interest.

According to a further embodiment, the heterologous nucleic acid sequences may encode for antigenic epitopes so that the recombinant strains may be used for vaccine purpose against a microorganism (bacteria, virus . . . ).

For example, said antigenic epitope can be selected from another poxviral or a vaccinia source.

Alternatively, the heterologous nucleic acid sequences may encode for an antigenic epitope, which may be selected from any non-vaccinia source. For example, said recombinant viral strain may express one or more antigenic epitopes from Plasmodium falciparum, Mycobacteria, Influenza virus, or from viruses selected from the family of Flaviviruses, Paramyxoviruses, Hepatitis viruses, Human immunodeficiency viruses or from viruses causing hemorrhagic fever such as Hantaviruses or Filoviruses, i.e., Ebola or Marburg virus.

According to a further preferred embodiment of the invention, the expression of heterologous nucleic acid sequence is preferably, but not exclusively, under the transcriptional control of a poxvirus promoter, more preferably of a vaccinia virus promoter.

According to still a further embodiment the insertion of heterologous nucleic acid sequence is preferably into a non-essential region of the virus genome.

Viral strains according to the invention may be obtained by methods well known to the person skilled in the art. Such a method is described in Example here below.

Pharmaceutical Compositions

Viral strains according to the invention (recombinant or not) may be used for the preparation of a pharmaceutical composition.

Hence, the present invention also provides a pharmaceutical composition comprising a viral strain according to the invention (recombinant or not). The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Since the viral strains according to the invention are highly attenuated as demonstrated by experimental infection of immunocompromised animals, they are ideal to immunize or treat a wide range of mammals including humans.

Hence, in a particular embodiment, pharmaceutical compositions according to the invention can be used as vaccine.

For example, the pharmaceutical composition according to the invention can be used as vaccine against smallpox.

Indeed, the pharmaceutical composition according to the invention may induce vaccinia virus neutralizing antibodies or vaccinia specific T cell responses of a similar magnitude to those induced by the standard smallpox vaccine.

In still a particular embodiment, the pharmaceutical composition according to the invention can be used as a vaccine against other infectious diseases (the infectious diseases can be but are not limited to malaria, tuberculosis, hepatitis), cancer or other non-infectious diseases.

Alternatively, pharmaceutical compositions according to the invention may be used for gene therapy.

For vaccination or therapy, pharmaceutical compositions according to the invention may be administered either systemically or locally, i.e. by parenterally, intramuscularly, subcutaneous or any other path of administration know to the skilled practitioner. The mode of administration, the dose and the number of administrations can be optimized by those skilled in the art in a known manner.

The invention will be further illustrated by the following figures and examples.

FIGURES

Figure 1B:
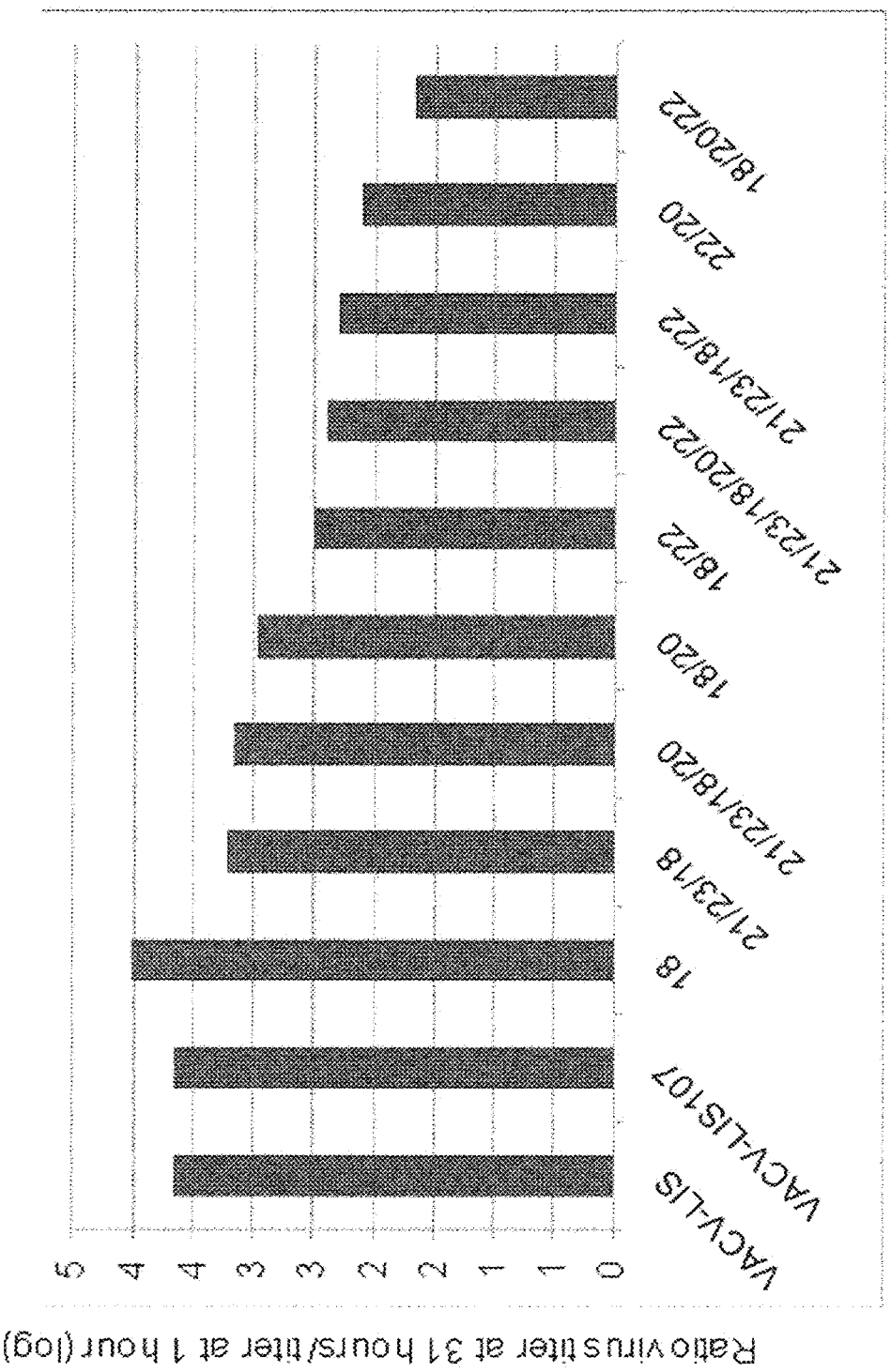

FIGS. 1a and 1b: Multiplication of Selected Deletion Mutants in Human HeLa Cells and Human MRC5 Fibroblasts HeLa cells grown in monolayers were infected with approximately 0.01 PFU/cell for one hour. Unadsobed virus was then removed and fresh medium was added. Samples of infected cells were harvested 3 hours or 48 hours post-infection and the virus titers in the samples were determined by titration on BHK21 cells. The X axis indicates the viruses examined and the Y axis the titer of each sample. MRC5 cells grown in monolayers were infected with approximately 0.01 PFU per cell for one hour. Unadsorbed virus was removed and fresh medium was added. Samples of infected cells were harvested 1 hour or 31 hours post-infection and the virus titers in the samples were determined by titration on Vero cells. The X axis indicates the viruses examined and the Y axis the log of the ratio of the titer of the sample taken at 31 hours over that taken at 1 hour.

FIGS. 2A and 2B: Weight Change in Athymic Nude Mice Vaccinated with Lister VACV-107 Deletion Mutants Groups of six Nude mice (athymic immunocompromized) were infected by tail scarification with $10^5$ PFU of the VACV deletion mutants in two separate experiments and the percentage in weight change was followed over the course of time.

Figure 3:
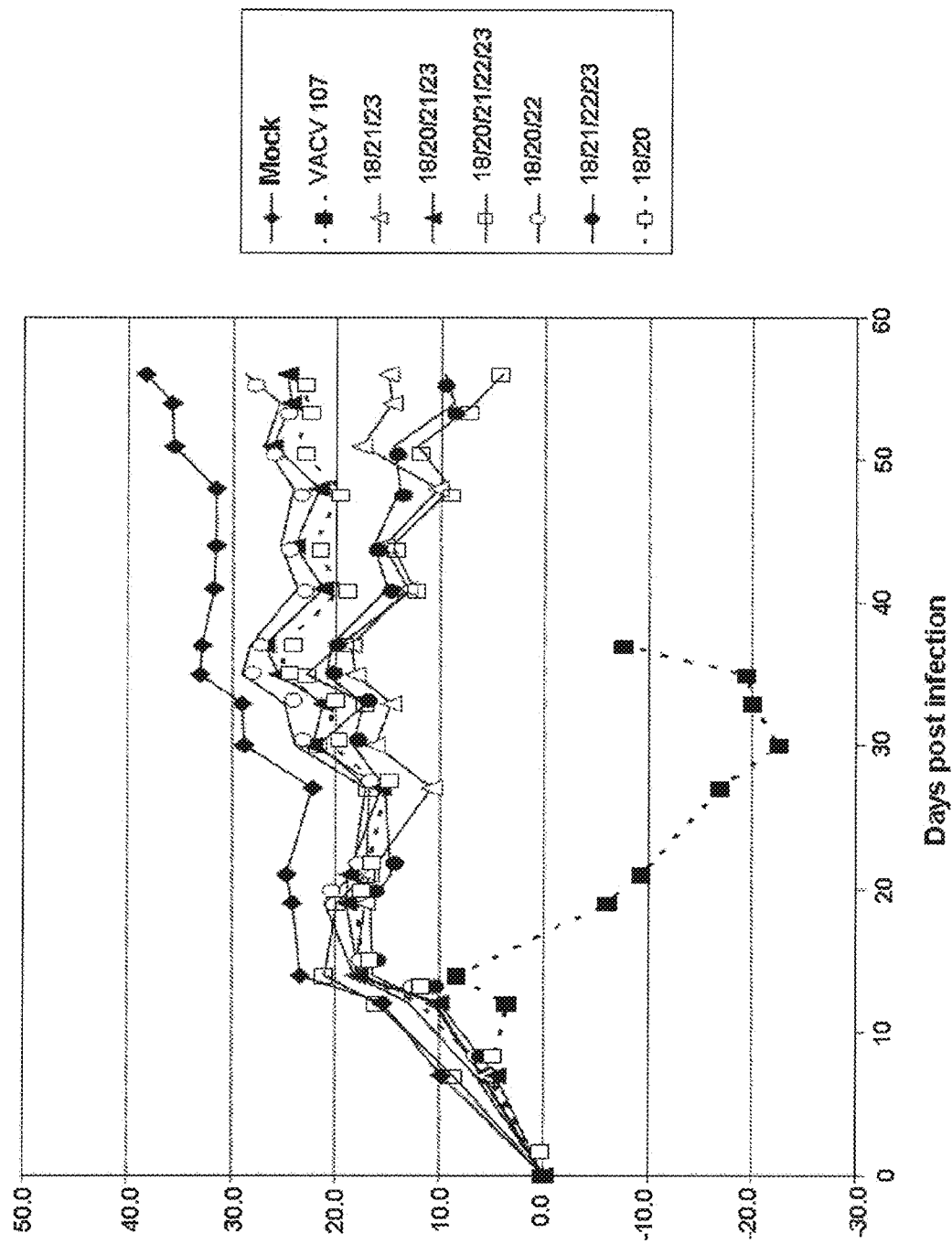

FIG. 3: Weight Change in Nude Mice Vaccinated with Lister VACV-107 Deletion Mutants Groups of six Nude mice were infected by tail scarification with $10^5$ PFU of the VACV deletion mutants and the percentage in weight change was followed over the course of time.

Figure 4A:
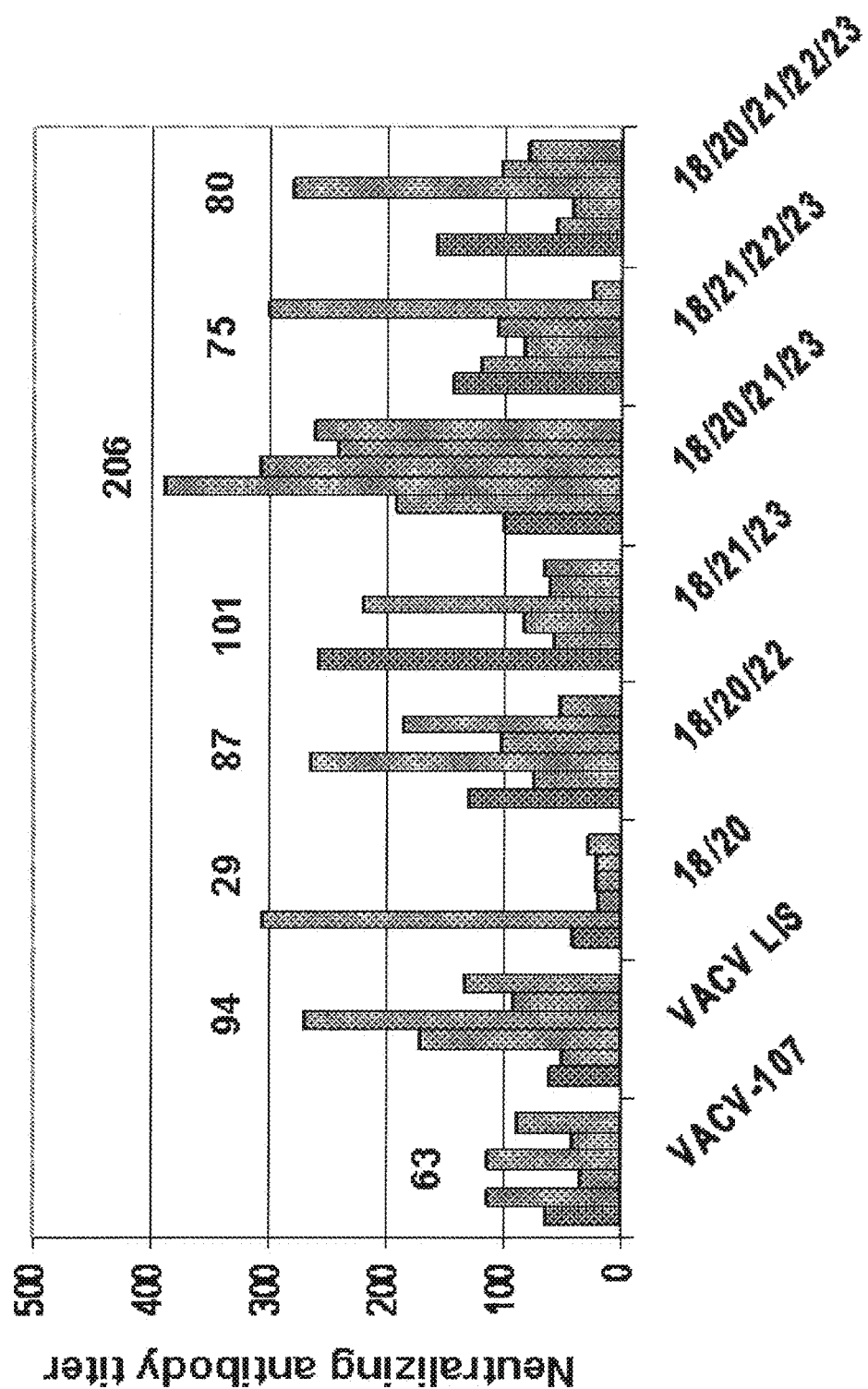

FIG. 4a: Induction of Neutralizing Antibodies in Mice Vaccinated with Lister VACV-107 Deletion Mutants BALB/C mice were vaccinated by scarification at the base of the tail with $10^5$ PFU (six animals per group). Four weeks later the mice were bled and vaccinia virus neutralizing antibodies in the serum of each animal were titrated. The graph depicts the reciprocal of the serum dilution which led to a 50% reduction in the VACV plaque count compared with a negative control and the mean of this dilution for each deletion mutant is indicated at the top of each series. Neutralization titers in serum samples from uninfected animals were less than 10, the threshold of neutralization (a 1/10 dilution of the serum resulted in no neutralization).

Figure 4B:
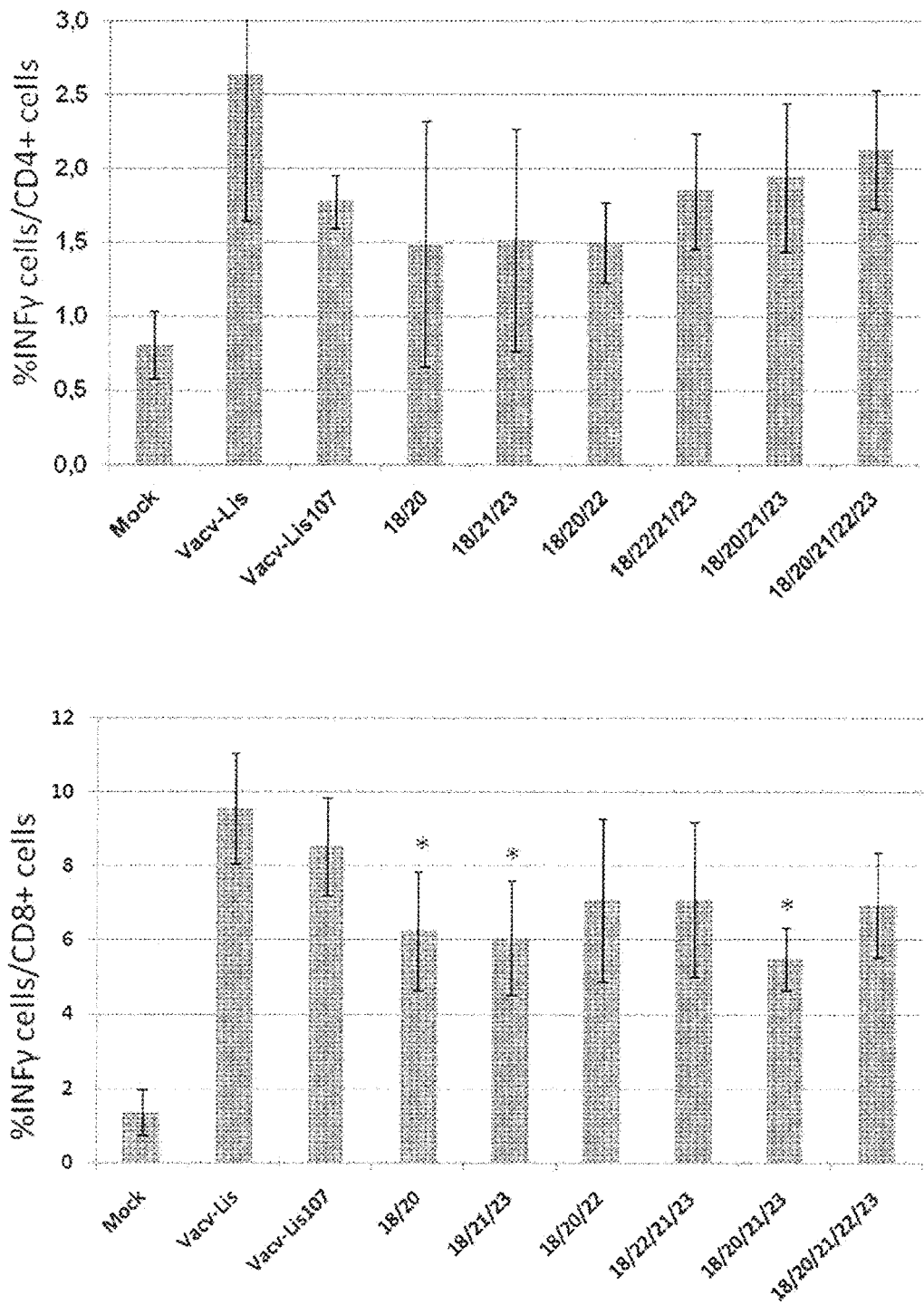

FIG. 4b: Induction of VACV-specific $CD4^+$ and $CD8^+$ Lymphocytes in Mice Vaccinated with VACV Lister Deletion Mutants BALB/C mice were vaccinated by scarification at the base of the tail with $10^5$ PFU (six animals per group). Four weeks later the mice were bled, spleens recovered and the percentage of CD4 (top panel) or CD8 T lymphocytes (bottom panel) able to secrete interferon γ in the presence of dendritic cells presenting VACV antigens was determined. The mean values for 6 animals in each group and the corresponding standard deviations are plotted. Asterisks are positioned above values that were significantly different from those obtained after infection with the VACV-107 virus (students T test p≤05).

Figure 5:
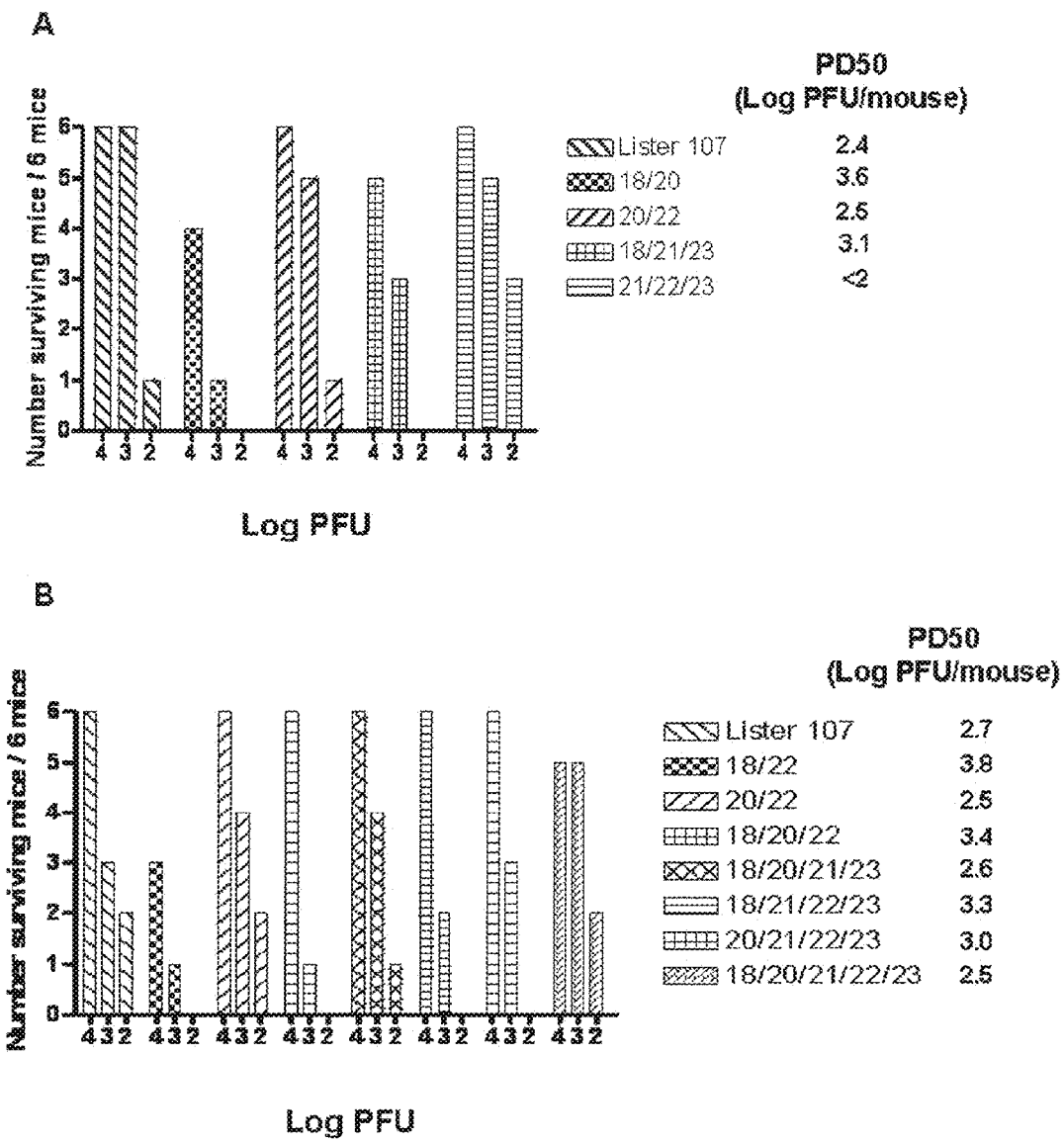

FIGS. 5A and 5B: Vaccination of BALB/c Mice Against Cowpox Virus Infection

Mice were vaccinated with either $10^4$, $10^3$ or $10^2$ PFU by tail scarification and challenged 28 days later with cowpox virus. The results are displayed as the number of surviving mice (Y axis) out of a total of 6 mice per group for each vaccine dose employed (X axis). The protective dose, theoretical dose able to protect 50% of the animals ($PD_{50}$) was calculated and is shown for each virus at the right of the graphs. Note that all unvaccinated mice succumbed to the challenge infection (not shown).

Figure 6:
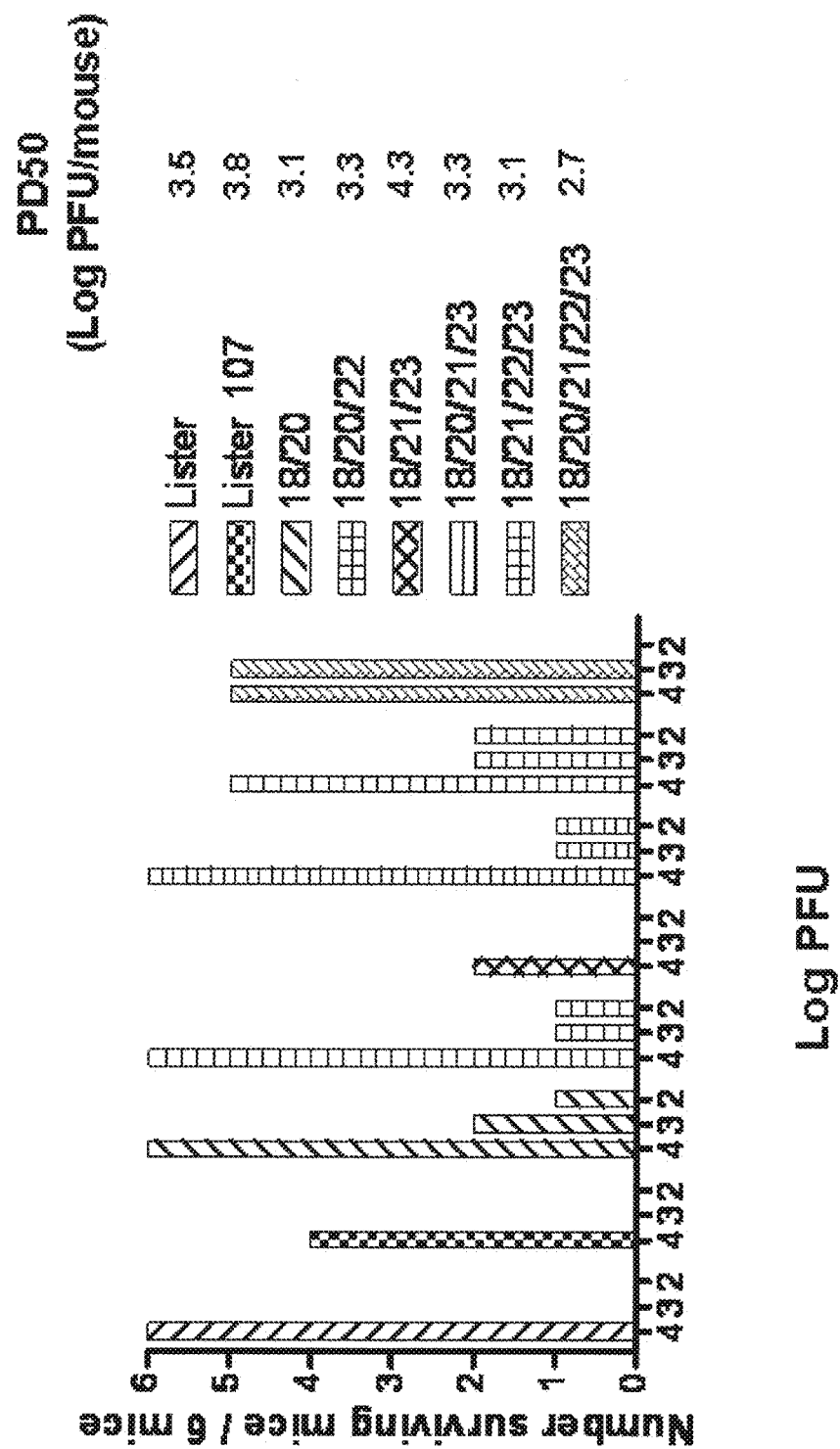

FIG. 6: Vaccination of BALB/c Mice Against Cowpox Virus Infection

Mice were vaccinated with either $10^4$, $10^3$ or $10^2$ PFU by tail scarification and challenged 28 days later with cowpox virus. The results are displayed as the number of surviving mice (Y axis) out of a total of 6 mice per group for each vaccine dose employed (X axis). The protective dose, theoretical dose able to protect 50% of the animals ($PD_{50}$) was calculated and is shown for each virus at the right of the graphs. Note that all unvaccinated mice succumbed to the challenge infection (not shown).

Figure 7:
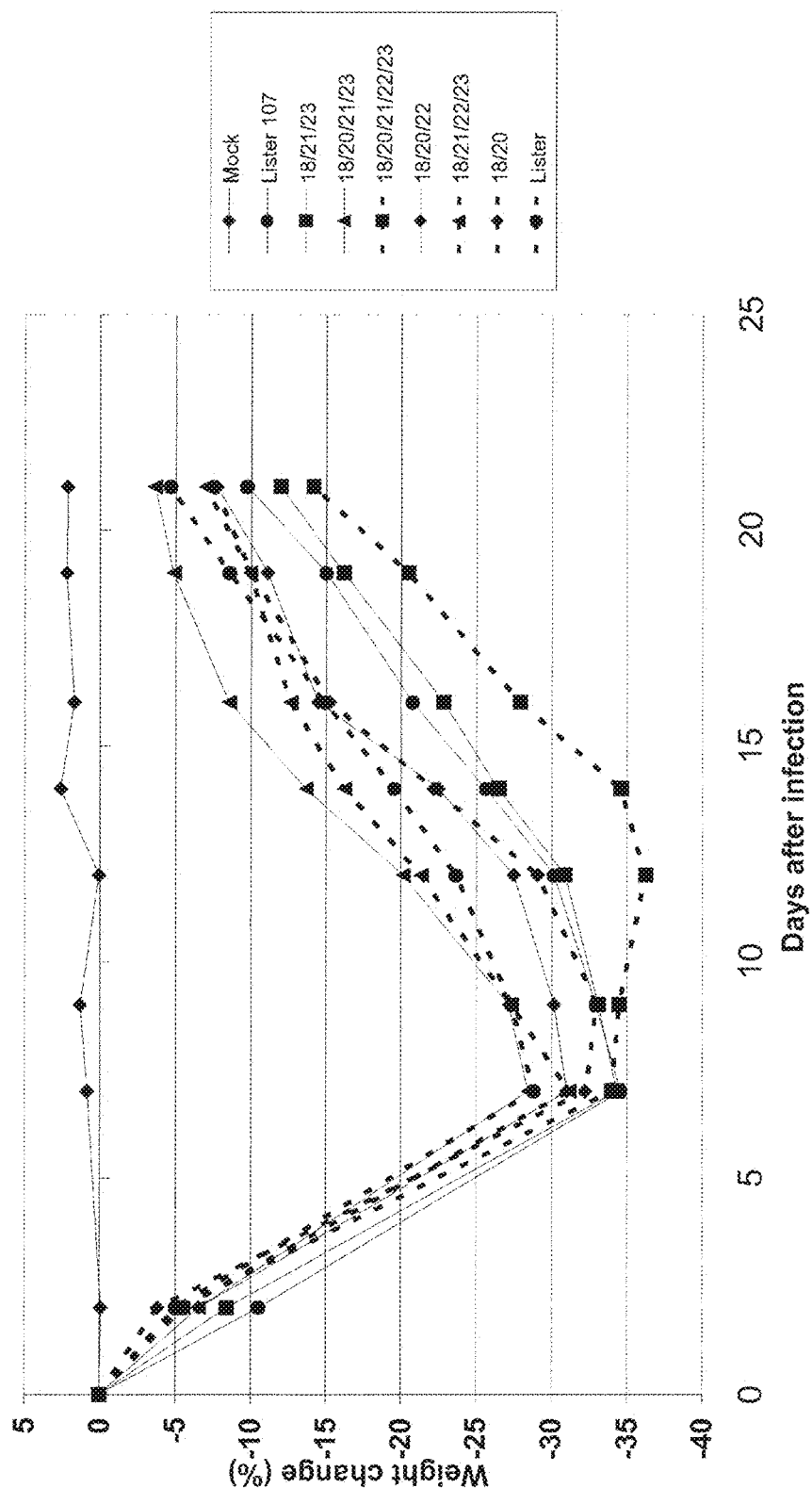

FIG. 7: Weight Loss in Vaccinated Mice Challenged with Cowpox Virus

The weight loss for mice vaccinated with $10^4$ PFU by tail scarification and challenged 28 days later with cowpox virus, as reported in FIG. 6, are plotted in this figure. The average weight of 6 mice per group is plotted as a function of time post-challenge.

TABLE 1a

Primers used to construct plasmids pEM20, pEM21, pEM22, pEM23 for targeted deletion in VACV-107.

| Plasmids (Deletion) | Deletion in MVA (kb) | Primers for leftmost fragment | Primers for rightmost fragment |
|---|---|---|---|
| pEM20 (Δ20) | 3.5 | 1° GCGCTCGAG ATAAAGTAGCCA TTCTTCC (SEQ ID N° 2) 2° GCGGGATCC TACCAGCCACCG AAAGAG (SEQ ID N° 3) | 3° CGCGGATCC TTTGGAAAGTT TTATAGGTAG (SEQ ID N° 4) 4° CGCGAGCTC ATGTCATAAAG AATGCACAT (SEQ ID N° 5) |
| pEM21 (Δ21) | 0.8 | 1° GCGGAGCTC CATGGAGCTAAT CTAAACG (SEQ ID N° 6) 2° GCGGGATCC AAGATAGGTAGA GATGGAAG (SEQ ID N° 7) | 3° GCGCTCGAG GAGAGTAACAG TCGAACA (SEQ ID N° 8) 4° GCGGGATCC GATCATTAAAT GTTTCATCAG (SEQ ID N° 9) |

TABLE 1a-continued

Primers used to construct plasmids
pEM20, pEM21, pEM22, pEM23
for targeted deletion in VACV-107.

| Plasmids (Deletion) | Deletion in MVA (kb) | Primers for leftmost fragment | Primers for rightmost fragment |
|---|---|---|---|
| pEM22 (Δ22) | 3.6 | 1° GCGCTCGAG GAGAGTAACAGT CGAACA (SEQ ID N° 10) | 3° CGCGGATC CTAAATTTCAG TTTATGTTTGT (SEQ ID N° 12) |
| | | 2° GCGGGATCC GATCATTAAATG TTTCATCAG (SEQ ID N° 11) | 4° GGCGAGCTCT AGCGTTTGTAAT TTCTGG (SEQ ID N° 13) |
| pEM23 (Δ23) | 1.8 | 1° GCGCTCGAG TCGAAATTCAGA GTGCAC (SEQ ID N° 14) | 3° CGCGGATCC ACATTGTTGAC AGAAACG (SEQ ID N° 16) |
| | | 2° GCGGGATCC GACGCGATCGTG TAACA (SEQ ID N° 15) | 4° CGCGAGCTCA CAGACTGAGATA CGCAA (SEQ ID N° 17) |

Plasmids used to create deletions are listed in the left column. The size of the corresponding deletions in the MVA strain relative to the VACV Copenhagen strain (Antoine et AL. 1998) is listed in the second column. The oligonucleotide primers used to amplify the fragments by PCR which flank the targeted regions are listed in the third and fourth columns.

TABLE 1b

Primers used to construct plasmid pEM18
for targeted deletion in VACV-107.

| Plasmid (Deletion) | Deletion in MVA (kb) | Primers for leftmost fragment | Primers for rightmost fragment |
|---|---|---|---|
| pEM18 (Δ18) | 4.8 + 2.8 | 1° TCGAGAAC TTGATATTGGA TATATCAC (SEQ ID N° 18) | 1° GATCCGAAT CATCCATTCCA CTGAATA (SEQ ID N° 22) |
| | | 2° GAACTTGATAT TGGATATATCAC (SEQ ID N° 19) | 2° CGAATCATCCA TTCCACTGAATA (SEQ ID N° 23) |
| | | 3 GATCCATAGAG AAAATAGCTCCAG AATA (SEQ ID N° 20) | 3° CCATGGTAG CTACGGCGAGAT (SEQ ID N° 24) |
| | | 4° CATAGAGAAAA TAGCTCCAGAATA (SEQ ID N° 21) | 4° AGCTCCATGG TAGCTACGGCGAG AT (SEQ ID N° 25) |

The plasmid used to create deletion Δ18 is listed in the left column and the corresponding deletion in the MVA strain as defined by Antoine et AL. 1998 is listed in the second column. The oligonucleotide primers used to amplify PCR fragments at the left end or right end of the targeted deletions are listed in the third and fourth columns.

TABLE 2

Primers used to screen for deletions by PCR.

| Deletion | Primer A | Primer A' | Primer B | Size (bp) VACV-107/Deletion |
|---|---|---|---|---|
| Δ18 | GATAGAATCA GACTCTAAAG (SEQ ID N° 26) | TAGAACATCA GTCTCCAA (SEQ ID N° 27) | ATGGATCTG TCACGAATT (SEQ ID N° 28) | 355/510 bp |
| Δ20 | GCTGATAATA GAACTCACG (SEQ ID N° 29) | GATAATGGTC ACGTGTTA (SEQ ID N° 30) | AAGACGTCG CTTTTAGCA (SEQ ID N° 31) | 375/520 bp |
| Δ21 | GCTATGAAG GAAAGACAT (SEQ ID N° 32) | GTCTCTCTAC AGGCTTCT (SEQ ID N° 33) | GCAATCATTC CTCATAAG (SEQ ID N° 34) | 350/510 bp |
| Δ22 | GCAATCATT CCTCATAAGA (SEQ ID N° 35) | ATAGAAACTG GAGAAATCAA (SEQ ID N° 36) | CAATATTGAA TGTGTTGCTG (SEQ ID N° 37) | 380/525 bp |
| Δ23 | GCGCTCGAG TCGAAATTC AGAGTGCAC (SEQ ID N° 14) | | CGCGAGCTCA CAGACTGAGA TACGCAA (SEQ ID N° 17) | 2692/1000 bp |

Deletions were checked by PCR analysis of total DNA extracted from infected cells using the 3 oligonucleotide primers A, A' and B as listed in table 2. Primers A and B together were designed to flank the areas deleted and generate fragments of approximately 500 bp. Primer A' was chosen so that it lies within the sequence expected to be deleted so that together with B it enables amplification of a fragment in the parental virus. Virus stocks containing mixtures of the two types of viruses generated the two PCR products listed in the fourth column whereas virus stocks containing only virus deleted in the targeted region generated only an approximately 500 bp fragment as listed in the fourth column except in the case of Δ23 which generated a 1000 bp fragment.

EXAMPLE

Material & Methods

General Outline of the Method Used to Construct New Viral Strains by Deletion of Selected Regions of a Clonal Isolate of the Vaccinia Virus (VACV) Lister-107 Strain:

Prior to this invention, biological clones of the virus contained within the smallpox Lister vaccine (production lot X5533 obtained from the Sanofi-Pasteur Company) were produced by standard virus cloning procedures on the human fibroblast cell line MRC-5. One clone, designated VACV-107, was selected for further study because it displayed similar properties to the parental virus population in that it protected mice from a lethal challenge infection with cowpox virus (an animal model of smallpox in man) as efficiently as the parental Lister strain and it displayed a similar level of pathogenicity upon intracerebral injection into newborn mice (Garcel et AL. 2009). Analysis of the genomic sequence of VACV-107 ($\approx$190 Kbp) demonstrated that its genotype is closely related to other isolates of VACV albeit with several distinctive features. For instance VACV-107 has a series of unique open reading frames from ORF 194 to ORF 196 as compared to a number of other VACV strains (Garcel et AL. 2007).

We then employed a strategy that was previously developed to create deletions in the VACV genome (Falkner et AL., 1990) and which operates in a similar manner to the strategy we had previously employed to delete unwanted selection markers from the fowlpox virus genome (Spehner et al., 1990). In a first step, we amplified by PCR of the VACV-107 genome, two approximately 500 bp fragments on each side of the regions to be deleted. The two amplified fragments surrounding each region to be deleted were then assembled together on one bacterial plasmid so as to replicate the desired deletions on the plasmids. We then added adjacent to the rightmost fragment on each plasmid both a gene encoding the green fluorescent protein (GFP) and a gene encoding the enzyme guanine phosphoribosyl-transferase (GPT) which confers resistance to mycophenolic acid (MPA). Both the GFP and GPT genes were positioned behind specific VACV promoters so as to ensure their expression.

The plasmids thus constructed for each region to be deleted were then transfected into cells that had been infected with VACV-107. Two days later, virus derived from this initial infection/transfection was used to infect fresh cells in the presence of MPA so as to select for virus clones that had integrated the entire plasmid. Observation of the fluorescence of plaque isolates at this stage confirmed that the entire plasmid was integrated into the viral genome. The strategy used implies an initial recombination event between virus DNA and plasmid DNA that generates virus recombinants that bear the region to be deleted as well as the entire plasmid DNA. After the initial isolation of an MPA resistant virus, further cloning steps are carried out in the presence of MPA to ensure that the virus population contains mostly virus harbouring the entire plasmid. The virus enriched in this manner is then plated on cells in the absence of MPA so as to allow detection of a second recombination event which can generate either virus deleted of the region targeted or parental virus. Both parental viruses and viruses that have deleted the GPT gene can be recognized because of their lack of GFP fluorescence and such viruses are picked and amplified on fresh cell monolayers. To distinguish viruses deleted in the regions targeted from parental virus, DNA extracted from cells infected with each virus isolate is analysed by PCR using specific oligonucleotides. Once a deleted virus is recognized it is cloned several times again to ensure its purity and the deletion is confirmed by PCR with selected oligonucleotides. In this way we isolated viruses containing deletions in 5 distinct regions of VACV-107 which correspond to 6 major regions deleted in the MVA strain. Two regions deleted in the MVA strain that are very close together (D4.8 and D2.8) were combined in one deletion in our study. Furthermore, we created viruses harboring combined deletions of each of the 5 deletions initially created by repeating the operations outlined above on previously deleted viruses. In addition, because it has previously been shown that inactivation of the VACV thymidine kinase gene (TK) leads to virus attenuation without loss of the vaccine potency (Lee et AL. 1992) we also deleted a portion of the TK gene and subsequently used this virus as a comparator in the evaluation of newly constructed deletion mutants. The pEM25 plasmid contains the deletion in the TK gene used to construct VACV-107Δ25.

Methods Used for PCR and Molecular Cloning:

PCR amplification of viral DNA and molecular cloning in plasmids was carried out according to the methods previously described (Sambrook et Russell, 2001). Approximately 500 bp DNA fragments of VACV-107 were amplified on both sides of the regions to be deleted using the oligonucleotides listed in table 1a and 1b. This table provides the name of the plasmid used to create the deletions in VACV-107, the designation of the corresponding deletion in the MVA virus (according to Antoine et AL., 1998) and the sequence of the oligonucleotides used to amplify the leftmost and rightmost regions surrounding each region targeted. In the case of plasmids pEM 23, pEM22, pEM20 and pEM21, DNA fragments were amplified using the indicated oligonucleotides, cut with the restriction enzymes positioned at each end and inserted into the appropriate plasmid as described in more detail in the results section for one plasmid. In the case of pEM18, each region was amplified by PCR with two different sets of oligonucleotide primers chosen so as to be able to generate the desired restriction sites at their ends upon denaturation of the fragments and reannealing of the two fragments together. The fragments surrounding each targeted deletion were then joined together two by two in a single bacterial plasmid so as to reproduce the deletions on the plasmid.

Virus Propagation and Cell Culture Methods:

The VACV Lister strain derived from the first generation smallpox vaccine was initially amplified and cloned in the human diploid fibroblast cell line MRC5 (obtained from bioMérieux) cultivated in RPMI 1640 Glutamax medium supplemented with 10% fetal calf serum (obtained from South America) and 40 μg/ml gentamycine. Lister clone VACV-107 and deletion mutants derived from it were amplified and cloned in the chicken embryonic stem cell line EbxR (obtained from Vivalis) cultivated in DMEM/F12 medium supplemented with 10% fetal calf serum, non essential amino acids, 1 mM sodium pyruvate and 40 μg/ml gentamycine. Baby hamster kidney cells (BHK21) were cultivated in BHK21 medium supplemented with 1.5 g/ml bacto-tryptose phosphate, gentamycine and 10% fetal calf serum. The BHK21 cell line was used to determine virus titers after infection of the majority of the cell lines examined but was never used to passage virus or produce virus stocks. Vero cells were cultivated in M199 medium supplemented with 5% fetal calf serum, 100 international units (IU) penicillin and 100 IU streptomycin. Human HeLa cells were cultivated in DMEM with 10% fetal calf serum and 40 μg/ml gentamycine. The titers obtained after infection of MRC5 cells were determined on Vero cells.

Assay for the Determination of Vaccinia Virus Neutralizing Antibodies and Vaccinia Virus T Lymphocyte Responses Mice were anesthetized with pentobarbital and bled by intracardiac puncture. Vaccinia virus neutralizing antibodies were then titrated according to the method described by Leparc-Goffart et AL. (2005). Serum samples were first incubated at 56° C. for 30 minutes then submitted to serial two-fold dilutions in PBS. The samples were then mixed with an equal volume of vaccinia virus containing 15-55 PFU/0.1 ml for one hour at 37° C. and added to Vero cell monolayers. Two days later virus plaques were counted. The neutralization titer was expressed as the reciprocal serum dilution that led to a 50% reduction in the number of plaques as compared to the control. The threshold of the titration was 10.

To measure T lymphocyte responses the percentage of $CD4^+$ and $CD8^+$ lymphocytes expressing intracellular IFN-γ was measured by flow cytometry as previously described by Ferrier-Rembert et al, (2007). Briefly, mature bone marrow dendritic cells from uninfected Balb/c mice were infected with VACV then incubated with spleen cell suspensions from infected animals for six hours at a ratio of one mature dendritic cell for two splenocytes. Brefeldin A (5 μg/ml) was added for the last four hours to block cytokine secretion. Cells were stained with FITC-coupled anti-CD8b2 and APC-couple anti-CD4 mAbs, fixed and permeabilised. Intracellular IFN-γ was stained with a PE-coupled anti-IFN-γ mAb and cells were fixed in 2% formaldehyde diluted in PBS. Flow cytometry was performed on a Beckman Coulter FC500 and the data analyzed with the CYTOMICS RXP® data analysis software (Beckman Coulter).

Methods Used to Obtain Virus Deletions: Transfection, Selection and Screening:

In order to isolate deletion mutants, EBxR cells were plated at approximately 300 000 cells per 35 mm² Petri dish and incubated overnight at 37° C. in a cell culture incubator containing 5% CO2. The cells were then infected with VACV-107 or one of its derivatives in which a deletion was to be introduced with approximately 0.1 PFU/cell for one hour. After this period of time the suspension containing unadsorbed virus was removed, the cells were washed twice with serum free medium and the appropriate plasmid was transfected into the cells using Lipofectamine (Invitrogen). About 1 µg of purified plasmid DNA in 10 µl DNA buffer was mixed with 100 µl EBxR culture medium without serum and 5 µl Lipofectamine were mixed with 100 µl of the EBxR culture medium without serum. The DNA mixture was then added to the Lipofectamine mixture and left to stand at room temperature for 15 minutes. Culture medium without serum (0.8 ml) and the DNA/Lipofectamine mix (0.2 ml) were then added to the previously infected cells. The cells were put into a 37° C. incubator under 5% $CO_2$. One day later cells were observed under the microscope by UV illumination to visualize expression of GFP, a marker of successful transfection and the cells were frozen down at −20° C. On the same day or several days later, the infected cells were thawed and then submitted to several additional rounds of freezing thawing to lyse all cells and the virus in the cell lysates was used to infect fresh EBxR cells in the presence of a selective pressure for the expression of the GPT gene. Selection was carried out under cell culture medium containing 1.2% low melting temperature agarose, 0.025 µg/ml mycophenolic acid, 0.25 µg/ml xanthine and 15 µg/ml hypoxanthine. One day later viral plaques formed in the presence of the selective medium were visualized by microscopy under UV light and fluorescent plaques were picked with a pipette and placed in 0.5 ml EBxR culture medium. The virus from each plaque was amplified by infection of EBxR cells in the presence of selective pressure but without agarose. This procedure of cloning the virus under selective pressure and amplification was repeated several times. Two to three independent virus clones able to form fluorescent plaques were then used to infect fresh EBxR cells after limiting dilution and in the absence of selective pressure but under an agarose overlay. This time only non fluorescent plaques were picked after two days infection and the virus was amplified on EBxR cells in the absence of selective pressure. A sample of the amplified virus stock was used to extract total DNA and the DNA was submitted to PCR using one of the appropriate pairs of primers indicated in table 2. The primers were designed so as to be able to detect the presence of the deleted viral DNA as well as undeleted viral DNA or a mixture of the two. The clones which contained only deleted viral DNA were submitted to two additional cloning steps in the absence of selective pressure, picking and amplification on EBxR cells. The viral deletions were again confirmed in another round of PCR analysis of DNA from the more thoroughly cloned virus mutants. Finally virus stocks were made by amplification on EBxR cells.

Animal Experiments:

Animal experiments were carried out using mice in accordance with French regulations on laboratory animals and received permission from the ethics committee where they were performed (CRSSA).

Protection of Mice Against a Lethal Intranasal Cowpox Virus Infection after Vaccination:

The ability of the deleted viruses to confer protective immunity after vaccination was assayed in 4 week old female BALB/c mice. Groups of 6 animals were tested and treated in the same manner for each condition studied. Before vaccination, mice were anesthetised by intraperitoneal injection of ketamine (75 mg/kg) and atropine (1.5 mg/kg). The mice were then scarified at the base of the tail with the tip of a 23 gauge needle. Three μl of virus at various concentrations was deposited at the scarification site. Twenty eight days after vaccination, the mice were anesthetised as described above and challenged by intranasal instillation with $2\times10^6$ 50% tissue culture infectious doses 50 ($TCID_{50}$) of cowpox virus (Brighton strain VR302 obtained from the ATCC and amplified in Vero cells) which corresponds to a dose of virus 30 fold higher than the dose that kills 50% of mice (Ferrier-Rembert et AL., 2007b). For the challenge, 50 μl of virus or 50 μl of NaCl 9°/°° were deposited in both nostrils using a micropipette with a sterile tip. Clinical signs of disease (weight loss, ruffling of the fur, and reduced mobility) and mortality were noted for the following three weeks. The animals were euthanized at the end of the experiment by cervical dislocation.

Assessment of Attenuation in Nude Mice Deficient in T Lymphocytes

Five week old Swiss Nude mice (Charles Rivers Laboratories) were anesthetised (100 mg/kg ketamine et 1.5 mg/kg atropine) and challenged with Lister VACV-107 or deletion mutants derived from it by tail scarification as described above using 5.0 log PFU of each virus. Clinical signs of disease and mortality were followed over an 8 week period.

Results

Construction of Plasmids Used to Isolate Deletion Mutants of VACV-107:

The construction of the plasmids used to delete targeted regions of the VACV-107 genome was carried out in the same manner for each of the deletions. First, the leftmost fragment of the targeted region in VACV-107, corresponding to the 3.5 Kb deletion in MVA, was first amplified by PCR using primers 1 and 2 designed for this deletion and indicated in table 1a. The DNA fragment obtained by PCR and separated by electrophoresis on an agarose gel was purified then cut with Xho I and Bam HI. The fragment was then inserted by ligation into a small bacterial plasmid, pEM8, to generate pEM9. The rightmost fragment of the targeted region (deletion 3.5 Kb in MVA) was then amplified by PCR using primers 3 and 4 indicated in table 1a and in the same manner as for the leftmost fragment was cut with Bam HI and Sac I then inserted by ligation into pEM9 to generate pEM10. We also constructed the pEM7 plasmid so as to contain side by side the GFP gene (gene encoding enhanced green fluorescent protein from BD Biosciences Clontech) under the control of a synthetic early promoter (Davison, A. J. and Moss, B., 1990; Howley et AL., 1996) and the GPT gene under the control of the p7.5 kd VACV promoter by modification of the pG08 plasmid (Sutter et AL., 1994). The juxtaposed GFP and GPT genes were flanked by an Eco RI site at the left end and a Pst I site at the right end. Thus a DNA fragment containing the GFP and GPT genes was cut out from pEM7 using Eco RI and Pst I and inserted by ligation into pEM10 previously cut with Sac I and Pst I. A single stranded oligonucleotide linker (5' gagctaattc3') was added to the ligation reaction to enable ligation of the Eco RI end of the fragment to the Sac I end of the pEM10 plasmid. This procedure generated plasmid pEM20 which was used in the transfection experiments described below. All of the other plasmids were constructed in the same manner except pEM18 in which case the oligonucleotides used for PCR amplification were designed to create the Xho I, Bam HI and Sac I sites after annealing together two PCR fragments for both the leftmost and rightmost regions targeted.

Isolation of Virus Deletion Mutants:

In a first step, mutants deleted in a single region were isolated after transfection of one of the plasmids into chicken EBxR cells infected with VACV-107 as described in detail in the methods section. Deletion mutants were designated according to the name of the plasmid from which they were isolated. For instance the use of pEM20 generated a virus named VACV-107Δ20 and for convenience virus names are sometimes shortened to the include only the deletion considered (for example VACV-107Δ20 may be shortened to Δ20). To isolate viruses deleted in two regions simultaneously, EBxR cells were infected with a virus deleted in one region and transfected with another plasmid required to delete another region. For instance virus Δ18/22 was isolated from cells infected with virus Δ18 and transfected with plasmid pEM22. The deletions were all confirmed by PCR analysis of DNA extracted from infected cells. Deletion Δ23 which is in an area of the genome that is repeated at both ends was initially isolated as a virus having only one end deleted. After cloning this virus on EBxR cells and analysis of several more virus clones we readily isolated a Δ23 virus with both ends deleted.

Multiplication of Deletion Mutants in Selected Cell Lines.

The deletion mutants were routinely propagated on the chicken embryonic stem cell line EbxR and all of them were found to multiply to high levels. Titration of virus was performed on hamster BHK21 cells and all of the deletion mutants produced similar and clearly visible plaques after a two day incubation period.

HeLa cells were also infected to investigate whether these human cells were permissive for multiplication of the mutants. Initial experiments showed that all of the mutants with single deletions multiplied well in HeLa cells except mutant Δ22 which induced virus yields about 5-10 fold lower than the parental VACV 107 strain. The influence of the Δ22 deletion within the background of other deletions was then investigated. Virus titers in the infected cell cultures were assayed on BHK21 cells after several cycles of freezing and thawing samples either 3 hours after infection (to determine the amount of input virus) or 48 hours after infection (to determine the yields). The input 3 hours post infection titers varied up to two fold. Forty eight hours after infection all deletion mutants containing the Δ22 deletion multiplied to levels 4 to 5 fold lower than the VACV 107 strain (FIG. 1a) indicating that this deletion indeed affected virus multiplication in human HeLa cells. However, there was no additional effect of the other deletions on virus multiplication indicating that only Δ22 contributed to the reduced virus yields. Similar experiments carried out in the human diploid fibroblast cell line MRC5 also indicated that the Δ22 deletion entailed reduced virus yields in this cell line (FIG. 1b). The other deletion mutants examined which did not harbor a Δ22 deletion multiplied as efficiently as the parental VACV 107 strain.

Figure 2:
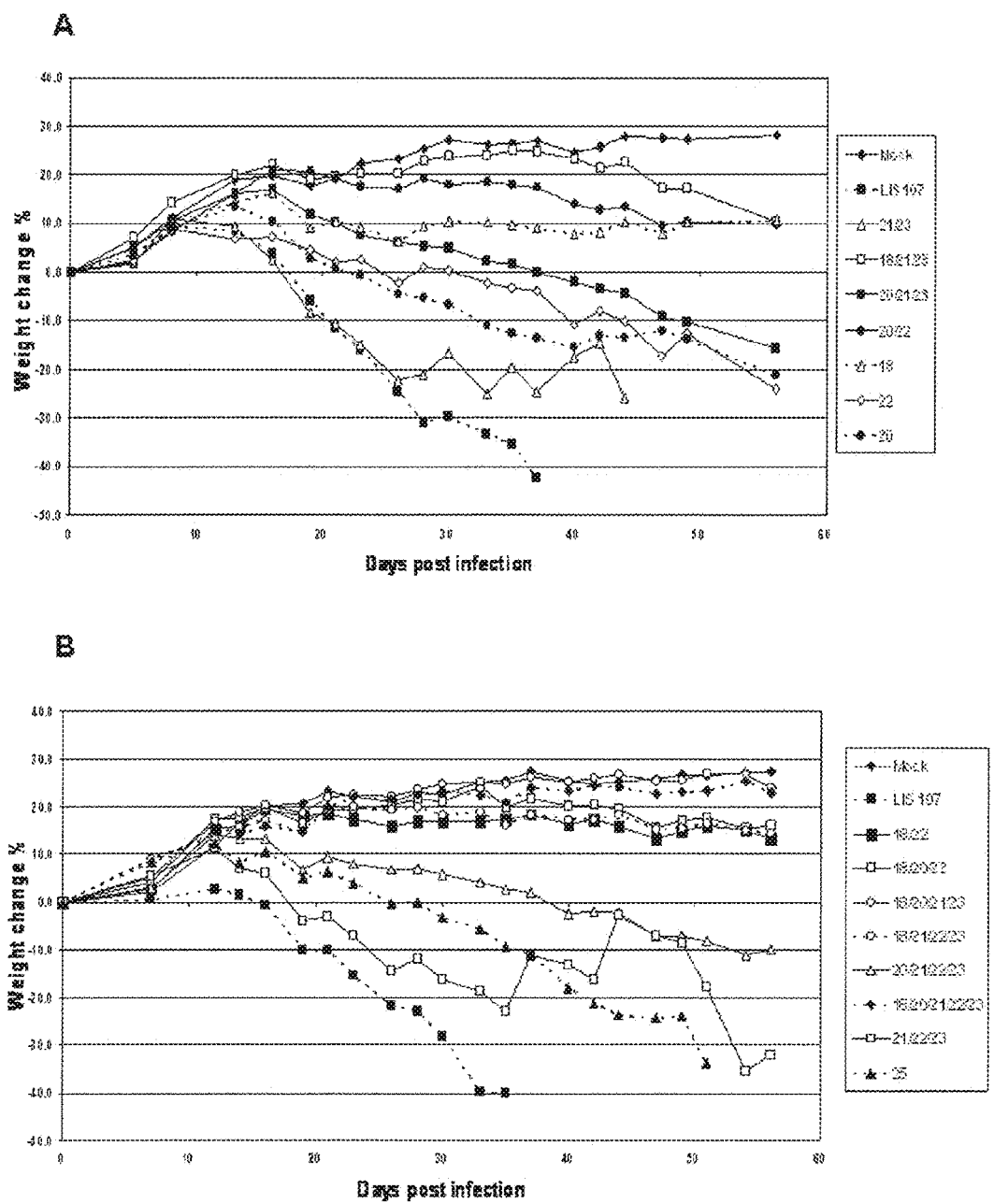

Assessment of Attenuation of the Deletion Mutants in Nude Mice:

Traditional smallpox vaccination can not be performed in immunocompromised people suffering from active HIV infection, drug induced or innate immunodepression. It should generally be recommended that these people and even their families are excluded from vaccination campaigns even though some may escape notice. In case of extensive exclusion from vaccination, too many people could be unvaccinated. Thus, it appears essential to have a vaccine available that is without any danger in immunocompromised individuals. In order to assess the potential danger associated with the use of the deletion mutants described above their pathogenicity upon vaccination of Nude mice lacking a thymus was studied. Nude mice are deficient in the production of antigen specific lymphocytes and T cell dependent antibody responses and therefore highly susceptible to vaccinia virus infection unlike immunocompetent mice (Ramshaw et AL. 1987). The experiments in FIG. 2 show that tail scarification of Nude mice with about $10^5$ PFU of VACV-107 or the traditional smallpox vaccine (not shown) inhibits the normal weight increase seen over time in Nude mice and leads to the death of all the animals starting around day 28 post infection. Mice infected with the deletion mutant VACV-107Δ20 (2 dead out of 6), VACV-107Δ22 (2 dead out of 6) VACV-107Δ21/23 (6 dead out of 6) and VACV-107Δ21/22/23 (5 dead out of 6) displayed a similar behaviour to those infected with VACV-107. All the other deletion mutants were significantly less virulent than VACV-107 or the first generation smallpox vaccine (data not shown for the latter virus) as testified by more weight increase and no mortality over time. In particular, the deletions mutants VACV-107Δ18/21/23, VACV-107Δ18/20/21/23, VACV-107Δ18/20/22 and VACV-107Δ18/20/21/22/23 displayed total attenuation in the Nude mouse model (no significant change in weight over time as compared to unvaccinated mice; Dunnett test p>0.05). It may also be pointed out that the majority of the deletion mutants described here were less virulent than VACV-Lis107Δ25 (6 dead out of 6), a virus which was deleted in the thymidine kinase gene to serve as a well known reference of attenuation.

Another experiment was performed to assess attenuation of one deletion mutant that had not been tested in the previous experiments (VACV-107Δ18/20) and others which appeared to be the most highly attenuated according to the experiments presented in FIG. 2. Again athymic Nude mice were scarified at the base of the tail with about $10^5$ PFU per animal and weight loss as well as animal survival were followed over time. Mice infected with VACV-107 died between 28 and 36 days after infection. All other animals infected with the deletion mutants survived the infection over the period of observation. Mice infected with some of the deletion mutants gained weight somewhat more slowly than uninfected mice (FIG. 3) and some of them developed slowly evolving lesions at the site of inoculation or at distant sites but no general morbidity was observed. In conclusion, all the deletion mutants tested in this experiment are highly attenuated in Nude mice as compared to the parental VACV strain.

Assessment of Immunogenicity

The ability of the some of the most severely attenuated deletion mutants to induce vaccinia virus neutralizing antibodies in mice was assessed using a standardized assay. (FIG. 4a). The cloned Lister strain 107 and the standard Lister vaccine induced a very similar level of neutralizing antibodies. All of the deletion mutants induced a level of antibodies comparable to that of the parental Lister strain with the exception of deletion VACV-LisΔ18/20 which was slightly lower and deletion VACV-LisΔ21/23/18/20 which was slightly higher.

The cell mediated immune responses were also assayed after tail scarification of groups of 6 Balb/C mice with $10^5$ PFU/animal (FIG. 4b). Spleens were recovered four weeks later and spleen cell suspensions were then stimulated with VACV-infected dendritic cells. The level of VACV-specific $CD4^+$ and $CD8^+$ lymphocytes was measured by assaying for the percentage of interferon-γ secreting cells in the spleen cell population using flow cytometry. The uncloned VACV-L is strain and the clonal isolate VACV-L is 107 induced a comparable and approximately two-fold increase in the VACV specific CD4+ lymphocyte response relative to mock-infected animals which was statistically significant (t-test de Student; P<0.05). Moreover, all of the deletion mutants induced a VACV-specific CD4+ response comparable to the response induced by VACV Lis-107 (p>0.05). In the case of the CD8+ cell response both the uncloned VACV-L is strain and the clonal isolate induced a similar response which was about 7 fold higher than the basal level measured for splenocytes from mock-infected animals. All of the deletions mutants induced a slightly weaker CD8+ response than VACV-L is 107 but this difference was only significant (p<0.05) for deletions mutants ΔII, III, V, ΔII, IV, V and ΔII, III, IV, V.

Vaccination of Mice by Deletion Mutants and Challenge with Cowpox Virus:

In order to quantitatively assess the ability of the most highly attenuated VACV mutants harboring specific deletions, BALB/c mice were vaccinated by scarification at the base of the tail with a total of $10^4$, $10^3$ or $10^2$ PFU per mouse. Each dose was administered to 6 mice then one month after vaccination the mice were challenged with cowpox virus and clinical signs of disease and mortality were noted. The survival of the animals after the challenge infection, performed in two independent experiments, is presented in FIG. 5. All animals in the unvaccinated groups (6 mice in each experiment) succumbed after infection with cowpox virus between the 6th and 10th day after infection and none of the unvaccinated, unchallenged animals (6 mice in each experiment) succumbed (data not shown in FIG. 5). All animals vaccinated with the $10^4$ PFU dose of the VACV-107 strain (one tenth of the dilution of the traditional vaccine) survived the challenge infection whereas animals vaccinated with the $10^3$ PFU dose and the $10^2$ dose were partially protected. The viral dose able to protect 50% of the animals ($PD_{50}$) was calculated using the method of Reed and Muench. The $PD_{50}$ results for each virus are provided on the right hand side of FIG. 5. Comparison of the efficiency of vaccination of the different deletion mutants shows that most of the mutants protected against mortality induced by the cowpox virus infection with similar efficiency as that of the parental vaccine with the exception of deletion mutants Δ18/20 et Δ18/22 in which case the $PD_{50}$ was significantly different from VACV-107 (Log-rank test: p<0.015 and p<0.017 respectively). Most remarkably, viruses deleted simultaneously in up to 4 and 5 regions of the genome protected mice as efficiently as the VACV-107 isolate. It may be pointed out as well that the $PD_{50}$ values obtained for the majority of the deletion mutants were about 100 fold lower than the value determined for the MVA strain (Ferrrier-Rembert et Al. 2008).

Another experiment was performed to assess vaccine efficacy of the most highly attenuated deletion mutants which were initially found to be as effective in vaccination as the parental VACV-107 strain. As previously, mice were vaccinated with either $10^4$, $10^3$ or $10^2$ PFU per animal by tail scarification. They were then challenged one month later with cowpox virus and animal deaths were recorded. The survival data are presented in FIG. 6 and the change in weight of the animals after challenge infection is presented in FIG. 7. Again all animals in the unvaccinated group succumbed to the cowpox challenge between the $6^{th}$ and $10^{th}$ day post infection and all the unvaccinated, unchallenged animals survived. All animals vaccinated with $10^4$ PFU of the traditional smallpox vaccine (Lister) survived the challenge infection whereas the animals immunized with the $10^3$ PFU and $10^2$ PFU doses were not protected. Except for VACV 107Δ18/21/23, the deletions mutants induced partial survival with the $10^3$ PFU and $10^2$ PFU doses and therefore were at least as effective as the traditional smallpox vaccine. The viral doses able to protect 50% of the animals ($PD_{50}$) were calculated using the Reed and Muench method (provided in FIG. 6) and according to these results all of the mutants were as effective as the parental Lister strain (Log-rank test: p>0.05) with the exception of VACV 107Δ18/21/23.

In order to study the protection against disease provided by vaccination, animal weight loss observed after the challenge infection reported above was recorded. Data for the $10^4$ vaccine dose are shown in FIG. 7. Statistical analysis (Dunnett test) revealed that there was no significant difference between protection against morbidity induced by VACV-107 or the traditional smallpox vaccine and the various deletion mutants (p≥0.05).

REFERENCES

Antoine, G., F. Scheiflinger, F. Dorner, and F. G. Falkner. 1998. The complete genomic sequence of the modified vaccinia Ankara strain: comparison with other orthopoxviruses. Virology 244:365-96.

Davison, A. J., and B. Moss. 1989. Structure of vaccinia virus early promoters. J Mol Biol 210:749-69.

Fenner F, Henderson D A, Arita I, Jezek Z, Ladnyi I D. Smallpox and its eradication. Geneva: WHO; 1988. p. 1460.

Fenner F. Smallpox, "the most dreadful scourge of the human species". Its global spread and recent eradication (2). Med J Aust 1984; 141(11):728-35.

Falkner, F. G., and B. Moss. 1990. Transient dominant selection of recombinant vaccinia viruses. J Virol 64:3108-11.

Ferrier-Rembert, A., Drillien, R., Tournier, J. N., Garin, D. and Crance, J. M. 2007b. Intranasal cowpox virus infection of the mouse as a model for preclinical evaluation of smallpox vaccines. Vaccine, 25, 4809-4817

Ferrier-Rembert A, Drillien R, Tournier J N, Garin D, Crance J M. Short- and long-term immunogenicity and protection induced by non-replicating smallpox vaccine candidates in mice and comparison with the traditional $1^{st}$ generation vaccine. Vaccine. 2008; 26, 1794-804

Garcel, A., J. M. Crance, R. Drillien, D. Garin, and A. L. Favier. 2007. Genomic sequence of a clonal isolate of the vaccinia virus Lister strain employed for smallpox vaccination in France and its comparison to other orthopoxviruses. J Gen Virol 88:1906-16. Garcel, A., J. Perino, J. M. Crance, R. Drillien, D. Garin, and A. L. Favier. Phenotypic and genetic diversity of the traditional Lister smallpox vaccine. Vaccine. 2009; 27(5):708-17.

Garcel A, Crance J M, Drillien R, Garin D, Favier A L. Genomic sequence of a clonal isolate of the vaccinia virus Lister strain employed for smallpox vaccination in France and its comparison to other orthopoxviruses. J Gen Virol 2007; 88:1906-16.

Howley, P. M., D. Spehner, and R. Drillien. 1996. A vaccinia virus transfer vector using a GUS reporter gene inserted into the I4L locus. Gene 172:233-7.

Leparc-Goffart, I., Poirier, B., Garin, D., Tissier, M-H., Fuchs, F. and Crance, J. M. 2005. Standardization of a neutralizing anti-vaccinia antibodies titration method: an essential step for titration of vaccinia immunoglobulins and smallpox vaccines evaluation. J. Clin. Virol. 32, 47-52.

Lee, M. S., J. M. Roos, L. C. McGuigan, K. A. Smith, N. Cormier, L. K. Cohen, B. E. Roberts, and L. G. Payne. 1992. Molecular attenuation of vaccinia virus: mutant generation and animal characterization. J Virol 66:2617-30.

Mahnel H, Mayr A. Experiences with immunization against *orthopox* viruses of humans and animals using vaccine strain MVA. Berl Munch Tierarztl Wochenschr. 1994 August; 107(8):253-6. Review. German.

Meisinger-Henschel C, Schmidt M, Lukassen S, Linke B, Krause L, Konietzny S, Goesmann A, Howley P, Chaplin P, Suter M, Hausmann J. Genomic sequence of chorioallantois vaccinia virus Ankara, the ancestor of modified vaccinia virus Ankara J Gen Virol. 2007 88, 3249-59.

Meyer, H., Sutter G., and Mayr A. Mapping of deletions in the genome of the highly attenuated vaccinia virus MVA and their influence on virulence. 1991. J Gen Virol 72 (Pt 5):1031-8)

Monath T P, Caldwell J R, Mundt W, Fusco J, Johnson C S, Buller M, et al. ACAM2000 clonal Vero cell culture vaccinia virus (New York City Board of Health strain) a second-generation smallpox vaccine for biological defense. Int J Infect Dis 2004; 8(Suppl. 2):S31-44.

Ramshaw, I. A., M. E. Andrew, S. M. Phillips, D. B. Boyle, and B. E. Coupar. 1987. Recovery of immunodeficient mice from a vaccinia virus/IL-2 recombinant infection. Nature 329:545-6.

Sambrook, J., and D. W. Russell. 2001. Molecular cloning: a laboratory manual 3ed. Cold Spring Harbor Laboratory Press, Cold Spring Harbor, N.Y.

Spehner, D., R. Drillien, and J. P. Lecocq. 1990. Construction of fowlpox virus vectors with intergenic insertions: expression of the beta-galactosidase gene and the measles virus fusion gene. J Virol 64:527-33.

Sutter, G., L. S. Wyatt, P. L. Foley, J. R. Bennink, and B. Moss. 1994. A recombinant vector derived from the host range-restricted and highly attenuated MVA strain of vaccinia virus stimulates protective immunity in mice to influenza virus. Vaccine 12:1032-40.

Weltzin R, Liu J, Pugachev K V, Myers G A, Coughlin B, Blum P S, et al. Clonal vaccinia virus grown in cell culture as a new smallpox vaccine. Nat Med 2003; 9(9):1125-30.

The invention claimed is:

1. A recombinant vaccinia virus, wherein said recombinant vaccinia virus comprises a genomic sequence SEQ ID NO: 1 with at least one deletion, and wherein said at least one deletion is selected from the group consisting of:

deletion of nucleotides 19758 to 28309 (Δ18) and deletion of nucleotides 161293 to 164811 (Δ20);

deletion of nucleotides 19758 to 28309 (Δ18) and deletion of nucleotides 181231 to 183304 (Δ21);

deletion of nucleotides 19758 to 28309 (Δ18) and deletion of nucleotides 6118 to 9677 (Δ22);

deletion of nucleotides 19758 to 28309 (Δ18) and a deletion of nucleotides 1833 to 3574 and 185848 to 187589 (Δ23);

deletion of nucleotides 19758 to 28309 (Δ18), deletion of nucleotides 161293 to 164811 (Δ20) and deletion of nucleotides 181231 to 183304 (Δ21);

deletion of nucleotides 19758 to 28309 (Δ18), deletion of nucleotides 161293 to 164811 (Δ20) and deletion of nucleotides 6118 to 9677 (Δ22);

deletion of nucleotides 19758 to 28309 (Δ18), deletion of nucleotides 161293 to 164811 (Δ20) and deletion of nucleotides 1833 to 3574 and 185848 to 187589 (Δ23);

deletion of nucleotides 19758 to 28309 (Δ18), deletion of nucleotides 181231 to 183304 (Δ21) and deletion of nucleotides 6118 to 9677 (Δ22);

deletion of nucleotides 19758 to 28309 (Δ18), deletion of nucleotides 181231 to 183304 (Δ21) and deletion of nucleotides 1833 to 3574 and 185848 to 187589 (Δ23);

deletion of nucleotides 19758 to 28309 (Δ18), deletion of nucleotides 6118 to 9677 (Δ22) and deletion of nucleotides 1833 to 3574 and 185848 to 187589 (Δ23);

deletion of nucleotides 19758 to 28309 (Δ18), deletion of nucleotides 161293 to 164811 (Δ20), deletion of nucleotides 181231 to 183304 (Δ21) and deletion of nucleotides 6118 to 9677 (Δ22);

deletion of nucleotides 19758 to 28309 (Δ18), deletion of nucleotides 161293 to 164811 (Δ20), deletion of nucleotides 181231 to 183304 (Δ21) and deletion of nucleotides 1833 to 3574 and 185848 to 187589 (Δ23);

deletion of nucleotides 19758 to 28309 (Δ18), deletion of nucleotides 181231 to 183304 (Δ21), deletion of nucleotides 6118 to 9677 (Δ22) and deletion of nucleotides 1833 to 3574 and 185848 to 187589 (Δ23); and deletion of nucleotides 19758 to 28309 (Δ18), deletion of nucleotides 161293 to 164811 (Δ20), deletion of nucleotides 181231 to 183304 (Δ21), deletion of nucleotides 6118 to 9677 (Δ22) and deletion of nucleotides 1833 to 3574 and 185848 to 187589 (Δ23).

2. The recombinant vaccinia virus of claim 1, wherein said recombinant vaccinia virus is derived from vaccinia virus Lister VACV-107.

3. The recombinant vaccinia virus of claim 1, wherein said recombinant vaccinia virus further comprises at least one heterologous nucleic acid sequence.

4. The recombinant vaccinia virus of claim 3, wherein said at least one heterologous nucleic acid sequence encodes an antigenic epitope.

5. An immunogenic composition comprising a recombinant vaccinia virus, wherein said recombinant vaccinia virus comprises a genomic sequence SEQ ID NO: 1 with at least one deletion, and wherein said at least one deletion is selected from the group consisting of:

deletion of nucleotides 19758 to 28309 (Δ18) and deletion of nucleotides 161293 to 164811 (Δ20);

deletion of nucleotides 19758 to 28309 (Δ18) and deletion of nucleotides 181231 to 183304 (Δ21);

deletion of nucleotides 19758 to 28309 (Δ18) and deletion of nucleotides 6118 to 9677 (Δ22);

deletion of nucleotides 19758 to 28309 (Δ18) and a deletion of nucleotides 1833 to 3574 and 185848 to 187589 (Δ23);

deletion of nucleotides 19758 to 28309 (Δ18), deletion of nucleotides 161293 to 164811 (Δ20) and deletion of nucleotides 181231 to 183304 (Δ21);

deletion of nucleotides 19758 to 28309 (Δ18), deletion of nucleotides 161293 to 164811 (Δ20) and deletion of nucleotides 6118 to 9677 (Δ22);

deletion of nucleotides 19758 to 28309 (Δ18), deletion of nucleotides 161293 to 164811 (Δ20) and deletion of nucleotides 1833 to 3574 and 185848 to 187589 (Δ23);

deletion of nucleotides 19758 to 28309 (Δ18), deletion of nucleotides 181231 to 183304 (Δ21) and deletion of nucleotides 6118 to 9677 (Δ22);

deletion of nucleotides 19758 to 28309 (Δ18), deletion of nucleotides 181231 to 183304 (Δ21) and deletion of nucleotides 1833 to 3574 and 185848 to 187589 (Δ23);

deletion of nucleotides 19758 to 28309 (Δ18), deletion of nucleotides 6118 to 9677 (Δ22) and deletion of nucleotides 1833 to 3574 and 185848 to 187589 (Δ23);

deletion of nucleotides 19758 to 28309 (Δ18), deletion of nucleotides 161293 to 164811 (Δ20), deletion of nucleotides 181231 to 183304 (Δ21) and deletion of nucleotides 6118 to 9677 (Δ22);

deletion of nucleotides 19758 to 28309 (Δ18), deletion of nucleotides 161293 to 164811 (Δ20), deletion of nucleotides 181231 to 183304 (Δ21) and deletion of nucleotides 1833 to 3574 and 185848 to 187589 (Δ23);

deletion of nucleotides 19758 to 28309 (Δ18), deletion of nucleotides 181231 to 183304 (Δ21), deletion of nucleotides 6118 to 9677 (Δ22) and deletion of nucleotides 1833 to 3574 and 185848 to 187589 (Δ23); and deletion of nucleotides 19758 to 28309 (Δ18), deletion of nucleotides 161293 to 164811 (Δ20), deletion of nucleotides 181231 to 183304 (Δ21), deletion of nucleotides 6118 to 9677 (Δ22) and deletion of nucleotides 1833 to 3574 and 185848 to 187589 (Δ23) and a pharmaceutically acceptable carrier.

6. The immunogenic composition of claim 5, wherein said recombinant vaccinia virus further comprises at least one heterologous nucleic acid sequence.

7. The immunogenic composition of claim 6, wherein said at least one heterologous nucleic acid sequence encodes an antigenic epitope.

* * * * *